United States Patent [19]
Somers et al.

[11] Patent Number: 6,034,216
[45] Date of Patent: Mar. 7, 2000

[54] LOW MOLECULAR WEIGHT PEPTIDOMIMETIC GROWTH HORMONE SECRETAGOGUES

[75] Inventors: Todd C. Somers, Foster City; Kathleen A. Elias, San Francisco; Ross G. Clark, Pacifica; Robert S. McDowell, San Francisco; Mark S. Stanley; John P. Burnier, both of Pacifica; Thomas E. Rawson, Mountain View, all of Calif.

[73] Assignee: Genentech Inc., South San Franciso, Calif.

[21] Appl. No.: 09/057,074

[22] Filed: Apr. 8, 1998

Related U.S. Application Data

[62] Division of application No. 08/340,767, Nov. 16, 1994, Pat. No. 5,798,337.

[51] Int. Cl.$^7$ .................................................. A61K 38/06
[52] U.S. Cl. ............................. 530/331; 514/18; 514/19; 548/496; 562/445
[58] Field of Search ................... 514/19, 18; 424/177; 530/331; 548/496; 562/445

[56] References Cited

U.S. PATENT DOCUMENTS

| | | | |
|---|---|---|---|
| 4,223,020 | 9/1980 | Momany | 424/177 |
| 4,223,021 | 9/1980 | Momany | 424/177 |
| 4,224,313 | 9/1980 | Zimmerman et al. | 424/94 |
| 4,224,316 | 9/1980 | Momany et al. | 424/177 |
| 4,226,857 | 10/1980 | Momany | 424/177 |
| 4,228,155 | 10/1980 | Momany | 424/177 |
| 4,228,156 | 10/1980 | Momany | 424/177 |
| 4,228,157 | 10/1980 | Momany et al. | 424/177 |
| 4,228,158 | 10/1980 | Momany | 424/177 |
| 4,410,512 | 10/1983 | Bowers | 424/177 |
| 4,410,513 | 10/1983 | Momany | 424/177 |
| 4,411,890 | 10/1983 | Momany | 424/177 |
| 4,839,344 | 6/1989 | Bowers et al. | 514/16 |
| 4,880,777 | 11/1989 | Momany | 424/177 |
| 5,206,235 | 4/1993 | Fisher et al. | 514/213 |
| 5,246,920 | 9/1993 | Bercu et al. | 514/12 |
| 5,268,360 | 12/1993 | Yoshikawa et al. | 514/18 |
| 5,283,241 | 2/1994 | Bochis et al. | 514/183 |
| 5,663,146 | 9/1997 | Bowers et al. | 514/16 |
| 5,663,171 | 9/1997 | Chen et al. | 514/19 |
| 5,767,085 | 6/1998 | Johansen et al. | 514/17 |

FOREIGN PATENT DOCUMENTS

| | | |
|---|---|---|
| 12724/95 | 7/1995 | Australia. |
| 018072 | 10/1980 | European Pat. Off.. |
| 274259 | 7/1988 | European Pat. Off.. |
| WO 89/07111 | 8/1989 | WIPO. |
| WO 89/10933 | 11/1989 | WIPO. |
| WO 92/01711 | 2/1992 | WIPO. |
| WO 93/04081 | 3/1993 | WIPO. |
| WO 94/08583 | 4/1994 | WIPO. |
| WO 94/11012 | 5/1994 | WIPO. |
| WO 94/13696 | 6/1994 | WIPO. |
| WO 95/11029 | 4/1995 | WIPO. |
| WO 95/13069 | 5/1995 | WIPO. |
| WO 95/14666 | 6/1995 | WIPO. |
| WO 95/17423 | 6/1995 | WIPO. |
| WO 95/34311 | 12/1995 | WIPO. |
| WO 96/22997 | 8/1996 | WIPO. |

OTHER PUBLICATIONS

Bowers et al., "On the in Vitro and in Vivo activity of a new synthetic hexapeptide that acts on the pituitary to specifically release growth hormone" *Endocrinology* 114(5):1537–1545 (1984).

Bowers et al., "Structure–activity relationships of a synthetic pentapeptide that specifically releases growth hormone in Vitro" *Endocrinology* 106(3):663–667 (1980).

Bowers, C.Y., "GH Releasing Peptides—Structure and Kinetics" *J. Pediatr. Endocrinology* 6(1):21–31 (1993).

Deghenghi et al., "GH–Releasing Activity of Hexarelin, A New Growth Homrone Releasing Peptide, in Infant and Adult Rats" *Life Sciences* 54(18):1321–1328 (1994).

Egorova et al., "Synthesis of shortened analogs of substance P with modification of the glutamine residue at position 6" *Chemical Abstracts* (abstract only) 116(11):abstract No. 106743 (1992).

Lin, Tsau–Yen et al., "Inhibition of Cathepsin D by Synthetic Oligopeptides" *Journal of Biological Chemistry* 254(23):11875–11883 (1979).

Lin, Tsau–Yen et al., "Inhibition of cathepsin D by synthetic oligopeptides" *Chemical Abstracts* (abstract only) 92(1):abstract No. 2280 (1980).

(List continued on next page.)

*Primary Examiner*—Cecilia J. Tsang
*Assistant Examiner*—David Lukton
*Attorney, Agent, or Firm*—Daryl B. Winter; Timothy R. Schwartz

[57] ABSTRACT

The present invention comprises growth hormone releasing peptides/peptidomimetics (GHRP) capable of causing release of growth hormone from the pituitary. Compositions containing the GHRP's of this invention are used to promote growth in mammals either alone or in combination with other growth promoting compounds, especially IGF-1. In a method of this invention GHRP's in combination with IGF-1 are used to treat Type II diabetes. An exemplary compound of this invention is provided below.

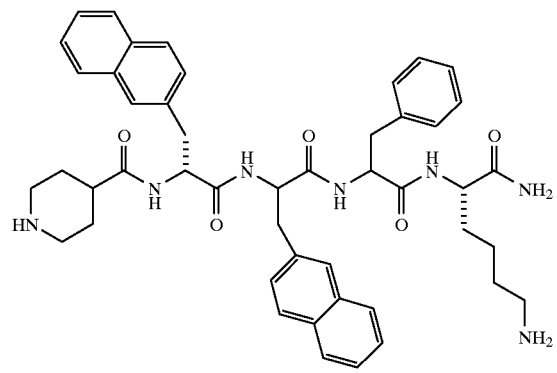

7 Claims, 23 Drawing Sheets

OTHER PUBLICATIONS

Momany et al., "Conformational energy studies and in Vitro and in Vivo activity data on growth hormone–releasing peptides" *Endocrinology* 114(5):1531–1536 (1984).

Momany et al., "Design, synthesis and biological activity of peptides which release growth hormone in Vitro" *Endocrinology* 108(1):31–39 (1981).

Schoen et al., "Growth Hormone Secretagogues" *Annual Reports in Medicinal Chemistry: Section IV–Endocrinology & Metabolic Diseases,* William K. Hagmann, Chapter 19, vol. 28:177–186 (1993).

Schoen, W.R. et al., "Structure–activity relationships in the amino acid sidechain of L–692,429" *Bioorg & Medicinal Chem. Lett.* 4(9):1117–1122 (1994).

Smith. R.G. et al., "A nonpeptidyl growth hormone secretagogue" *Science* 260:1640–1643 (1993).

Stavropoulos et al., "Synthesis of potent agonists of Substance P by replacement of Met11 with Glu(OBzl) and N–terminal glutamine with Glp of the C–terminal hexapeptide and heptapeptide of Substance P" *Int. J. Peptide Protein Res.* 45(6):508–513 (1995).

Wu, Danxing et al., "The effect of GH–releasing peptide–2 (GHRP–2 or KP 102) on GH secretion from primary cultured ovine pituitary cells can be abolished by a specific GH–releasing factor (GRF) receptor antagonist" *J. Endocrin.* 140:R9–R–13 (1994).

☐ Excipient

○ (inip) b b F K-NH2 Infusion

△ (inip) b b F K-NH2 Injection

LOW MOLECULAR WEIGHT PEPTIDOMIMETIC GROWTH HORMONE SECRETAGOGUES

This is a divisional of application Ser. No. 08/340,767 filed on Nov. 16, 1994, now U.S. Pat. No. 5,798,337.

FIELD OF THE INVENTION

The invention relates to synthetic peptidomimetics having growth hormone releasing activity in mammals. The peptidomimetics of this invention are used to stimulate the release of endogenous growth hormone (GH) in mammals needing elevation of serum growth hormone levels.

BACKGROUND OF THE INVENTION

GH secretion is known to be inhibited by the hypothalamic hormone somatostatin (SS) and stimulated by GH-releasing hormone (GHRH) in all mammalian species studied including humans. In man, GH is released from the anterior pituitary somatotrophs in pulsatile secretory bursts occurring about 4–8 times in each 24 hour period (Devesa, J., et al., *Trends Endocrinol Metab.* 3:175–183 [1992] and Mason, W. T., et al.,*Acta Paediatr Suppl* 388:84–92 [1993]). This episodic release pattern seems to be optimal for inducing the physiological effects of GH since many target tissues appear to be more sensitive to the frequency than the total amount of GH arriving at the target tissue (Robinson and Clark *Growth Hormone: Basic and Clinical Aspects* Isaksson, Binder, Hall and Hokfelt eds., Amsterdam, p109–127 [1987]). It is believed the episodic secretion of GH is caused by the rhythmic alternate release of the excitatory 44-amino acid peptide GHRH and the inhibitory tetradecapeptide SS, regulated through the "pituitary-hypothalamus axis" (see FIG. 1). Secreted GH, in turn, both directly and indirectly through IGF-1 appears to maintain this rhythm by stimulating SS and inhibiting GHRH release. Other neurotransmitters also modulate GH release usually by stimulating or inhibiting SS release. Additionally, other factors including exercise, sleep, glucocorticoids, thyroid hormones (e.g. TSH), sex steroids (e.g. testosterone and 17-β-estradiol), free fatty acids, amino acids (e.g. arginine and ornithine), and glucose levels further modulate GH release.

In addition to the two primary endogenous regulators of GH release, SS and GHRH, a number of other peptidyl/nonpeptidyl compounds have been shown to stimulate GH release primarily through the pituitary-hypothalamus axis. These include the peptides galanin, pituitary adenylate cyclase-activation peptide (PACAP), delta sleep-inducing peptide (DSIP), and angiotensin II. These peptides, however, generally lack specificity for GH release. A number of structurally diverse nonpeptidyl GH secretagogues (e.g. Talipexole and Clonidine) are reported to stimulate GH release in vitro and in vivo, but these compounds are believed to mediate their effect through cholinergic, adrenergic, dopaminergic or serotonergic pathways and thus also lack GH releasing specificity.

Apart from GHRH, the GH secretagogues having the greatest GH releasing specificity and thus having the greatest therapeutic potential are the growth hormone releasing peptides/peptidomimetics (GHRP's) (Bowers, *J. Pediatr. Endocrinol.* 6:21–31 [1993]; and Schoen et al., *Annual Reports in Medicinal Chemistry,* 28:177–186 [1993]). These compounds can activate the pituitary-hypothalamus axis (Dickson et al., *Neuroscience* 53:303–306 [1993]) and act directly on the pituitary somatotroph (see FIG. 1) by an independent (non-GHRH, non-opiate and non-SS) secretory pathway. Compounds of this class can therefore be characterized by their independent GH releasing pathway. For example, somatotroph cells maximally stimulated with GHRP's can release additional GH when treated with GHRH and vice versa. Similarly the inhibitory effects of specific antagonists to GHRH or GHRP's have no effect on stimulation of GH release by the opposite secretagogue in vitro. These compounds also exhibit dose-dependent desensitization or attenuation of GH release after continuous exposure with the same or different compounds of the GHRP class. Furthermore, structurally related biologically inactive cognate GHRP compounds capable of inhibiting GH release of a particular GHRP have no effect on GHRH agonism. These effects support the independent pathway model and serve as experimental criteria for compounds belonging to the GHRP class. Surprisingly, while the GHRH receptor has been cloned in a number of species including man (Gaylin et al., *Mol. Endo.* 7:77–84 [1993], the GHRP receptor has remained elusive.

The paradigm compounds of the GHRP class are the synthetic methionine-enkaphalin derived GHRP's identified by Bowers et al., *Endocrinology* 106:663–667 (1980) and Momany et al., *Endocrinology* 108:31–39 (1981). The most widely studied GHRP is referred to as "GHRP-6" (Momany et al., *Endocrinology* 114:1531–1536 [1984]; and Bowers et al., *Endocrinology* 114:1537–1545 [1984]) which has been shown; to be specific for GH release, has no reported long term toxicity, is well tolerated, and can elevate serum GH in a dose-dependent manner in normal humans (Bowers, *J. Pediatr. Endocrinol.* 6:21–31 [1993]). GHRP-6 is active in a dose-dependent manner when administered either iv, intranasally or orally, though it is poorly absorbed orally (~0.3%). More potent second generation hepta- and hexapeptides, "GHRP-1" and "GHRP-2" (also known as KP 102), of this class have been described more recently, though these compounds are also expected to be poorly absorbed orally.

His-D Trp-Ala-Trp-D Phe-Lys-NH$_2$ (HwAWfK-NH2)

GHRP-6

Ala-His-D βNal-Ala-Trp-D Phe-Lys-NH$_2$ (AHbAWfK-NH2)

GHRP-1

D Ala-D βNal-Ala-Trp-D Phe-Lys-NH$_2$ (abAWfK-NH2)

GHRP-2

More recently, nonpeptidyl benzolactam GH secretagogues that appear to use the same alternative signal transduction pathway as GHRP-6 have been described (Smith, R. G. et al., *Science* 260:1640–1643 [1993] and U.S. Pat. No. 5,206,235). The benzolactam L-692,429 in combination with GHRP-6 at concentrations that maximally stimulated GH release produced no additional GH release. Conversely, GHRH and L-692,429 were reported to give a synergistic increase in GH secretion. GHRH and L-692,429 were also reported to effect a common transient desensitation pattern indicating these compounds operate through a common receptor pathway. L-692,429 is reported to be about 6-fold less potent that GHRP-6 and to be specific for GH release, except for some in vivo ACTH and cortisol release.

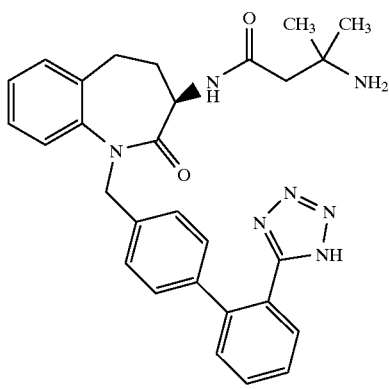

L-692,429

A more potent analogue of L-692,429 having a potency in the rat pituitary cell assay slightly greater than GHRP-6 has also been reported (Schoen W. R. et al., *Bioorg. & Medicinal Chem. Lett.* 4:1117–1122 [1994]). This compound, L-692, 585, presumably causes GH release by the same alternative pathway as GHRP-6.

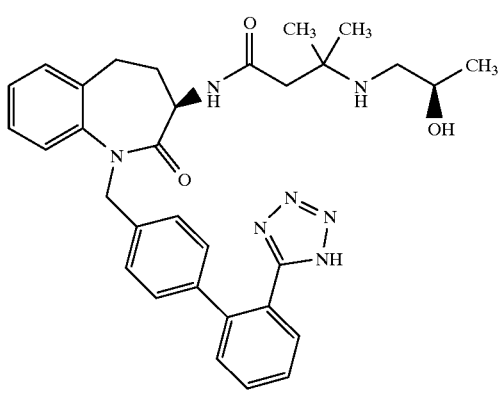

L-692,585

A number of these compounds (e.g., "GHRP-6" and L-692,429) are reported to be safe and effective in promoting endogenous GH release in humans, however, there remain problems with oral availability and specificity.

OBJECTS OF THE INVENTION

It is an object of this invention to provide novel GH secretagogues that promote the release of endogenous growth hormone in mammals. It is a further object to provide GH secretagogues that provide a synergistic increase in GH secretion when combined with GHRH. It is still a further object of this invention to provide more potent GH secretagogues than those of the prior art, especially "GHRP-6", "GHRP-1", "GHRP-2", L-692,429 and L-692, 585. It is a further object to provide GH secretagogues that are specific for GH release and do not cause significant release of other hormones, especially; LH, FSH, TSH, ACTH, prolactin, vasopressin, oxytocin, insulin and cortisol. These and other objects of the invention will be apparent from the following specification.

SUMMARY OF THE INVENTION

The objects of this invention have been achieved by providing a compound represented by structural formula (I):

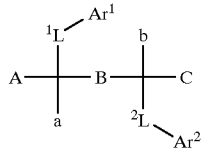

where the symbols in formula (I) define the following groups:

A is selected from

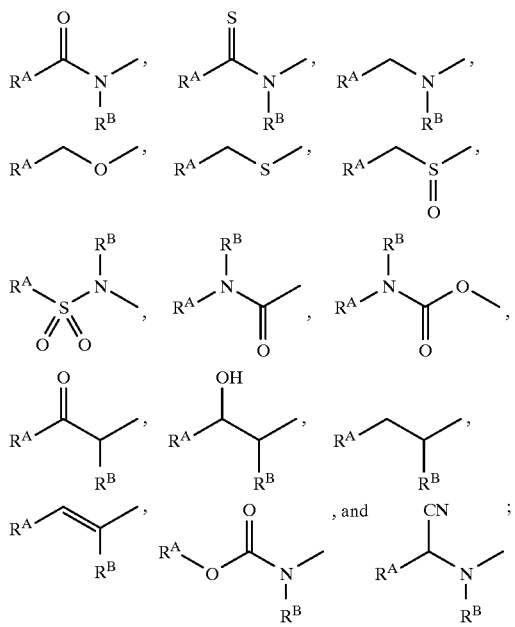

B is selected from

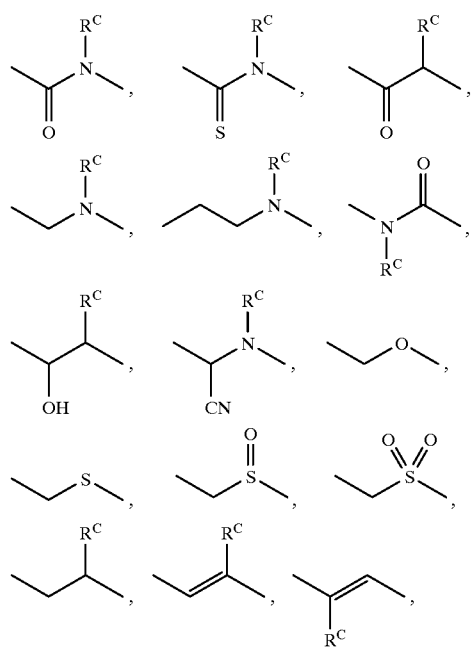

-continued

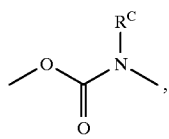

and $C_1$–$C_6$alkyl substituted with

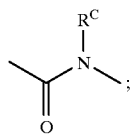

B may optionally be selected from the group a covalent bond, and $C_1$–$C_3$alkyl, when $L^2$ is —N($R^C$)—Q;

C is selected from the group hydrogen,

D—Y, and

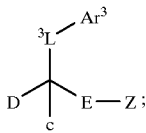

D is selected from the group

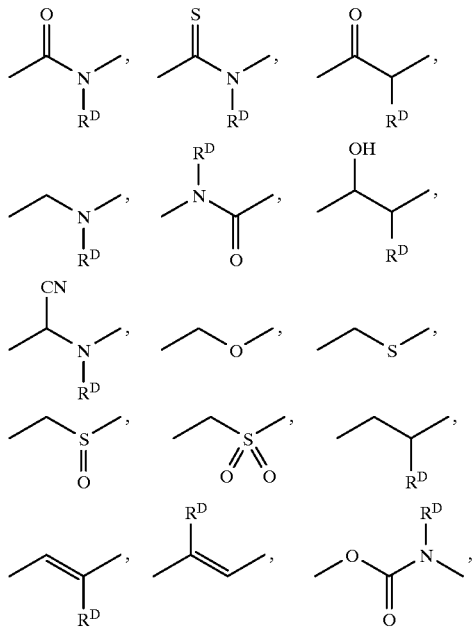

and $C_1$–$C_6$alkyl substituted with

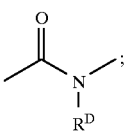

E is selected from the group

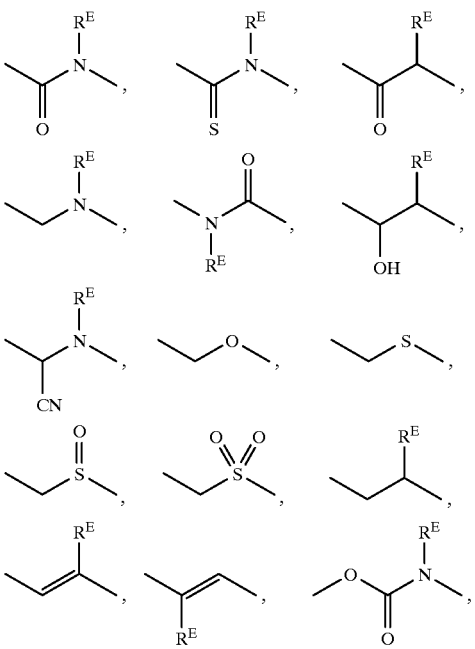

and $C_1$–$C_6$alkyl substituted with

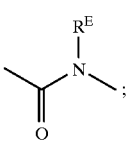

$Ar^1$ and $Ar^2$ are each independently selected from substituted or unsubstituted aryl and substituted or unsubstituted heterocycle, preferably indoyl substituted with

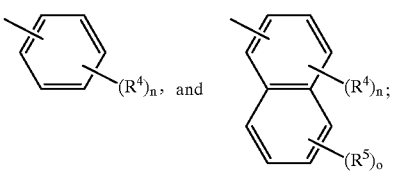

$Ar^1$ and $Ar^2$ are independently selected from hydrogen, and $C_1$–$C_6$alkyl; when $R^B$ or $R^C$ are $L^1$—$Ar^1$ or $L^2$—$Ar^2$;

$Ar^3$ is selected from the group

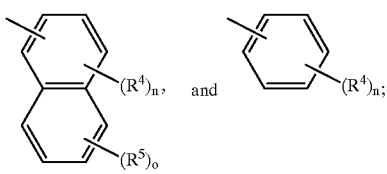

$Ar^3$ is selected from hydrogen, and $C_1$–$C_6$alkyl; when $R^D$ is $L^3$—$Ar^3$, $Ar^1$ together with a, $Ar^2$ together with b and $Ar^3$ together with c, each pair together with the carbon to which they are attached may independently form a 5 or 6 member carbocyclic ring;

a, b and c are independently selected from hydrogen, and $C_1$–$C_6$alkyl;

n and o are independently 1, 2 or 3;

$L^1$ is selected from —$CH_2$—O—, —$CH_2$—$CH_2$—O—, —$CH_2$—, —$CH_2$—$CH_2$—, and —$CH_2$—$CH_2$—$CH_2$—;

$L^2$ and $L^3$ are independently selected from a covalent bond, —O—, —O—$CH_2$—, —N($R^C$)—Q, and $L^1$;

Q is selected from the group —$L^2$—, —S(=O)$_2$—$L^2$—, —C(=O)—, —C(=O)—O—, —CH(X)—, and —CH(X)—$CH_2$—;

$R^A$ is selected from the group $C_0$–$C_3$alkyl-heterocycle where the heterocycle comprises a mono-, bi-, or tricycle containing 5–12 ring atoms, one or two of which are heteroatoms selected from O, S, and N, provided at least one heteroatom is N, where any N atom is optionally substituted with $R^1$, $C_0$–$C_6$alkyl substituted with one or two substituents selected from the group $NR^2R^3$, imidazolinyl, pyridinyl, dihydropyridinyl, and piperidinyl;

$R^B$, $R^C$ and $R^D$ are selected from the group $R^A$, $L^1$—$Ar^1$, $L^2$—$Ar^2$, hydrogen, $C_1$–$C_6$alkyl, and halo (F, Cl, Br, I)$C_1$–$C_6$alkyl;

$R^A$ and $R^B$ together with the N to which they are bonded may form a 5- or 6-member heterocycle, optionally containing one additional heteroatom selected from O, S, and N where any N is optionally substituted with $R^1$, any carbon is optionally substituted with $R^6$ and where the heterocycle is optionally fused to a phenyl ring, optionally substituted with $R^4$;

$R^1$ is selected from hydrogen, $C_1$–$C_6$alkyl, C(=O)—$C_1$–$C_6$alkyl, C(=O)—$NR^2R^3$, C(=$NR^2$)—$NR^2R^3$, C(=O)O—$C_1$–$C_6$alkyl, and halo(F, Cl, Br, I)$C_1$–$C_6$alkyl, hydroxy$C_1$–$C_6$alkyl, dihydroxy$C_1$–$C_6$alkyl;

$R^2$ and $R^3$ are independently selected from $R^1$ and piperidinyl;

$R^2$ and $R^3$ together with the N to which they are bonded may form a 5- or 6-membered heterocycle, optionally containing one additional hetero atom selected from O, S, and N where any N is optionally substituted with $R^1$, any carbon is optionally substituted with $R^6$ and where the heterocycle is optionally fused to a phenyl ring, optionally substituted with $R^4$;

$R^4$ and $R^5$ are independently selected from the group hydrogen, halo(F, Cl, Br, and I), cyano, amino, amido, nitro, hydroxy, $C_1$–$C_6$alkyl optionally substituted with 1–3 $R^6$, $C_2$–$C_6$alkynyl optionally substituted with 1–3 $R^6$, $C_1$–$C_6$alkyloxy optionally substituted with 1–3 $R^6$, $C_1$–$C_6$acylamino optionally substituted with 1–3 $R^6$, $C_1$–$C_6$alkylcarbonyl optionally substituted with 1–3 $R^6$, $C_1$–$C_6$alkyloxycarbonyl optionally substituted with 1–3 $R^6$, N—($C_1$–$C_6$alkyl), N—($C_1$–$C_6$acyl)amino optionally substituted with 1–3 $R^6$, N—($C_1$–$C_6$alkyl)carboxamido optionally substituted with 1–3 $R^6$, N,N-di($C_0$–$C_6$alkyl)amino optionally substituted with 1–3 $R^6$, N,N-di($C_1$–$C_6$alkyl)carboxamido optionally substituted with 1–3 $R^6$, $C_1$–$C_4$perfluoroalkyl, and $C_1$–$C_3$perfluoroalkoxy;

$R^6$ is selected from the group $COOR^2$, O(C=O)$R^2$, $CONR^2R^3$, cyano, $NR^2R^3$, $NR^2COR^3$, azido, nitro, and hydroxy;

$R^7$ is selected from the group $R^6$, $C_6$–$C_{10}$aryl optionally substituted with halo(F, Cl, Br, and I), cyano, amino, amido, nitro, hydroxy, $C_1$–$C_4$perfluoroalkyl, and $C_1$–$C_3$perfluoroalkoxy;

X is selected from the group hydrogen, $C_0$–$C_6$alkyl optionally substituted with 1–3 $R^6$, $C_0$–$C_6$alkyl-O—$C_1$–$C_6$alkyl optionally substituted with 1–2 $R^6$, and $C_1$–$C_6$acyl optionally substituted with a group selected from $L^2$—$Ar^2$, $R^A$, and $R^6$;

Y is selected from the group —(C=O)—$R^A$, $C_1$–$C_6$alkyl substituted with 1–2 $R^7$, $C_2$–$C_6$alkynyl optionally substituted with 1–2 $R^7$, $C_2$–$C_6$alkyenyl optionally substituted with 1–2 $R^7$, and $C_1$–$C_6$alkyloxy optionally substituted with 1–2 $R^7$, Y and $R^D$ together with the N to which they are bonded may form a 5- or 6-member heterocycle, optionally containing one additional hetero atom selected from O, S, and N where any N is optionally substituted with $R^1$, any carbon is optionally substituted with $R^7$ and where the heterocycle is optionally fused to a phenyl ring;

Z is selected from the group $C_1$–$C_6$alkyl substituted with 1–2 $R^7$, $C_2$–$C_6$alkynyl optionally substituted with 1–2 $R^7$, $C_2$–$C_6$alkyenyl optionally substituted with 1–2 $R^7$, $C_1$–$C_6$alkyloxy optionally substituted with 1–2 $R^7$ and piperidinyl; and pharmaceutically acceptable salts thereof.

In one embodiment of the invention the compound preferably has a molecular weight between 400–650 da and is represented by formula II

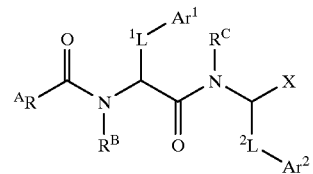

II where the symbols in formula II are defined as follows:

$Ar^1$ and $Ar^2$ are each independently selected from indoyl,

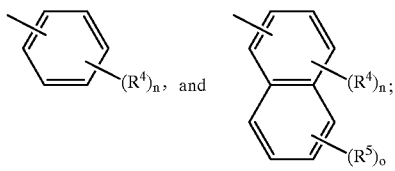

n and o are independently 1, 2 or 3;

$L^1$ is selected from —$CH_2$—O—, —$CH_2$—$CH_2$—O—, —$CH_2$—, —$CH_2$—$CH_2$—, and —$CH_2$—$CH_2$—$CH_2$—;

$L^2$ is selected from a covalent bond, —O—, and $L^1$;

$R^A$ is selected from the group $C_0$–$C_3$alkyl-heterocycle, —O—$C_0$–$C_3$alkyl-heterocycle, and —$NR^2$—$C_2$–$C_6$alkyl-heterocycle, where the heterocycle comprises a mono-, bi-, or tricycle containing 5–12 ring atoms, one or two of which are heteroatoms selected from O, S, and N, provided at least one heteroatom is N, where any N atom is optionally substituted with $R^1$, $C_0$–$C_6$alkyl substituted with one or two substituents, O—$C_2$-$C_6$alkyl substituted with one or two substituents, and $NR^2$—$C_2$-$C_6$alkyl substituted with one or two substituents where the substituents are selected from the group $NR^2R^3$, imidazolinyl, pyridinyl, dihydropyridinyl, and piperidinyl;

$R^B$ and $R^C$ are selected from the group hydrogen, $C_1$-$C_6$alkyl optionally substituted with a group selected from $NR^2R^3$, and phenyl-$C_1$-$C_3$-alkyl-$NR^2R^3$, and halo(F, Cl, Br, I)$C_1$-$C_6$alkyl;

$R^1$ is selected from hydrogen, $C_1$-$C_6$alkyl, C(=O)—$C_1$-$C_6$alkyl, C(=O)—$NR^2R^3$, C(=$NR^2$)—$NR^2R^3$, C(=O)O—$C_1$-$C_6$alkyl, and halo(F, Cl, Br, I)$C_1$-$C_6$alkyl, $C_1$-$C_6$alkoxyalkyl or (hydroxylalkyl);

$R^2$ and $R^3$ are independently selected from hydrogen, $C_1$-$C_6$alkyl, piperidinyl, and halo(F, Cl, Br, I)$C_1$-$C_6$alkyl;

$R^2$ and $R^3$ together with the N to which they are bonded may form a 5- or 6-membered heterocycle, optionally containing one additional hetero atom selected from O, S, and N where any N is optionally substituted with $R^1$, any carbon is optionally substituted with $R^6$ and where the heterocycle is optionally fused to a phenyl ring, optionally substituted with $R^4$;

$R^4$ and $R^5$ are independently selected from the group hydrogen, halo(F, Cl, Br, and I), cyano, amino, amido, nitro, hydroxy, $C_1$-$C_6$alkyl optionally substituted with 1–3 $R^6$, $C_2$-$C_6$alkynyl optionally substituted with 1–3 $R^6$, $C_1$-$C_6$alkyloxy optionally substituted with 1–3 $R^6$, $C_1$-$C_6$acylamino optionally substituted with 1–3 $R^6$, $C_1$-$C_6$alkylcarbonyl optionally substituted with 1–3 $R^6$, $C_1$-$C_6$alkyloxycarbonyl optionally substituted with 1–3 $R^6$, N—($C_1$-$C_6$alkyl), N—($C_1$-$C_6$acyl)amino optionally substituted with 1–3 $R^6$, N—($C_1$-$C_6$alkyl)carboxamido optionally substituted with 1–3 $R^6$, N,N-di($C_0$-$C_6$alkyl)amino optionally substituted with 1–3 $R^6$, N,N-di($C_1$-$C_6$alkyl)carboxamido optionally substituted with 1–3 $R^6$, $C_1$-$C_4$perfluoroalkyl, and $C_1$-$C_3$perfluoroalkoxy;

$R^6$ is selected from the group $COOR^2$, O(C=O)$R^2$, $CONR^2R^3$, cyano, $NR^2R^3$, $NR^2COR^3$, azido, nitro, and hydroxy;

X is selected from the group hydrogen, oxo (=O), $COOR^2$, $CONR^2R^3$, $C_0$-$C_6$alkyl-O—$C_1$-$C_6$alkyl optionally substituted with 1–2 $R^6$, and $C_1$-$C_6$alkyl optionally substituted with 1–2 $R^6$; and pharmaceutically acceptable salts thereof.

Alternative compounds of this embodiment may be represented by formula IIa–IIg

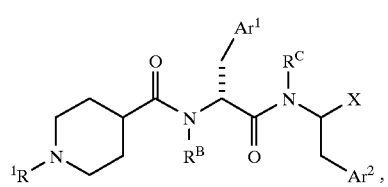

IIa

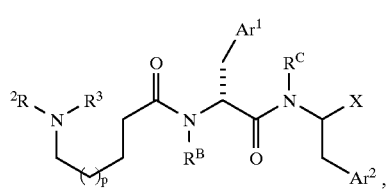

IIb

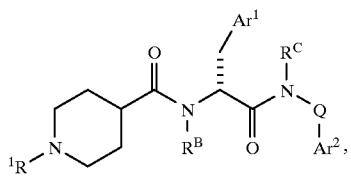

IIc

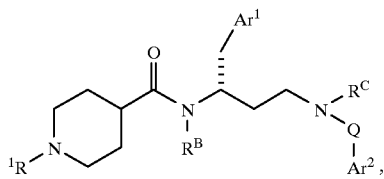

IId

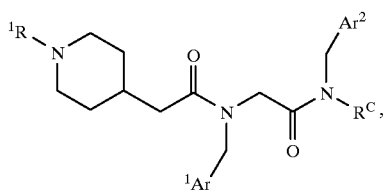

IIe

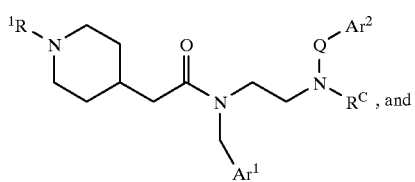

IIf

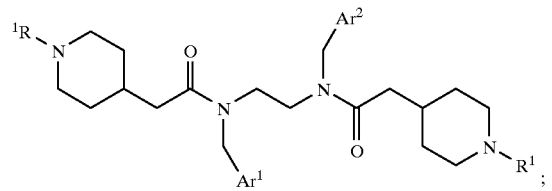

IIg where $Ar^1$, $Ar^2$, $R^B$, $R^C$, $R^1$, $R^2$, $R^3$, $R^6$, Q and X are defined above, and p is 0, 1 or 2.

Optionally the $Ar^1$, $Ar^2$, $R^B$, $R^C$, $R^1$, $R^2$, $R^3$, $R^6$ and X are defined as follows:

$Ar^1$ and $Ar^2$ are each independently selected from indoyl, and

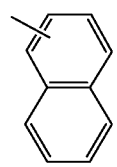

;

$R^B$ and $R^C$ are selected from the group hydrogen, and methyl;

$R^1$ is selected from hydrogen, $C_1$-$C_6$alkyl, $C_2$-$C_6$alkyl substituted with 1 or 2 hydroxy groups, C(=O)—$C_1$-$C_6$alkyl, C(=O)—$NR^2R^3$, C(=$NR^2$)—$NR^2R^3$, C(=O)O—$C_1$-$C_6$alkyl, and halo (F, Cl, Br, I)$C_1$-$C_6$alkyl;

$R^2$ and $R^3$ are independently selected from hydrogen, $C_1$-$C_6$alkyl, piperidinyl, and halo(F, Cl, Br, I)$C_1$-$C_6$alkyl;

$R^2$ and $R^3$ together with the nitrogen to which they are attached may form piperidinyl, pyrroylidinyl, piperazinyl, and morpholinyl;

$R^6$ is selected from the group $COOR^2$, $O(C=O)R^2$, $CONR^2R^3$, cyano, $NR^2R^3$, $NR^2COR^3$, azido, nitro, and hydroxy;

X is selected from the group hydrogen, oxo (=O), $COOR^2$, $CONR^2R^3$, $C_0$-$C_6$alkyl-O—$C_1$-$C_6$alkyl optionally substituted with 1–2 $R^6$, and $C_1$-$C_6$alkyl optionally substituted with 1–2 $R^6$; and pharmaceutically acceptable salts thereof.

In an alternative embodiment of the invention the compound is represented by structural formula III–IIIi

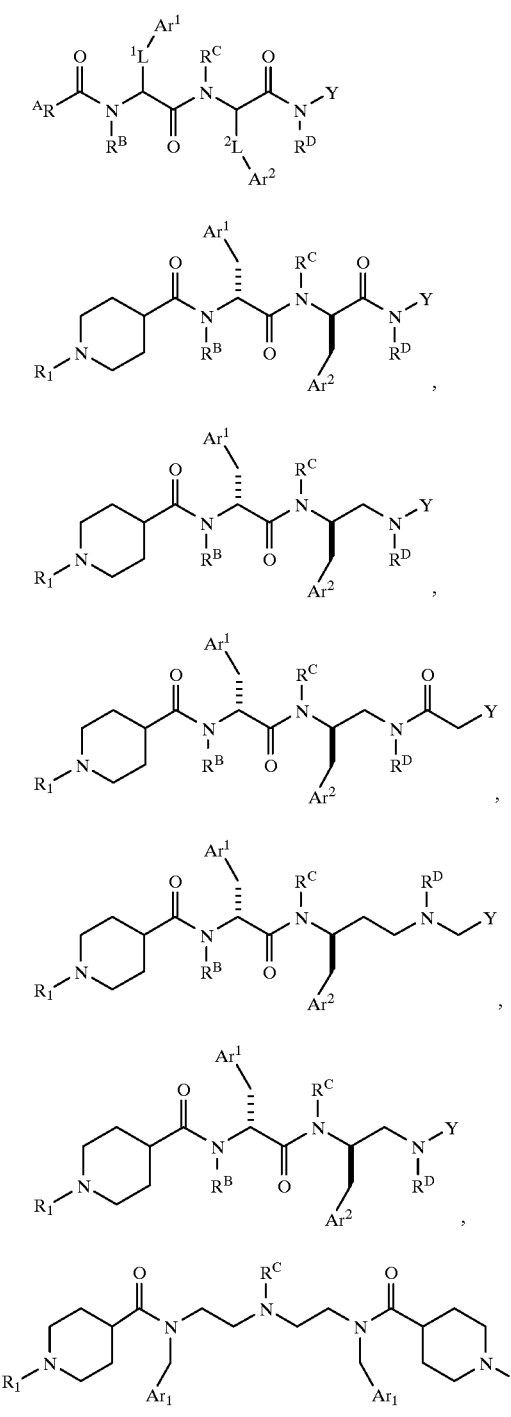

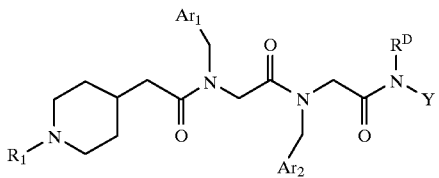

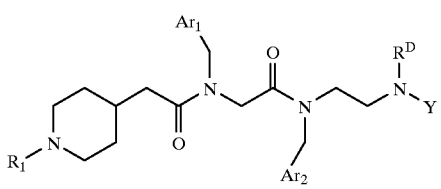

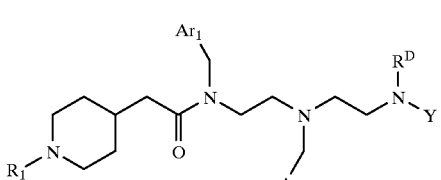

where the symbols in formula III–IIIi are defined as follows:

$Ar^1$ and $Ar^2$ are each independently selected from indoyl,

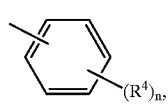

and

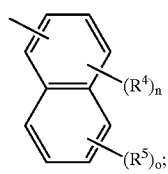

n and o are independently 1, 2 or 3;

$L^1$ and $L^2$ are independently selected from —$CH_2$—O—, —$CH_2$—$CH_2$—$CH_2$—O—$CH_2$, —$CH_2$—$CH_2$—, and —$CH_2$—$CH_2$—$CH_2$—;

$R^A$ is selected from the group $C_0$-$C_3$alkyl-heterocycle, —O—$C_0$-$C_3$alkyl-heterocycle, and —$NR^2$—$C_2$-$C_6$alkyl-heterocycle, where the heterocycle comprises a mono-, bi-, or tricycle containing 5–12 ring atoms, one or two of which are heteroatoms selected from O, S, and N, provided at least one heteroatom is N, where any N atom is optionally substituted with $R^1$, $C_0$-$C_6$alkyl substituted with one or two substituents, O—$C_2$-$C_6$alkyl substituted with one or two substituents, and $NR^2$—$C_2$-$C_6$alkyl substituted with one or two substituents where the substituents are selected from the group $NR^2R^3$, imidazolinyl, pyridinyl, dihydropyridinyl, and piperidinyl;

$R^B$, $R^C$ and $R^D$ are selected from the group hydrogen, $C_1$-$C_6$alkyl optionally substituted with a group selected from $NR^2R^3$, and phenyl-$C_1$-$C_3$-alkyl-$NR^2R^3$, and halo(F, Cl, Br, I)$C_1$-$C_6$alkyl;

$R^1$ is selected from hydrogen, $C_1$-$C_6$alkyl, C(=O)—$C_1$-$C_6$alkyl, hydroxyalkyl C(=O)—$NR^2R^3$, C(=$NR^2$)—$NR^2R^3$, C(=O)O—$C_1$-$C_6$alkyl, and halo(F, Cl, Br, I)$C_1$-$C_6$alkyl;

$R^2$ and $R^3$ are independently selected from hydrogen, $C_1$–$C_6$alkyl, piperidinyl, and halo(F, Cl, Br, I)$C_1$–$C_6$alkyl;

$R^2$ and $R^3$ together with the N to which they are bonded may form a 5- or 6-membered heterocycle, optionally containing one additional hetero atom selected from O, S, and N where any N is optionally substituted with $R^1$, any carbon is optionally substituted with $R^6$ and where the heterocycle is optionally fused to a phenyl ring, optionally substituted with $R^4$;

$R^4$ and $R^5$ are independently selected from the group hydrogen, halo(F, Cl, Br, and I), cyano, amino, amido, nitro, hydroxy, $C_1$–$C_6$alkyl optionally substituted with 1–3 $R^6$, $C_2$–$C_6$alkynyl optionally substituted with 1–3 $R^6$, $C_1$–$C_6$alkyloxy optionally substituted with 1–3 $R^6$, $C_1$–$C_6$acylamino optionally substituted with 1–3 $R^6$, $C_1$–$C_6$alkylcarbonyl optionally substituted with 1–3 $R^6$, $C_1$–$C_6$alkyloxycarbonyl optionally substituted with 1–3 $R^6$, N—($C_1$–$C_6$alkyl), N—($C_1$–$C_6$acyl)amino optionally substituted with 1–3 $R^6$, N—($C_1$–$C_6$alkyl)carboxamido optionally substituted with 1–3 $R^6$, N,N-di($C_0$–$C_6$alkyl)amino optionally substituted with 1–3 $R^6$, N,N-di($C_1$–$C_6$alkyl) carboxamido optionally substituted with 1–3 $R^6$, $C_1$–$C_4$perfluoroalkyl, and $C_1$–$C_3$perfluoroalkoxy;

$R^6$ is selected from the group $COOR^2$, $O(C=O)R^2$, $CONR^2R^3$, cyano, $NR^2R^3$, $NR^2COR^3$, azido, nitro, and hydroxy;

$R^7$ is selected from the group $R^6$, and $C_6$–$C_{10}$aryl optionally substituted with halo(F, Cl, Br, and I), cyano, amino, amido, nitro, hydroxy, $C_1$–$C_4$perfluoroalkyl, and $C_1$–$C_3$perfluoroalkoxy;

Y is selected from the group $C_1$–$C_6$alkyl substituted with 1–2 $R^7$, $C_2$–$C_6$alkynyl optionally substituted with 1–2 $R^7$, $C_2$–$C_6$alkyenyl optionally substituted with 1–2 $R^7$, and $C_1$–$C_6$alkyloxy optionally substituted with 1–2 $R^7$, and pharmaceutically acceptable salts thereof.

In a further alternative embodiment of this invention the compound is represented by structural formula IV

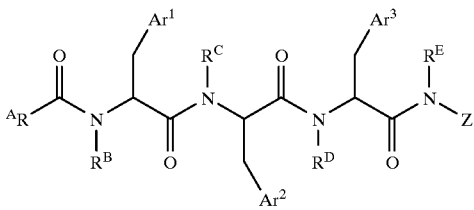

where the symbols of formula IV are defined as follows:
$Ar^1$ and $Ar^2$ are each independently selected from indoyl,

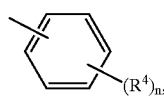
and
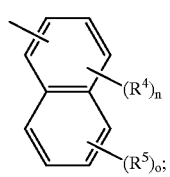

$Ar^3$ is selected from the group

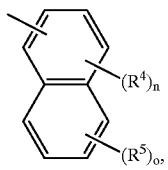
and
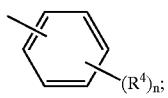

n and o are independently 1, 2 or 3;

$R^A$ is selected from the group $C_0$–$C_3$alkyl-heterocycle, —O—$C_0$–$C_3$alkyl-heterocycle, and —$NR^2$—$C_2$–$C_6$alkyl-heterocycle, where the heterocycle comprises a mono-, bi-, or tricycle containing 5–12 ring atoms, one or two of which are heteroatoms selected from O, S, and N, provided at least one heteroatom is N, where any N atom is optionally substituted with $R^1$, $C_0$–$C_6$alkyl substituted with one or two substituents, O—$C_2$–$C_6$alkyl substituted with one or two substituents, and $NR^2$—$C_2$–$C_6$alkyl substituted with one or two substituents where the substituents are selected from the group $NR^2R^3$, imidazolinyl, pyridinyl, dihydropyridinyl, and piperidinyl;

$R^B$, $R^C$, $R^D$, and $R^E$ are selected from the group hydrogen, $C_1$–$C_6$alkyl optionally substituted with a group selected from $NR^2R^3$, and phenyl-$C_1$–$C_3$-alkyl-$NR^2R^3$, and halo(F, Cl, Br, I)$C_1$–$C_6$alkyl;

$R^1$ is selected from hydrogen, $C_1$–$C_6$alkyl, $C(=O)$—$C_1$–$C_6$alkyl, $C(=O)$-hydroxyalkyl $NR^2R^3$, $C(=NR^2)$—$NR^2R^3$, $C(=O)O$—$C_1$–$C_6$alkyl, and halo(F, Cl, Br, I)$C_1$–$C_6$alkyl;

$R^2$ and $R^3$ are independently selected from hydrogen, $C_1$–$C_6$alkyl, piperidinyl, and halo(F, Cl, Br, I)$C_1$–$C_6$alkyl;

$R^2$ and $R^3$ together with the N to which they are bonded may form a 5- or 6-membered heterocycle, optionally containing one additional hetero atom selected from O, S, and N where any N is optionally substituted with $R^1$, any carbon is optionally substituted with $R^6$ and where the heterocycle is optionally fused to a phenyl ring, optionally substituted with $R^4$;

$R^4$ and $R^5$ are independently selected from the group hydrogen, halo(F, Cl, Br, and I), cyano, amino, amido, nitro, hydroxy, $C_1$–$C_6$alkyl optionally substituted with 1–3 $R^6$, $C_2$–$C_6$alkynyl optionally substituted with 1–3 $R^6$, $C_1$–$C_6$alkyloxy optionally substituted with 1–3 $R^6$, $C_1$–$C_6$acylamino optionally substituted with 1–3 $R^6$, $C_1$–$C_6$alkylcarbonyl optionally substituted with 1–3 $R^6$, $C_1$–$C_6$alkyloxycarbonyl optionally substituted with 1–3 $R^6$, N—($C_1$–$C_6$alkyl), N—($C_1$–$C_6$acyl)amino optionally substituted with 1–3 $R^6$, N—($C_1$–$C_6$alkyl)carboxamido optionally substituted with 1–3 $R^6$, N,N-di($C_0$–$C_6$alkyl)amino optionally substituted with 1–3 $R^6$, N,N-di($C_1$–$C_6$alkyl) carboxamido optionally substituted with 1–3 $R^6$, $C_1$–$C_4$perfluoroalkyl, and $C_1$–$C_3$perfluoroalkoxy;

$R^6$ is selected from the group $COOR^2$, $O(C=O)R^2$, $CONR^2R^3$, cyano, $NR^2R^3$, $NR^2COR^3$, azido, nitro, and hydroxy;

$R^7$ is selected from the group $R^6$, $C_6$–$C_{10}$aryl optionally substituted with halo(F, Cl, Br, and I), cyano, amino, amido, nitro, hydroxy, $C_1$–$C_4$perfluoroalkyl, and $C_1$–$C_3$perfluoroalkoxy;

Z is selected from the group $C_1$–$C_6$alkyl substituted with 1–2 $R^7$, $C_2$–$c_6$alkynyl optionally substituted with 1–2 $R^7$, $C_2$–$C_6$alkyenyl optionally substituted with 1–2 $R^7$, and $C_1$–$C_6$alkyloxy optionally substituted with 1–2 $R^7$, Z and $R^E$ together with the N to which they are bonded may form a 5- or 6-membered heterocycle, optionally containing one additional hetero atom selected from O, S, and N where any N is optionally substituted with $R^1$, any carbon is optionally substituted with $R^7$ and where the heterocycle is optionally fused to a phenyl ring; and pharmaceutically acceptable salts thereof.

An optional compound of this embodiment is represented by structural Formula (IVa)

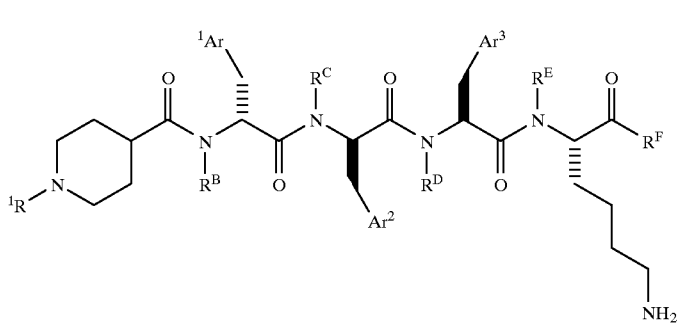

IVa where the symbols in formula IVa are defined as follows:

$R^B$, $R^C$, $R^D$ and $R^E$ are selected from the group hydrogen, and $C_1$–$C_6$alkyl;

$Ar^1$ and $Ar^2$ are each independently selected from indoyl, and

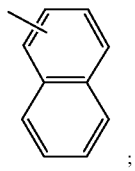

;

$Ar^3$ is selected from the group

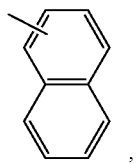

, and

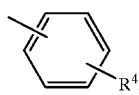

$R^F$ is selected from the group OH, $C_1$–$C_4$alkyloxy, $NR^5R^6$, and 1 to 4 α-amino acid residues;

$R^4$ is selected from hydrogen, halo(F, Cl, Br, and I), cyano, amino, amido, nitro, hydroxy, $C_1$–$C_4$alkoxy, $C_1$–$C_4$perfluoroalkyl, and $C_1$–$C_3$perfluoroalkoxy;

$R^5$ and $R^6$ are independently selected from hydrogen, and $C_1$–$C_6$alkyl; and pharmaceutically acceptable salts thereof.

In still another embodiment of this invention the compound is referred to as a "retroinverso" of the compound of formula II and is represented by formula V

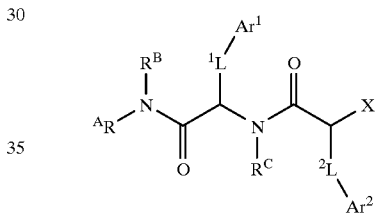

V where $Ar^1$, $Ar^2$, $L^1$, $L^2$, $R^A$, $R^B$, $R^C$ and X are defined above for the compound of formula I.

The invention further comprises a pharmaceutical composition comprising a pharmaceutically acceptable excipient and any of the compounds represented by structural formula I–V. Additionally the invention provides a method for increasing the level of endogenous growth hormone in a mammal comprising administering to the mammal a pharmaceutically effective amount of the forgoing composition to the mammal. The method further comprises administering the composition in combination with a growth factor selected from; growth hormone releasing hormone (GHRH), insulin like growth factor-1 (IGF-1), and insulin like growth factor-2 (IGF-2). In an alternative method of this invention GHRP's represented by formulae I–V, as well as other GHRP's, are used in combination with IGF-1 to treat diseases in which long term IGF-1 is indicated including but not limited to Type II diabetes.

DETAILED DESCRIPTION OF THE INVENTION

A. Definitions

Figure 1:
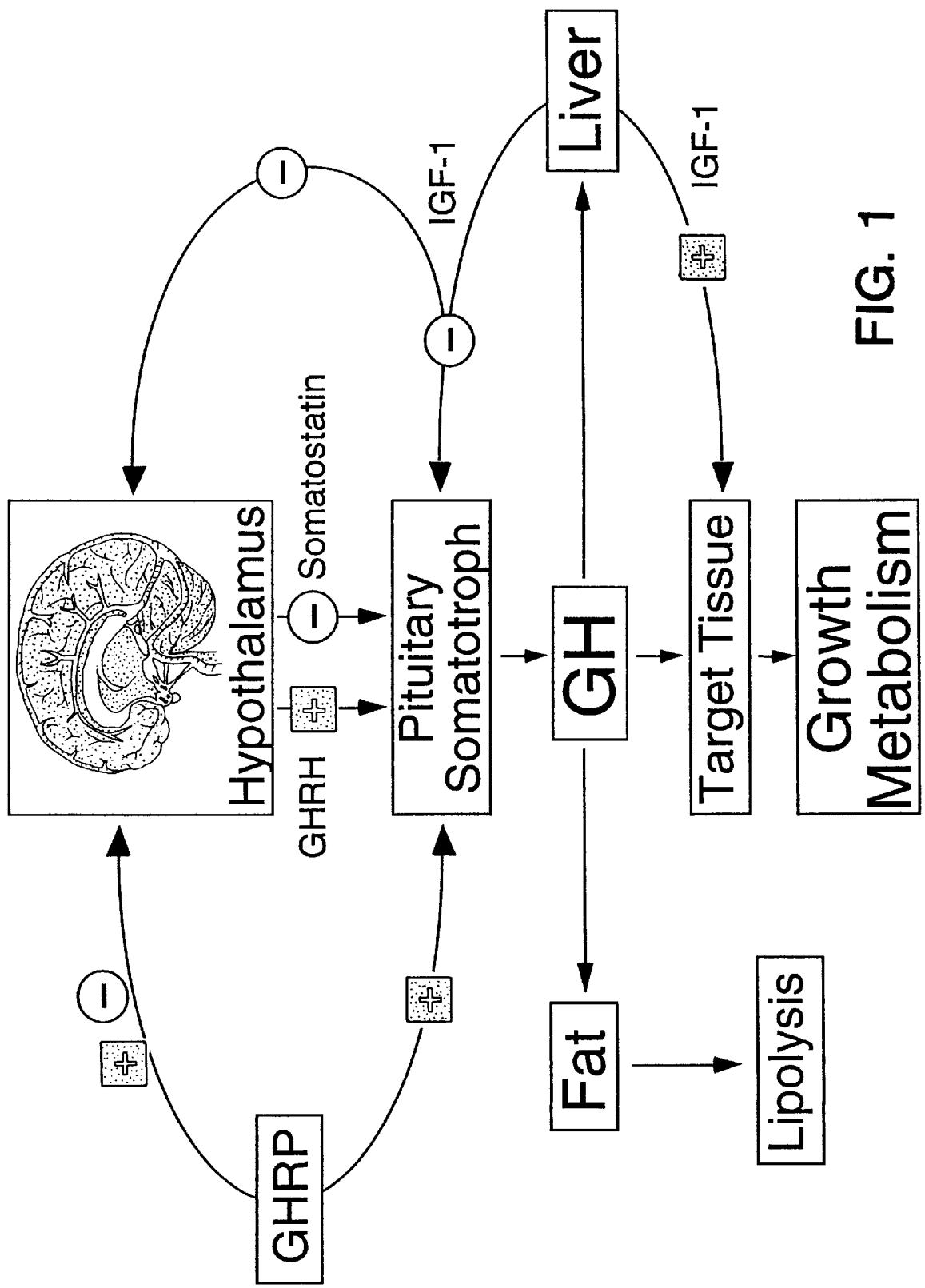
FIG. 1. A cartoon showing regulation of growth hormone (GH) release by the "pituitary-hypothalamus axis" and the alternative "GHRP pathway". Some of the stimulatory (+) and inhibitory (−) effects that growth hormone releasing hormone/factor (GHRH/F), growth hormone releasing peptides/peptidomimetics (GHRP's ), somatostatin (SS), GH, and insulin-like growth factor 1 (IGF-1) have on selected glands, organs, and tissues are also shown.

Terms used in the claims and specification are defined as set forth below unless otherwise specified.

The terms growth hormone releasing hormone (GHRH) or factor (GHRF/GRF) are used interchangeably and refer to the endogenous hypothalamic GH secretagogue, from any species, having the capability of binding to the pituitary somatotroph and inducing a rapid dose-dependent release of GH and biologically active analogs thereof. Included in this definition are; GHRH(1–44), GHRH(1–43), GHRH(1–40), and GHRH (1–29). Other examples of GHRH analogs are described in U.S. Pat. No. 4,622,312.

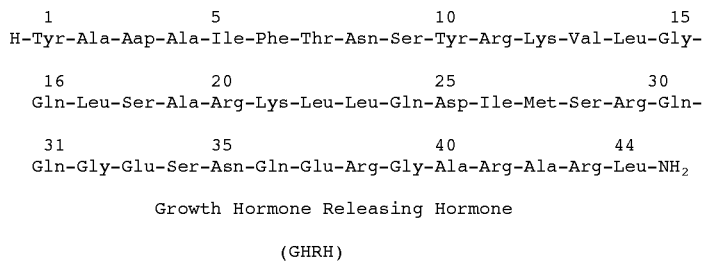

Growth Hormone Releasing Hormone (GHRH)

The term somatostatin (SS) refers to the inhibitory hypothalamic tetradecapeptide capable of antagonizing in a dose-dependent manner the GH-releasing effect of GHRH. 1

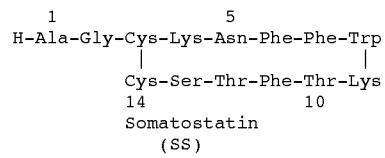

Somatostatin
(SS)

As used herein, "IGF-1" refers to insulin-like growth factor from any species, including bovine, ovine, porcine, equine, avian, and preferably human, in native-sequence or in variant form, and from any source, whether natural, synthetic, or recombinant. Preferred herein for animal use is that form of IGF-1 from the particular species being treated, such as porcine IGF-1 to treat pigs, ovine IGF-1 to treat sheep, bovine IGF-1 to treat cattle, etc. Preferred herein for human use is human native-sequence, mature IGF-1, more preferably without a N-terminal methionine, prepared, for example, by the process described in EP 230,869 published Aug. 5, 1987; EP 128,733 published Dec. 19, 1984; or EP 288,451 published Oct. 26, 1988. More preferably, this native sequence IGF-1 is recombinantly produced and is available from Genentach, Inc., South San Francisco, Calif. for clinical investigations. Also preferred for use is IGF-1 that has a specific activity greater than about 14,000 units/ mg as determined by redioreceptor assay using placenta membranes, such as that available from KabiGen AB, Stockholm, Sweden.

The most preferred IGF-1 variants are those described in U.S. Pat. No. 5,077,276 issued Dec. 31, 1991, in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-1, des(1-3)IGF-1, or des-IGF-1).

The term "GHRP" as used herein refers to compounds that cause release of endogenous GH in a dose-dependent manner, where such release is synergized by GHRH but not by other GHRP's such as GHRP-6, and where such release causes a desensitization after continuous exposure to the GHRP while maintaining the ability to respond to GHRH.

The term "$C_n$–$C_m$alkyl" means a cyclic or linear, branched or unbranched, saturated aliphatic hydrocarbon radical, having the number of carbon atoms specified, where m and n are zero or integers identifying the range of carbon atoms contained in the alkyl group. When n is zero (0) the term becomes a chemical bond, usually a covalent bond. Examples of alkyl radicals include methyl, ethyl, n-propyl, isopropyl(iPr), n-butyl, iso-butyl, sec-butyl, tert-butyl(tBu), n-pentyl, 2-methylbutyl, 2,2-dimethylpropyl, n-hexyl, 2-methylpentyl, 2,2-dimethylbutyl, n-heptyl, 2-methylhexyl, cyclohexyl, and the like. The terms "lower alkyl" and "$C_1$–$C_6$alkyl" are synonymous and used interchangeably.

The term "$C_2$–$C_m$alkenyl" means a cyclic or linear, branched or unbranched hydrocarbon radical containing at least one carbon—carbon double bond, having the number of carbon atoms specified, each double bond being independently cis, trans, E or Z, or a non-geometric isomer.

The term "$C_2$–$C_m$alkynyl" means a cyclic or linear, branched or unbranched hydrocarbon radical containing at least one carbon—carbon triple bond, having the number of carbon atoms specified, The terms "$C_1$–$C_{12}$acyloxy" or "$C_1$–$C_{12}$alkanoyloxy" are used interchangeably and denote herein groups of the formula $C_0$–$C_{12}$alkyl-C(=O)—O— such as; formyloxy, acetoxy, propionyloxy, butyryloxy, pentanoyloxy, hexanoyloxy, heptanoyloxy, and the like.

The term "N,N-di($C_0$–$C_6$)alkylamino" denotes herein groups of the formula ($C_0$–$C_6$alkyl)$_2$—N— where both, one or none of the hydrogen atoms of $H_2$N— are substituted with $C_1$–$c_6$alkyl.

The term "N—($C_1$–$C_6$alkyl), N—($C_1$–$C_6$acyl)amino" denotes herein an amino group where one hydrogen is substituted with a $C_1$–$C_6$alkyl group and the other hydrogen is substituted with a $C_1$–$C_6$acyl group.

The terms "$C_1$–$c_6$alkyloxycarbonyl" and "$C_1$–$C_6$carboalkoxy" are used interchangeably herein and denote groups of the formula $C_1$–$c_6$alkyl-O—C(=O)—.

The terms "N—($C_1$–$C_6$alkyl)carboxamido" and "N—($C_1$–$C_6$alkyl)-aminocarbonyl" are used interchangeably herein and denote groups of the formula $C_1$–$C_6$alkyl-NH—C(=O)—.

The terms "$C_1$–$C_{12}$alkylcarbonyl", "$C_1$–$C_{12}$alkanoyl" and "$C_1$–$C_{12}$acyl" are used interchangeably herein and denote groups of the formula $C_0$–$C_{12}$alkyl-C(=O)— and encompass groups such as formyl, acetyl, propionyl, butyryl, pentanoyl, hexanoyl, heptanoyl, benzoyl and the like.

The term "$C_1$–$C_6$acylamino" denotes groups of the formula $C_1$–$c_6$alkyl-C(=O)—NH—.

The terms "$C_1$–$C_{12}$alkyloxy" and "$C_1$–$C_{12}$ substituted alkyloxy" denote $C_1$–$C_{12}$alkyl and $C_1$–$C_{12}$ substituted alkyl groups, respectively, attached to an oxygen which is in turn the point of attachment for the alkyloxy or substituted alkyloxy group to the group or substituent designated (e.g. $C_1$–$C_{12}$alkyl-O—). These include groups such as methoxy, ethoxy, n-propoxy, isopropoxy, n-butoxy, t-butoxy, cyclohexyloxy and like groups.

The term "aryl" when used alone means a homocyclic hydrocarbon aromatic radical, whether or not fused, having the number of carbon atoms designated or if none are designated—from 6 to 14. Aromatic radicals may be mononuclear or polynuclear. Examples of aryl groups include phenyl, napthyl anthranyl, phenanthranyl, azulyl and the like.

Preferred aryl groups include phenyl, napthyl, biphenyl, phenanthrenyl, naphthacenyl, and the like (see e.g. *Lang's Handbook of Chemistry* (Dean, J. A., ed) 13$^{th}$ ed. Table 7-2 [1985]).

Optionally the "aryl" is substituted with one or more substituents usually designated by a group "—R'"', where n is any integer. Examples of substituted phenyl groups include mono- or di(halo)phenyl groups such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; mono- or di(hydroxy)phenyl groups such as 4-hydroxyphenyl, 3-hydroxyphenyl, 2,4-dihydroxyphenyl, the protected-hydroxy derivatives thereof and the like; nitrophenyl groups such as 3- or 4-nitrophenyl; cyanophenyl groups, for example, 4-cyanophenyl; mono- or di(lower alkyl)phenyl groups such as 4-methylphenyl, 2,4-dimethylphenyl, 2-methylphenyl, 4-(isopropyl)phenyl, 4-ethylphenyl, 3-(n-propyl)phenyl and the like; mono or di(alkoxy)phenyl groups, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; mono- or dicarboxyphenyl or (protected carboxy)phenyl groups such 4-carboxyphenyl; mono- or di(hydroxymethyl)phenyl or (protected hydroxymethyl)phenyl groups such as 3-(protected hydroxymethyl)phenyl or 3,4-di (hydroxymethyl)phenyl, 2,3- and 3,4-methylene dioxy; mono- or di(aminomethyl)phenyl or (protected aminomethyl)phenyl groups such as 2-(aminomethyl) phenyl or 2,4-(protected aminomethyl)phenyl; or mono- or di(N-(methylsulfonylamino))phenyl groups such as 3-(N-methylsulfonylamino))-phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, 4-fluoro or chlorophenyl the 4-hydroxyphenyl, the 2-aminomethylphenyl and the 3-(N-(methylsulfonylamino))phenyl groups.

The term "arylalkyl" means one, two, or three aryl groups having the number of carbon atoms designated, appended to an alkyl radical having the number of carbon atoms designated including but not limited to; benzyl, napthylmethyl, phenethyl, benzyhydryl (diphenylmethyl), trityl, and the like. A preferred arylalkyl group is the benzyl group.

The term "substituted $C_6$–$C_{12}$aryl-$C_1$–$C_6$alkyl" denotes a $C_1$–$C_6$alkyl group substituted at any carbon with a $C_6$–$C_{12}$aryl group bonded to the alkyl group through any aryl ring position and substituted on the $C_1$–$C_6$alkyl portion with one, two or three groups chosen from halogen(F, Cl, Br, I), hydroxy, protected hydroxy, amino, protected amino, $C_1$–$C_6$acyloxy, nitro, carboxy, protected carboxy, carbamoyl, carbamoyloxy, cyano, $C_1$–$C_6$alkylthio, N-(methylsulfonylamino) $C_1$–$c_6$alkoxy, or other groups specified. Optionally, the aryl group may be substituted with one, two, or three groups chosen from halogen(especially F), cyano, hydroxy, protected hydroxy, nitro, $C_1$–$C_6$alkyl, $C_1$–$C_4$alkoxy, carboxy, protected carboxy, carboxymethyl, protected carboxymethyl, hydroxymethyl, protected hydroxymethyl, aminomethyl, protected aminomethyl, or an N-(methylsulfonylamino) group. As before, when either the $C_1$–$C_6$alkyl portion or the aryl portion or both are disubstituted, the substituents can be the same or different.

Examples of the term "substituted $C_6$–$C_{10}$aryl-$C_1$–$C_6$alkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethyl-phenyl)n-propyl, 4-chloro-3-aminobenzyl, 6-(4-methoxyphenyl)-3-carboxy(n-hexyl), 5-(4-aminomethyl phenyl)-3-(aminomethyl)(n-pentyl), and the like.

Unless otherwise specified, the terms "heterocycle", "heterocyclic group", "heterocyclic" or "heterocyclyl" are used interchangeably herein and refer to any mono-, bi-, or tricyclic saturated, unsaturated, or aromatic ring having the number of ring atoms designated where at least one ring is a 5-, 6- or 7-membered hydrocarbon ring containing a designated number of heteroatoms selected from nitrogen, oxygen, and sulfur, preferably at least one heteroatom is nitrogen (*Lang's Handbook of Chemistry,* supra). The heterocycle is a 5- or 6-member saturated, unsaturated, or aromatic hydrocarbon ring usually containing 1,2 , or 3 heteroatoms, preferably 1 or 2, selected from O, N, and S. Typically, the 5-membered ring has 0 to 2 double bonds and the 6- or 7-membered ring has 0 to 3 double bonds and the nitrogen or sulfur heteroatoms may optionally be oxidized, and any nitrogen heteroatom may optionally be substituted or quarternized. Included in the definition are any bicyclic groups where any of the above heterocyclic rings are fused to a benzene ring. Heterocyclics in which nitrogen is the heteroatom are preferred.

The following ring systems are examples of the heterocyclic (whether substituted or unsubstituted) radicals denoted by the term "heterocyclic": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydro-pyrimidyl, tetrazolo[1,5-b] pyridazinyl and purinyl, as well as benzo-fused derivatives, for example benzoxazolyl, benzthiazolyl, benzimidazolyl and indolyl.

Heterocyclic 5-membered ring systems containing a sulfur or oxygen atom and one to three nitrogen atoms are also suitable for use in the instant invention. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl, and tetrazolyl, preferably 1H-tetrazol-5-yl. A preferred group of examples of benzo-fused derivatives are benzoxazol-2-yl, benzthiazol-2-yl and benzimidazol-2-yl.

Further suitable specific examples of the above heterocyclic ring systems are 6-membered ring systems containing one to three nitrogen atoms. Such examples include pyridyl, such as pyrid-2-yl, pyrid-3-yl, and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl radicals, are a preferred group. Optionally preferred 6-membered ring heterocycles are; piperazinyl, piperazin-2-yl, piperidyl, piperid-2-yl, piperid-3-yl, piperid-4-yl, morpholino, morpholin-2-yl, and morpholin-3-yl.

An optional group of "heterocyclics" include; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,-dioxo-as-triazin-3-yl, 2,5-dihydro-5-oxo-6-hydroxy-as-triazin-3-yl, 2,5-dihydro-5-oxo-6-hydroxy-as-triazin-3-yl sodium salt, 2,5-dihydro-5-oxo-6-hydroxy-2-methyl-as-triazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazan-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl.

An alternative group of "heterocyclics" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

The terms "heteroaryl group" or "heteroaryl" are used interchangeably herein and refer to any mono-, bi-, or tricyclic aromatic rings having the number of ring atoms designated where at least one ring is a 5-, 6- or 7-membered hydrocarbon ring containing from one to four heteroatoms selected from nitrogen, oxygen, and sulfur, preferably at least one heteroatom is nitrogen. The aryl portion of the term "heteroaryl" refers to aromaticity, a term known to those skilled in the art and defined in greater detail in *Advanced Organic Chemistry J.* March, $3^{rd}$ ed., pages 37–69, John Wiley & Sons, New York (1985).

"Optical isomers", "diastereomers", and "geometric isomers" of some of the compounds represented by the formulae described herein are comprehended to be within the scope of the instant invention, as well as racemic and resolved enantiomerically pure forms and pharmaceutically acceptable salts thereof.

"Pharmaceutically acceptable salts" include both acid and base addition salts.

"Pharmaceutically acceptable acid addition salt" refers to those salts which retain the biological effectiveness and properties of the free bases and which are not biologically or otherwise undesirable, formed with inorganic acids including but not limited to hydrochloric acid, hydrobromic acid, sulfuric acid, sulfamic nitric acid, phosphoric acid and the like, and organic acids such as acetic acid, propionic acid, glycolic acid, pyruvic acid, lactic acid, oxalic acid, maleic acid, malic acid, maloneic acid, succinic acid, fumaric acid, tartaric acid, citric acid, stearic acid, ascorbic acid, benzoic acid, cinnamic acid, mandelic acid, methanesulfonic acid, ethanesulfonic acid, isethionic acid, p-toluenesulfonic acid, salicyclic acid, naturally occurring amino acids and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucasamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

In general, unless otherwise specified, the abbreviations used for the designation of amino acids and the protective groups used therefor are based on recommendations of the IUPAC-IUB Commission of Biochemical Nomenclature (*Biochemistry,* 11:1726–1732 (1972). Table 1 provides a list of commonly used symbols or abbreviations (abbr.) used to describe the compounds of this invention.

TABLE I

| ABBR | (SMILES) STRUCTURE | R/S | COMMON NAME OF COMPOUND |
|---|---|---|---|
| A | NC(C)C(=O) | S | L-Alanine |
| a | NC(C)C(=O) | R | D-Alanine |
| Ab | NCCCC(=O) | | 4-aminobutyric acid |
| Ac | C(C=O) | | Acetyl |
| Abx | NC2(CCCCC2)C(=O) | | 1-amino-1-cyclohexanecarboxylic acid |
| Ahp | NCCCCCCC(=O) | | 7-aminoheptanoic acid |
| Ahx | NCCCCCC(=O) | | 6-aminohexanoic acid |
| amb | NCc4ccc(cc4)C(=O) | | p-aminomethylbenzoic acid |
| amF | NC(C)(Cc1ccccc1)C(=O) | S | alpha-methyl-L-Phenylalanine |
| apc | N3CCC(N)CC3 | | 1-(4-amino-piperidine) |
| api | NC3CCNCC3 | | 4-(4-amino-piperidine) |
| Ava | NCCCCC(=O) | | 5-aminovaleric acid |
| B | NC(Cc1cc2ccccc2cc1)C(=O) | S | L-beta-naphthylalanine |
| b | NC(Cc1cc2ccccc2cc1)C(=O) | R | D-beta-naphthylalanine |
| bA | NCCC(=O) | | beta-Alanine |
| bam | NCCCCN | | 1,4-butanediamine |
| Bmn | NC(Cc1cc2ccccc2cc1)CN | S | L-2-amino-3-(2-naphthyl)propylamine |
| bmn | NC(Cc1cc2ccccc2cc1)CN | R | D-2-amino-3-(2-naphthyl)propylamine |
| BOC | C(C)(C)OC(=O) | | tert-Butoxycarbonyl |
| Bol | NC(Cc1cc2ccccc2cc1)CO | S | L-beta-naphthylalanol |
| bol | NC(Cc1cc2ccccc2cc1)CO | R | D-beta-naphthylalanol |
| chA | NC(CC1CCCCC1)C(=O) | | 3-cyclohexylalanine |
| chf | NC(Cc1ccc(C1)cc1)C(=O) | R | D-4-chloro-Phenylalanine |
| cho | C4CCC(CC4)C(=O) | | cyclohexane carboxylic acid |
| cxa | NC3CCC(N)CC3 | | trans-1,4-cyclohexane diamine |
| Cxp | N4CCN(CC4)C(=O) | | 1-carboxypiperazine |
| dam | N(C)C | | N,N-dimethylamine |
| F | NC(Cc1ccccc1)C(=O) | S | L-Phenylalanine |
| f | NC(Cc1ccccc1)C(=O) | R | D-Phenylalanine |
| fbd | N(CCc1ccccc1)CCCN | | N-(2-phenylethyl) butane diamine |
| feb | N(CCc1ccccc1)CCC(=O) | | N-(2-phenylethyl) beta-Alanine |
| feg | N(CCc1ccccc1)CC(=O) | | N-(2-phenylethyl) Glycine |
| fem | NCCc1ccccc1 | | 1-phenethyl amine |
| G | NCC(=O) | | Glycine |
| H | NC(Cc1[nH]cnc1)C(=O) | S | L-Histadine |
| h | NC(Cc1[nH]cnc1)C(=O) | R | D-Histadine |
| hcF | NC(Cc1ccccc1)CC(=O) | S | 3-(S)-benzyl-beta-alanine |

TABLE I-continued

| ABBR | (SMILES) STRUCTURE | R/S | COMMON NAME OF COMPOUND |
|---|---|---|---|
| hF | NC(CCc1ccccc1)C(=O) | S | homo-L-Phenylalanine |
| hf | NC(CCc1ccccc1)C(=O) | R | homo-D-Phenylalanine |
| inip | N4CCC(CC4)C(=O) | | isonipecotic acid |
| isog | N4CC=C(CC4)C(=O) | | isoguvacine |
| K | NC(CCCCN)C(=O) | S | L-Lysine |
| k | NC(CCCCN)C(=O) | R | D-Lysine |
| mab | N(C)CCCC(=O) | | N-methyl-4-aminobutyric acid |
| mam | NC | | methylamine |
| man | NCCc1cc2ccccc2cc1 | | N-(2-naphthylmethyl)amine |
| mBm | N(C)C(Cc1cc2ccccc2cc1)CN | S | N-methyl-[2-amino-3-(2-naphthyl)propyl]amine |
| mbm | N(C)C(Cc1cc2ccccc2cc1)CN | R | N-methyl-[2-amino-3-(2-naphthyl)propyl]amine |
| men | N(C)CCc1cc2ccccc2cc1 | | N-Methyl-2-(2-naphthylethylamine) |
| miz | N(C)C(Cc1cc2ccccc2cc1)CN(=N)N | R | 2(R)-2-(N-Methylamino)-1-azido-3-(2-naphthyl)propane |
| mor | N1CCOCC1 | | morpholine |
| N | NC(CC(=O)N)C(=O) | S | L-Asparagine |
| n | NC(CC(=O)N)C(=O) | R | D-Asparagine |
| nba | NC(C)(C)CC(=O) | | 3,3-dimethyl-3-aminopropionic acid |
| nbol | N(C)C(Cc1cc2ccccc2cc1)CO | S | N-Methyl-D-beta-naphthylalanol |
| nL | NC(CCCC)C(=O) | S | L-Norleucine |
| nl | NC(CCCC)C(=O) | R | D-Norleucine |
| nmB | N(C)C(Cc1cc2ccccc2cc1)C(=O) | S | N-Methyl-L-beta-naphthylalanine |
| nmb | N(C)C(Cc1cc2ccccc2cc1)C(=O) | R | N-Methyl-D-beta-naphthylalanine |
| nmF | N(C)C(Cc1ccccc1)C(=O) | S | N-Methyl-L-Phenylalanine |
| nmK | N(C)C(CCCCN)C(=O) | S | N-Methyl-L-Lysine |
| npA | NC(Cc1c2ccccc2cc1)C(=O) | S | L-alpha-Naphthylalanine |
| npa | NC(Cc1c2ccccc2cc1)C(=O) | R | D-alpha-Naphthylalanine |
| npe | NCCc1cc2ccccc2cc1 | | 2-(2-naphthyl)ethylamine |
| O | NC(CCCN)C(=O) | S | L-Ornithine |
| o | NC(CCCN)C(=O) | R | D-Ornithine |
| P | N1C(CCC1)C(=O) | S | L-Proline |
| p | N1C(CCC1)C(=O) | R | D-Proline |
| pac | n4ccc(cc4)CC(=O) | | Pyridine-4-acetic acid |
| pam | NCCCCCN | | 1,5-pentanediamine |
| Pg | NC(c1ccccc1)C(=O) | S | L-Phenylglycine |
| pG | NC(c1ccccc1)C(=O) | R | D-Phenylglycine |
| Pol | NC(Cc1ccccc1)CO | S | L-Phenylalanol |
| ppc | N1CCC(CC1)C(=O) | | Piperidine-4-carboxylic acid |
| ppz | N3CCNCC3 | | piperazine |
| pyc | n4ccc(cc4)C(=O) | | Pyridine-4-carboxylic acid |
| ram | NCCCN | | 1,3-propane diamine |
| S | NC(CO)C(=O) | S | L-Serine |
| tam | NCCN | | 1,2-ethane diamine |
| tbm | NC(C)(C)C | | tert-butylamine |
| tic | N7C(Cc8ccccc8C7)C(=O) | S | D-tetrahydroisoquinoline |
| Tic | N7C(Cc8ccccc8C7)C(=O) | R | L-tetrahydroisoquinoline |
| W | NC(Cc1[nH]c2ccccc2c1)C(=O) | S | L-Tryptophane |
| w | NC(Cc1[nH]c2ccccc2c1)C(=O) | R | D-Tryptophane |
| wol | NC(Cc1[nH]c2ccccc2c1)CO | R | D-Tryptophanol |
| Y | NC(Cc1ccc(O)cc1)C(=O) | S | L-Tyrosine |
| y | NC(Cc1ccc(O)cc1)C(=O) | R | D-Tyrosine |
| Y(I) | NC(Cc1ccc(O)c(I)c1)C(=O) | S | 3-Iodo-L-Tyrosine |

Notes:
a)The above structures are depicted in the SMILES format ("SMILES, 1. Introduction to Encoding Rules" Weinenger, D. J. Chem. Inf. Comput. Sci. 1988, 28, 31.). They are generally written N- to C-terminal with the points of attachment at the left- and/or right hand atoms depending on sequence position. In cases where attachment would be ambiguous, two different acronyms are used to depict the two modes, if both are used.
b)It will be understood that when attached at a terminal position, the appropriate C-terminal function indicated in the table (i.e. —OH, —NH2, OMe) is added to complete the structure (acid, amide, Me ester, respectively). Also, hydrogen atoms are to be added to the terminal amine functions to fill out the valence.

B. Utility

The compounds of Formula I can be administered to mammals, including man, to release endogenous growth hormone in vivo. For example, the compounds can be administered to commercially important mammals such as swine, cattle, sheep and the like to accelerate and increase their rate and extent of growth and the efficiency of their conversion of feed into body tissue, and to increase milk production in such mammals. In addition, these compounds can be administered to humans in vivo as a diagnostic tool to determine whether the pituitary is capable of releasing growth hormone. The compounds of Formula I can be administered in vivo to adults and children to stimulate growth hormone release.

Accordingly, the present invention includes within its scope pharmaceutical compositions comprising, as an active ingredient, at least one of the compounds of Formula I in association with a pharmaceutical carrier or diluent. Optionally, the active ingredient of pharmaceutical compositions can comprise a growth promoting agent in addition to at least one of the compounds of Formula I.

Growth promoting agents include but are not limited to; TRH, diethylstilbestrol, theophylline, enkephalins, E series prostaglandins, peptides of the VIP-secretin-glucagon-GRF family and other growth hormone secretagogues such as GHRP-6, GHRP-1 as described in U.S. Pat. No. 4,411,890; benzo fused lactams such as those disclosed in U.S. Pat. No. 5,206,235; and growth hormone releasing hormone (GHRH) and its analogs or growth hormone (GH) and its analogs or somatomedins including IGF-1 and IGF-2 and their analogs.

The compounds of this invention are shown to induce release of growth hormone and IGF-1. It is known to those skilled in the art that there are many uses for growth hormone and the IGF's. Therefore administration of the compounds of this invention for purposes of stimulating the release of endogenous growth hormone or IGF-1 can have the same effects or uses as growth hormone or the somatomedins themselves. These uses of growth hormone and IGF-1 include the following: stimulating growth hormone release in elderly humans; prevention of catabolic side effects of glucocorticoids, treatment of osteoporosis, stimulation of the immune system, treatment of retardation, acceleration of wound healing, accelerating bone fracture repair, treatment of growth retardation, treating renal failure or insufficiency resulting in growth retardation, treatment of physiological short stature, including growth hormone deficient children, treating short stature associated with chronic illness, treatment of obesity and growth retardation associated with obesity, treating growth retardation associated with Prader-Willi syndrome and Turner's syndrome; accelerating the recovery and reducing hospitalization of burn patients; treatment of intrauterine growth retardation, skeletal dysplasia, hypercortisolism and Cushings syndrome; Induction of pulsatile growth hormone release; replacement of growth hormone in stressed patients; treatment of osteochondrodysplasias, Noonans syndrome, schizophrenia, depression, Alzheimer's disease, diseases of demeylination, multiple sclerosis, delayed wound healing, and psychosocial deprivation; treatment of pulmonary dysfunction and ventilator dependency; attenuation of protein catabolic response after a major operation; reducing cachexia and protein loss due to chronic illness such as cancer or AIDS; treatment of hyperinsulinemia including Type II diabetes; adjuvant treatment for ovulation induction; stimulating thymic development and prevent the age-related decline of thymic function; treatment of immunosuppressed patients; treatment of bone marrow transplanted patients, improvement in muscle strength, mobility, diseases of muscle function, muscular dystrophy's, maintenance of skin thickness, metabolic homeostasis, enhancing renal function and hemeostasis including acute and chronic renal failure, stimulation of osteoblasts, bone remodeling, and cartilage growth; stimulation of the immune system in companion animals; growth promotion in livestock including stimulation of milk production in ruminates and wool or hair growth.

An alternative use of the GHRP's of this invention, represented by formulae I–V, as well as other GHRP's as defined herein, including but not limited to GHRP-6 and GHRP-1 as described in U.S. Pat. No. 4,411,890; GHRP-2; benzo fused lactam GHRP's such as those disclosed in U.S. Pat. No. 5,206,235; are used in combination with IGF-1 to treat diseases in which long term IGF-1 treatment is indicated. This use of GHRP's is to bring serum GH levels back to normal when long-term IGF-1 therapy down-regulates the pituitary GH secretion. Such use includes but is not limited to use in the treatment of Type II diabetes.

Other uses of the instant compounds will be apparent from the following references; Amato et al., *Journal of Clinical Endocrinology and Metabolism* 77(6):1671–1676 (1993), Bengtsson et al., *Journal of Clinical Endocrinology and Metabolism* 76(2):309–317 (1993), Binnerts et al., *Clinical Endocrinology* 37:79–87 (1992), Bowers, *Journal of Clinical Endocrinology and Metabolism* 76(4):817–823 (1993), Cuneo et al., *J. Applied Physiol.* 70(2):688–694 (1991), Cuneo et al., *J Applied Physiol.* 70(2):695–700 (1991), Degerblad et al., *Acta Endocrinologica* 126:387–93 (1992), Edén et al., *Arteriosclerosis and Thrombosis* 13(2):296–301 (1993), Hartman et al., *Horm Res* 40:37–47 (1993), Ho et al., *Horm Res* 40:80–86 (1993), Jøgensen et al., *Acta Endocrinologica* 125:449–453 (1991), Jøgensen et al., *The Lancet* June 3:1221–1224 (1989), Lamberts et al., *Clinical Endocrinology* 37:111–115 (1992), McGauley et al., *Horm Res* 33(suppl 4):52–54 (1990), Møller et al., *Clinical Endocrinology* 39:403–408 (1993), O'Halloran et al., *Journal of Clinical Endocrinology and Metabolism* 76(5):1344–1348 (1993), Orme et al., *Clinical Endocrinology* 37:453–459 (1992), Rodriguez-Arnao et al., *Horm Res* 39:87–88 (1993), Rosén et al., *Clinical Endocrinology* 40:111–116 (1994), Rosén et al., *Acta Endocrinologica* 129:195–200 (1993), Rudman et al., *The New England Journal of Medicine* 323(1):1–6 (1990), Salomon et al., *The New England Journal of Medicine* 321(26):1797–1803 (1989), Shibasaki et al., *Journal of Clinical Endocrinology and Metabolism* 58(1):212–214 (1984), Sönksen et al., *Acta Paediatr Scand [Suppl]* 379:139–146 (1991), Tauber et al., *Journal of Clinical Endocrinology and Metabolism* 76(5):1135–1139 (1993), Vandeweghe et al., *Clinical Endocrinology* 39:409–415 (1993), Whitehead et al., *Clinical Endocrinology* 36:45–52 (1992), and Bercu et al., U.S. Pat. No. 5,246,920.

Additionally, the most potent compounds of this invention can be used as GH antagonists. It is known that hypothalamic hormones that are super agonists can also be used as antagonists. For example super agonists of Gonadotrophin Releasing Hormone (GnRH) such as GONADORELIN and LEUPROLIDE act either as agonists or antagonists depending on the method of administration. The actions of the GnRH super agonists are summarized in Goodman and Gilmans, *The Pharmacological Basis of Therapertics*, 8th Ed., McGraw Hill Inc., p. 1353 (1993). By analogy, it is believed the continuous administration of the compounds of formula I–V will lead to down-regulation of the growth response. These molecules can therefore be used as functional antagonists of pituitary GH secretion, thereby antagonizing GH or IGF-1 action.

The uses of such antagonists of GH secretion include but are not limited to; treatment of excess GH secretion as in acromegaly or gigantism; in cancer of the breast, colon and prostate; in diabetes especially in Type I adolescent patients to counteract the down phenomenon; and in Type I and Type II patients to directly control blood glucose, and to control the long-term affects of diabetes, as for example in retinopathy.

The compounds of this invention can be administered by oral, parenteral (e.g., intramuscular, intraperitoneal, intravenous or subcutaneous injection or infusion, or implant), nasal, pulmonary, vaginal, rectal, sublingual, or topical routes of administration and can be formulated in dosage forms appropriate for each route of administration.

C. Methods of Making

1. General Peptide Synthesis

One method of producing GHRP's involves chemical synthesis of the "polypeptide". This can be accomplished using methodologies well known to those skilled in the art (see Stewart, J. M. & Young, J. D. *Solid Phase Peptide Synthesis* Pierce Chemical Co. Rockford, Ill.[1984]; see also U.S. Pat. No. 's 4,105,603; 3,972,859; 3,842,067; and 3,862, 925).

Figure 2:
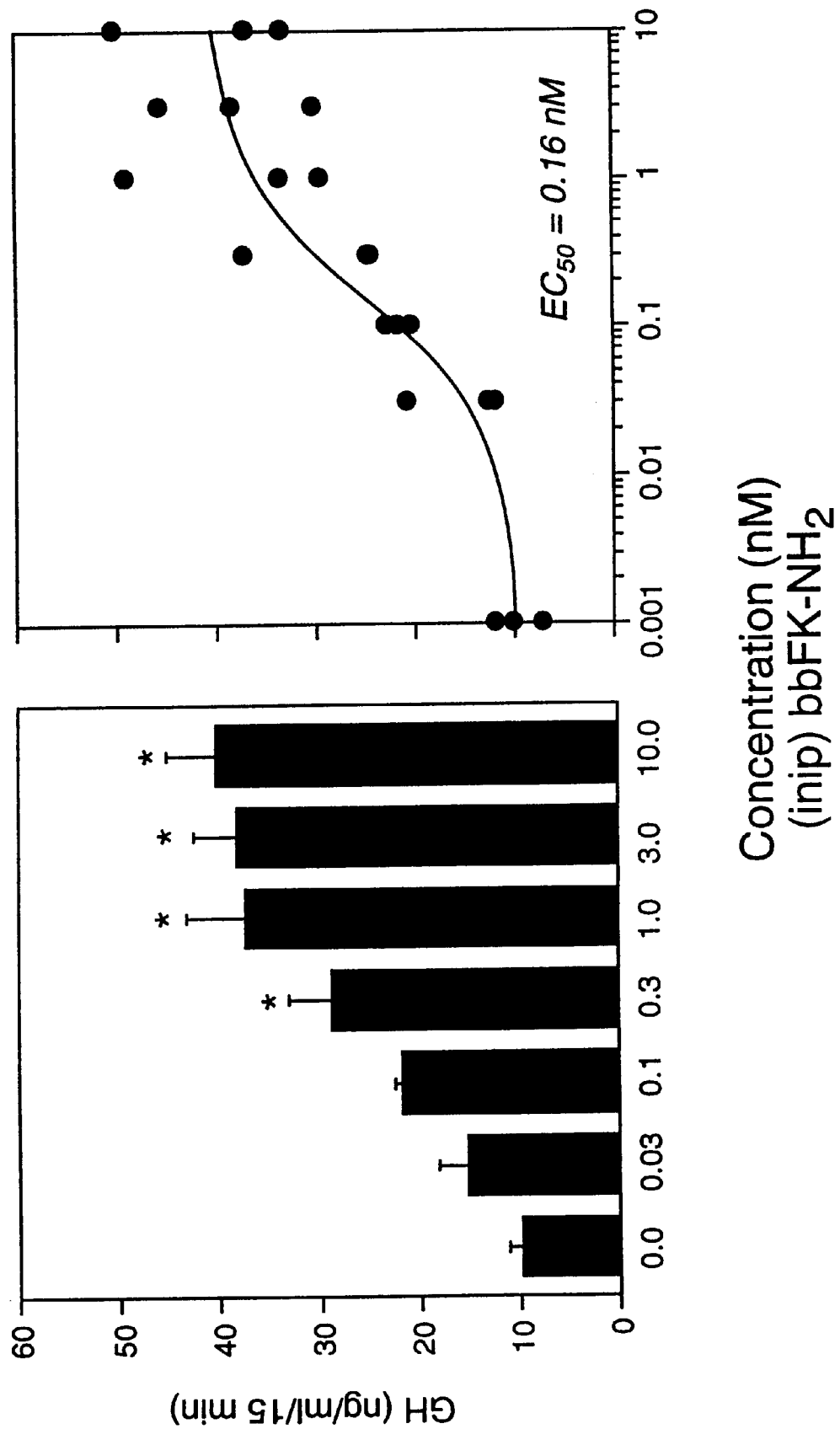
FIG. 2. A representative rat "pit" cell assay dose response of GH release over a 15 min. exposure to increasing concentrations of (inip)-bbFK-NH$_2$. GH release is significantly (P<0.05) increased at 0.3 nM and reaches a plateau by 1 nM with an EC$_{50}$ of 0.16 nM (see right panel for data points and curve used to calculate EC$_{50}$). The mean (n=3) EC$_{50}$ for inip-bbFK-NH$_2$ was 0.18±0.04 nM, over 30-fold more potent than HwAWfK-NH$_2$ ("GHRP-6") (6.2±1.5 nM; n=5).

"Polypeptides" of the invention may be conveniently prepared using solid phase peptide synthesis (Merrifield, *J. Am. Chem. Soc.,* 85:2149 [1964]; Houghten, *Proc. Natl. Acal. Sci USA* 82:5132 [1985]). Solid phase synthesis begins at the carboxy-terminus of the putative peptide by coupling a protected amino acid to a suitable resin (e.g. chloromethylated polystyrene resin) as shown in FIGS. 1-1 and 1-2, on pages 2 and 4 of Stewart and Young supra. After removal of the α-amino protecting group with, for example, trifluoroacetic acid (TFA) in methylene chloride and neutralizing in, for example TEA, the next α-amino- and if necessary, side-chain-protected amino acids are added. The remaining α-amino- and, if necessary, side-chain-protected amino acids are then coupled sequentially in the desired order by condensation to obtain an intermediate compound connected to the resin. Alternatively, some amino acids may be coupled to one another forming a peptide prior to addition of the peptide to the growing solid phase polypeptide chain.

The condensation between two amino acids, or an amino acid and a peptide, or a peptide and a peptide can be carried out according to the usual condensation methods such as the azide method, mixed acid anhydride method, DCC (N,N'-dicyclohexylcarbodiimide) or DIPC (N,N'-diisopropylcarbodiimide)methods, active ester method (p-nitrophenyl ester method, BOP [benzotriazole-1-yl-oxytris (dimethylamino) phosphonium hexafluorophosphate] method, N-hydroxysuccinic acid imido ester method, etc., and Woodward regent K method.

Common to chemical syntheses of peptides is the protection of any reactive side-chain groups of the amino acids with suitable protecting groups. Ultimately these protecting groups are removed after the desired polypeptide chain has been sequentially assembled. Also common is the protection of the α-amino group on an amino acid or a fragment while that entity reacts at the carboxyl group followed by the selective removal of the α-amino-protecting group to allow subsequent reaction to take place at that location. Accordingly, it is common in polypeptide synthesis that an intermediate compound is produced which contains each of the amino acid residues located in the desired sequence in the peptide chain with various of these residues having side-chain protecting groups attached. These protecting groups are then commonly removed substantially at the same time so as to produce the desired resultant product following removal from the resin.

Suitable protective groups for protecting the α- and ε-amino side chain groups are exemplified by benzyloxycarbonyl (CBZ), isonicotinyloxycarbonyl(iNOC), O-chlorobenzyloxycarbonyl (2-Cl-CBZ), p-nitrobenzyloxycarbonyl [Z(NO$_2$)], p-methoxybenzyloxycarbonyl [Z(OMe)], t-butoxycarbonyl (BOC), t-amyloxycarbonyl (AOC), isobormyloxycarbonyl, adamatyloxycarbonyl, 2-(4-biphenyl)-2-propyl-oxycarbonyl (BPOC), 9-fluorenylmethoxycarbonyl (FMOC), methylsulfonyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt) and the like.

Protective groups for the carboxy functional group are exemplified by; benzyl ester (OBzl), cyclohexyl ester (Chx), 4-nitrobenzyl ester (ONb), t-butyl ester (OtBu), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenylsulfonyl (Mts), and the like. The thiol group of cysteine may be protected with p-methoxybenzyl, triphenylmethyl, acetylaminomethyl ethylcarbamoyle, 4-methylbenzyl, 2,4,6-trimethy-benzyl (Tmb) etc., and the hydroxyl group of serine can be protected with benzyl, t-butyl, acetyl, tetrahydropyranyl and the like.

Stewart and Young supra provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151.

After the desired amino acid sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the peptide residue is washed with ether, and extracted from the resin by washing with aqueous acetonitrile and acetic acid.

Preferably in order to avoid alkylation of residues in the polypeptide, (for example, alkylation of methionine, cysteine, and tyrosine residues) a thio-cresol and cresol scavenger mixture is used.

2. Other General Procedures

The peptidomimetic compounds of the invention may also be conveniently prepared by the methods for peptide synthesis described in monographs such as ("Principles of Peptide Synthesis, M. Bodanszky, Spring-Verlag, 2nd Ed., 1993; "Synthetic Peptides; A Users Guide", G. A. Grant, Ed, W. H. Freeman and Co., 1992; and references sited therein), or by other methods generally known to one skilled in the art. The synthesis of compounds of this invention that are peptidomimetric in nature (i.e. contain other than standard amide bond linkages) may be prepared by extension of the methods described in the specific Examples 1–37 and the methods laid forth in Schemes I–IV below, by the general synthetic methods described in "Comprehensive Organic Transformations", R. C. Larock, VCH Publishers, 1989, and by methods generally known to one skilled in the art.

For compounds of claim 1 where the amide linkages (—C(=O)—NH—) are replaced with amide isostere linkages such as; —CH$_2$—NH—, —CH$_2$—S—, —CH$_2$—CH$_2$—, —CH=CH— (cis and trans), —C(=O)—CH$_2$—, —CH(OH)—CH$_2$—, —CH(CN)—NH—, —O—C(=O)—NH— and —CH$_2$—SO—, amide bond replacing methods known in the art are employed. The following references describe preparation of amide isostere linkages which include these alternative-linking moieties: Spatola, A. F., Vega Data 1(3): "Peptide Backbone Modifications" (General Review) (March 1983), Spatola, A. F., in "Chemistry and biochemistry of Amino Acids Peptides and Proteins", B. Weinstein, ed., Marcel Dekker, New York, P. 267 (1983); Morley, J. S., *Trends Pharm. Sci* pp. 463–468; Hudson, D. et al. *Int. J. Pept. Prot. Res.* 14:177–185 (1979) (—CH$_2$NH—, —CH$_2$CH$_2$—); Spatola, A. F., et al., *Life Sci.* 38:1243–1249 (1986) (—CH$_2$—S—); Hann, M. M., *J. Chem. Soc. Perkin. Trans I* 307–314 (1982) (—CH=CH—, cis and trans); Almquist, R. G., et al., *J. Med. Chem.*

23:1392–1398 (1980) (—C(=O)—CH$_2$—); Jennings-White C., et al., *Tetrahedron Lett* 23:(1982) (—C(=O)—CH$_2$—); Szelke, M., et al., EP Application No. 45665 (1982) *Chem Abs*:9739405 (1982) (—CH(OH)—CH$_2$); Holladay, M. W., et al., *Tetrahedron Lett* 24:4401–4404 (1983) (—C(OH)—CH$_2$—); Hruby, V. J. *Life Sci* 31:189–199 (1982) (—CH$_2$S—); and Cho, C. Y. et al, *Science* 261:1303–1305 (1993) (—O—C(=O)—NH—).

In one embodiment, compounds of the invention are specifically prepared by the methods described in Schemes I–IV. The N-terminal amino group is shown as isonipecotic acid for clarity, but it is understood that the compounds of this invention with other groups (R$^A$) at this position are prepared by substitution of the appropriately protected reagent for the protected isonipecotic acid in the scheme. One may in general use a range of methods for the coupling of the components such as preformed active esters, acid chlorides, and coupling reagents. For connections other than amides, alkylation, acylation, and sulfonylation, for example, may be accomplished using the appropriately activated reagent and methods described in ("Comprehensive Organic Transformations", R. C. Larock, VCH Publishers, 1989).

3. Specific Schemes

As shown in Scheme I, protected amino acids of the type 1 may be alkylated according to the procedure of Benoitin (Can. J. Chem. 55, 906, 1977) to give a variety of N-substituted compounds (2).

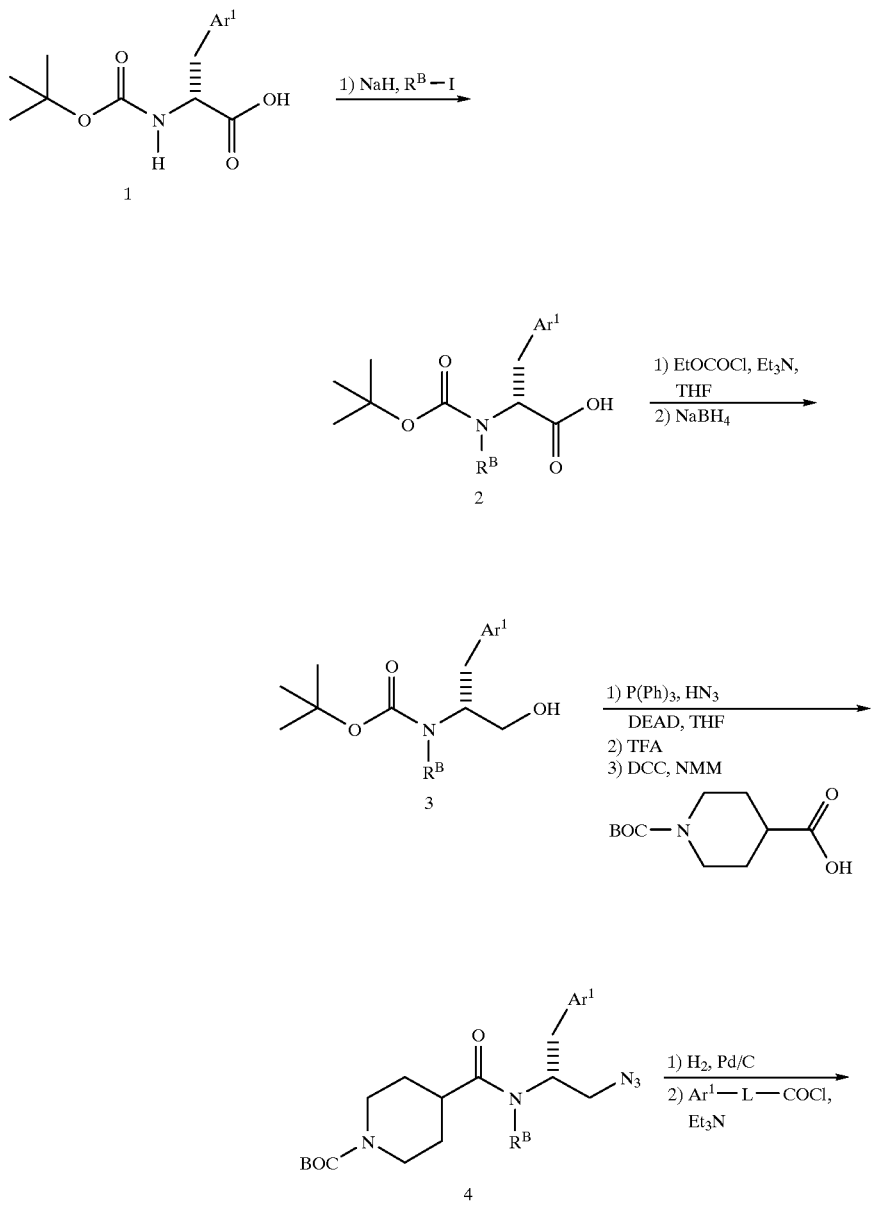

Scheme I

-continued

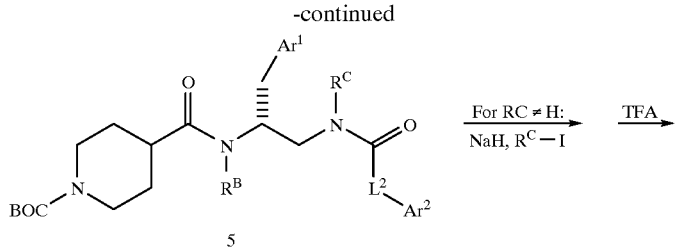

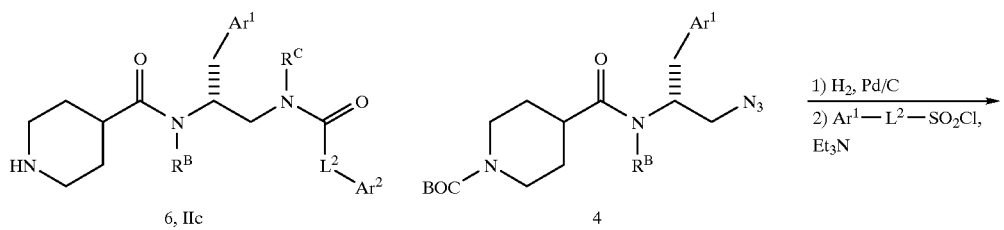

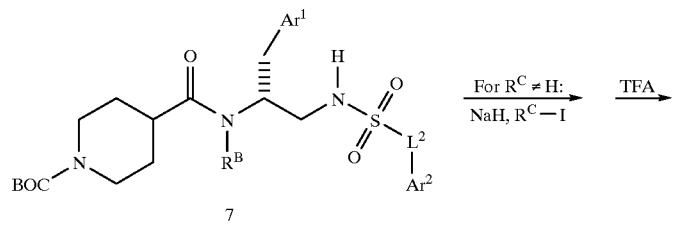

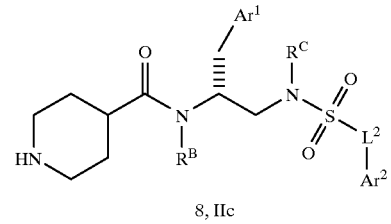

To produce reduced or inverted amide compounds of the Type IIc, (2) may be reduced through the preformed mixed anhydride with sodium borohydride to give protected amino alcohols (3). Conversion of the hydroxyl function to an amine may be accomplished via Mitsunobu coupling of (3) with hydrazoic acid to give an intermediate protected amino azide. Deblocking of the amino function and coupling to the N-terminal group is conveniently performed at this differentiated stage. In this example, the N-BOC is removed with TFA and the resulting free-based amino azide coupled to N-BOC-isonipecotic acid using the reagent DCC to give (4).

The intermediate azide (4) can be converted to a variety of compounds of this invention. For example, hydrogenation of the azido function gives an amine which can be acylated with a variety of groups, for example, $Ar^1$-$L^2$-COCl to give (5) (Scheme I). For the synthesis of the range of $L^2$'s herein claimed, it is understood that $Ar^1$-$L^2$-COCl may be substituted with a variety of different acylating agents like chloro carbonates, activated esters, isocyanates, and the like. For example, 2-naphthoylchloride, benzylchloroformate, phenylacetyl chloride, dihydrocinnamoyl chloride, and phenylisocyanate may be used to give compounds (6) with a range of linkers $L^2$. Global deprotection then gives 6, for $R^C$=H. Incorporation of the N-substitution $R^C$, into (5) can be accomplished via alkylation of (5), for example via deprotonation with sodium hydride and reaction with an alkyl halide. Deprotection gives (6) ($R^C$ H).

For synthesis of N-sulfonamido compounds, the amine produced via reduction of (4) can be sulfonylated, alternately alkylated at nitrogen (for $R^C$ H), and deprotected to give (8).

For the synthesis of compounds (6) and (8) where $R^B$=H and $R^C$ H, it may be more convenient to incorporate the substituent $R^C$ via reductive amination. For example, using one equivalent of an appropriate aldehyde and sodium cyanoborohydride, $R^C$ can be introduced into the amine from reduction of (4), prior to acylation or sulfonylation to (6) or (8), respectively.

Compounds IIc in which X=H, alkyl, substituted alkyl, and the like, may be synthesized via the route shown in Scheme II.

Scheme II

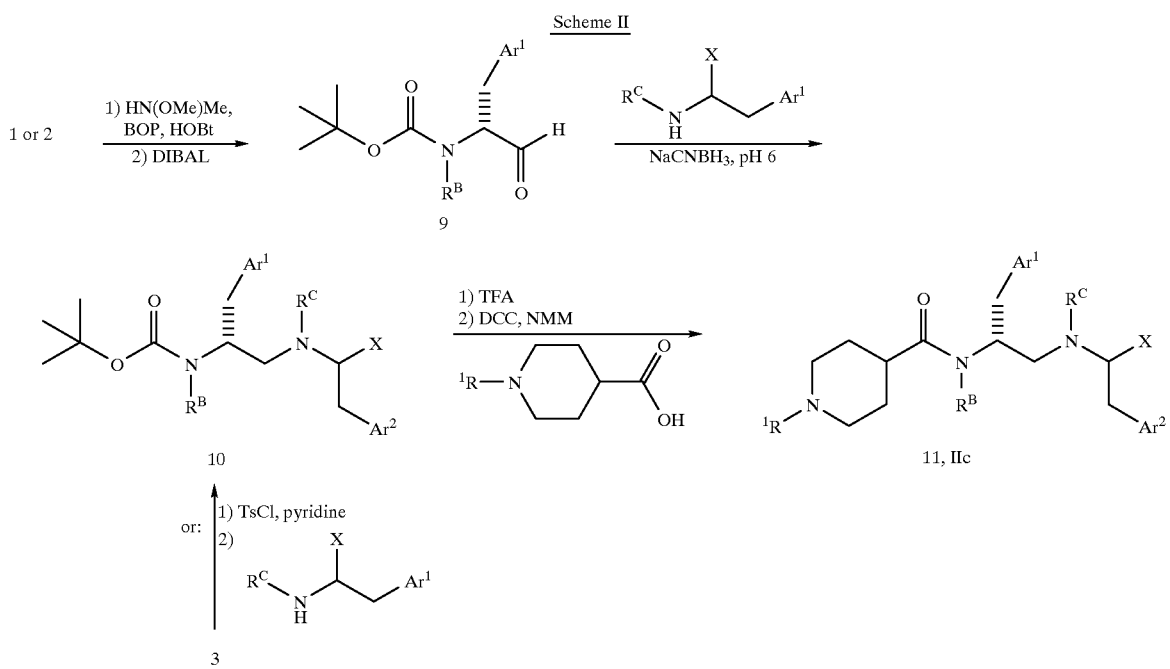

The intermediate protected amino acids (1) or (2) (from Scheme I) are converted to protected amino aldehydes (9), conveniently via DIBAL reduction of the derived N-methyl-N-methoxy-amide. Subsequent reductive amination with an appropriately substituted amine gives (10). Alternatively, (10) can be prepared from (3) via conversion of the alcohol to a tosylate or other suitable leaving group, and displacement with an appropriately substituted amine (Scheme II). It should be apparent that a wide variety of amines could be used in these two routes to (10) including tryptamine, N-methyl-(2-naphthyl)ethyl amine, alpha-methylphenethylamine, tryptophanol, and N-methyl-beta-naphthylalanol. The amine may also be part of a heterocycle, i.e. 2-benzyl- or naphthylmethyl-piperidine.

This reductive amination strategy is a general method for incorporation of a reduced amide isostere into a polyamide chain. Thus, substitution of an appropriately protected amino acid derivative or peptide with a free alpha-amine, for the amine component in Scheme II (9) to (10) provides a protected, reduced amide isostere, intermediate. In this manner, compounds IIIb–IIIe may be prepared using appropriate orthogonal protecting groups for the reactive functionality. This method may also be employed when the amine component is attached to a solid support, suitable for peptide synthesis, providing a convenient method for the synthesis of longer peptidic compounds.

Completion of the synthesis of compounds of the type 11 (Scheme II) (and by analogy, compounds IIIb–IIIe), requires deprotection of the amino group and coupling to an appropriately protected N-terminal moiety, shown in Scheme II as N-$R^1$-isonipecotic acid for clarity. Depending on the particular substituents X, $R^B$, and $R^C$ in (10), it may be necessary to orthogonally protect reactive functionality prior to removal of the N-terminal blocking group. For example, for (10) ($R^C$=X=H) the secondary amine in (10) can be acylated with FMOC-Cl (e.g. $R^C$=FMOC) prior to removal of the N-terminal BOC. This ensures that the subsequent acylation occurs only at the terminal amine.

It will be noted that a wide variety of N-terminal groups can be attached to the intermediate deprotected (10). Any suitably protected amino acid, i.e. BOC-4-aminobutyric acid, N-alkyl-isonipecotic acid, may be attached using a standard coupling reagent. Also, protected active esters, anhydrides, and acid chlorides, may be used. For the synthesis of urea type linkages, the intermediate deprotected (10) may be reacted with carbonyl diimidazole or phosgene, followed by addition of a suitably protected or symmetrical amine. In particular, reaction with piperazine, propane diamine, or N1,N4-dimethylpropanediamine, give preferred compounds.

For the synthesis of compounds with an N-terminal carbamate linkage, the intermediate deprotected (10) ($R^C$ H) may be reacted with carbonyl diimidazole or phosgene, followed by addition of a suitably N-protected amino alcohol such as BOC-aminoethanol, BOC-aminopropanol, and BOC-2- or 3-hydroxypiperidine. Alternatively, the intermediate deprotected (10) can be reacted directly with a preformed N-blocked-chloroformate.

The final step necessary for completion of the synthesis of the compounds of type 11 is removal of the protecting functionality using appropriate conditions (for a general monograph on protecting groups, see Greene, W. T., Wuts P. G. M. *Protective Groups in Organic Synthesis,* 2nd Ed., John Wiley & Sons, NY [1991]).

It will be noted that these methods for incorporation of different N-terminal groups (e.g. $R^A$'s) are generally applicable to the compounds of this invention and not limited to the particular example of Scheme II.

The synthesis of the peptidomimetic compounds IId–IIg, are shown below in Schemes III–VI. For the synthesis of IId (Scheme III), protected amino acid (2) or (1 for $R^B$=H) is converted to the homologous methyl ester via rearrangement of the diazoketone with Ag(I) in methanol.

Scheme III

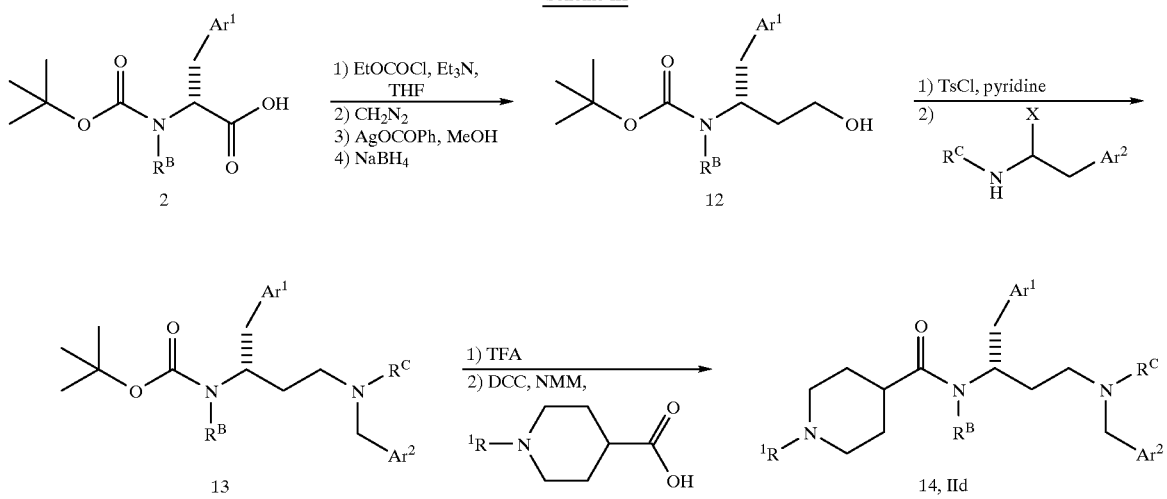

Reduction of the ester provides alcohol (12) which, when converted to a tosylate or similar leaving group, can be displaced by a large range of substituted amines, as exemplified by the conversion of 3 to 10 (Scheme II). Deprotection of the product (13) and acylation provides (14) after deprotection.

Compounds of the type IIe can be prepared as shown in Scheme IV.

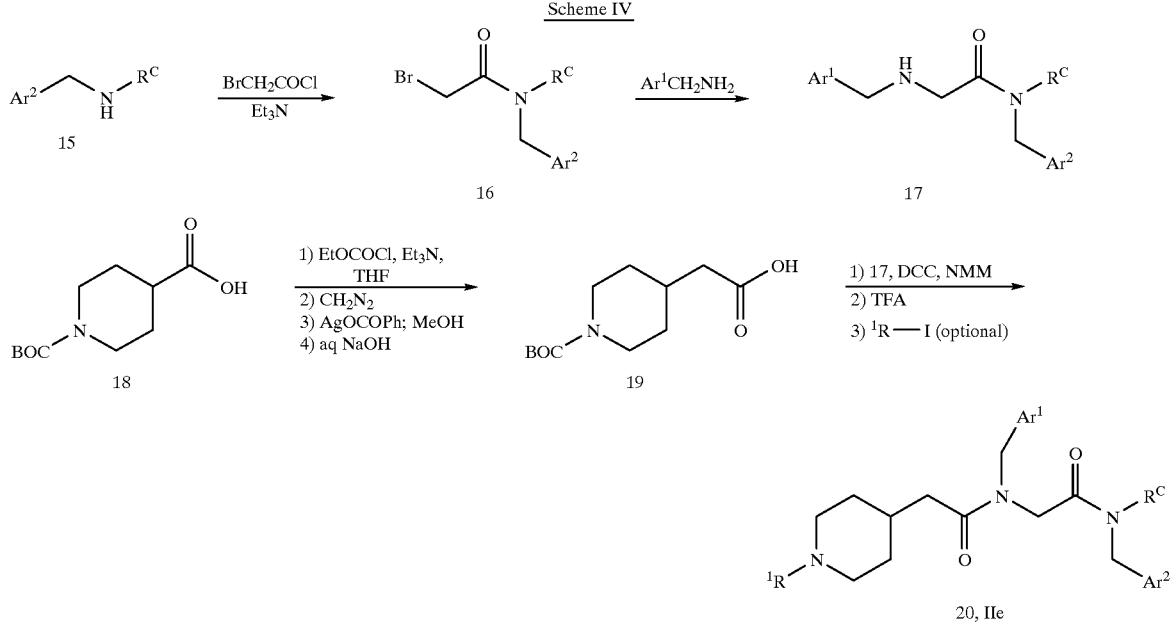

Substituted amine (15) is acylated with bromoacetyl bromide to give (16), which is reacted with a second amine to give (17). Acylation with an appropriate N-terminal moiety gives (20). For example, a prefered N-terminus, 4-carboxymethylpiperidine (19), is prepared via homologation of BOC-isonipecotic acid (18), and acylated onto (17) with DCC. Deprotection and optional alkylation of the terminal amine provides (20). Reductive amination with an appropriate aldehyde is an alternate method for the incorporation of $R^1$ substituents onto the terminal amine. This is a generally applicable method, useful for many compounds of this invention.

Compounds of the type IIf (Scheme V) can be prepared from (17) via LAH reduction of the amide functionality. Acylation with (19), deprotection, and optional N-alkylation provides (21).

Scheme V

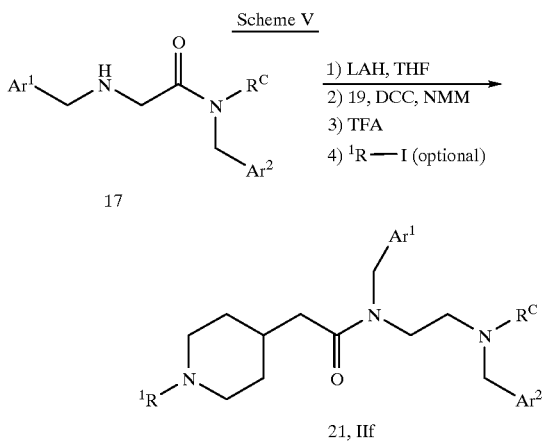

17

21, IIf

The pseudo symmetrical compounds of type IIg are preparable via the route shown in Scheme VI. Conversion of arylamine (22) to (23) is analogous to the preparation of (17) above.

Scheme VI

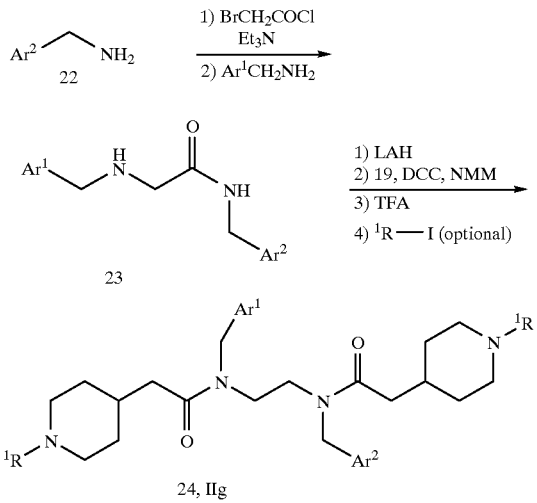

23

24, IIg

LAH reduction provides a symmetrical or unsymmetrical substituted ethane diamine which is acylated simultaneously at both nitrogens with 19 or another appropriate reagent. Deblocking as above gives (24).

D. Preferred Embodiments

The present invention is based on the discovery of several new classes of small peptidomimetics that cause the release of growth hormone in mammals. It is a preferable object of the present invention to provide agents that are selective for GH release and have suitable safety and efficacy for chronic administration to mammals. In a more prefered embodiment, the present invention provides compounds which are suitable for oral, intranasal, or pulmonary delivery. It is an aim of the most prefered embodiments of the present invention to provide compounds that are superior to the prior art by the above criteria. It is further prefered that the compounds be readily synthesizable in optically pure form where necessary.

In view of the foregoing, the prefered compounds of this invention have an $EC_{50}$ in the rat "pit" cell assay of less than about 1.0 nM and most preferably less than about 0.5 nM. Prefered compounds of this invention also have a molecular weight less than 650 da and most preferably less than 600 da. Prefered embodiments of the compounds of this invention are represented by structural Formula (I)

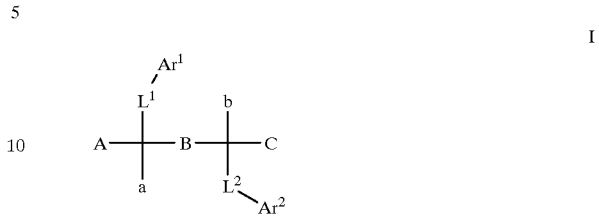

I where the symbols of formula (I) are selected from the following:

From the substructures shown for group A of Formula (I), those prefered A's are selected from;

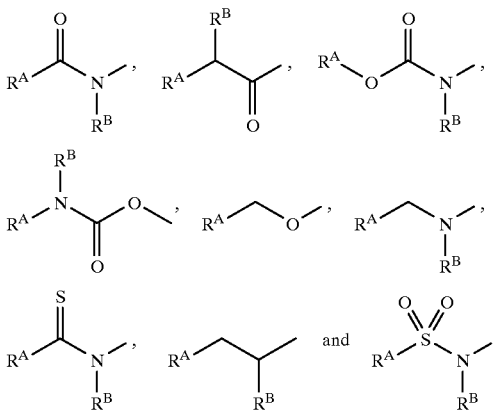

while the most preferred A's incorporate either an amide or carbamate linkage as in;

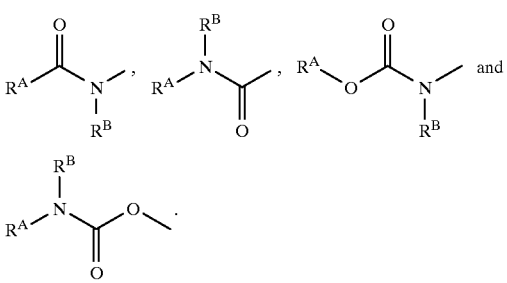

With respect to certain combinations of $L^1$-$Ar^1$ and B, it is prefered to use a commercially available amino acid as a starting material.

For the groups $R^A$, of substructure A, prefered embodiments incorporate functionality that places a basic nitrogen atom (or prodrug form thereof) at a distance of approximately 4 to 8 C—C bonds from the attachment point of $L^1$-$Ar^1$, in a through-bond measurement. For example, preferred $R^A$'s, of the most prefered A substructures above, include alkyl amines $(CH_2)_n NR^2 R^3$ (where n=2 to 4) and saturated six-membered ring heterocycles containing 1 or 2 nitrogen atoms, for the amide-linked A's, and $(CH_2)_n NR^2 R^3$ (where n=2 or 3) and 3- or 4-substituted saturated six-membered ring heterocycles containing 1 or 2 nitrogen atoms, for the carbamate-linked A's. Prefered R's attached at the nitrogen atom of $R^A$ include hydrogen, methyl, ethyl, 2-hydroxyethyl, and 2-hydroxypropyl. More prefered, are those $R^A$'s that place the amine at approximately 6 C—C bonds from the attachment point of $L^1$-$Ar^1$, measured in a through-bond manner, as is the case with the most prefered $R^A$'s $(CH_2)_3NR^2R^3$, 4-piperidinyl, and piperazinyl, for the amide linked A's, and $(CH_2)_3NR^2R^3$ for the carbamate linked A's, where $R^2$ and $R^3$ are chosen from the group hydrogen and methyl. In the case of the carbamate where $R^A$ is attached directly to nitrogen, an additionally prefered $R^A$ forms a piperazine, where the carbamate nitrogen is incorporated as a ring atom. Thus, a most prefered embodiment of the present invention incorporates a substructure A of the following composition:

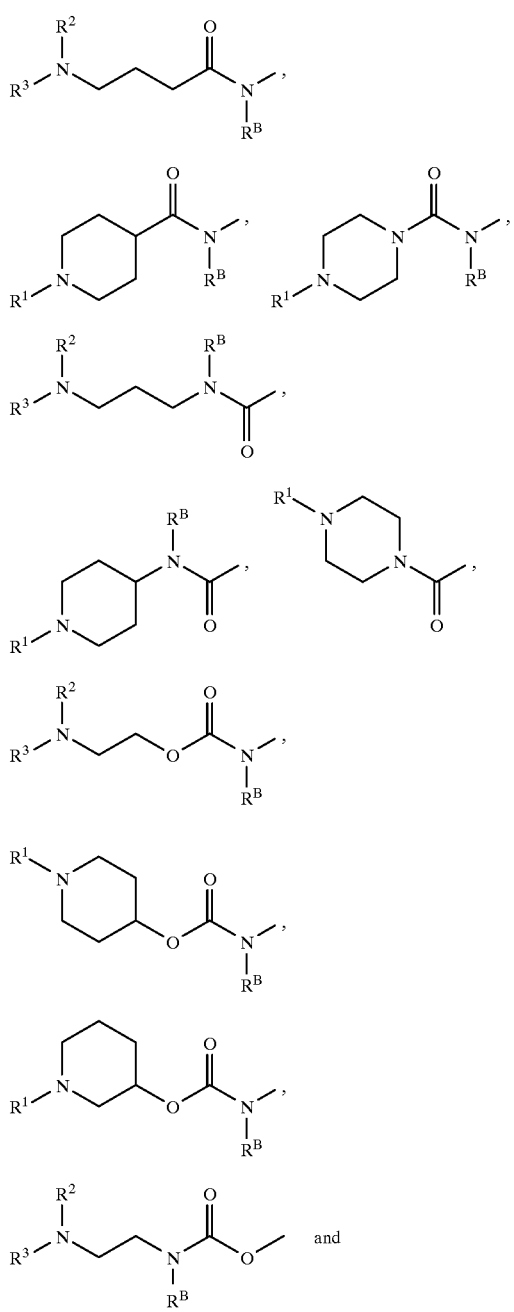

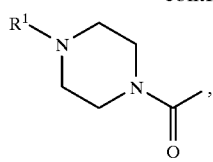

where the groups $R^B$ are hydrogen or lower alkyl.

In the most prefered embodiment of the instant invention, the A substructure of Formula (I) is an amide derived from attachment of isonipecotic (inip) acid (piperidine-4-carboxylic acid)

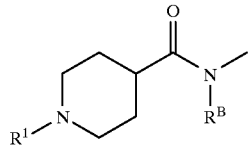

where the groups $R^B$ and $R^1$ are hydrogen or lower alkyl.

As is taught in the present invention, the above substructure A's display the amine functionality at a near optimal distance from $L^1$-$Ar^1$ in Formula (I) and thus it is prefered that the appended $R^A$'s for other substructure A's of the instant invention mimic this distance as closely as possible, preferably through the incorporation of a rigidifying carbo- or heterocyclic substructure.

Prefered embodiments of the other substructures of the compound represented in Formula (I) are as follows:

For the groups a and b, hydrogen and methyl, independently selected, are more prefered. In a most preferred embodiment a and b are both hydrogen.

For the substructure B, which links the two aromatic sidechains, the amide, amine, and ether of the following functions are more prefered;

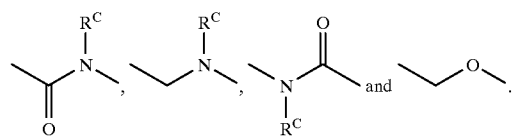

The most preferred B's are selected from:

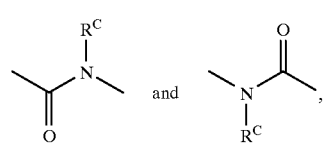

where $R^C$ is additionally preferred to be hydrogen or methyl.

Moreover, when the substructure A, B, and/or C are comprised of the amide function C(=O)NH, the present invention teaches that the NH is replacable by MNe with retention of biological activity. It is therefore a most prefered embodiment of the present invention that the groups $R^B$, $R^C$, and $R^D$ be independently selected from methyl and hydrogen, a particular combination chosen so as to optimize for desired properties of the molecule, such as stability and lipophilicity.

From the prefered list of substructures C, of Formula I, the more prefered embodiments are conveniently discussed by class. For the "pentapeptide, short series", exemplified by the most prefered (inip)bwFK-NH$_2$ (where C is —C(=O)—Phe—Lys-amide), and Formula Ia below, prefered embodiments include, in addition to the most prefered —C(=O)—Phe—Lys-amide, the substitution for Lys (Y) by the n-alkyl diamines H$_2$N(CH$_2$)$_n$NH$_2$, where n=2–6, and amino amides selected from the common amino acids.

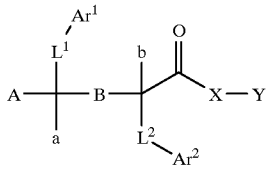
(Ia)

As is taught in the present invention, a wide range of substitution is allowable at the Lys (Y) and, to a lesser extent, the Phe (X) position. It is therefore preferable to select from all possible C-terminal groups, those that are inexpensive, and improve the overall physical properties of the compound.

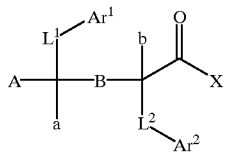
(Ib)

For the Phe (X) position in the above formula (Ib) and the "tetrapeptide, short series", the Phe is most prefered when a C-terminal amide is included, as are L-alpha-naphthylalanine, L-beta-naphthylalanine, and Tyr. In the short series, exemplified by (inip)bbF-NH$_2$, the C-terminal carboxamide is a prefered embodiment. Also prefered are the amides N,N-dimethyl, N-methyl and morpholinyl. In a further prefered embodiment, the carboxamide is replaced with the free acid and the reduced congener CH$_2$OH and hydrogen.

An additional class of most prefered compounds (Formula Ic) are obtained by the replacement of the Phe in the above structures with a non-aromatic residue. Most prefered among this class are the compounds where X (below) is an amide derived from the lower alkyl diamines and the lower alkyl aminocarboxamides. Most preferable is when X is butane diamine.

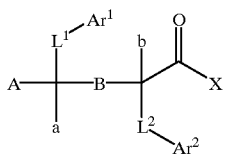
(Ic)

Most preferable is a compound where X is butane diamine and B is a N-methyl amide. Further most preferable compounds include those where X is NH$_2$, alkyl amides therefrom, OH, and it's lower alkyl esters.

In the "micro series", exemplified by (inip)b(wol), and depicted below, Z is prefered to be CH$_2$OH, CH$_2$OC(=O)R$^2$, CH$_2$NR$^2$R$^3$, CH$_2$OR, and hydrogen. Most prefered is Z=CH$_2$OH or hydrogen.

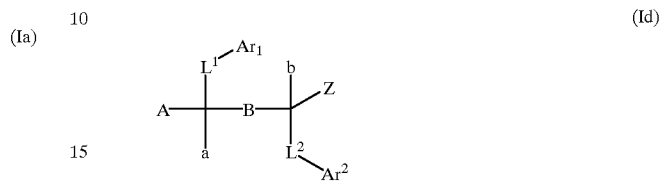
(Id)

From the prefered list of L$^1$-Ar$^1$'s and L$^2$-Ar$^2$'s detailed in claim 1, the most prefered are chosen from CH$_2$Ar, where Ar is preferably 1- or 2-naphthyl, 3-indoyl, or substituted phenyl. In a most highly prefered embodiment, L$^1$-Ar$^1$ is CH$_2$(2-naphthyl) and L$^2$-Ar$^2$ is CH$_2$(3-indoyl) or CH$_2$(2-naphthyl).

Other most prefered compounds of the present invention include:

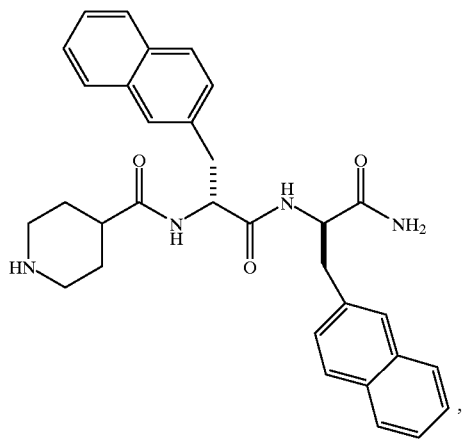
,

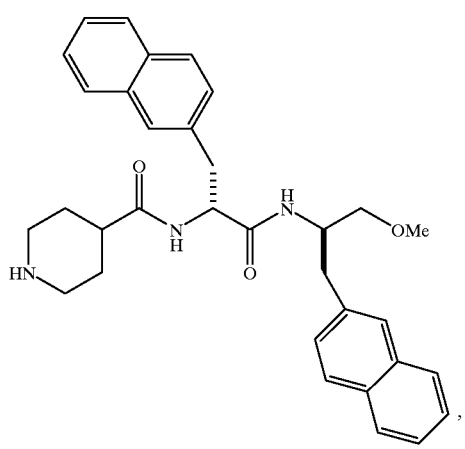
,

47
-continued
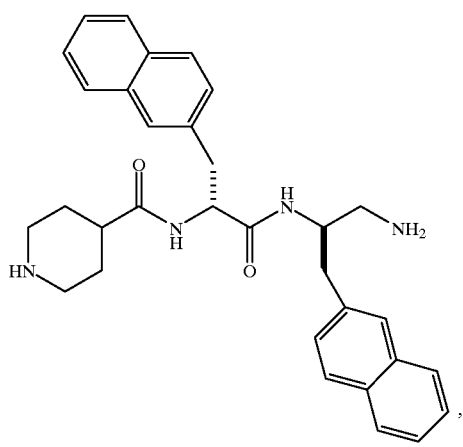
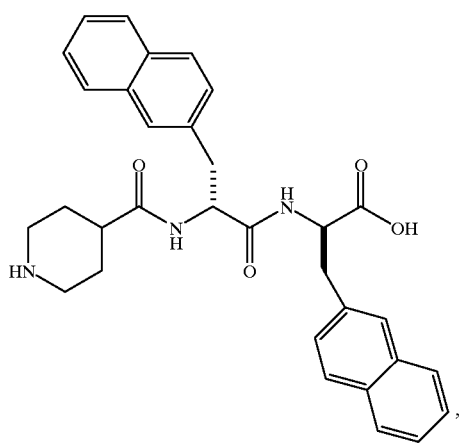
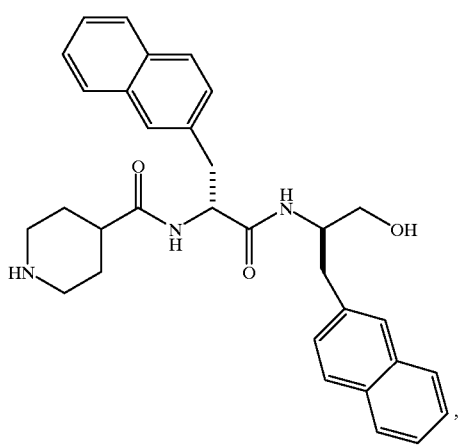
48
-continued
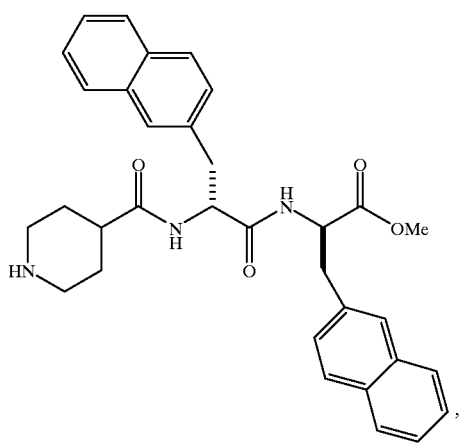
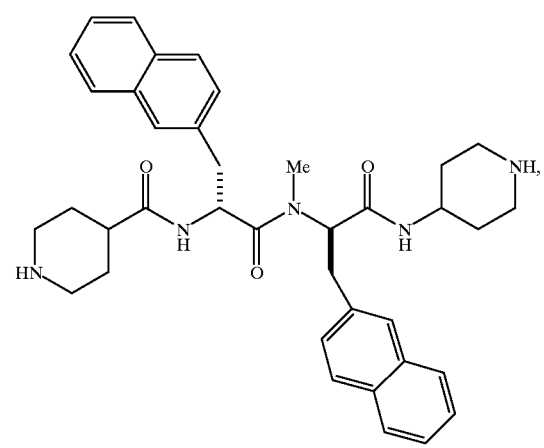
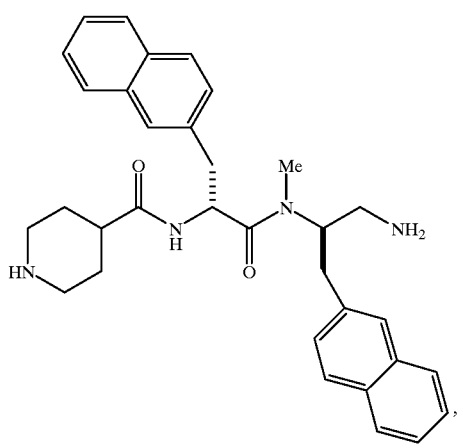

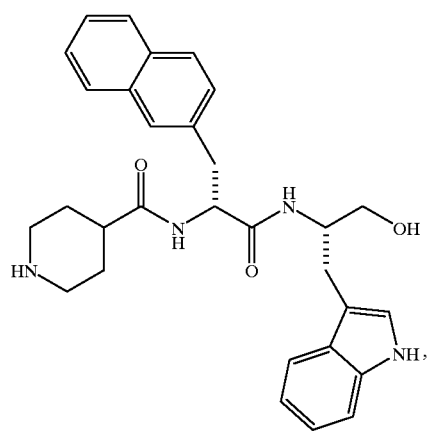
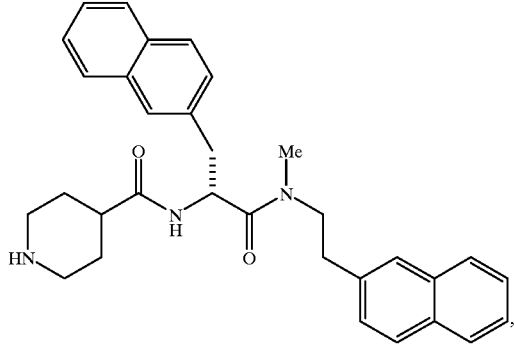
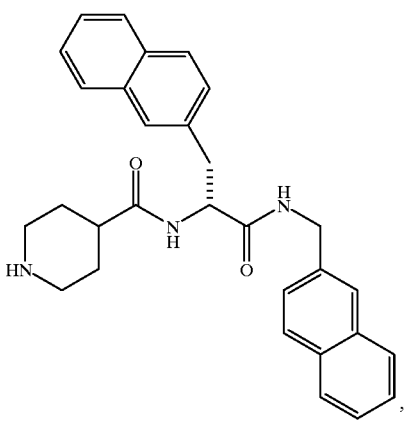
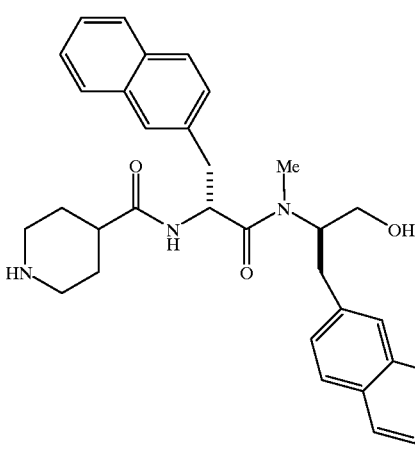
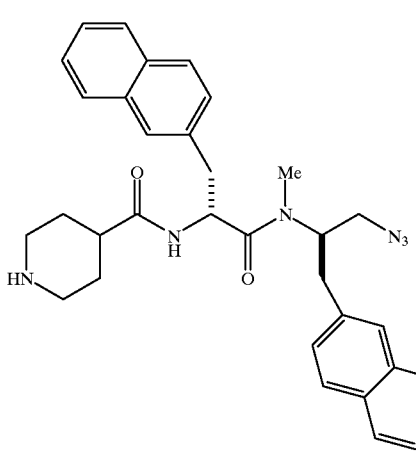

51
-continued
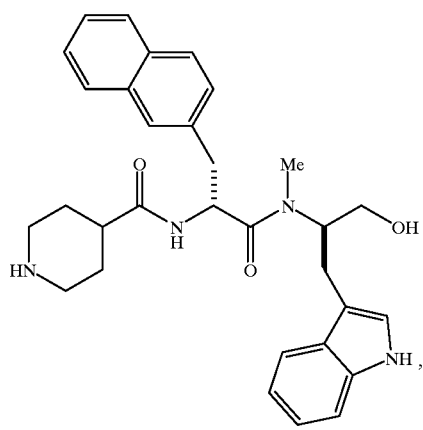
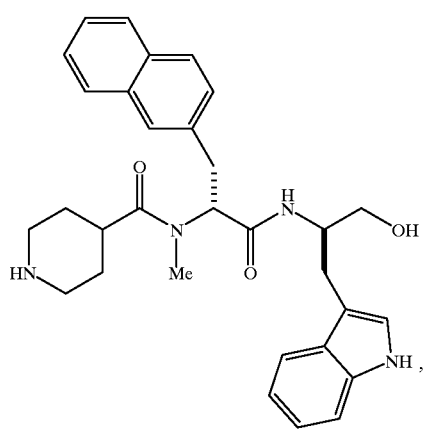
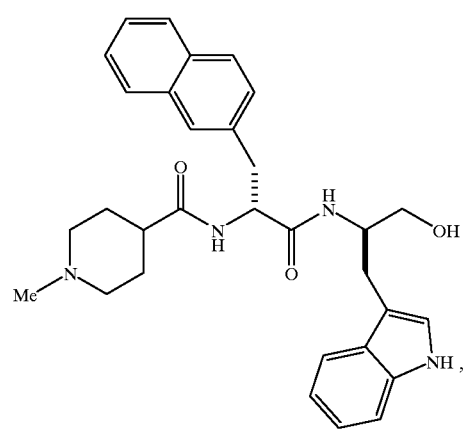
52
-continued
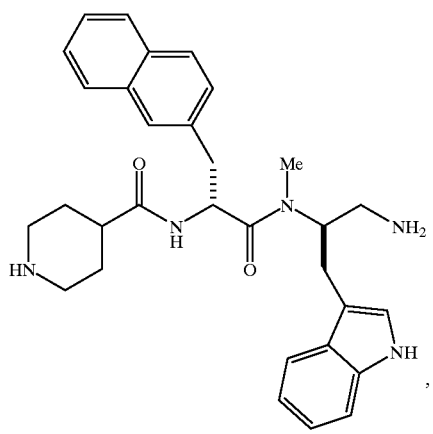
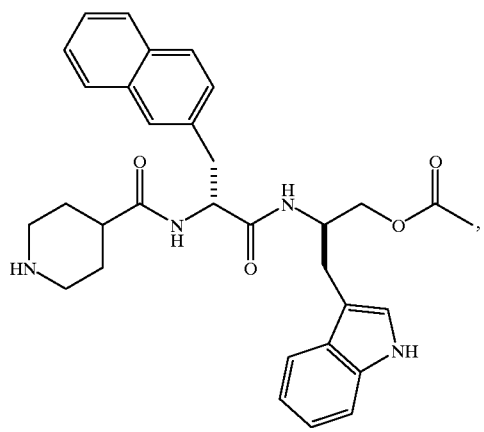
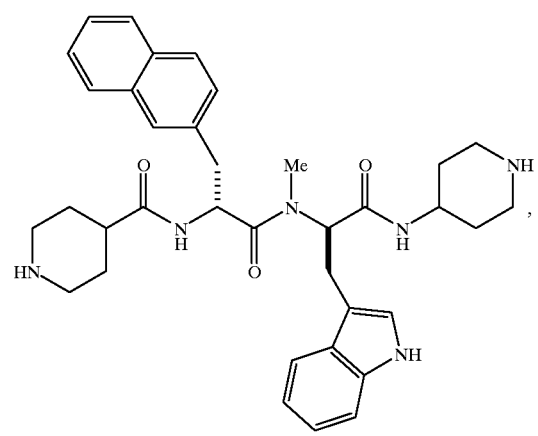

53
-continued
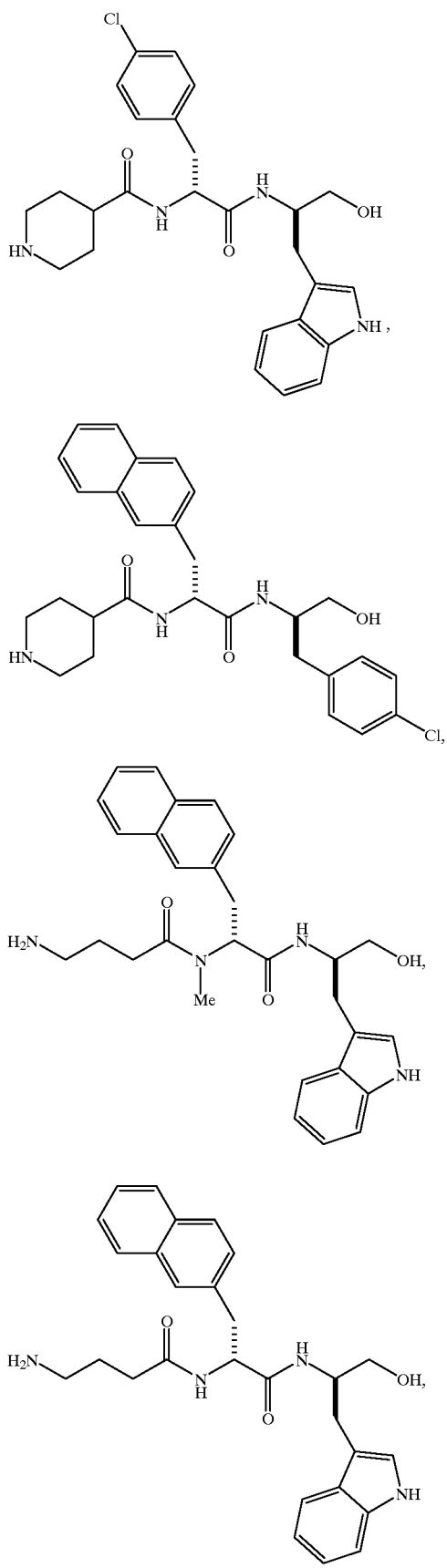
54
-continued
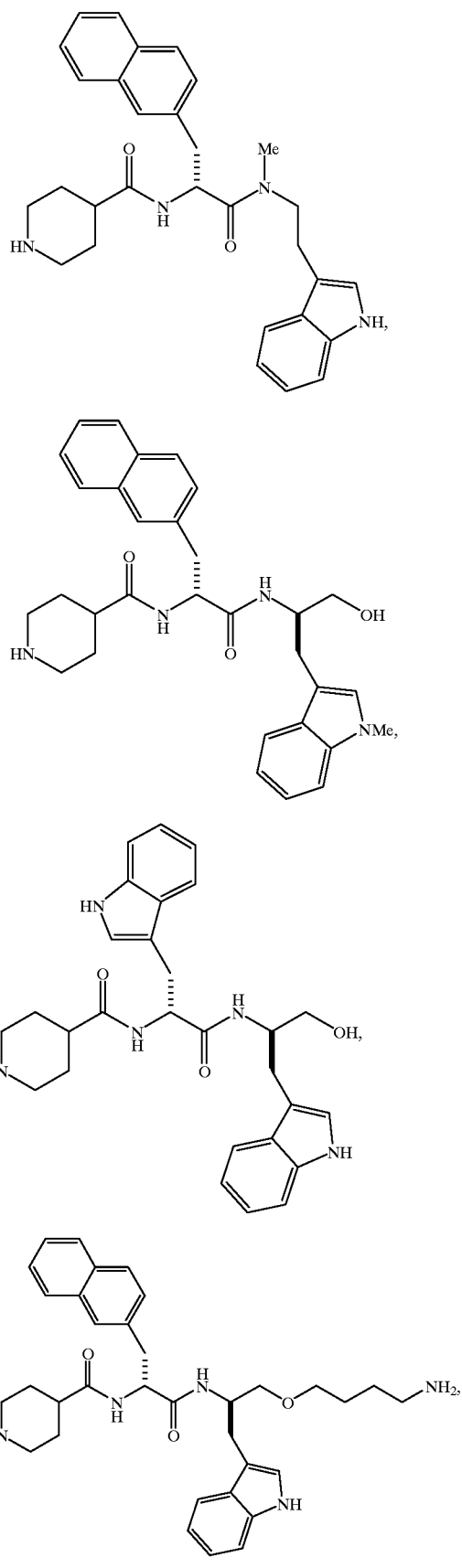

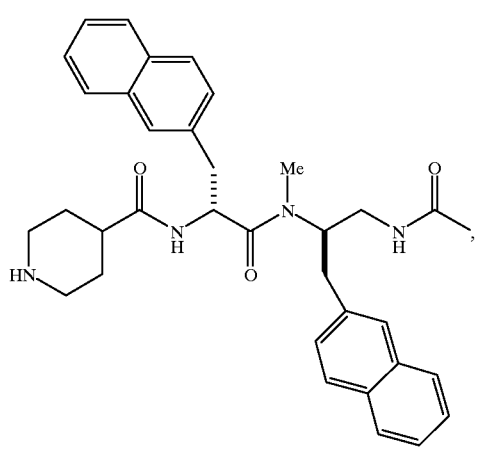
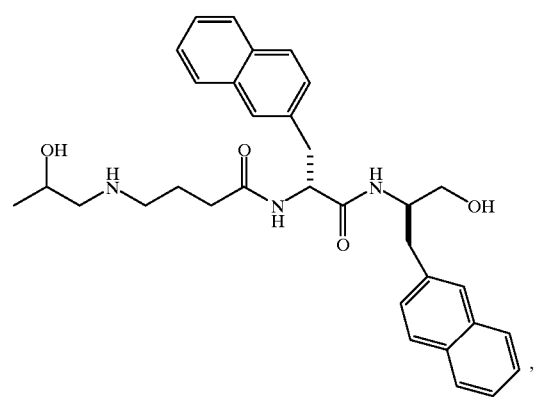
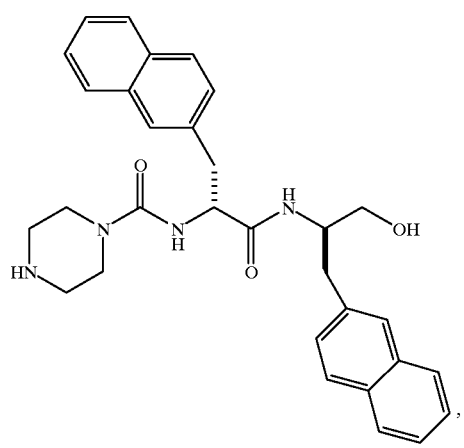
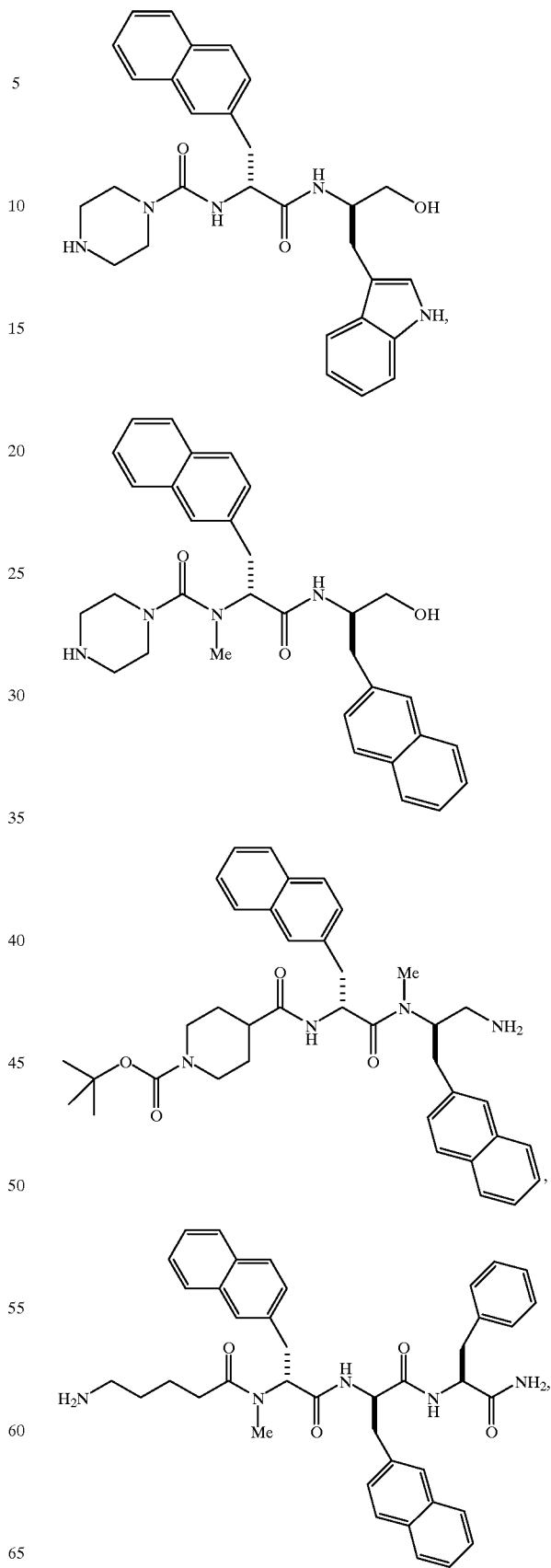

57
-continued
58
-continued
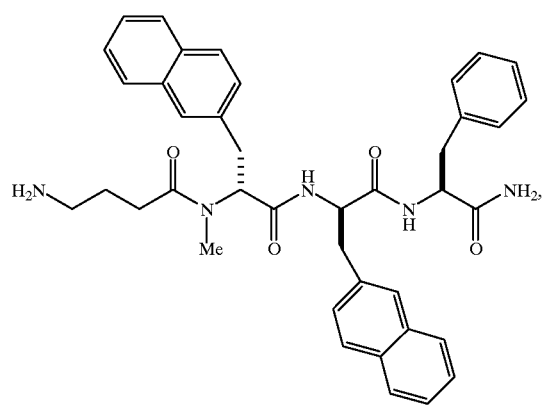
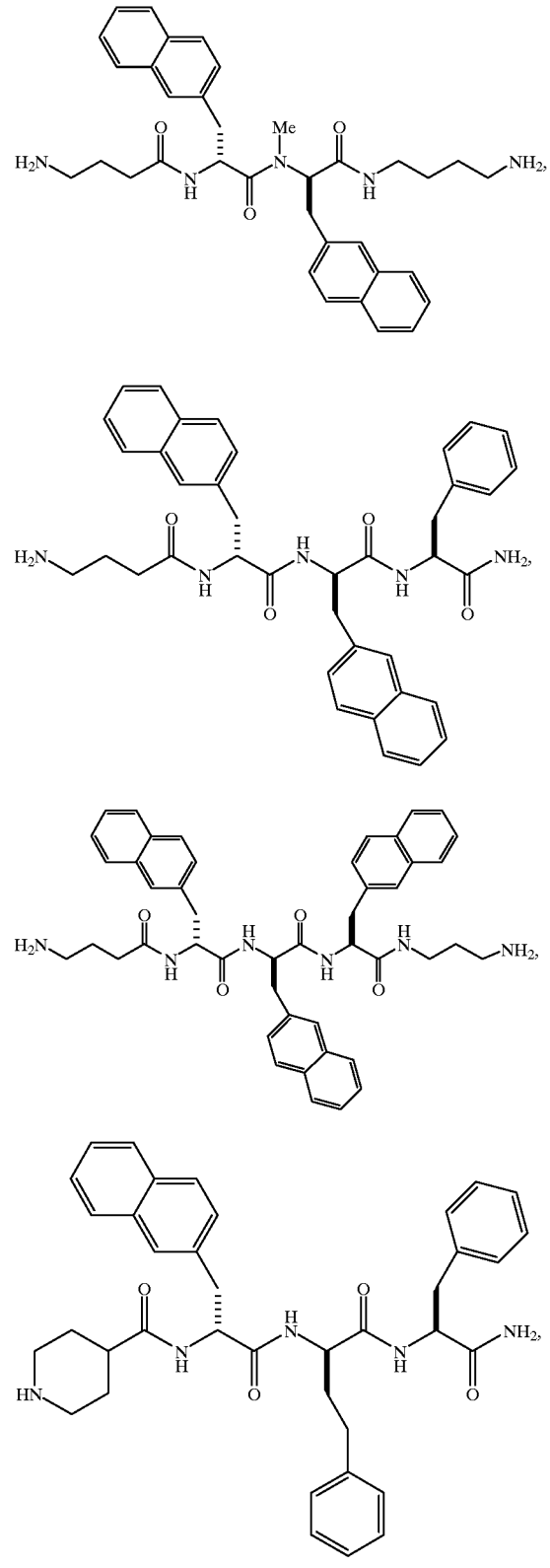

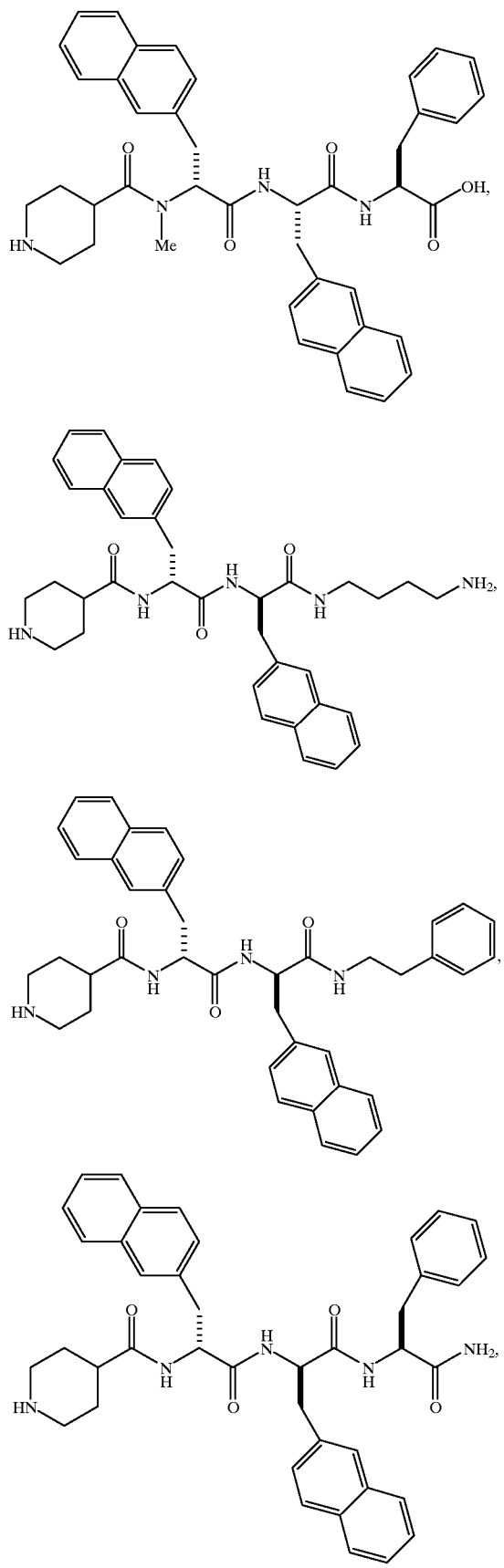
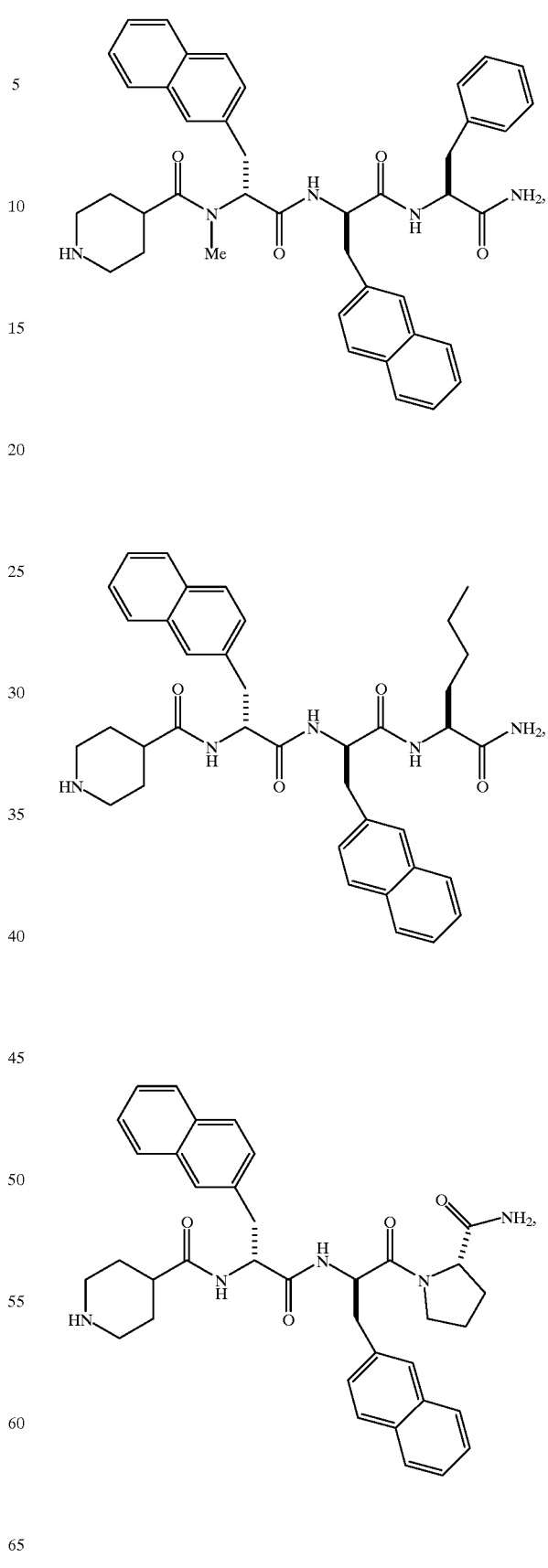

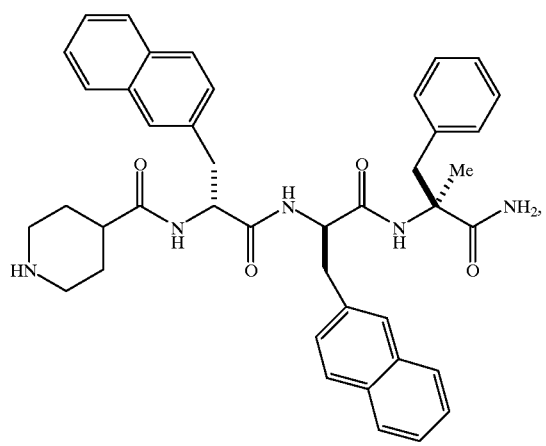
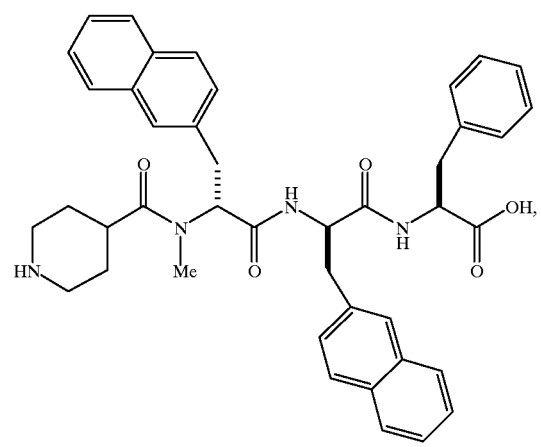
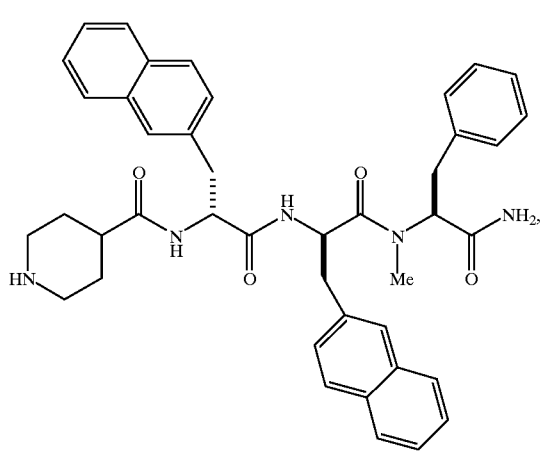
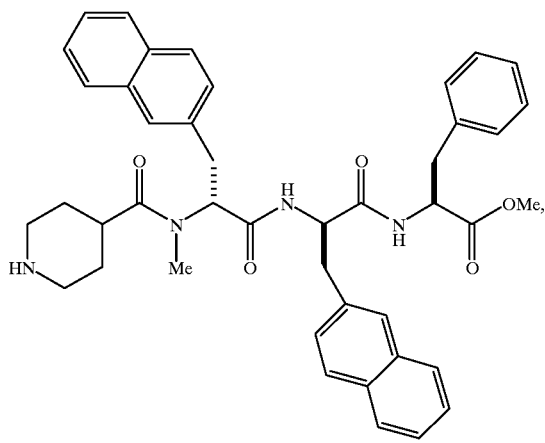
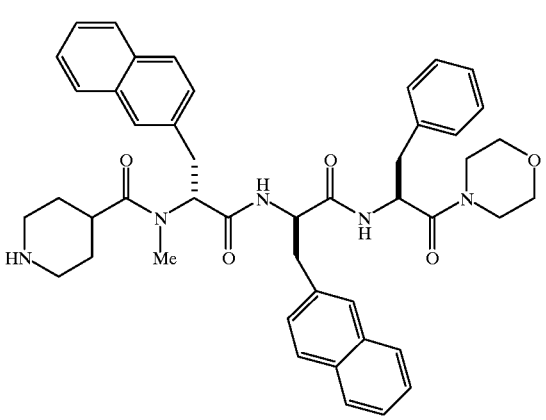
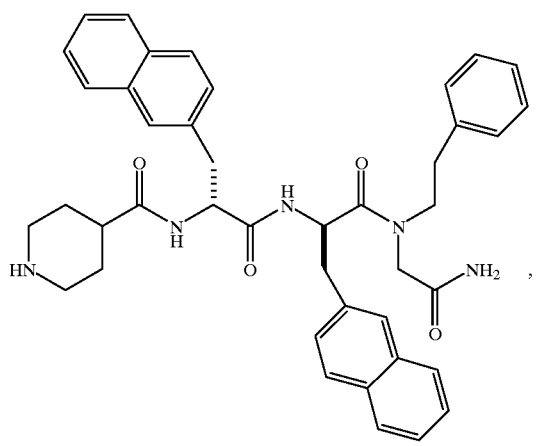

63
-continued
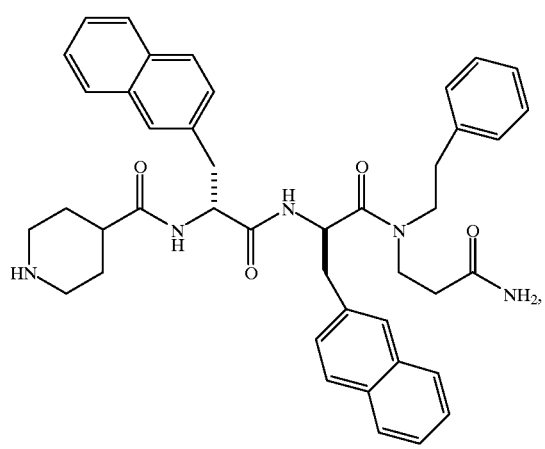
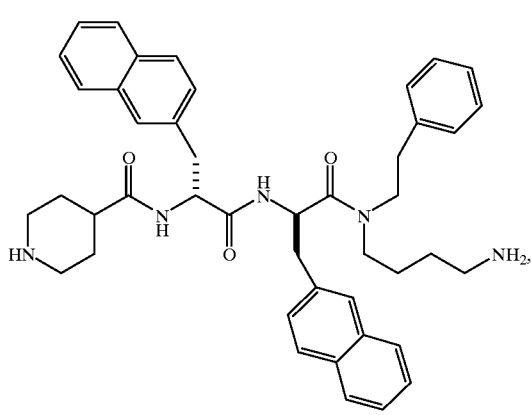
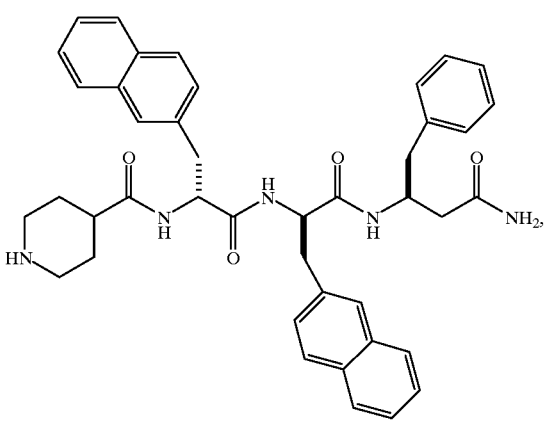
64
-continued
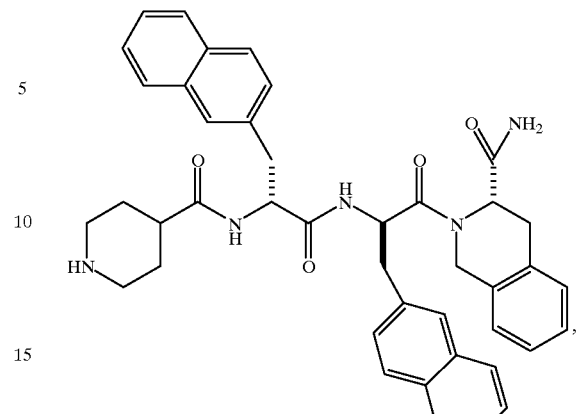
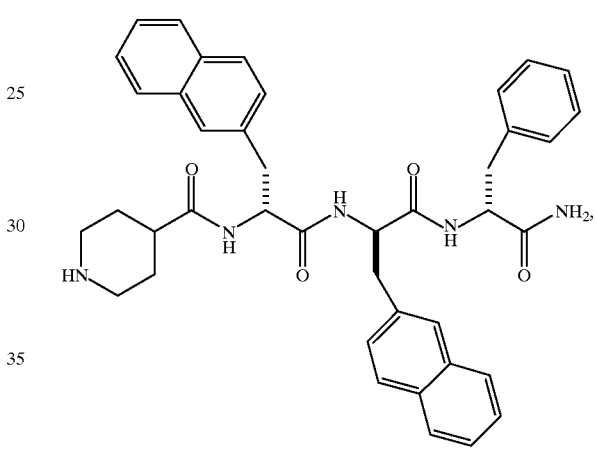
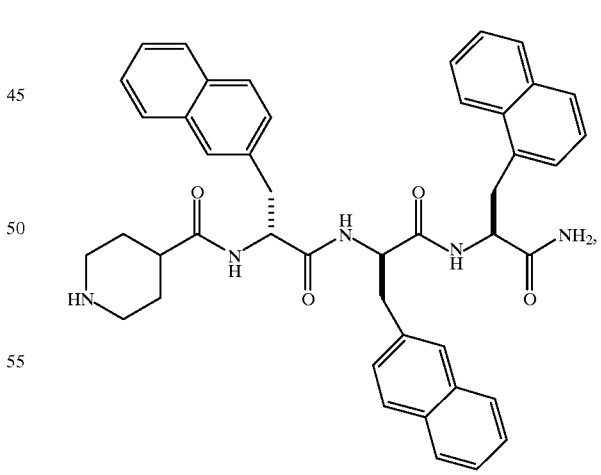

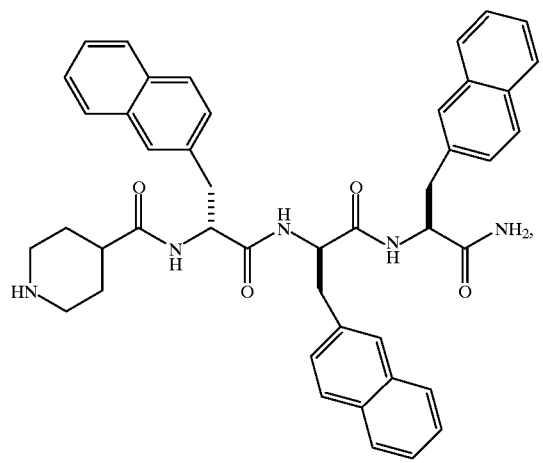
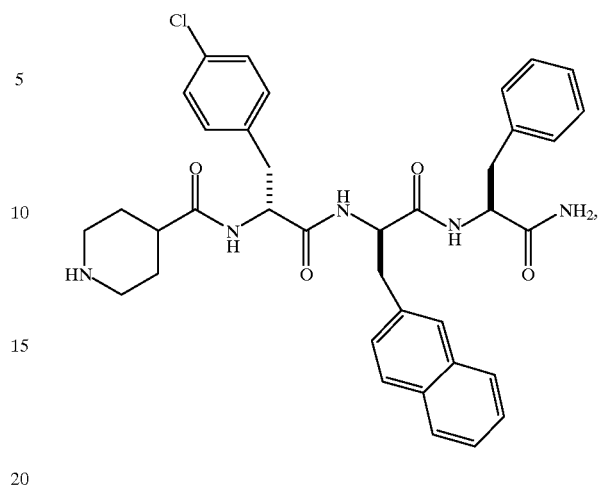
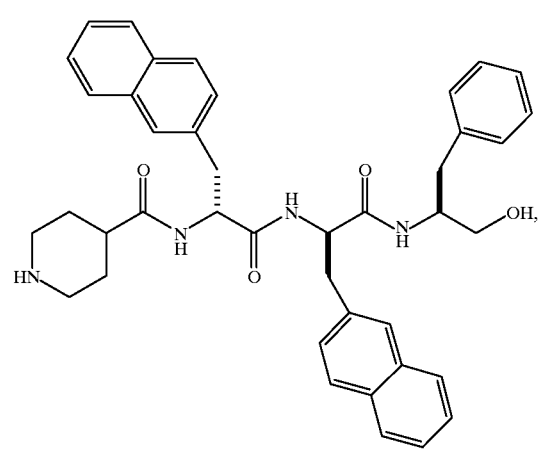
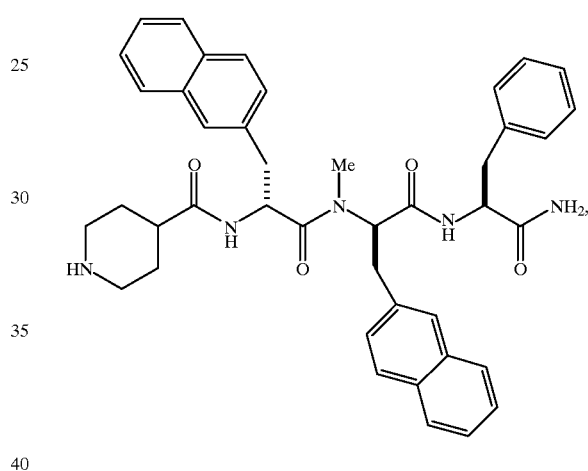
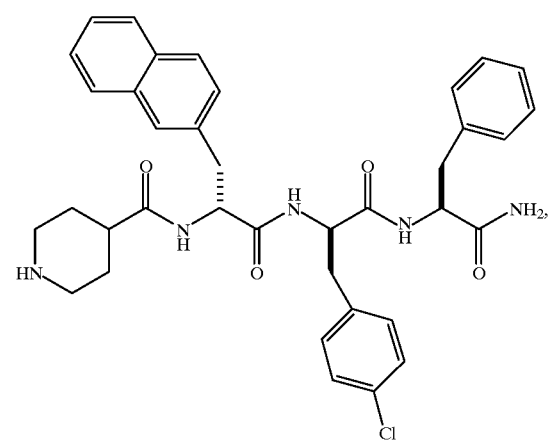
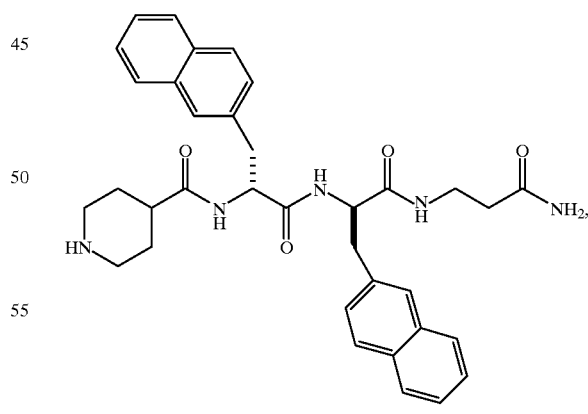

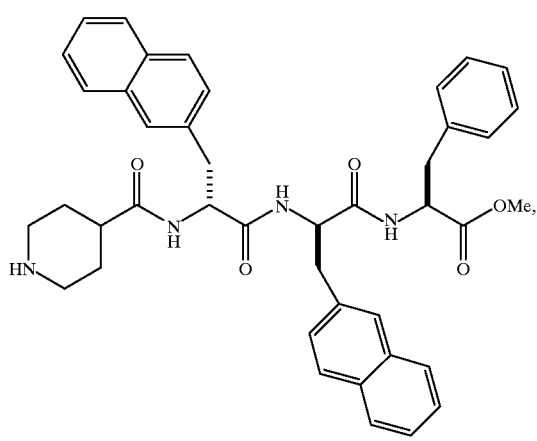
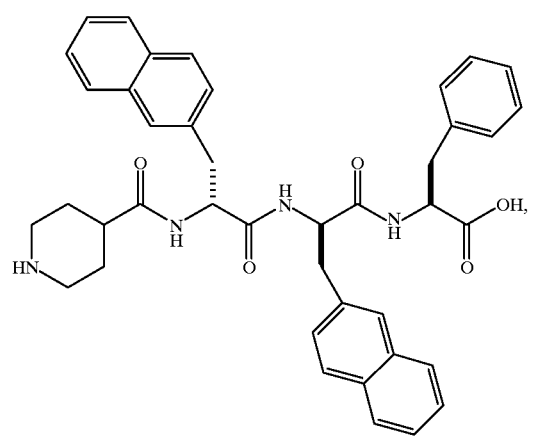
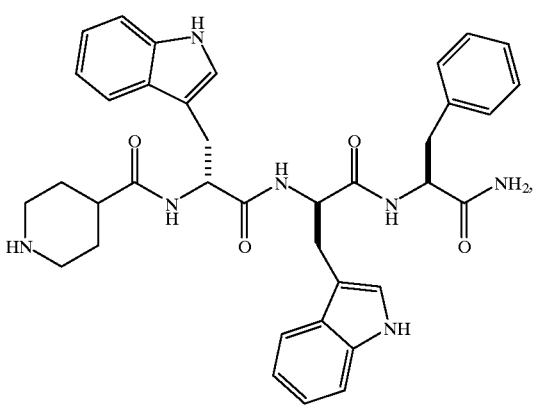
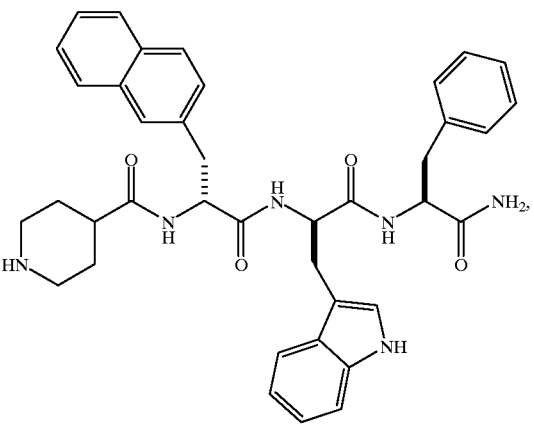
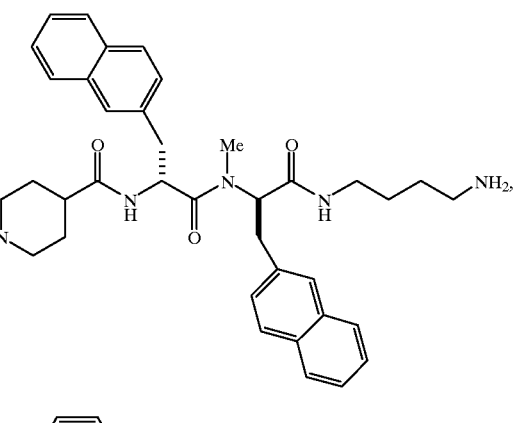
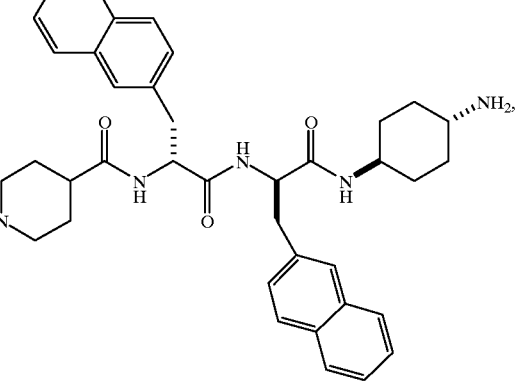
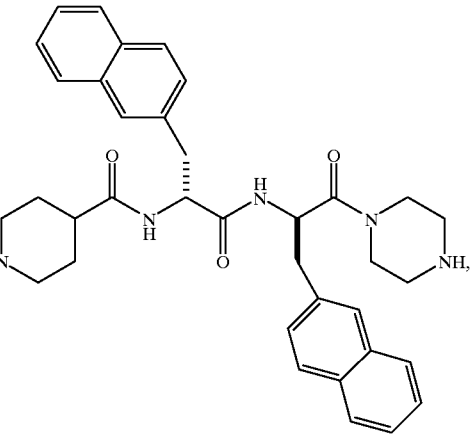

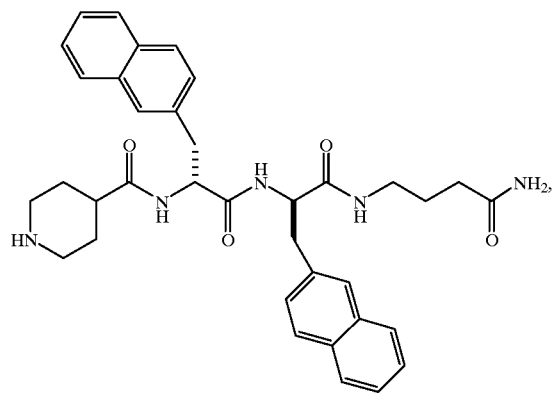
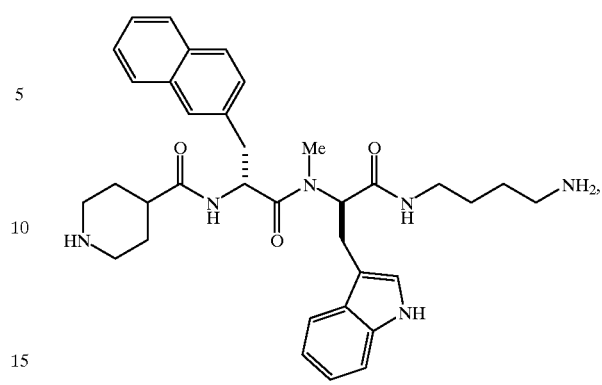
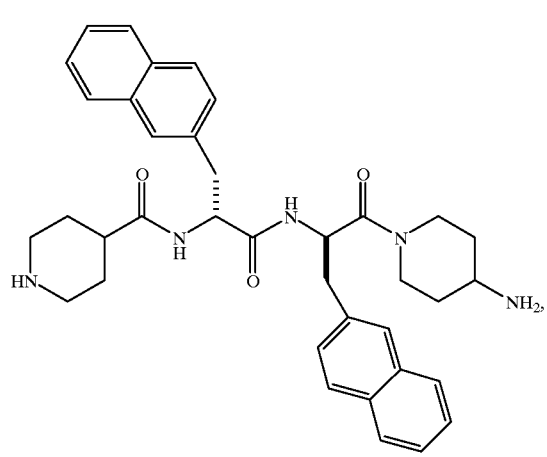
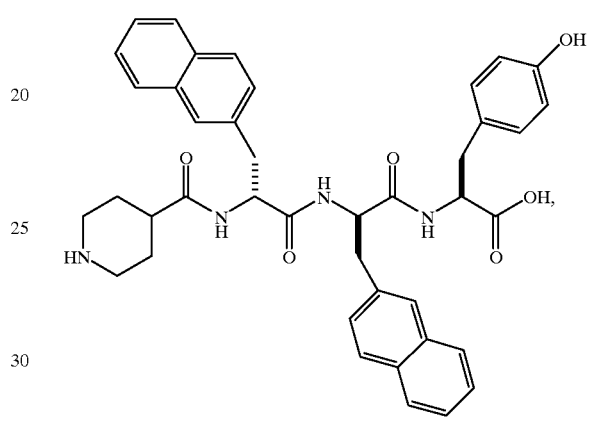
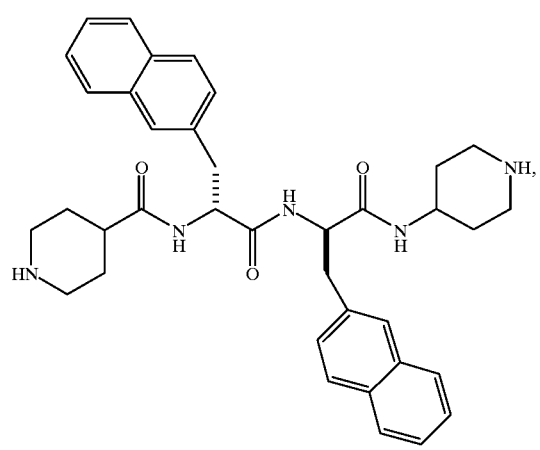
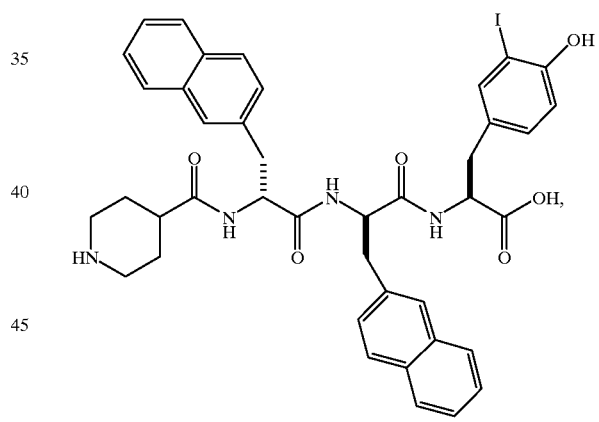
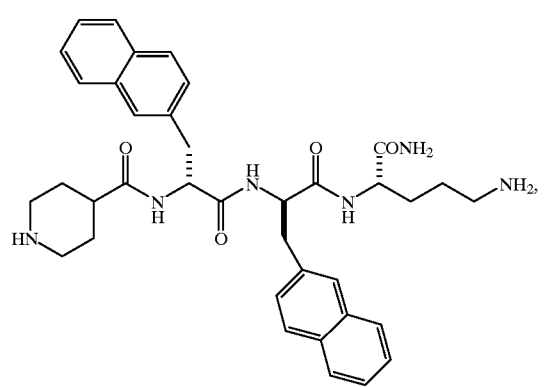
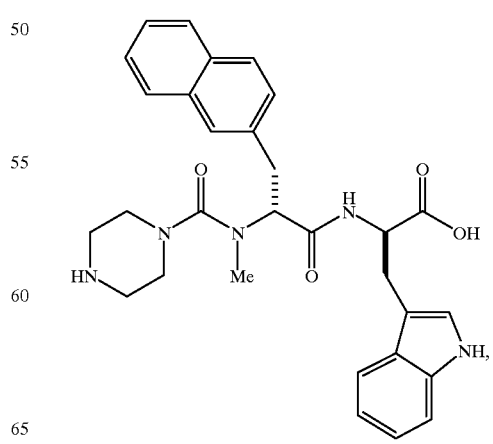

71
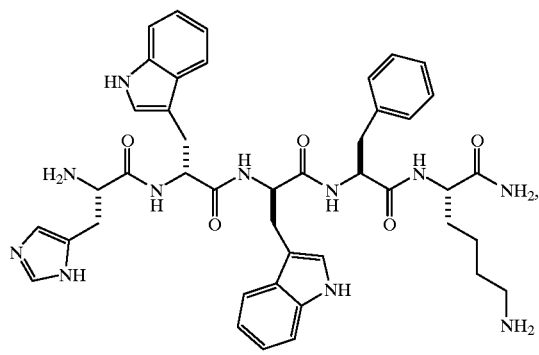
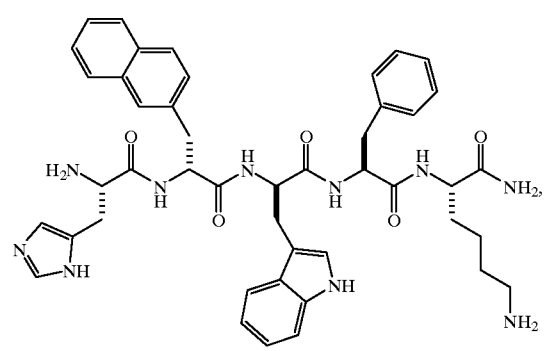
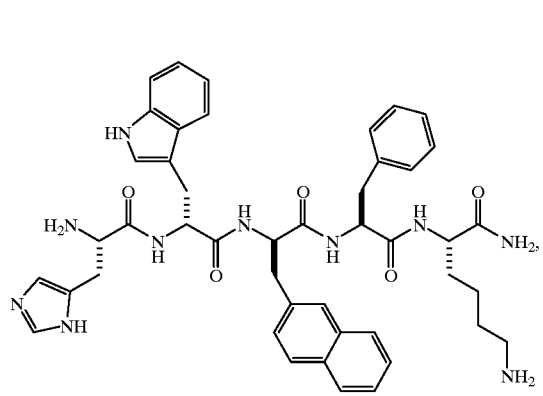
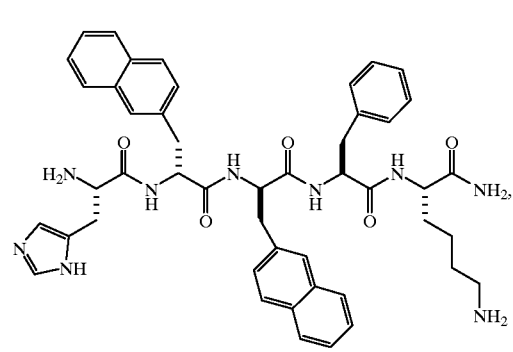
72
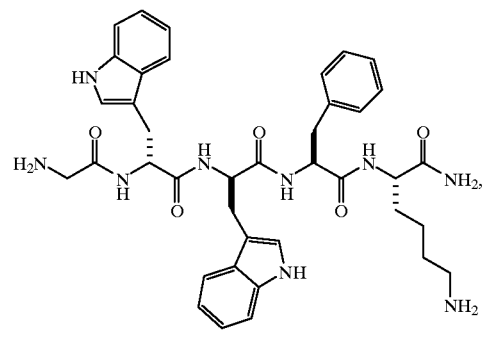
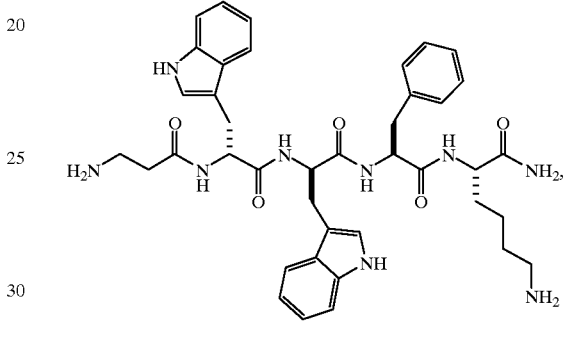
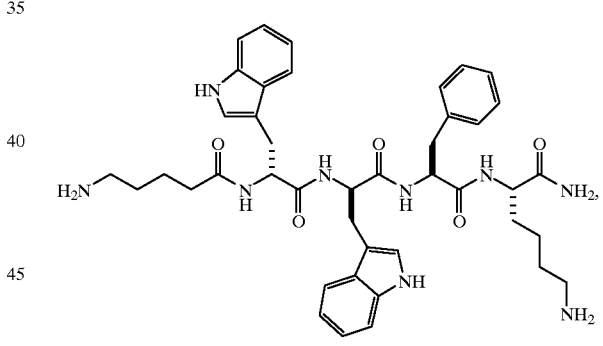
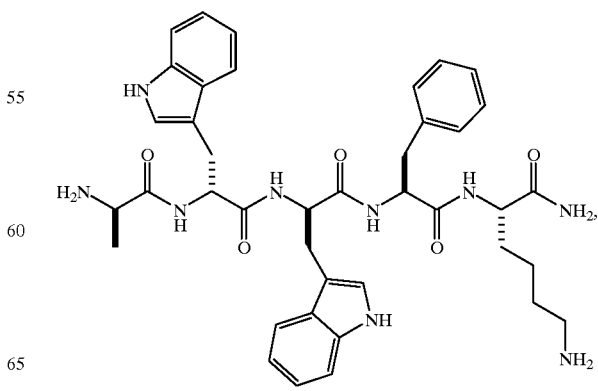

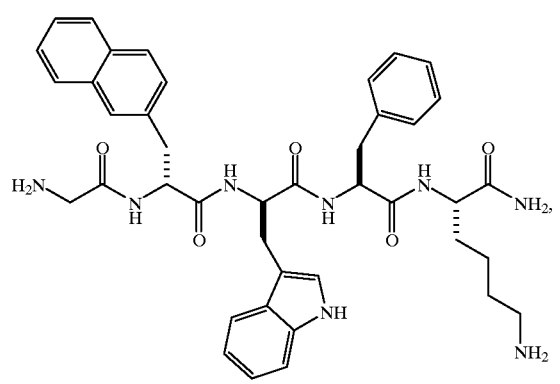
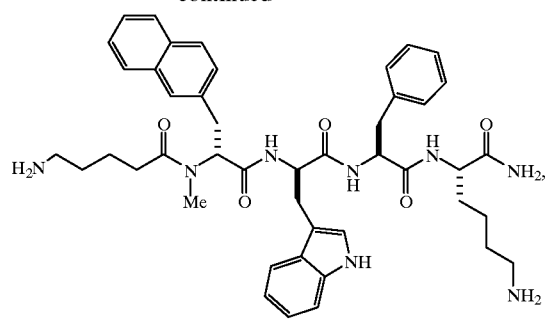
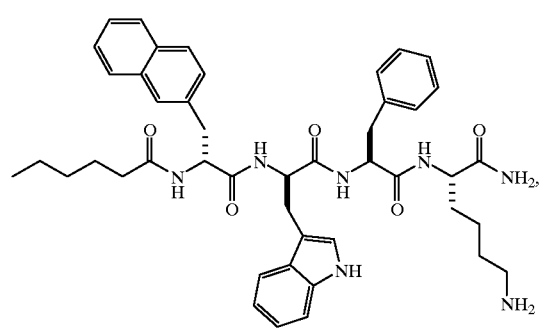
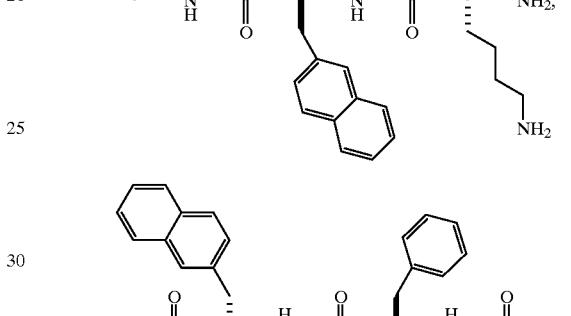
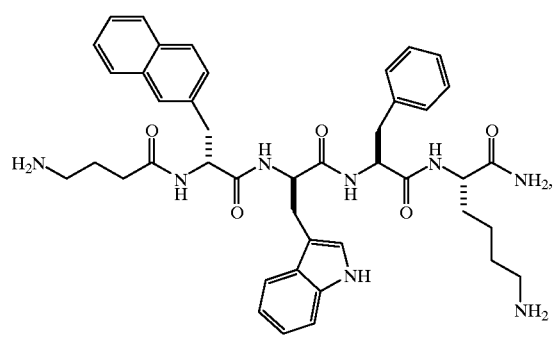
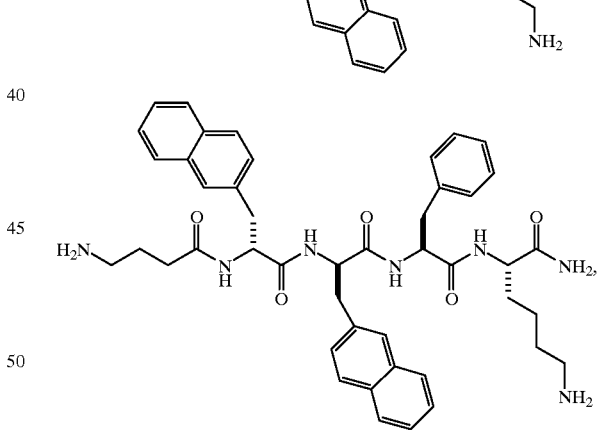
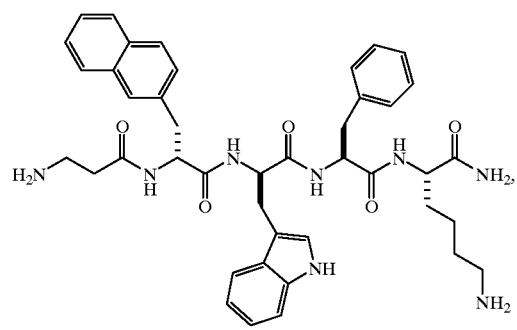
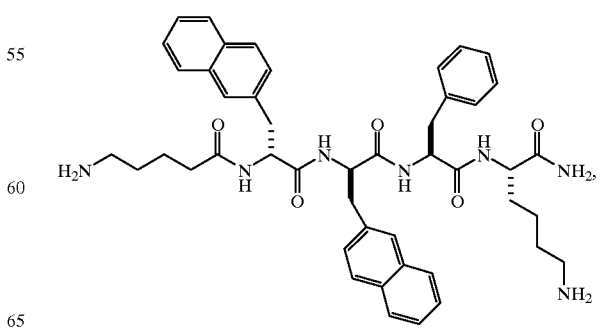

75
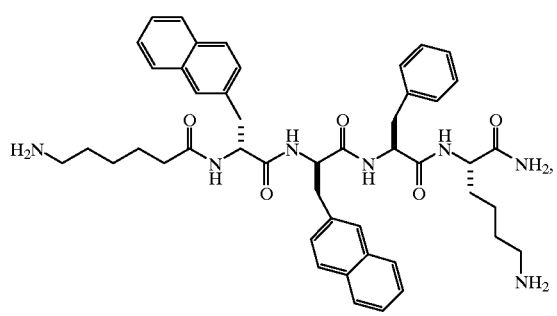
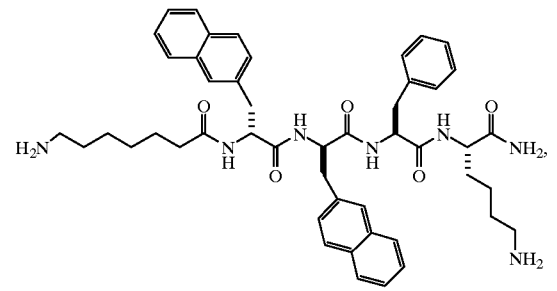
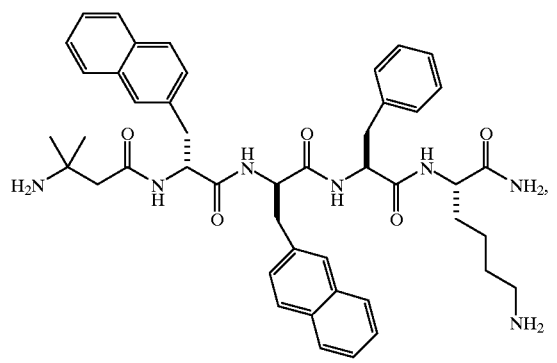
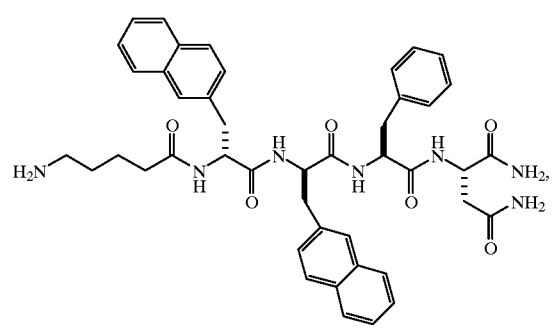
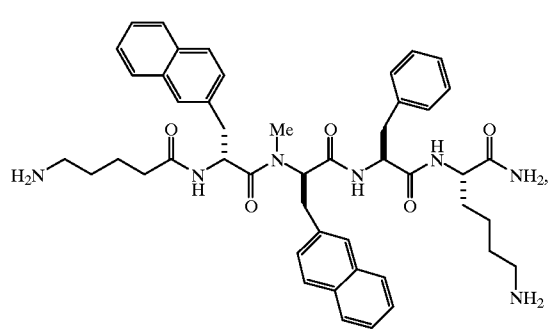
76
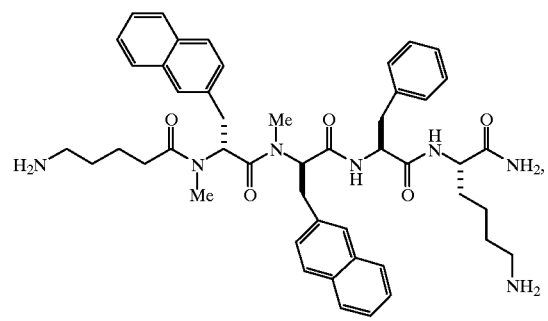
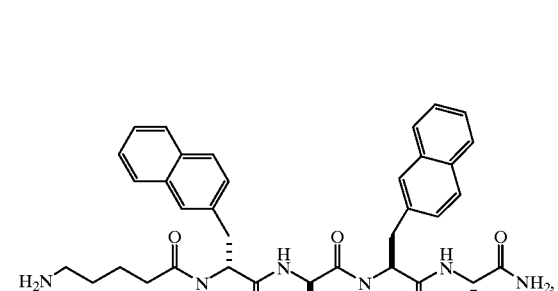
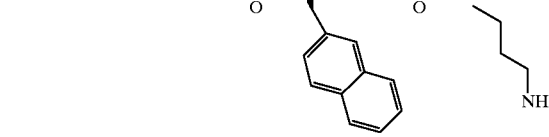
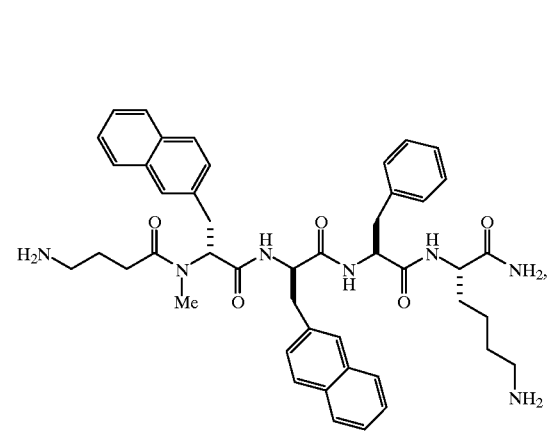
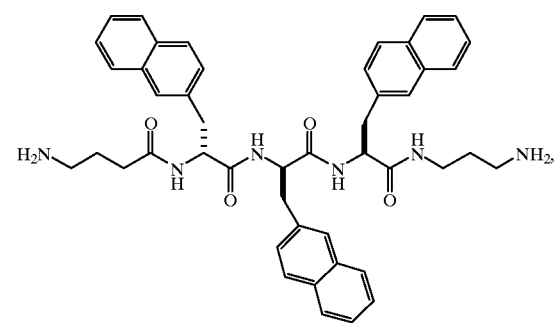

77
-continued
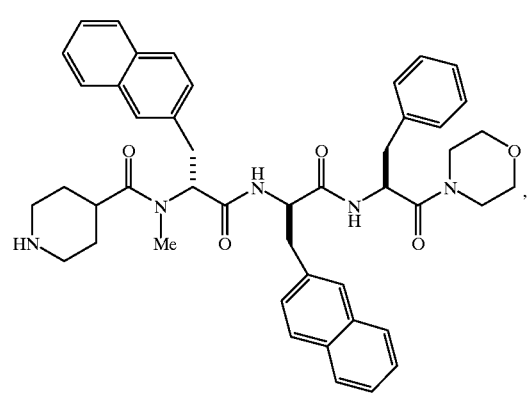
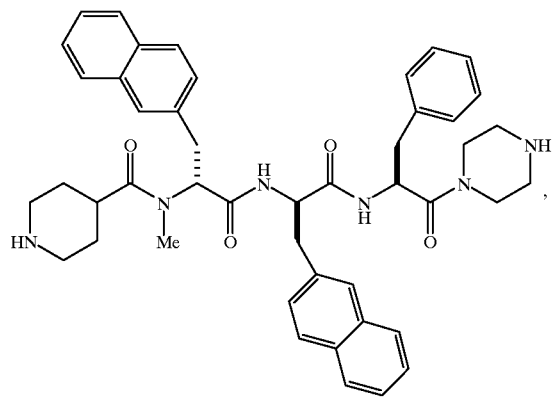
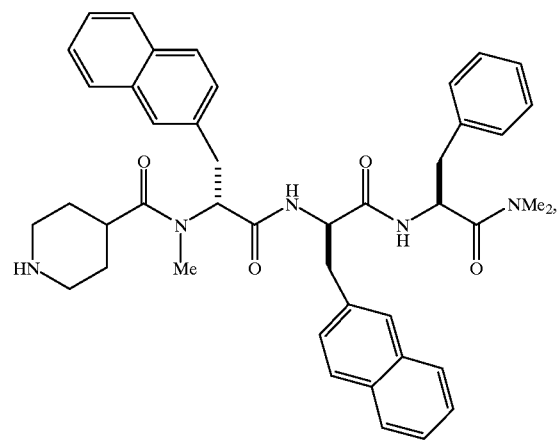
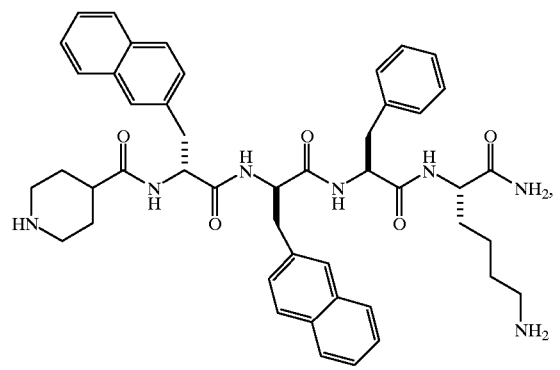
78
-continued
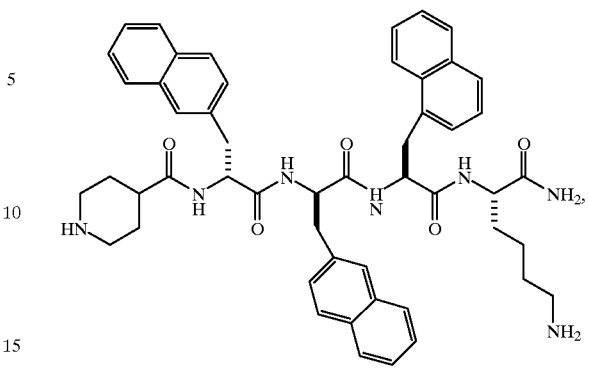
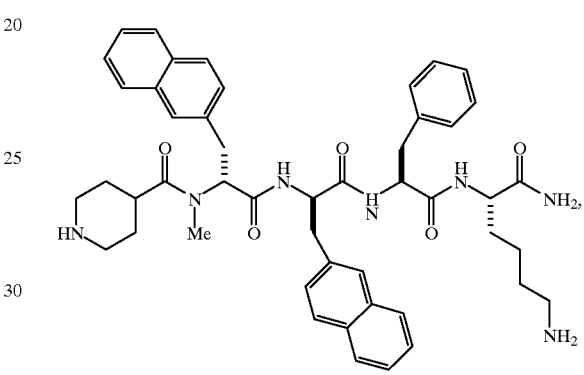
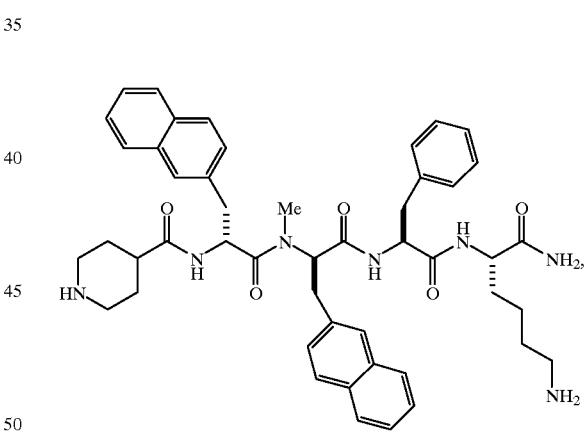
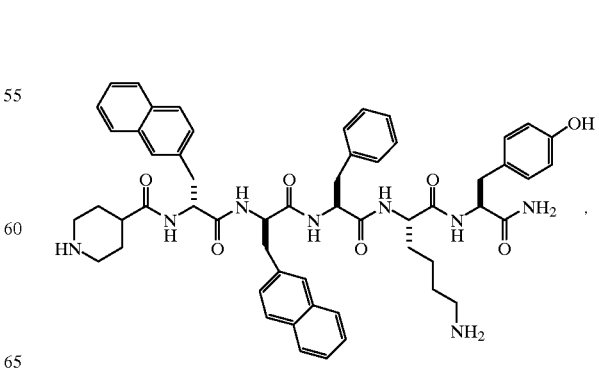

79
-continued
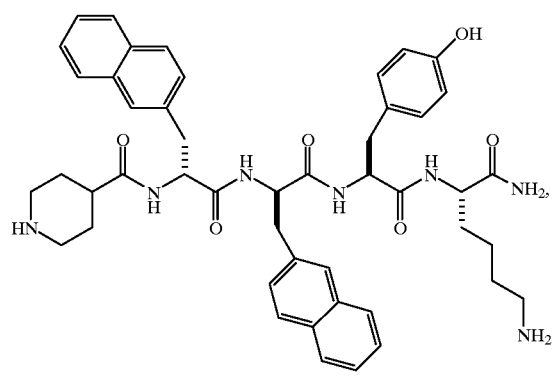
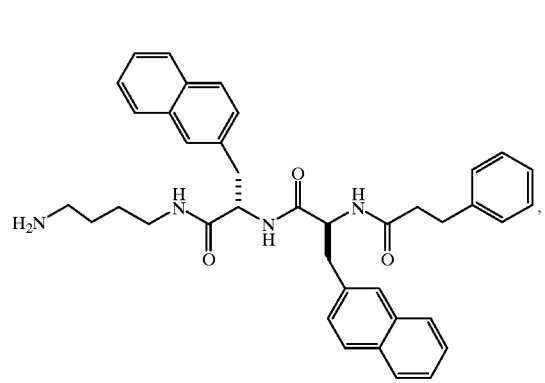
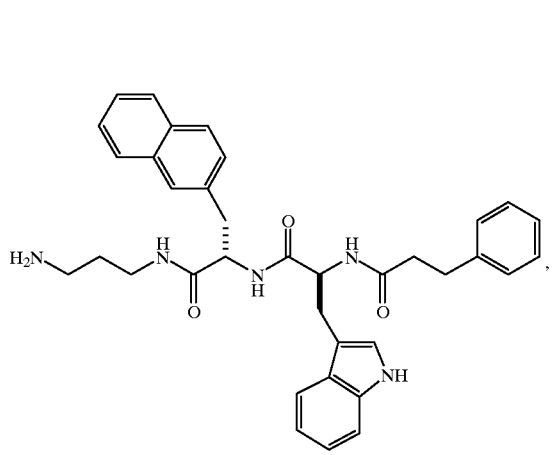
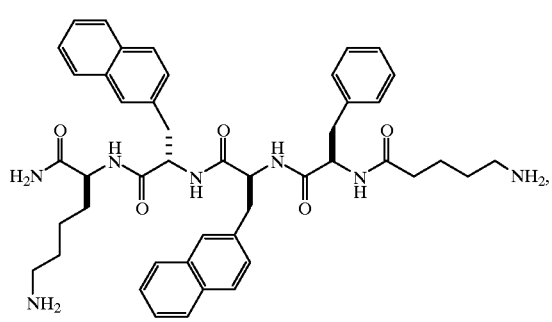
80
-continued
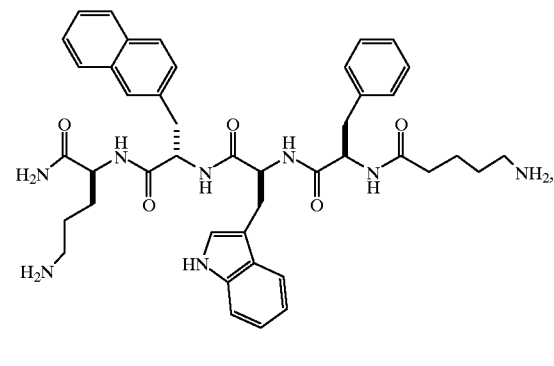
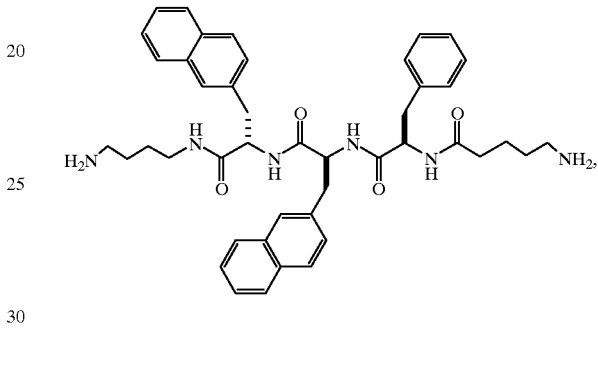
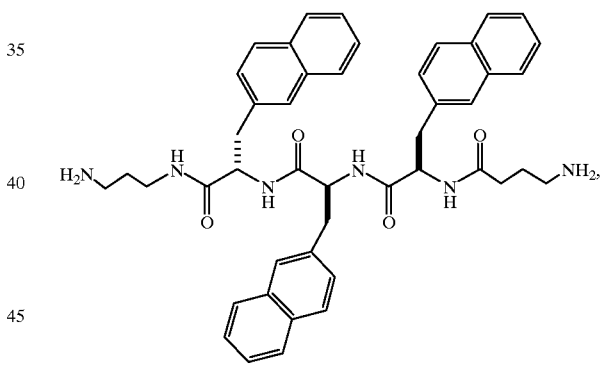
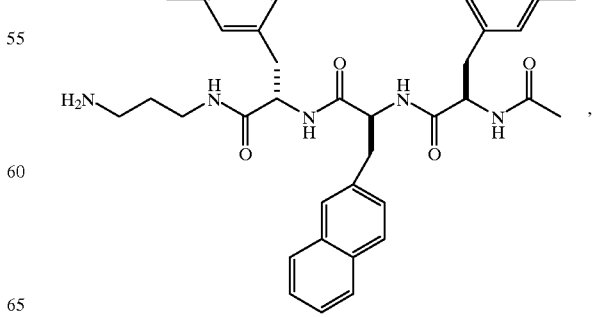

81
-continued
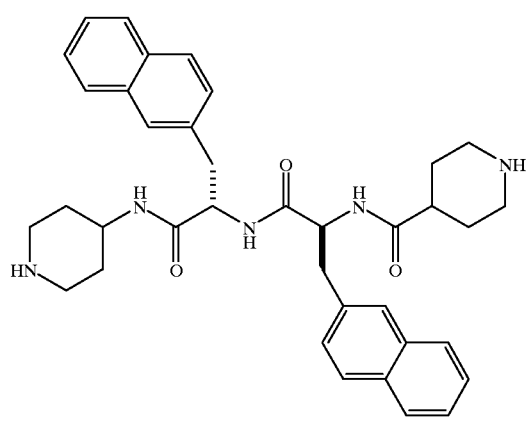
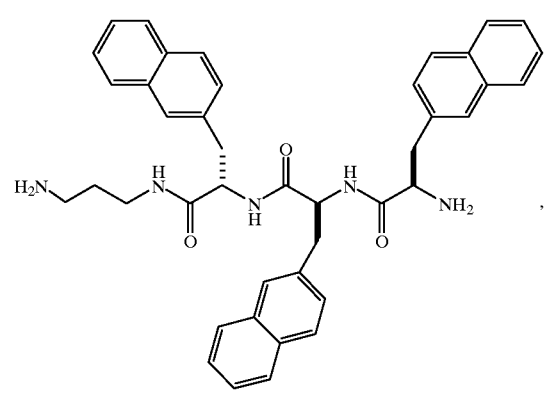
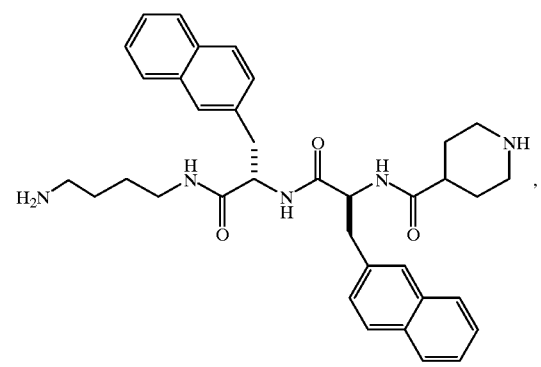
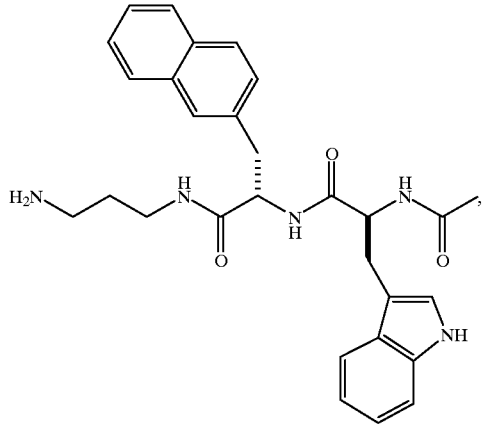
82
-continued
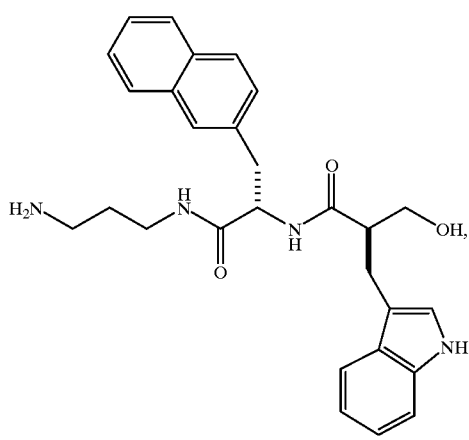
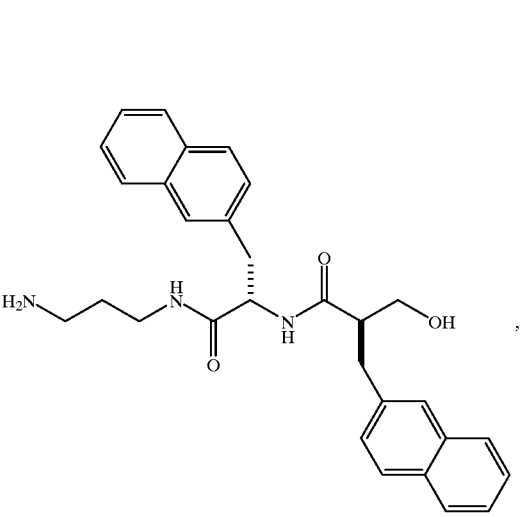
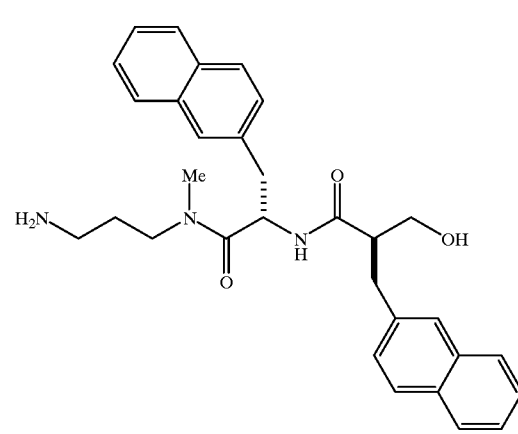

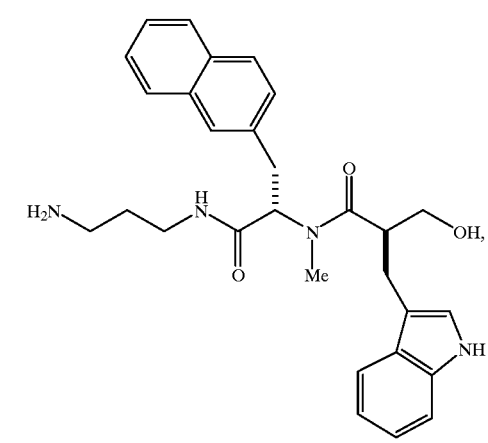
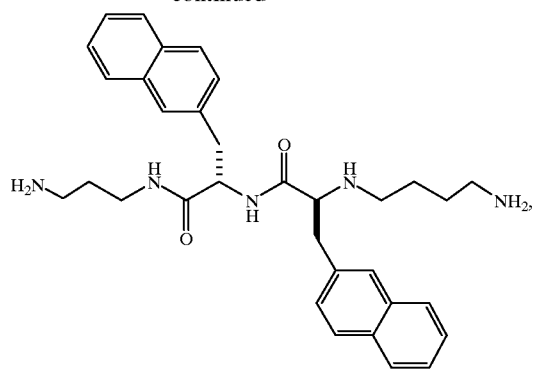
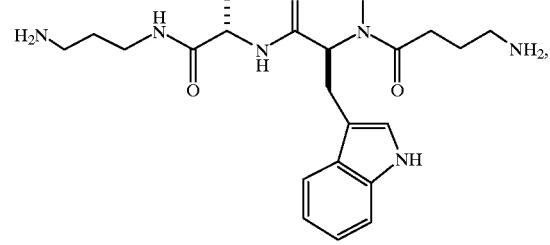
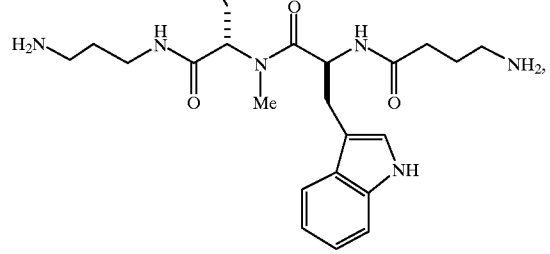
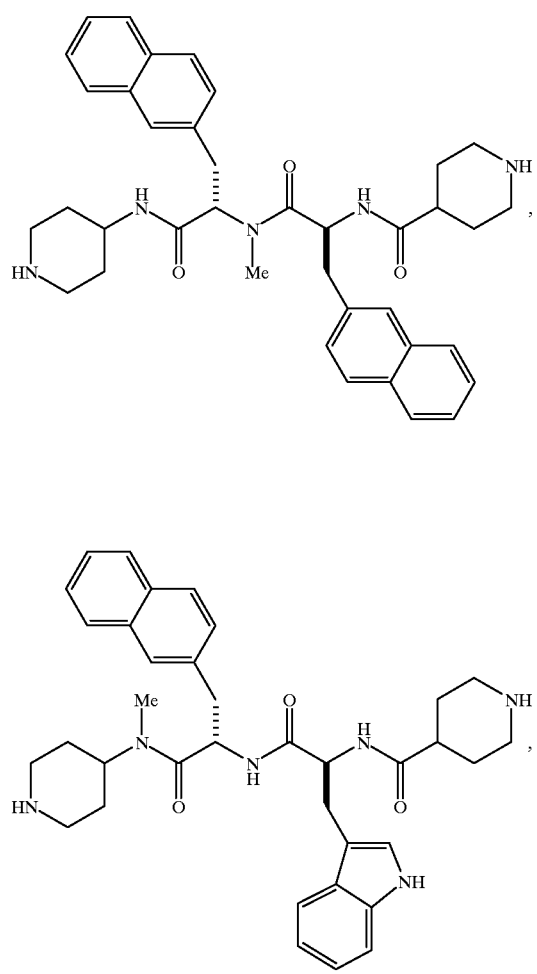
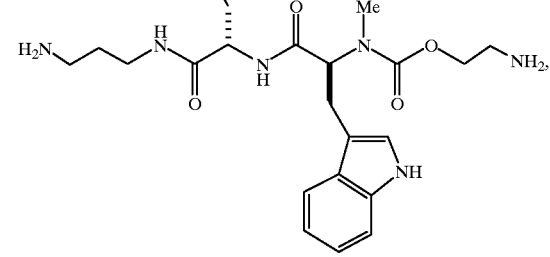

85
-continued
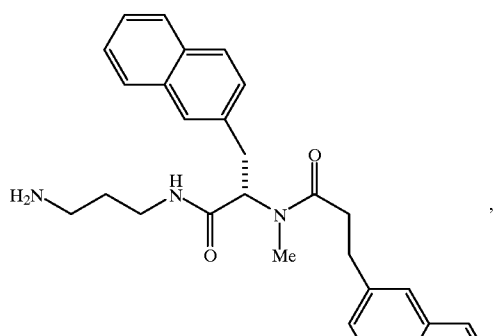
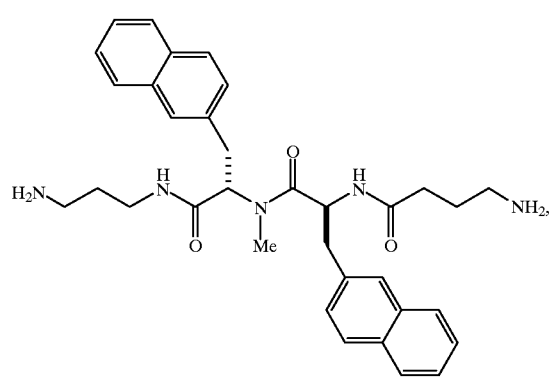
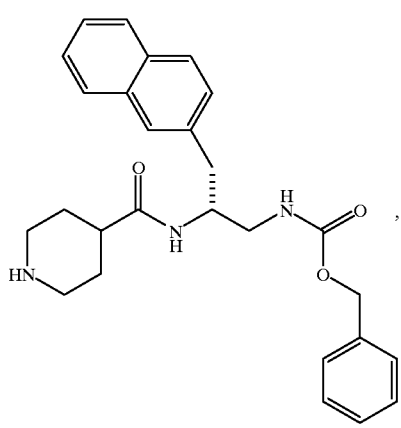
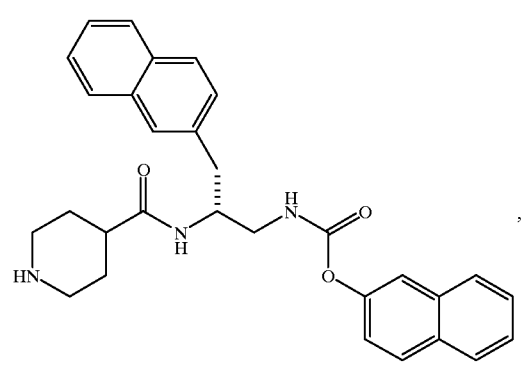
86
-continued
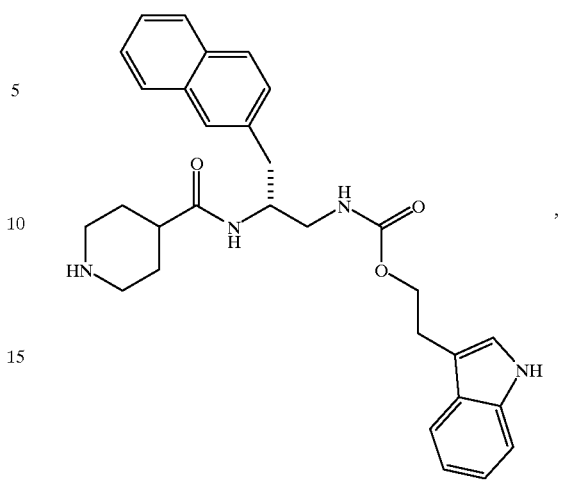
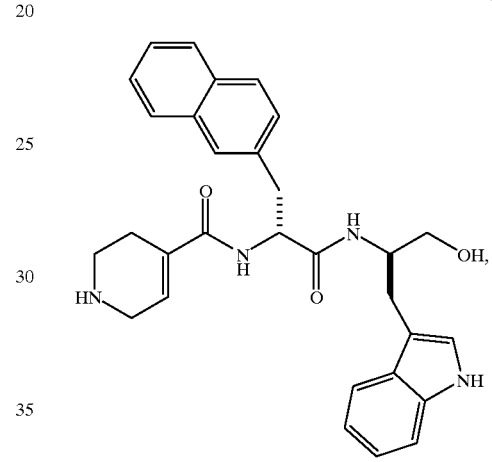
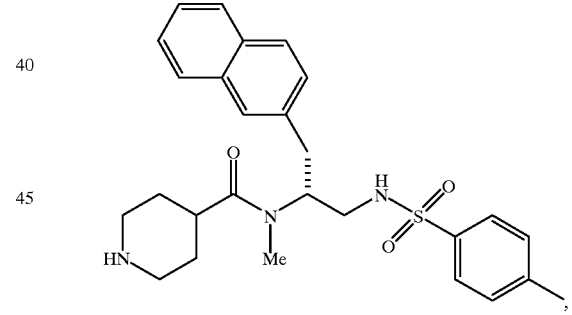
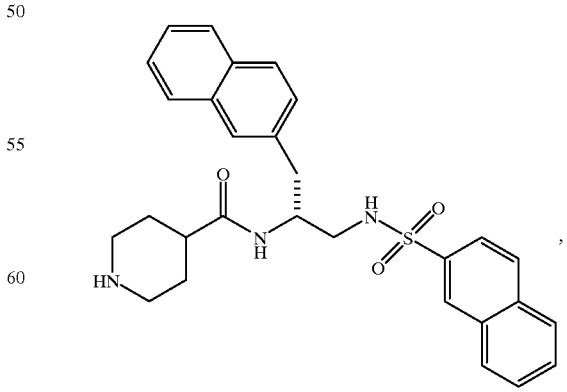

87
-continued
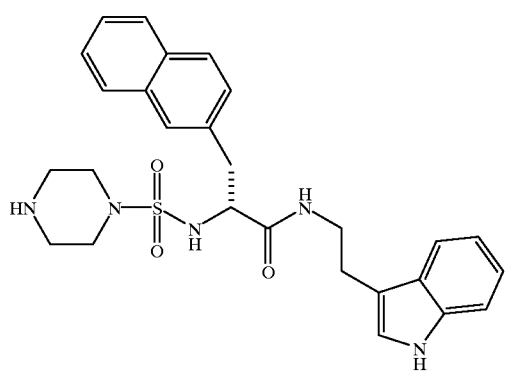,
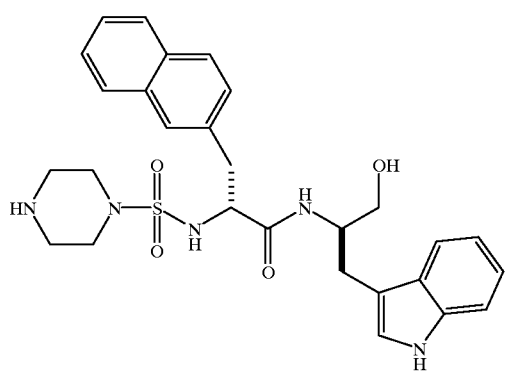,
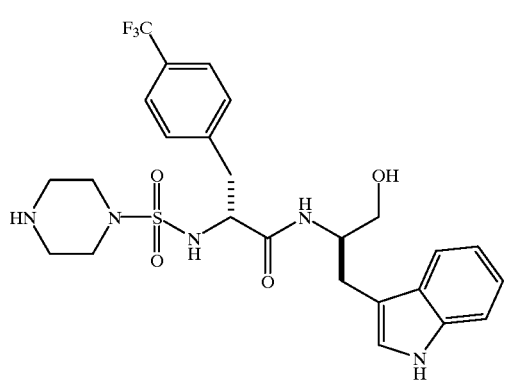,
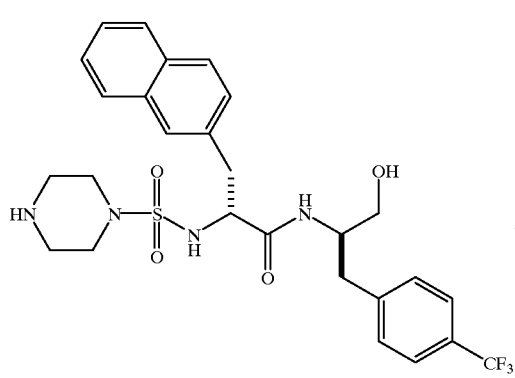,
88
-continued
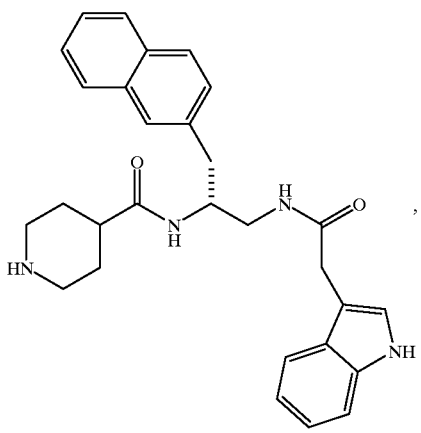,
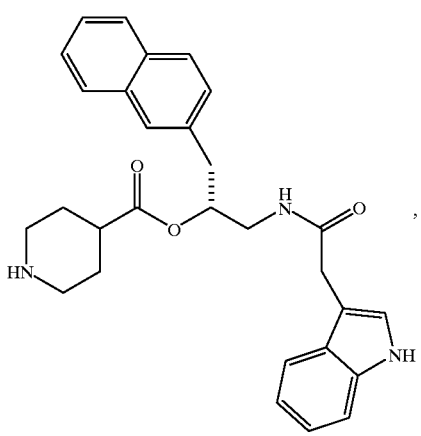,
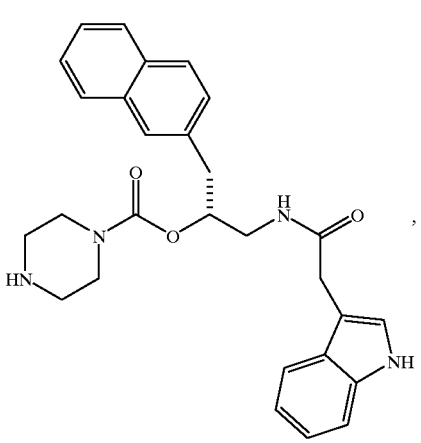, 89
-continued
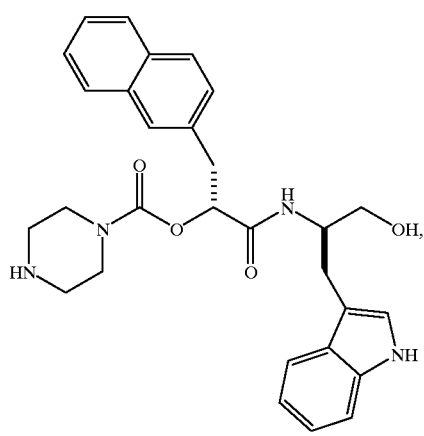
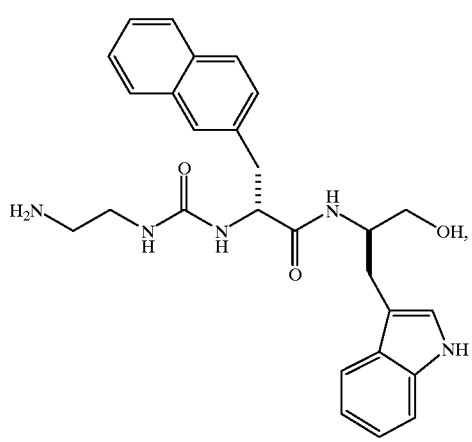
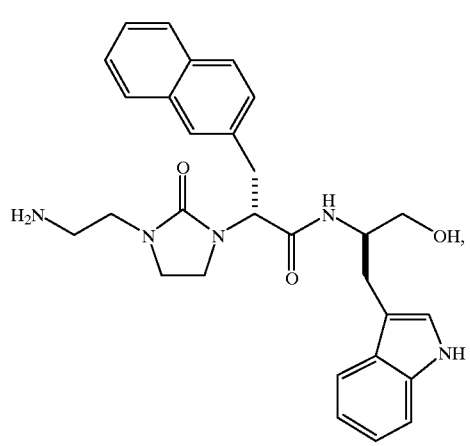
90
-continued
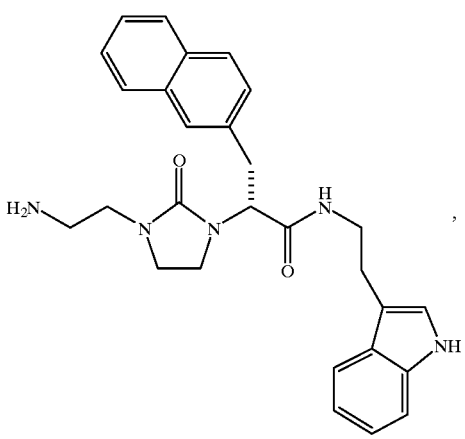
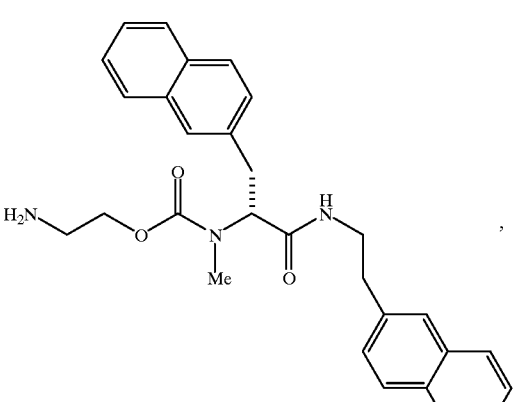

91
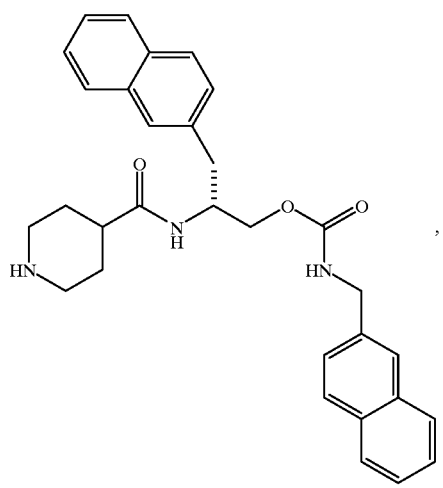
,
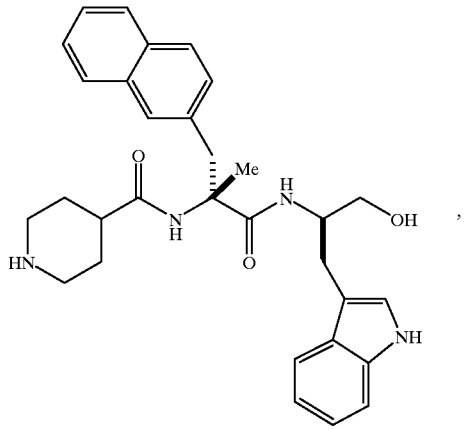
,
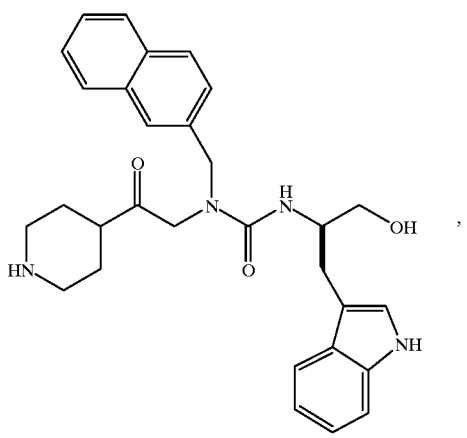
,
92
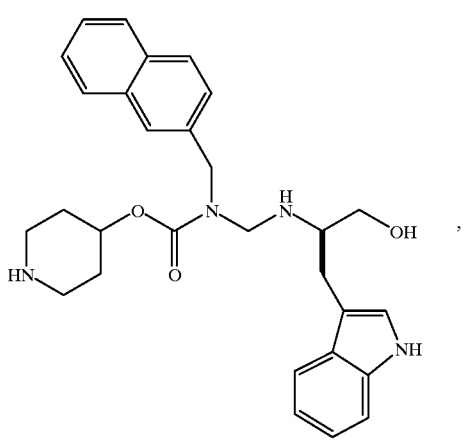
,
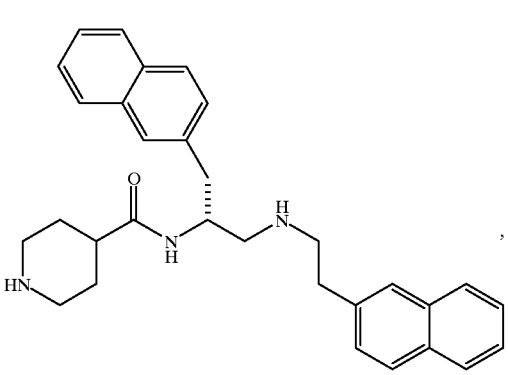
,

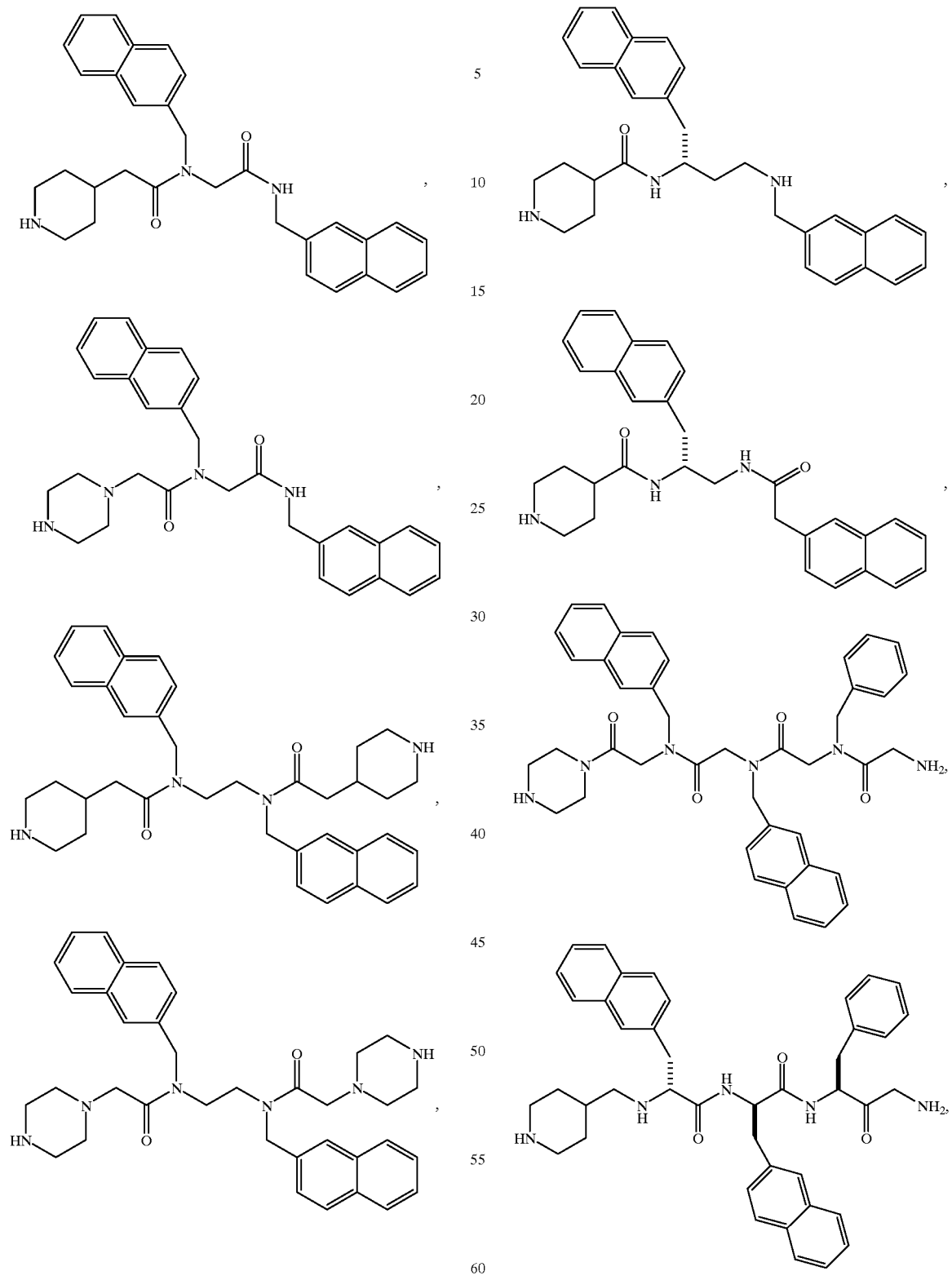

95
-continued
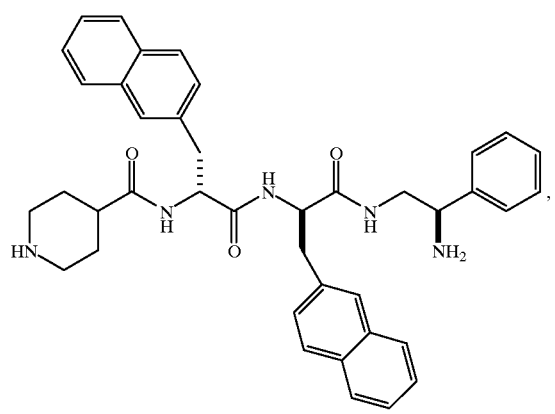
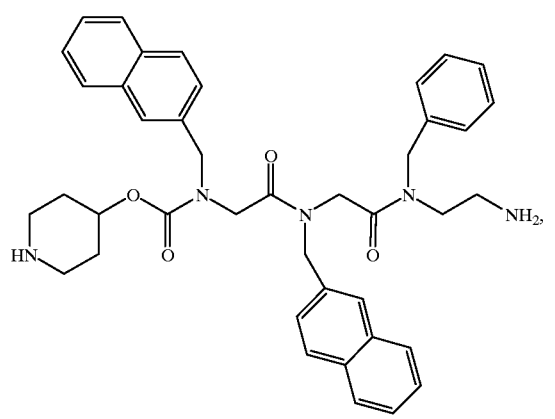
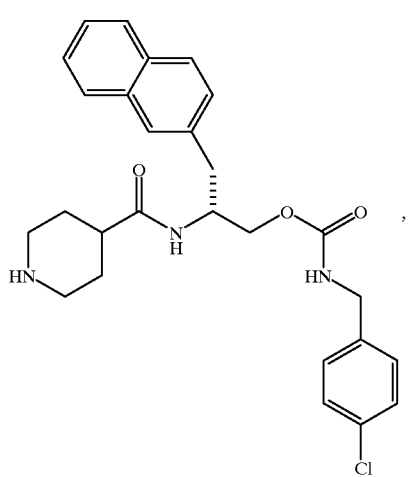
96
-continued
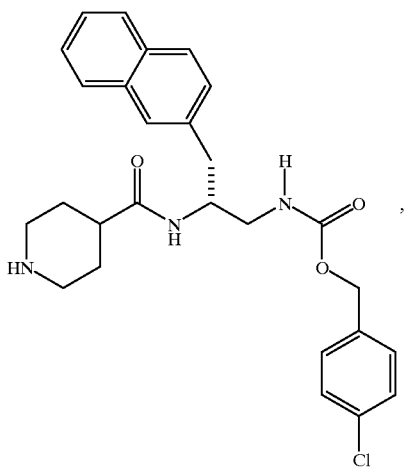
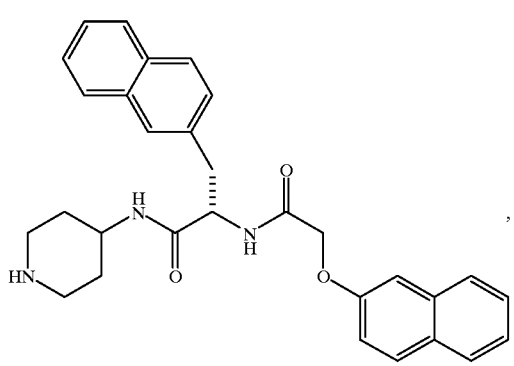
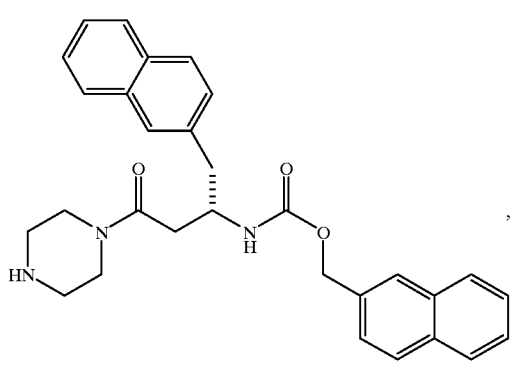
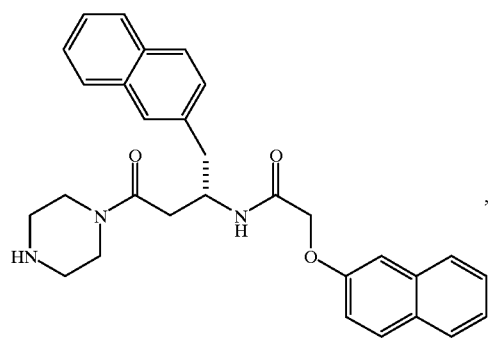

97
-continued
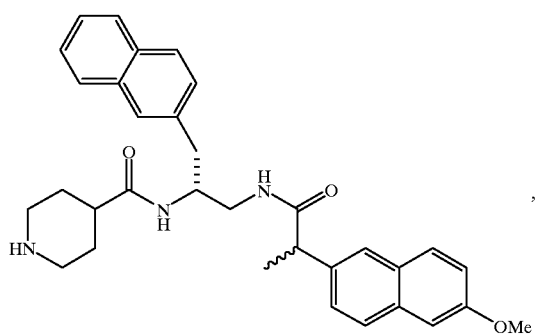,
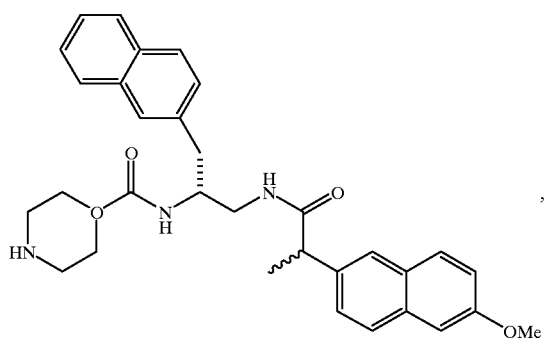,
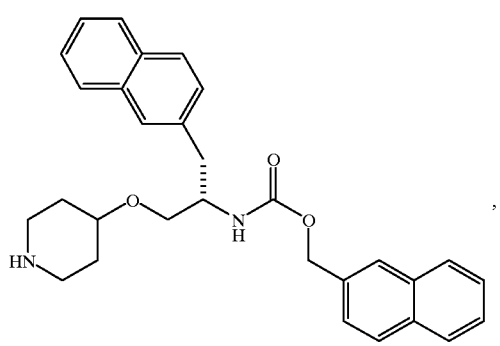,
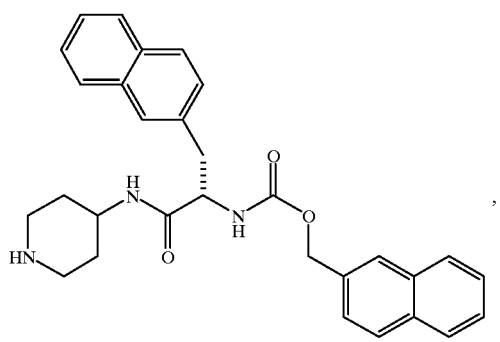,
98
-continued
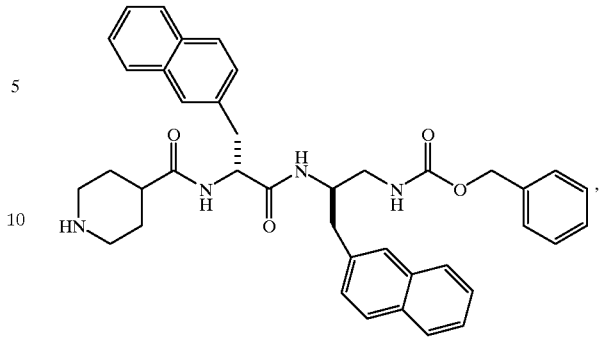,
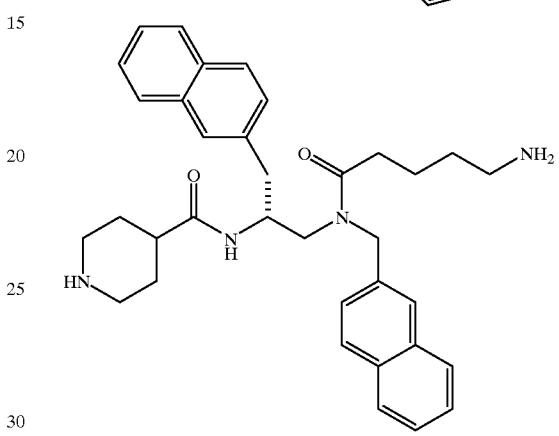,
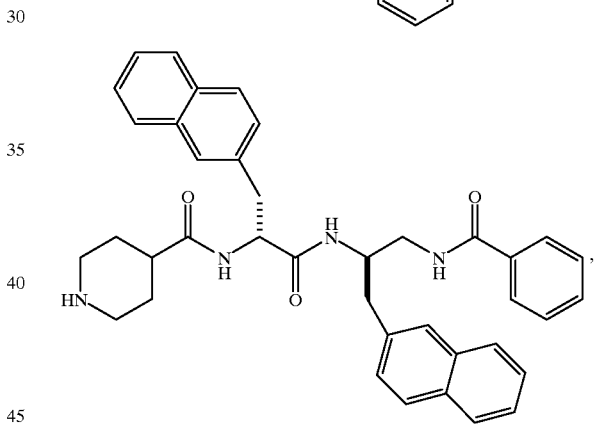,
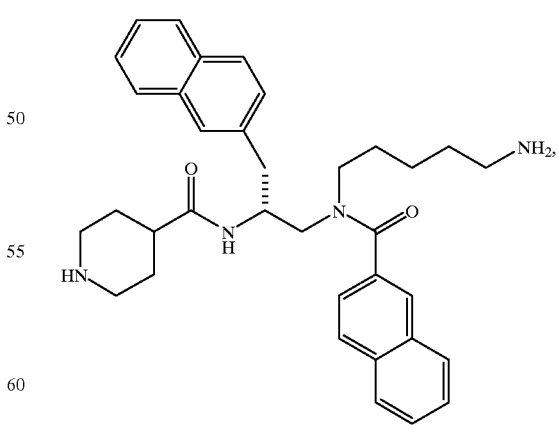,

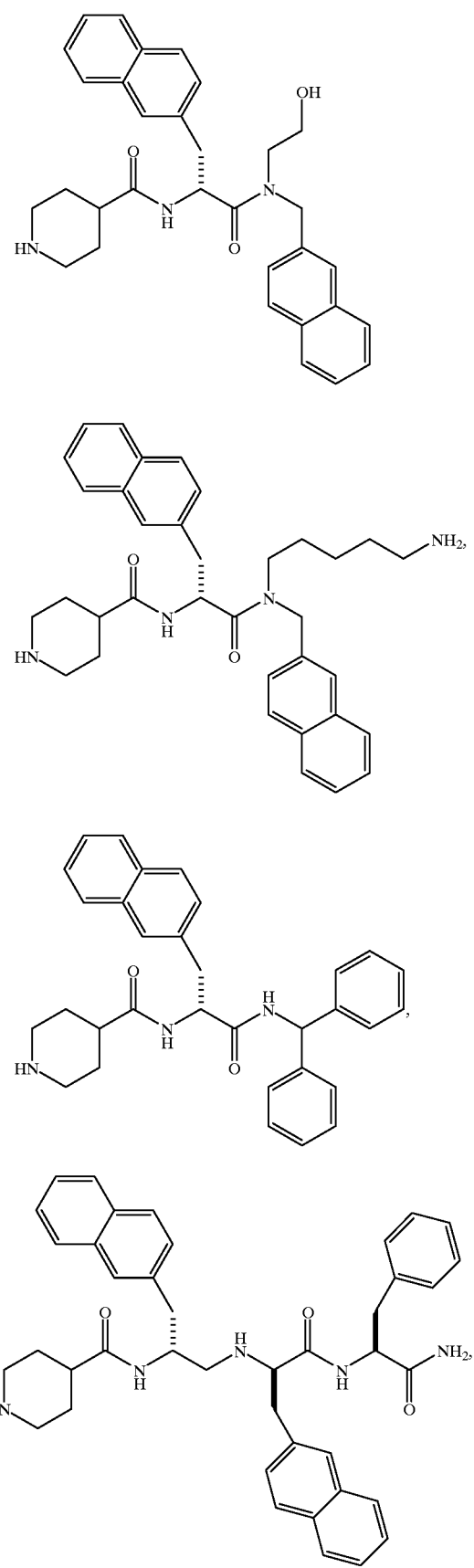
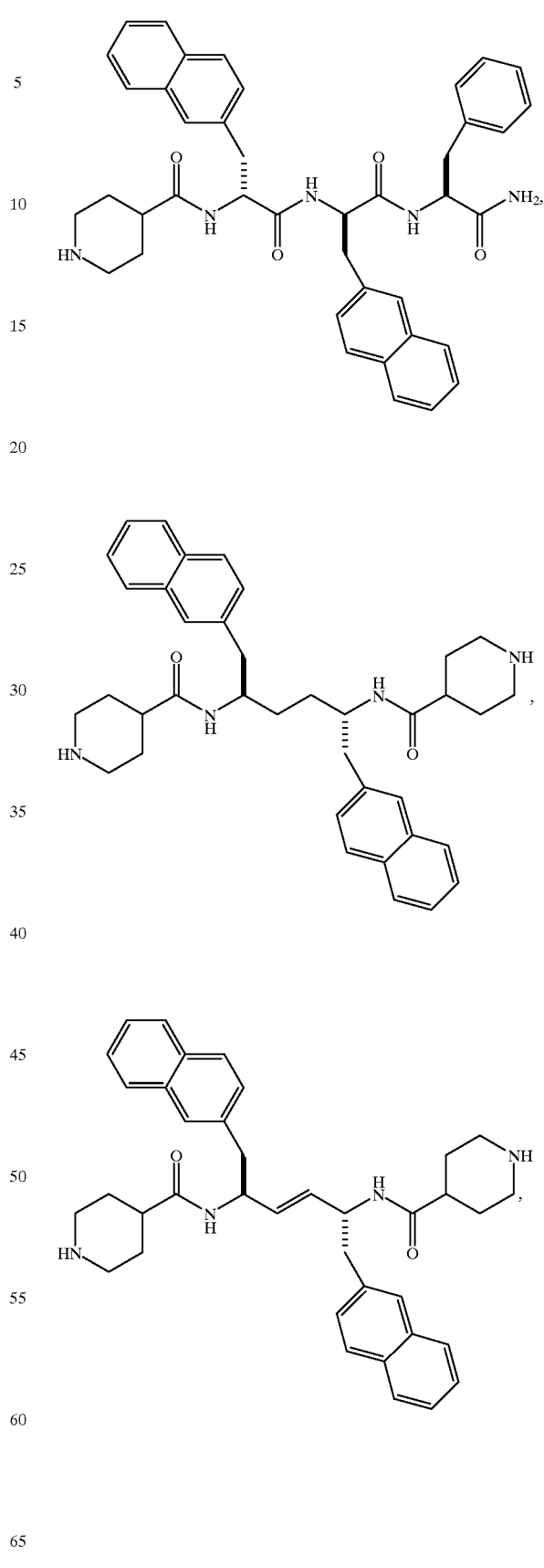

-continued

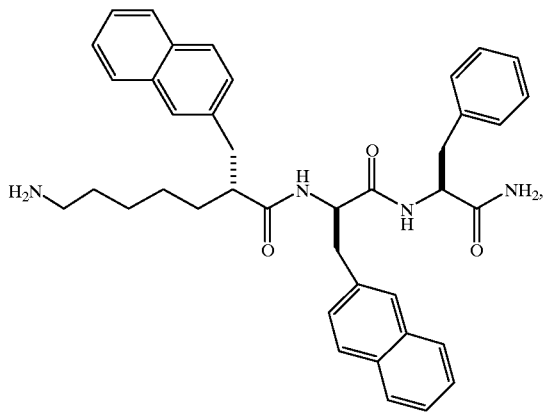

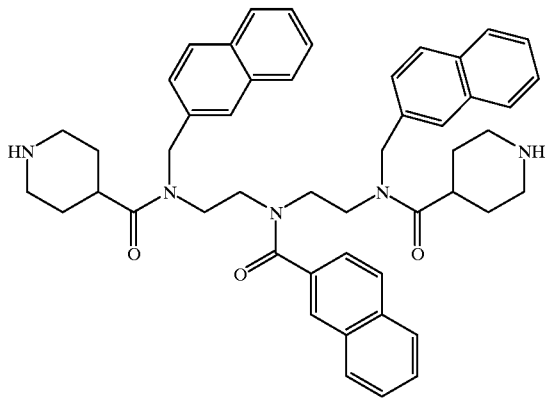

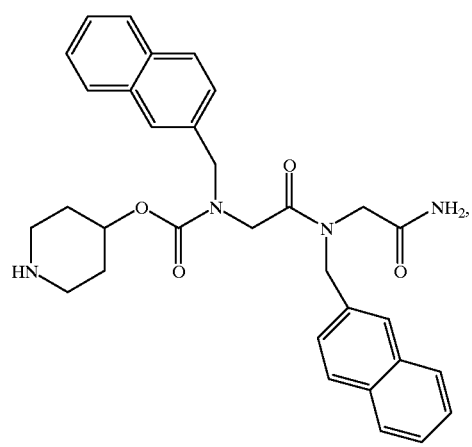

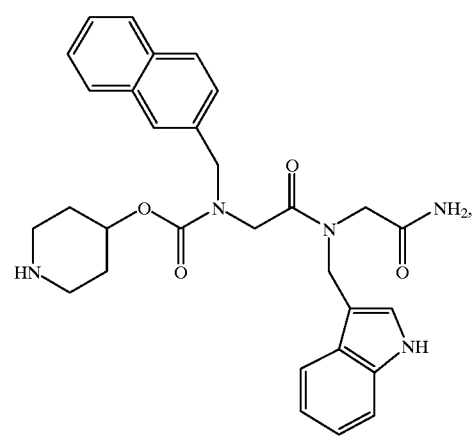

-continued

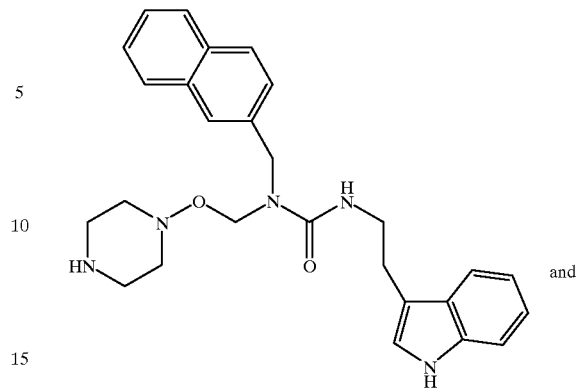

and

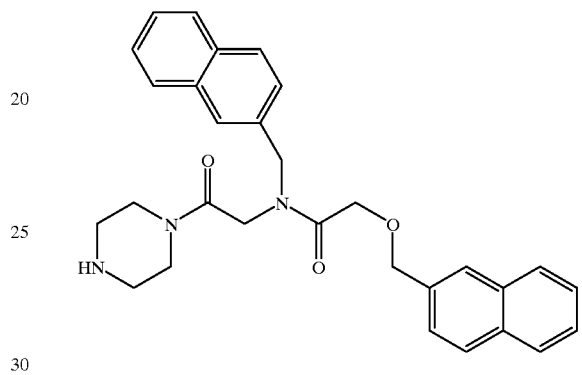

E. Biological Activity

1. In Vitro Activity

A. In Vitro $EC_{50}$

The "pit" $EC_{50}$ values for all GHRPs were determined by the GH dose-response to the GHRP using the rat pituitary monolayer culture system detailed in Example 38. The results are provided in Tables II–VI in Example 39. Table II details selected biological data for prior art compounds including GHRP-6 with a "pit cell" $EC_{50}$ of 6.2±1.5 nM (n=5). Table III details selected biological data from 64 compounds from formula IV. Included in this novel class of compound, which is significantly smaller than GHRP-6, is (inip)-bbFK-NH$_2$ with an $EC_{50}$ of 0.18±0.04, over 30fold more potent than GHRP-6. Table IV details selected biological data from 63 compounds derived from formula III, including (inip)bb(feg) with an $EC_{50}$ of 0.25±0.19 (n=3); almost 25-fold more potent than GHRP-6. Table V details selected biological data from 23 compounds from formula II including (inip)b(wol) ($EC_{50}$=10.6±6.2; n=3) with a EC50 roughly equivalent to GHRP-6. Table VI details selected biological data from "retroinverso" compounds including the most potent, (Ab)bBB(ram), with an $EC_{50}$ of 2 nM (n=2).

B. In Vitro Characterization

In addition, representatives from novel classes of GHRP were further characterized in vitro to determine whether these compounds were acting in a manner analogous to "GHRP-6". The representatives include: from formula IV (inip)-bbFK-NH$_2$, from formula III (inip)bb(feg) and from formula II (inip)b(wol). The characterization results are detailed below. All experiments had a minimum of three replicates.

1. Representative from Formula IV

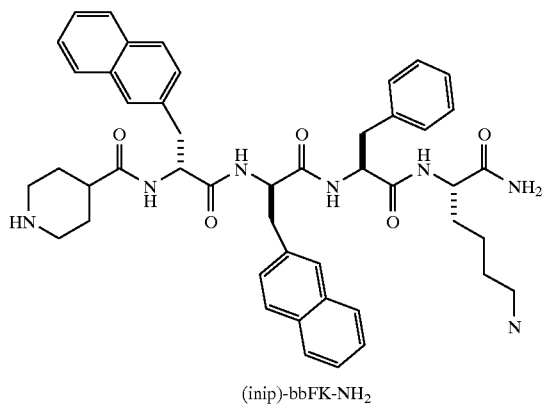

(inip)-bbFK-NH$_2$

A representative dose response for GH release in the rat "pit" cell assay over a 15 min. exposure to increasing concentrations of (inip)-bbFK-NH$_2$ is demonstrated in FIG. 2 (see Example 38 for all assay protocols). GH release is significantly (P<0.05) increased at 0.3 nM and reaches a plateau by 1 nM with an EC$_{50}$ of 0.16 nM. The mean (n=3) EC$_{50}$ for (inip)-bbFK-NH$_2$ was 0.18±0.04 nM, over 30-fold more potent than (GHRP-6) (6.2±1.5 nM; n=5).

Figure 3:
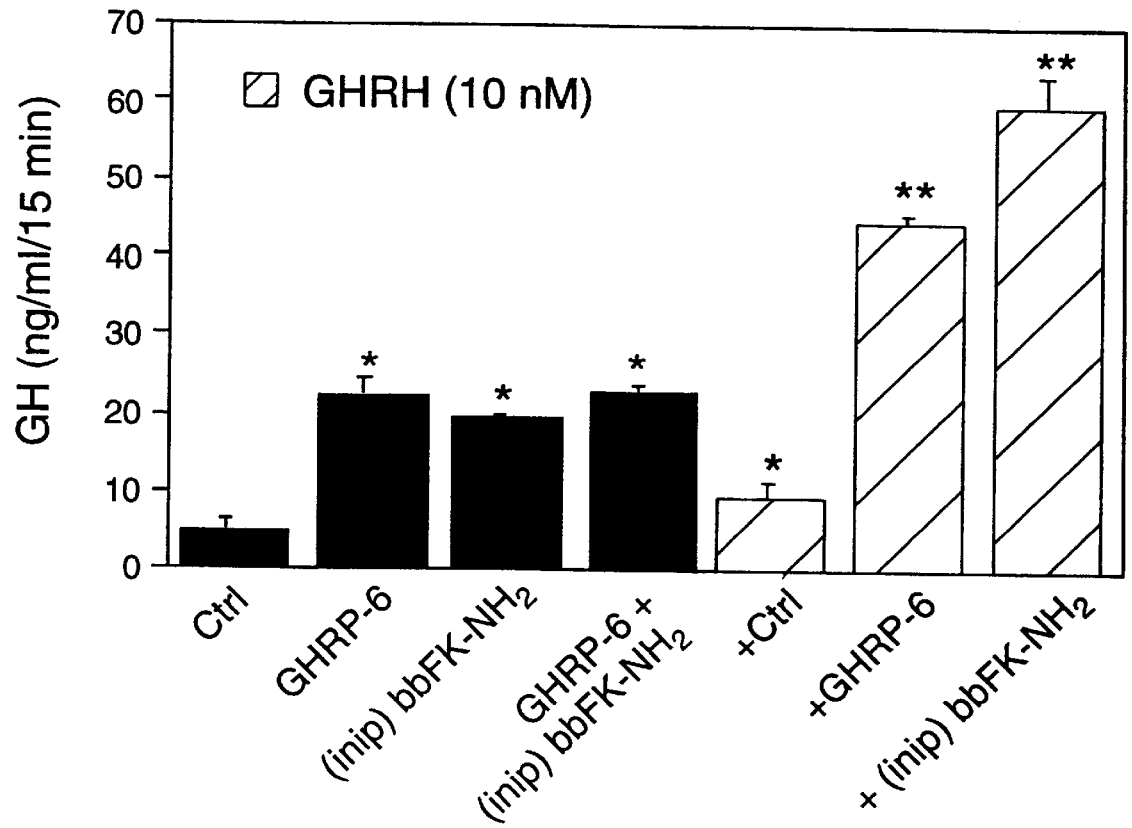
FIG. 3. Demonstration that (inip)-bbFK-NH$_2$ acts at the proposed "GHRP receptor". Rat "pit" cell challenges were carried out using combinations of GHRP-6, (inip)-bbFK-NH$_2$ and GHRH. GHRP-6 and (inip)-bbFK-NH$_2$ (100 nM) both caused 3-fold increases in GH levels over control (ctrl), but no additional or synergistic increase was observed when used in combination (solid black bars). In contrast, both GHRP-6 and (inip)-bbFK-NH$_2$ show synergy with 10 nM GHRH indicating that neither GHRP-6 nor (inip)-bbFK-NH$_2$ act via the GHRH receptor (cross hatched bars).

To demonstrate that the novel (inip)-bbFK-NH$_2$ was acting in a manner analogous to "GHRP-6", challenges were carried out using combinations of (GHRP-6), (inip)-bbFK-NH$_2$ and GHRH (see FIG. 3). GHRP-6 and (inip)-bbFK-NH$_2$ (100 nM) both caused 3-fold increases in GH levels, but no additional increase was observed when these two GHRP's were used in combination. This suggests that both GHRP's may act at the same site. In contrast, both GHRP's showed synergy with GHRH in the rat "pit" cell assay indicating that neither GHRP acts via the GHRH receptor.

Figure 4:
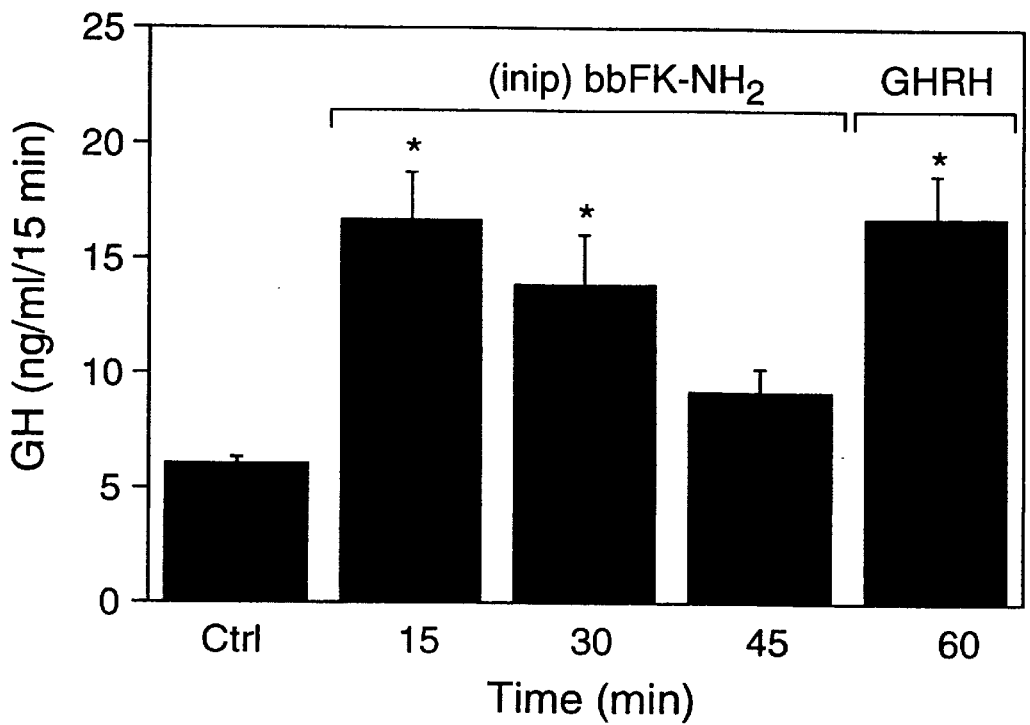
FIG. 4. Desensitization effect of the "GHRP receptor" upon challenging rat pituitary cells with three sequential 15 min. incubations with fresh (inip)-bbFK-NH$_2$. The GH release was decreased after the second 15 min. incubation (total 30 min. exposure to (inip)-bbFK-NH$_2$) and no significant GH release compared to control occurred during the final challenge with (inip)-bbFK-NH$_2$. However when GHRH (10 nM) was added to the next 15 min. incubation, a significant GH response occurred, consistent with the separate receptor model.

A desensitization effect on the putative GHRP receptor was observed when cells were sequentially challenged with fresh (inip)-bbFK-NH$_2$ every 15 min. (FIG. 4). The GH release was decreased after the second 15 min. incubation (total 30 min. exposure to (inip)-bbFK-NH$_2$) and no significant GH release compared to control occurred during the final (inip)-bbFK-NH$_2$ challenge. However when GHRH (10 nM) was added to the next 15 min. incubation, a significant GH response occurred, consistent with the model of separate receptors for GHRH and the GHRP's.

Figure 5:
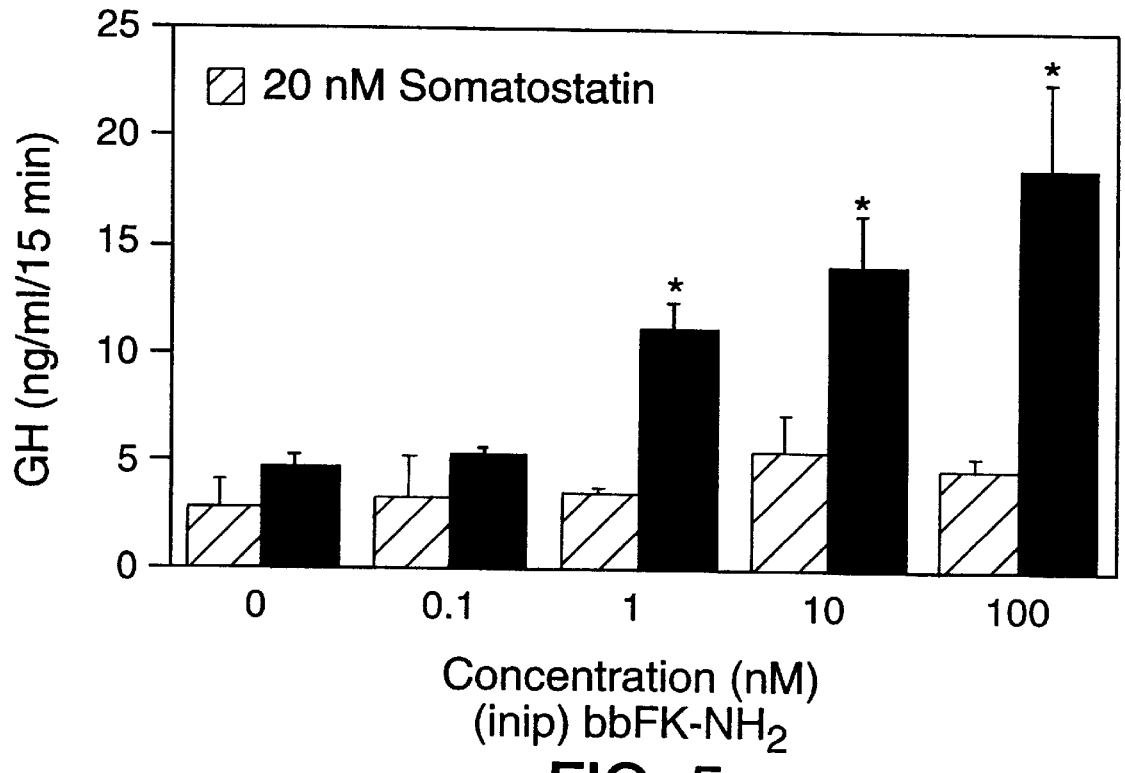
FIG. 5. Somatostatin suppression of GHRP-stimulated GH release. (Inip)-bbFK-NH$_2$ at 0.1, 1, 10 and 100 nM significantly elevates GH release (solid black bars). Coincubation of (inip)-bbFK-NH$_2$ with 20 nM somatostatin suppressed this release (crosshatched bars).

Somatostatin is known to suppress GHRP-stimulated GH release. At 1, 10 and 100 nM (inip)-bbFK-NH$_2$ significant elevations of GH were observed. Somatostatin (20 nM) coincubation with (inip)-bbFK-NH$_2$ at the same concentrations suppressed this enhanced release (FIG. 5).

Figure 6:
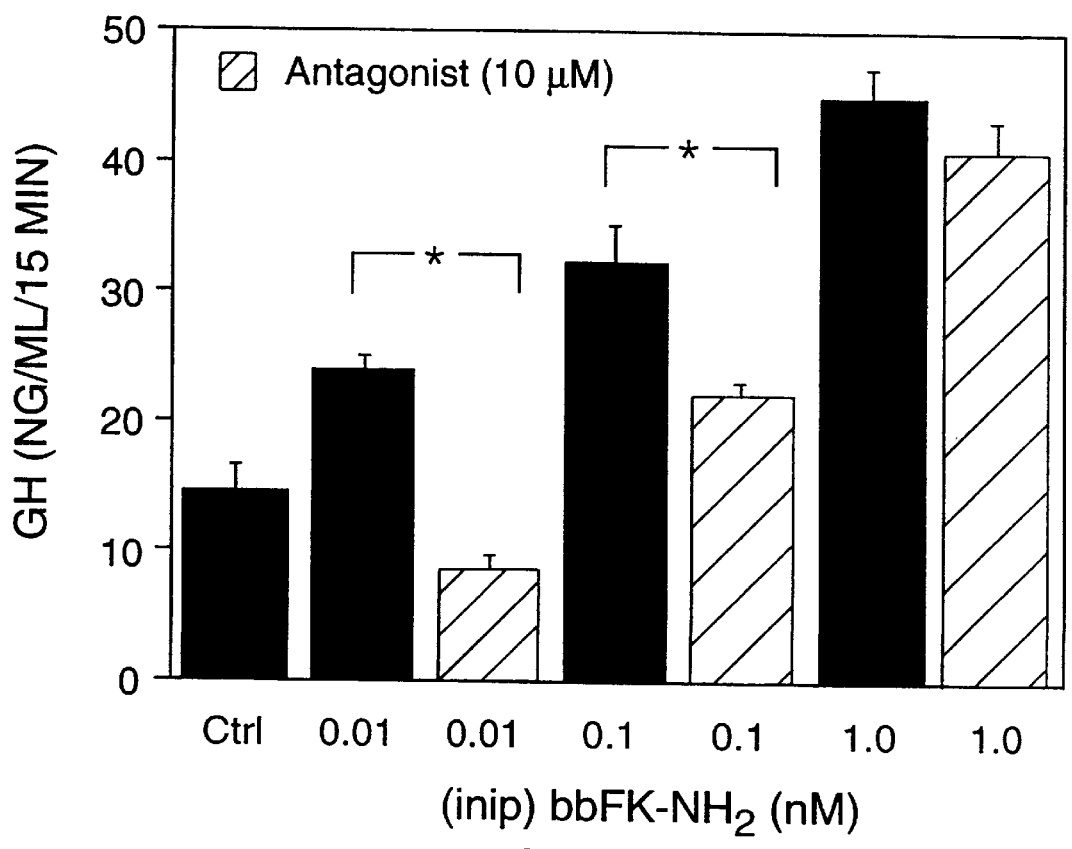
FIG. 6. Antagonism of (inip)-bbFK-NH$_2$ induced GH release in the absence (solid black bars) and presence of 10 μM of the "GHRP-6" antagonist HwkWfK-NH$_2$ (crosshatched bars).

Other evidence that (inip)-bbFK-NH$_2$ evokes the GHRP receptor includes the response to the GHRP receptor antagonist HwkWfK. As demonstrated in FIG. 6, while high doses (10 μM) were required, HwkWfK did antagonize (inip)-bbFK-NH$_2$.

Figure 7:
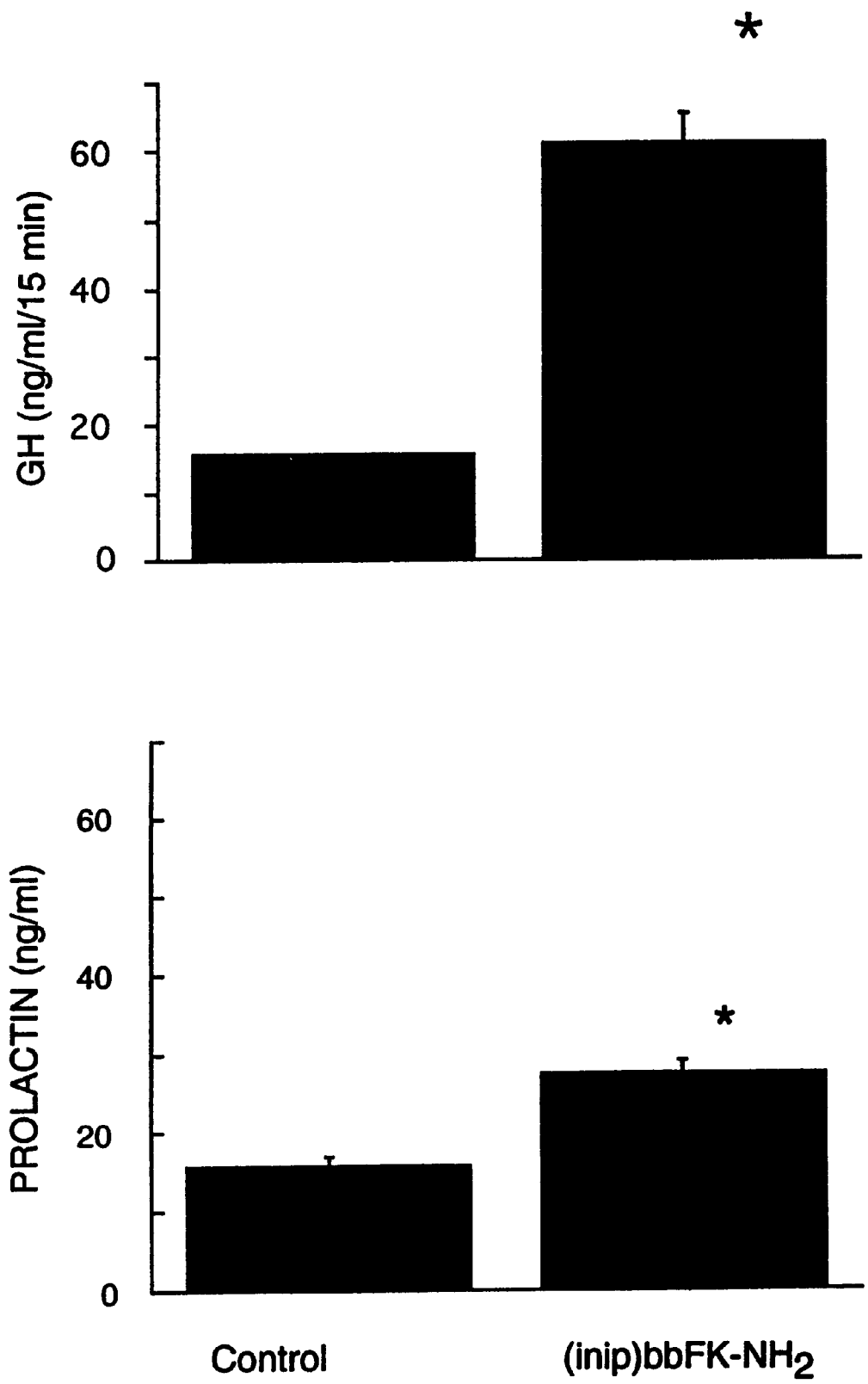
FIG. 7. Specificity for GH release compared to prolactin release induced with (inip)-bbFK-NH$_2$. GH and prolactin levels in the same media from cells challenged with 100 nM (inip)-bbFK-NH$_2$. GH release was 3-fold while prolactin levels increased 1.6 fold.
Figure 8:
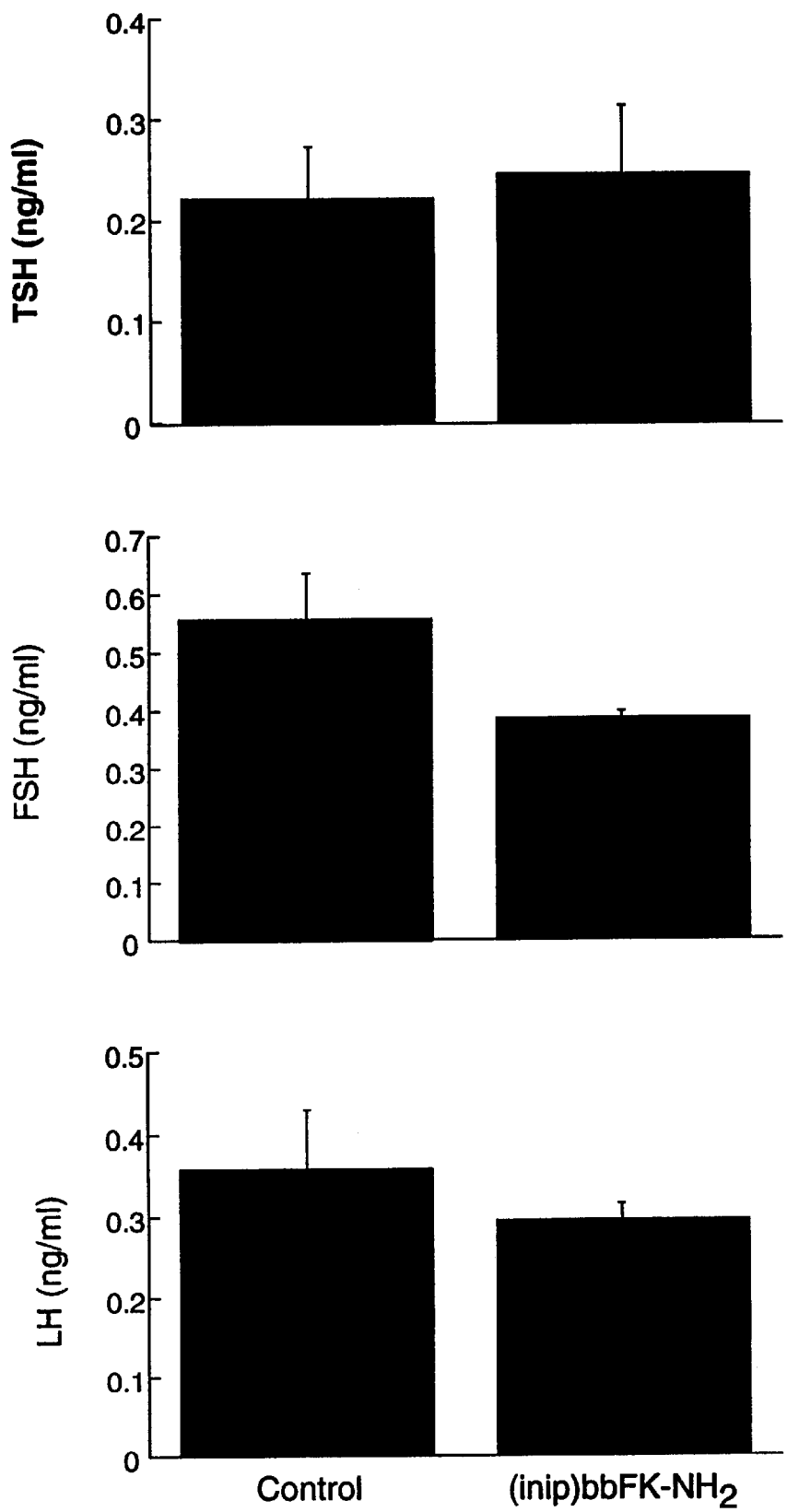
FIG. 8. TSH, FSH and LH release induced with (inip)-bbFK-NH$_2$. Pituitary cells challenged with (inip)-bbFK-NH$_2$ had no effect on these hormone concentrations.
Figure 9:
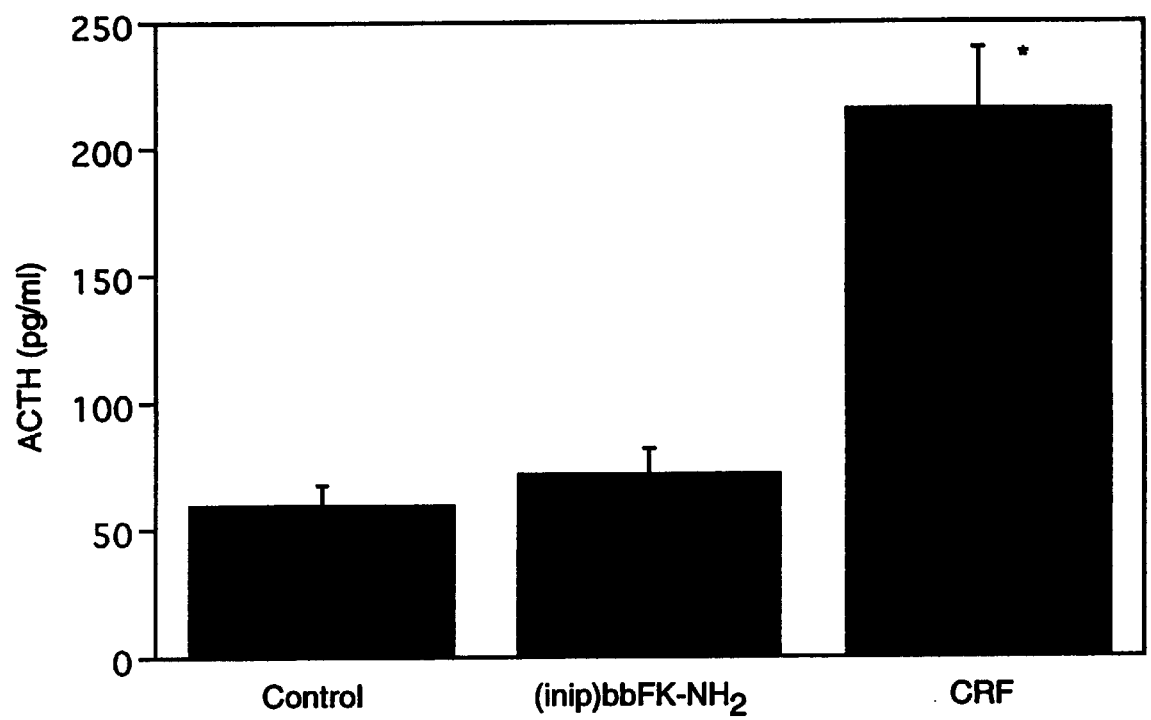
FIG. 9. ACTH release induced with corticotrophin releasing factor (CRF) or (inip)-bbFK-NH$_2$. ACTH levels rose 3-fold when stimulated with CRF but no significant change was observed with 100 nM (inip)-bbFK-NH$_2$.
Figure 10A:
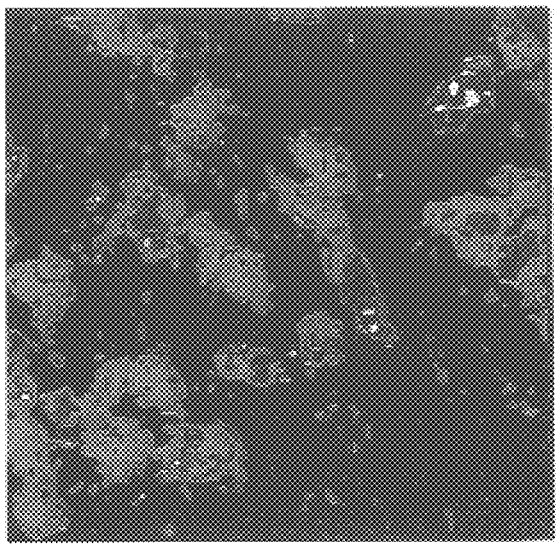
FIGS. 10A–10D. Ca$^{++}$ release in pituitary cells by (inip)-bbFK-NH$_2$. Basal Ca$^{++}$ in Indol-1 AM loaded pituitary cells after 4-day monolayer culture (FIG. 10A and FIG. 10C). Twenty-one (21) seconds after (inip)-bbFK-NH$_2$ addition, the increased Ca$^{++}$ flux in FIG. 10D is demonstrated by lighter areas in some of the cells of this heterologous population. Addition of vehicle did not change Ca$^{++}$ levels (FIG. 10B).
Figure 10B:
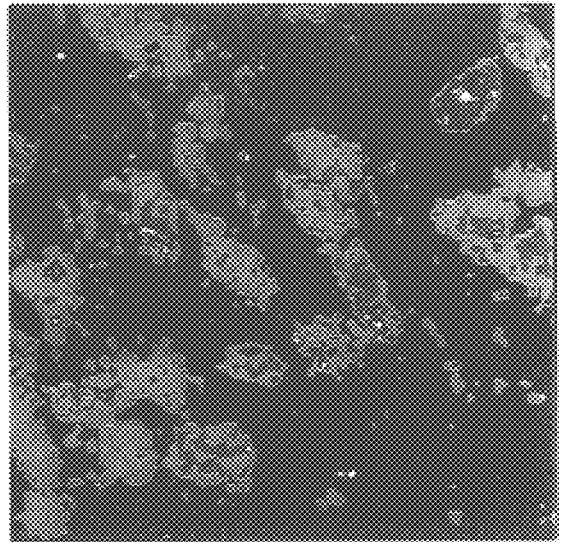
Figure 10C:
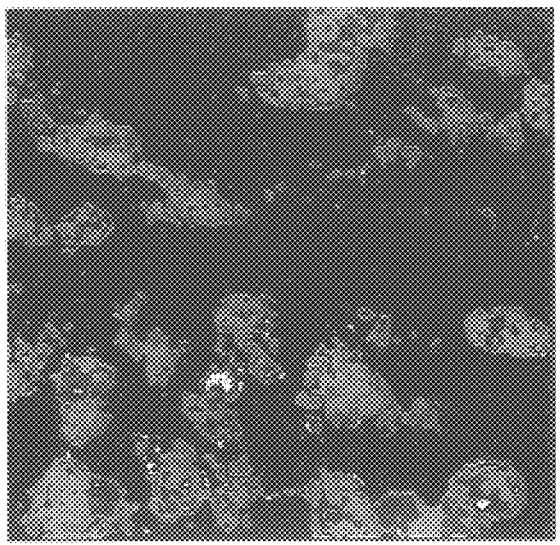
Figure 10D:
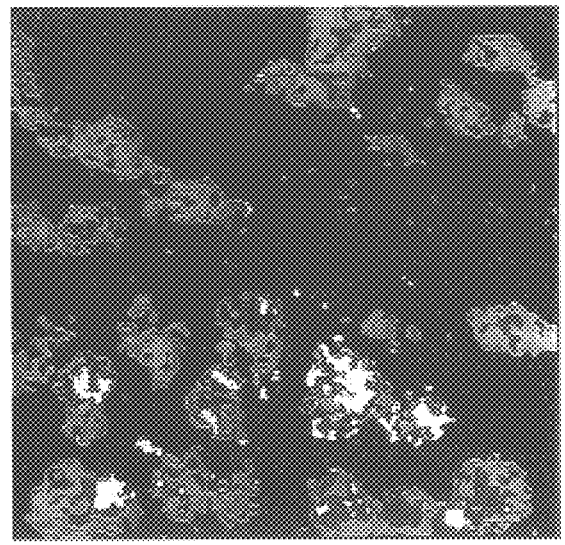

The specificity of (inip)-bbFK-NH$_2$ in vitro was demonstrated in that LH, FSH, TSH or ACTH release was unchanged by 100 nM (inip)-bbFK-NH$_2$. Prolactin concentrations were significantly increased but less than 2 fold (FIGS. 7–9).

Ca$^{++}$ flux determinations are shown in FIG. 10. The left panels (A and C) show the basal Ca$^{++}$ pattern immediately prior to addition of vehicle or (inip)-bbFK-NH$_2$. Twenty-one (21) seconds after (inip)-bbFK-NH$_2$ application the increased Ca flux in panel D is demonstrated by lighter colors in some of the cells of this heterologous population. As a control, addition of vehicle did not alter the Ca$^{++}$ profile (B), but addition of the calcium secretagogue ionomycin resulted in maximal stimulation of all the cells (data not shown).

2. Representative from Formula III

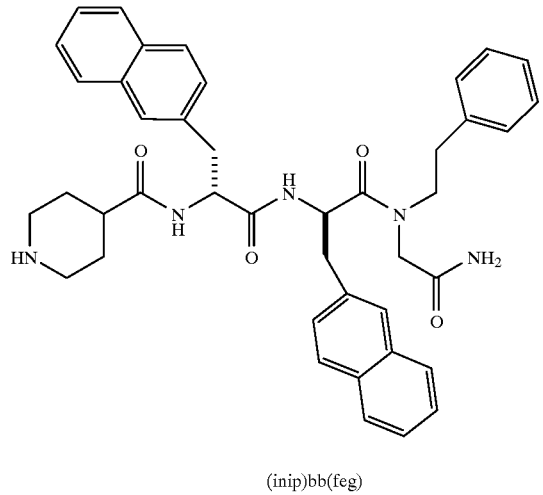

(inip)bb(feg)

Figure 11:
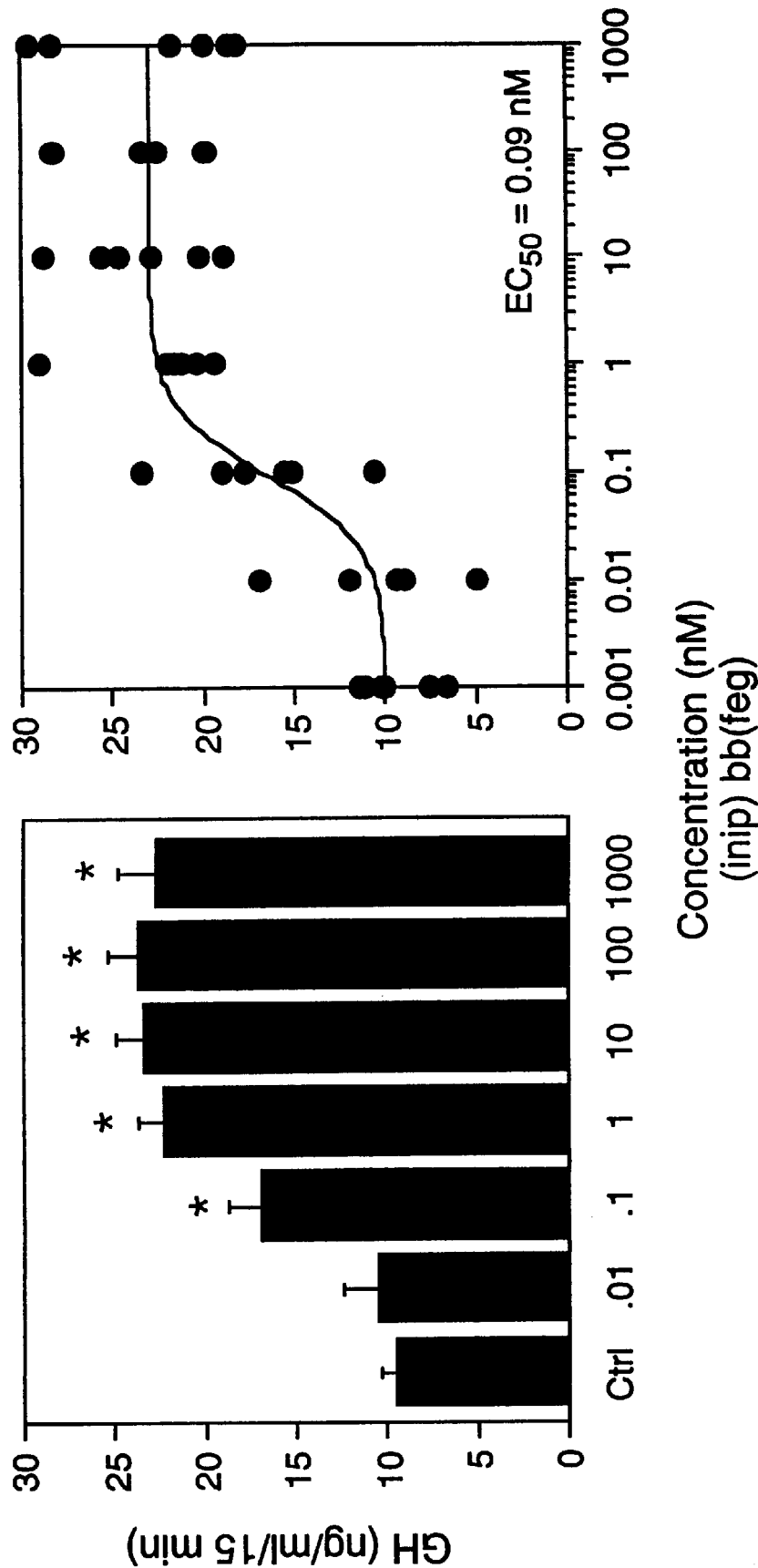
FIG. 11. Dose dependent GH release with (inip)bb(feg). GH release by rat pituitary cells to increasing concentrations of (inip)bb(feg) (left panel) over a 15 minute incubation. Right panel shows data points and curve used to calculate the EC$_{50}$ of 0.09 nM.

This novel GHRP is smaller by about one (lysine) amino acid residue compared to (inip)-bbFK-NH$_2$ described above. Dose dependent GH release with (inip)bb(feg) is shown in FIG. 11. GH release by rat pituitary cells to increasing concentrations of (inip)bb(feg) (left panel) over a 15 minute incubation shows a dose dependent increase. The right panel shows data points and curve used to calculate the EC$_{50}$ of 0.09 nM for the GHRP (inip)bb(feg). The mean EC$_{50}$ (n=3) for (inip)bb(feg) was 0.25±0.19 nM.

Figure 12:
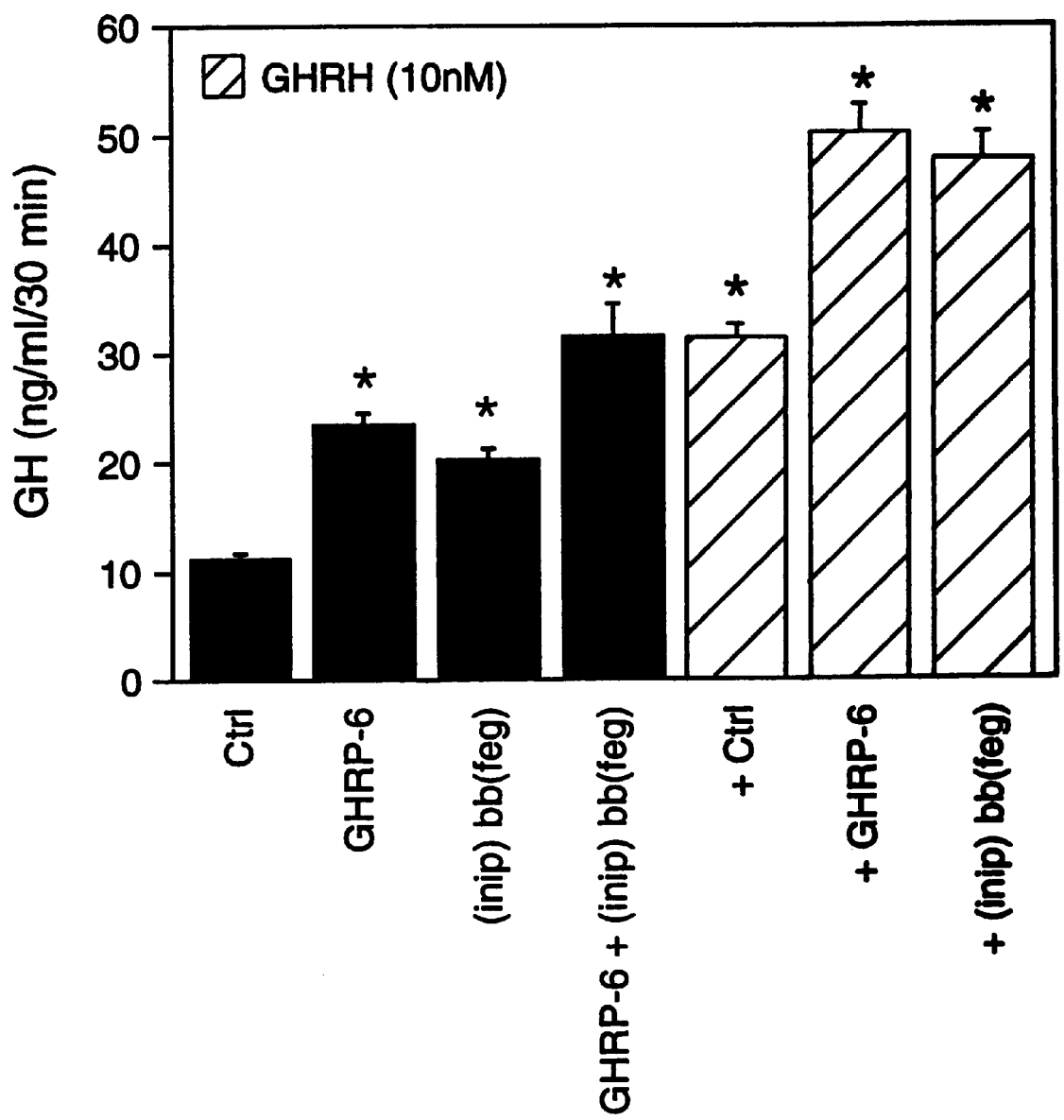
FIG. 12. Demonstration that (inip)bb(feg) acts at the proposed "GHRP receptor". GH response to GHRP-6 (100 nM) and (inip)bb(feg) (100 nM) was significantly greater than control but GH release was not synergistic when both were added in combination. GHRH (100 nM) elicited a mild GH response which was synergistic in combination with either GHRP-6 or (inip)bb(feg).

To demonstrate that (inip)bb(feg) also acts at the proposed "GHRP receptor", GH response to GHRP-6 (100 nM) and (inip)bb(feg) (100 nM) was measured as shown in FIG. 12. The combination of these two GHRP's produced a GH release significantly greater than the control but GH release was not synergistic when these GHRP's were added in combination. GHRH (100 nM) elicited a mild GH response which was synergistic in combination with either GHRP-6 or (inip)bb(feg) indicating these GHRP's evoke a receptor different from GHRH.

Figure 13:
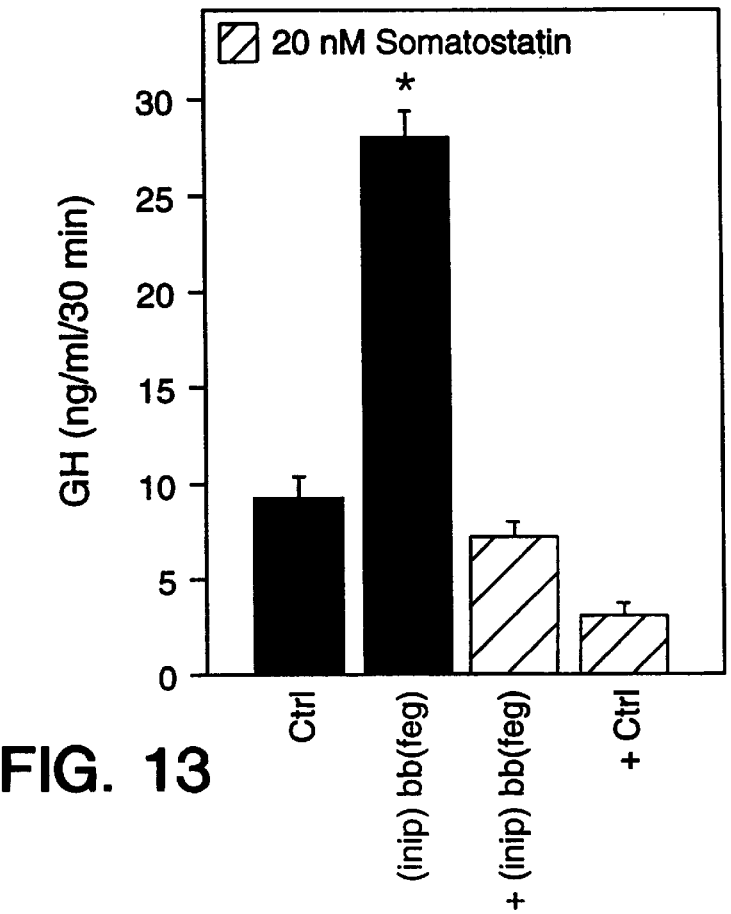
FIG. 13. Somatostatin suppression of (inip)bb(feg)-stimulated GH release. GH release with 100 nM (inip)bb (feg) was totally suppressed in the presence of 20 nM somatostatin.

Somatostatin suppression of (inip)bb(feg)-stimulated GH release is shown in FIG. 13. GH release with 100 nM (inip)bb(feg) was totally suppressed in the presence of 20 nM somatostatin consistent with the SS suppression response of other GHRP's.

Figure 14:
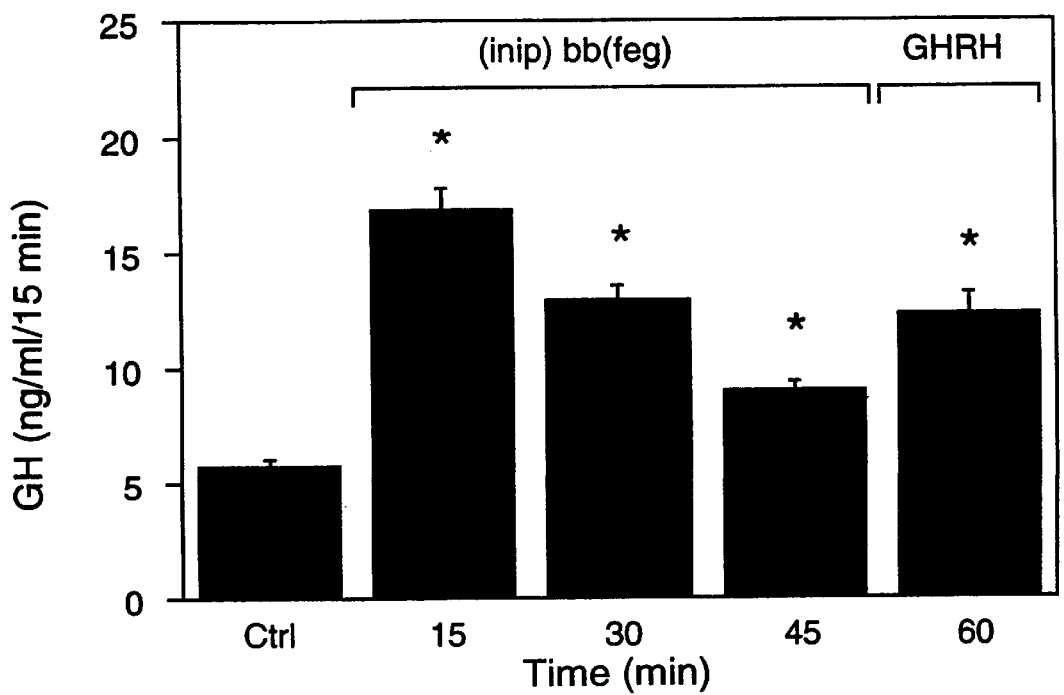
FIG. 14. Desensitization of the "GHRP receptor" upon challenging rat pituitary cells with three sequential 15 min. incubations with fresh (inip)bb(feg). GH release from the same pituitary cells over three sequential 15 minute incubations with (inip)bb(feg) (100 nM). After a total of 45 minutes, GH release was markedly decreased in response to (inip)bb(feg) but these cells were able to release more GH in response to a final 15 minute incubation with GHRH (10 nM).

Similarly, desensitization of the "GHRP receptor" upon challenging rat pituitary cells with three sequential 15 min. incubations with fresh (inip)bb(feg) is demonstrated in FIG. 14. GH release from the same pituitary cells over three sequential 15 minute incubations with (inip)bb(feg) (100 nM) demonstrated a classic GHRP desensitization pattern. After a total of 45 minutes, GH release was markedly decreased in response to (inip)bb(feg) but these cells were able to release more GH in response to a final 15 minute incubation with GHRH (10 nM).

3. Representative from Formula II

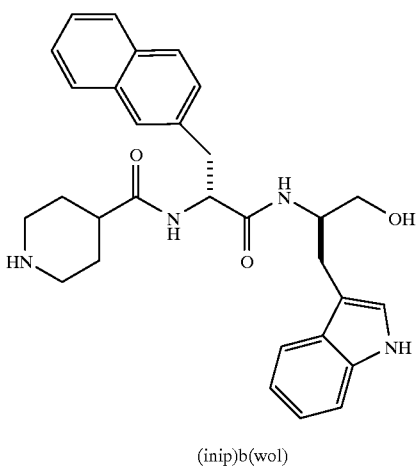

(inip)b(wol)

Figure 15:
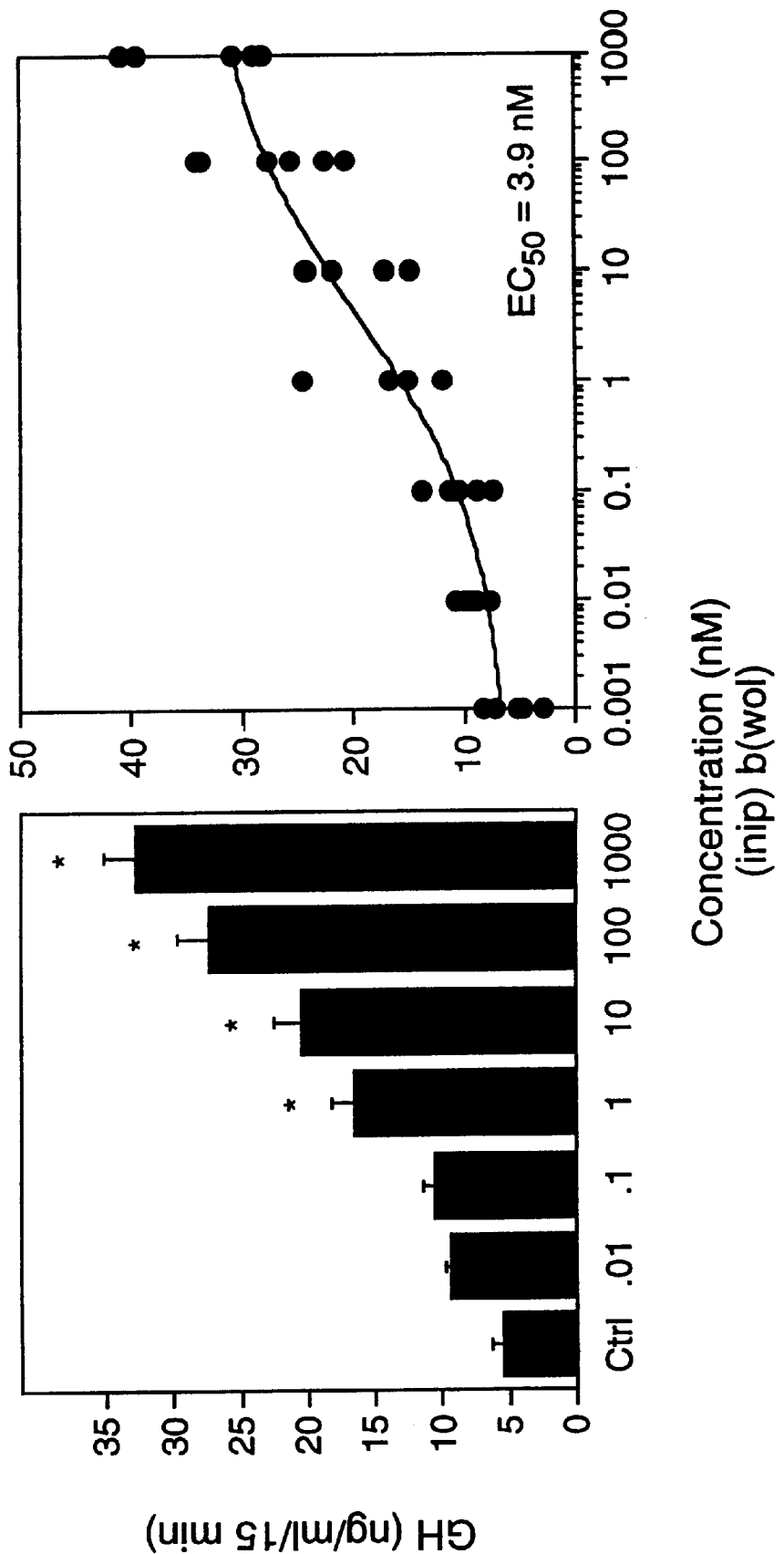
FIG. 15. Dose dependent GH release with (inip)b(wol). GH release by rat pituitary cells to increasing concentrations of (inip)b(wol) (left panel) over a 15 minute incubation. Right panel shows the data points and curve used to calculate the EC$_{50}$ of 3.9 nM.

This novel GHRP is still smaller than (inip)bb(feg), containing only two aromatic residues (b-wol) compared to the three for (inip)-bbFK-NH$_2$ and (inip)bb(feg). A dose dependent GH release with (inip)b(wol) is demonstrated in FIG. 15. GH release by rat pituitary cells to increasing concentrations of (inip)b(wol) (left panel) over a 15 minute incubation shows a dose dependent increase. The right panel shows the data points and curve used to calculate the EC$_{50}$ of 3.9 nM for the GHRP (inip)b(wol). The mean EC$_{50}$ (n=3) for (inip)b(wol) was 10.6±6.2 nM.

Figure 16:
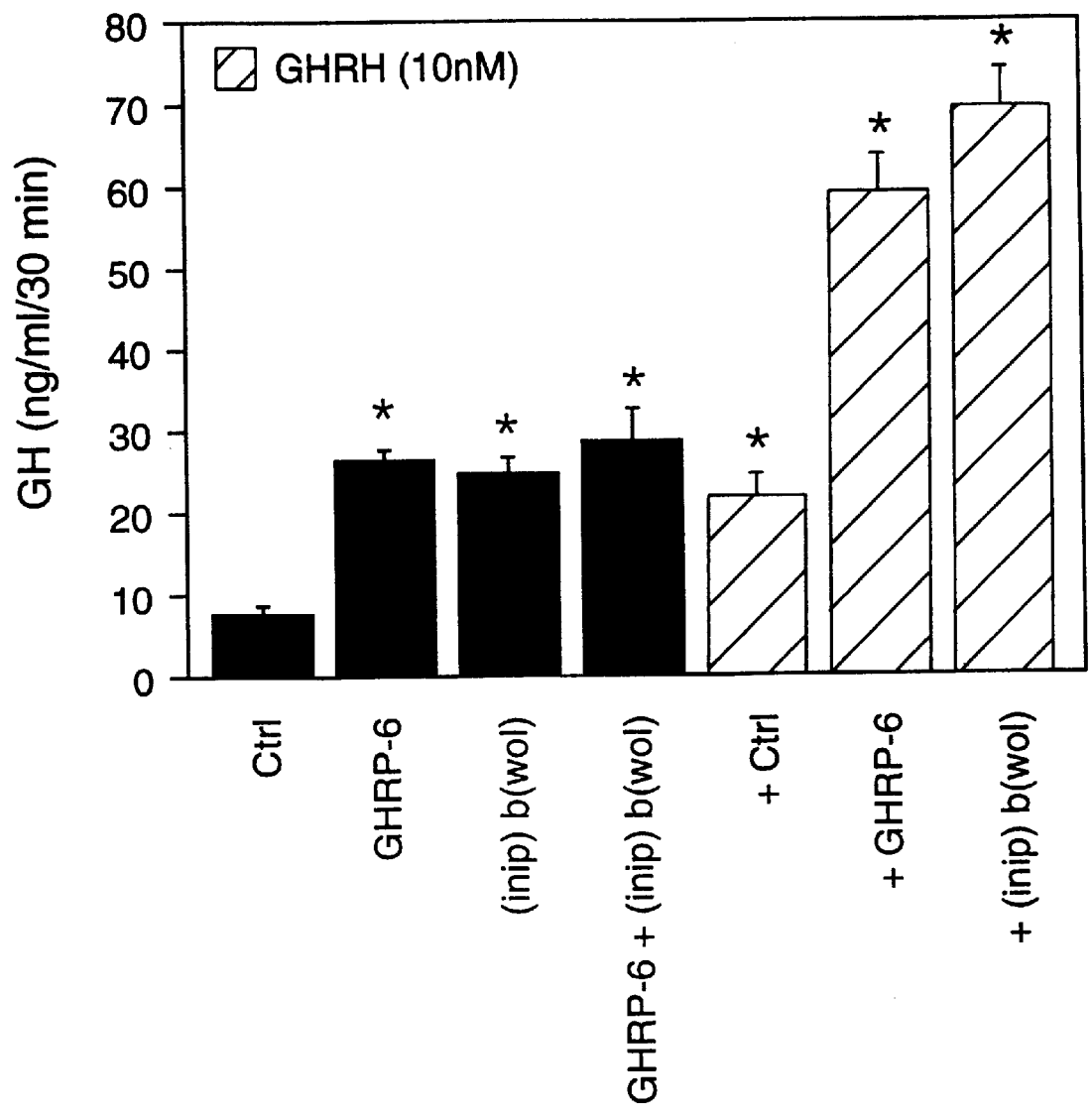
FIG. 16. Demonstration that (inip)b(wol) acts at the proposed "GHRP receptor". GH response to GHRP-6 (100 nM) and (inip)b(wol) (100 nM) was significantly greater than control but GH release was not synergistic when both were added in combination. GHRH (100 nM) elicited a mild GH response which was synergistic in combination with either GHRP-6 or (inip)b(wol).

Again, to demonstrate that (inip)b(wol) acts at the proposed "GHRP receptor", GH response to GHRP-6 (100 nM) and (inip)b(wol) (100 nM) was measured as shown in FIG. 16. GH release with there two GHRP's was significantly greater than control but not synergistic. In contrast, GHRH (100 nM) elicited a mild GH response which was synergistic in combination with either GHRP-6 or (inip)b(wol).

Figure 17:
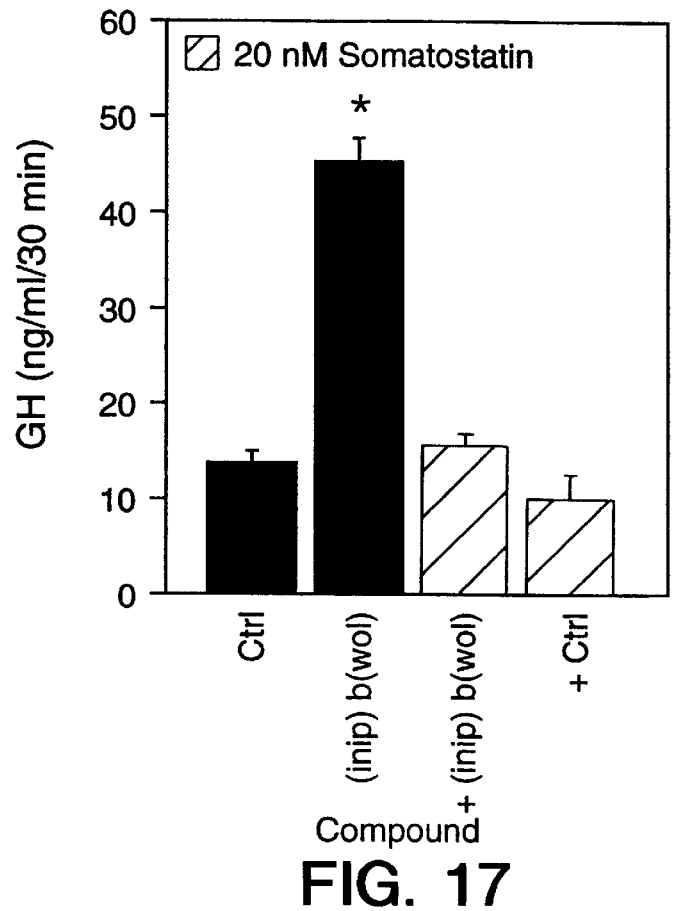
FIG. 17. Somatostatin suppression of (inip)b(wol)-stimulated GH release. GH release to 100 nM (inip)b(wol) was totally suppressed in the presence of 20 nM somatostatin.

Somatostatin suppression of (inip)b(wol)-stimulated GH release is demonstrated in FIG. 17. GH release to 100 nM (inip)b(wol) was totally suppressed in the presence of 20 nM somatostatin consistent with the SS suppression response of other GHRP's.

Figure 18:
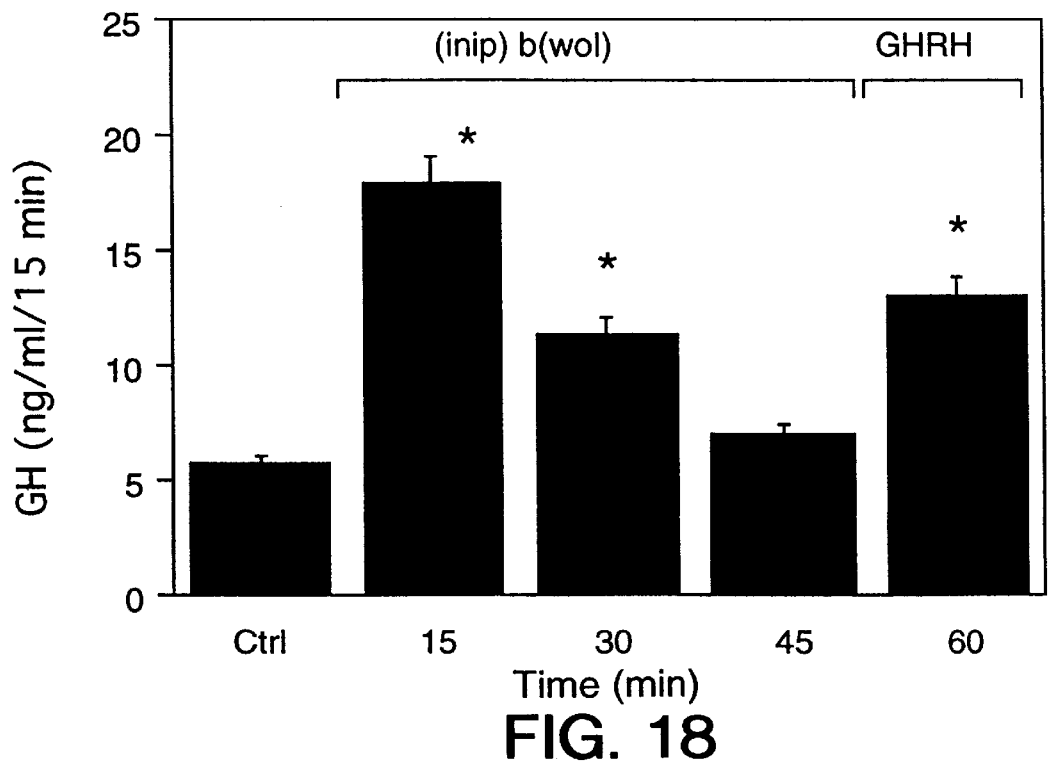
FIG. 18. Desensitization effect of the "GHRP receptor" upon challenging rat pituitary cells with three sequential 15 min. incubations with fresh (inip)b(wol). GH release from the same pituitary cells over three sequential 15 minute incubations with (inip)b(wol) (100 nM). After a total of 45 minutes, no significant release of GH was observed in response to (inip)b(wol) but these cells were able to release GH in response to a final 15 minute incubation with GHRH (10 nM).

Finally, the desensitization effect of the "GHRP receptor" upon challenging rat pituitary cells with three sequential 15 min. incubations with fresh (inip)b(wol) is shown in FIG. 18. GH release from the same pituitary cells over three sequential 15 minute incubations with (inip)b(wol) (100 nM) demonstrated a classic GHRP desensitization pattern. After a total of 45 minutes, no significant release of GH was observed in response to (inip)b(wol) but these cells were able to release GH in response to a final 15 minute incubation with GHRH (10 nM)

4. Summary of In Vitro Characterization

Clearly, by the functional assays demonstrated herein, representatives from each novel class of compound (Formulas II, III, IV and V) elicit GH release in a manner analogous to "GHRP-6". All these classes of compounds released GH in a dose-dependent manner, were synergized by GHRH but not GHRP-6, and had receptor desensitization after continuous exposure to the GHRP while maintaining the ability to respond to GHRH; all consistent with these compounds working through the putative "GHRP receptor". These assays are well-accepted and have been used extensively in the literature. (Cheng et al., *Endocrinology* 132:2727–2731 [1993]; Blake and Smith, *Journal of Endocrinology* 129:11–19 [1991]; Cheng et al., *Endocrinology* 124:2791–2798 [1989]; Smith *Science* 260:1640–1643 [1993]; and Akman et al., Endocrinology 132:1286–1291 [1993]).

Additionally, a representative from Formula IV, (inip) bbFK-NH$_2$, was further characterized and demonstrated a selective GH release from heterogeneous pituitary cells (excepting a mild, but significant increase in prolactin), ability to release GH via a Ca$^{++}$ flux mechanism, and to be inhibited by a GHRP antagonist. (Bowers et al., *Endocrinology* 128:2027–2035 [1991]).

These data are consistent with the view that all four novel classes of GHRP's elicit GH release in a manner analogous to "GHRP-6", and thus may opperate via the same mechanism to release GH in vitro.

2. In Vivo Activity in Normal Rats

To determine if the new GHRP molecules showed efficacy in vivo, young (90 day old) and adult (120 day old) rats were treated with the GHRP's of this invention and GHRH according to the protocols in Examples 41 and 44. Rat GHRH, which has been shown to increase body weight in normal young female rats was used as a positive control in these experiments (Clark and Robinson, *Nature* 314:281–283 [1985]).

A. Body Weight Gain in Normal Rats

Figure 19:
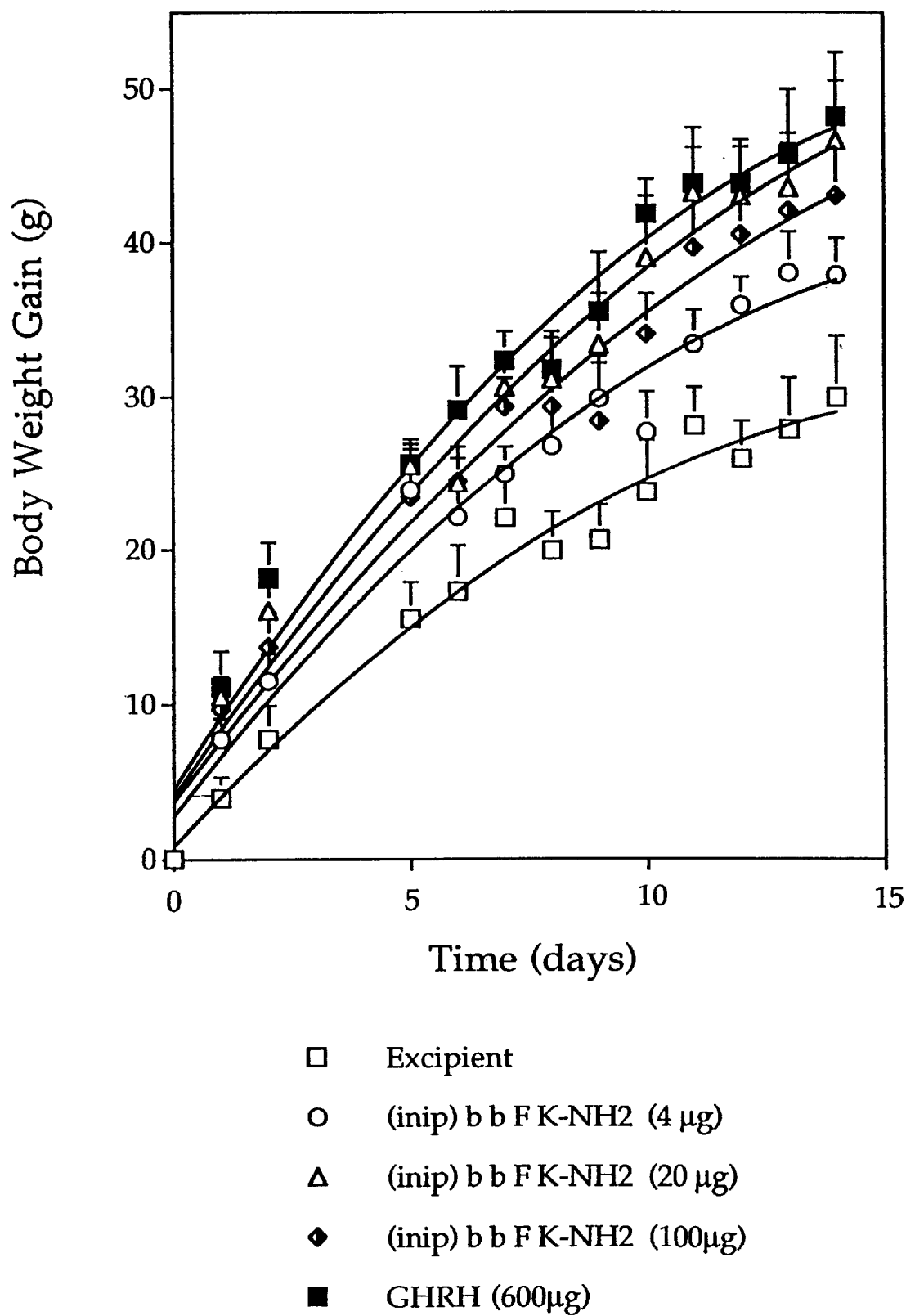
FIG. 19. Body weight gain in normal adult female rats in response to excipient (open squares), three doses of (inip) bbFK-NH2 (4 μg/d open circles, 20 μg/d open triangles, 100 μg/d half-filled diamonds), or one dose of GHRH (600 μg/d, filled squares); delivery was by subcutaneous minipump infusion for 14 days. There was a dose-related weight gain in response to (inip)bbFK-NH2, that at 20 μg/d reached the response to GHRH. Means and standard errors are shown.

Body weight gains plotted against time for the 5 treatment groups are shown in FIG. 19. Both (inip)bbFK-NH$_2$ and rat GHRH induced significant body weight gain compared to the vehicle excipient rats. By Day 5 of treatment the weight gains of all the treated groups were statistically significantly greater than the excipient treated rats. The dose-related nature of the body weight gains to (inip)bbFK-NH$_2$ is presented in FIG. 19. The weight gain in response to the much larger dose of rat GHRH (600 µg/day) was very similar to that induced by the medium dose (20 µg/day) of (inip)bbFK-NH$_2$. In addition, as little as 4 µg/day (equal to 166 ng/hr) of (inip)bbFK-NH$_2$ induced a significant weight gain in young normal rats. The great potency of (inip)bbFK-NH$_2$ can be seen from this comparison with GHRH and from the very low dose required to induce a significant anabolic effect in vivo.

Figure 20:
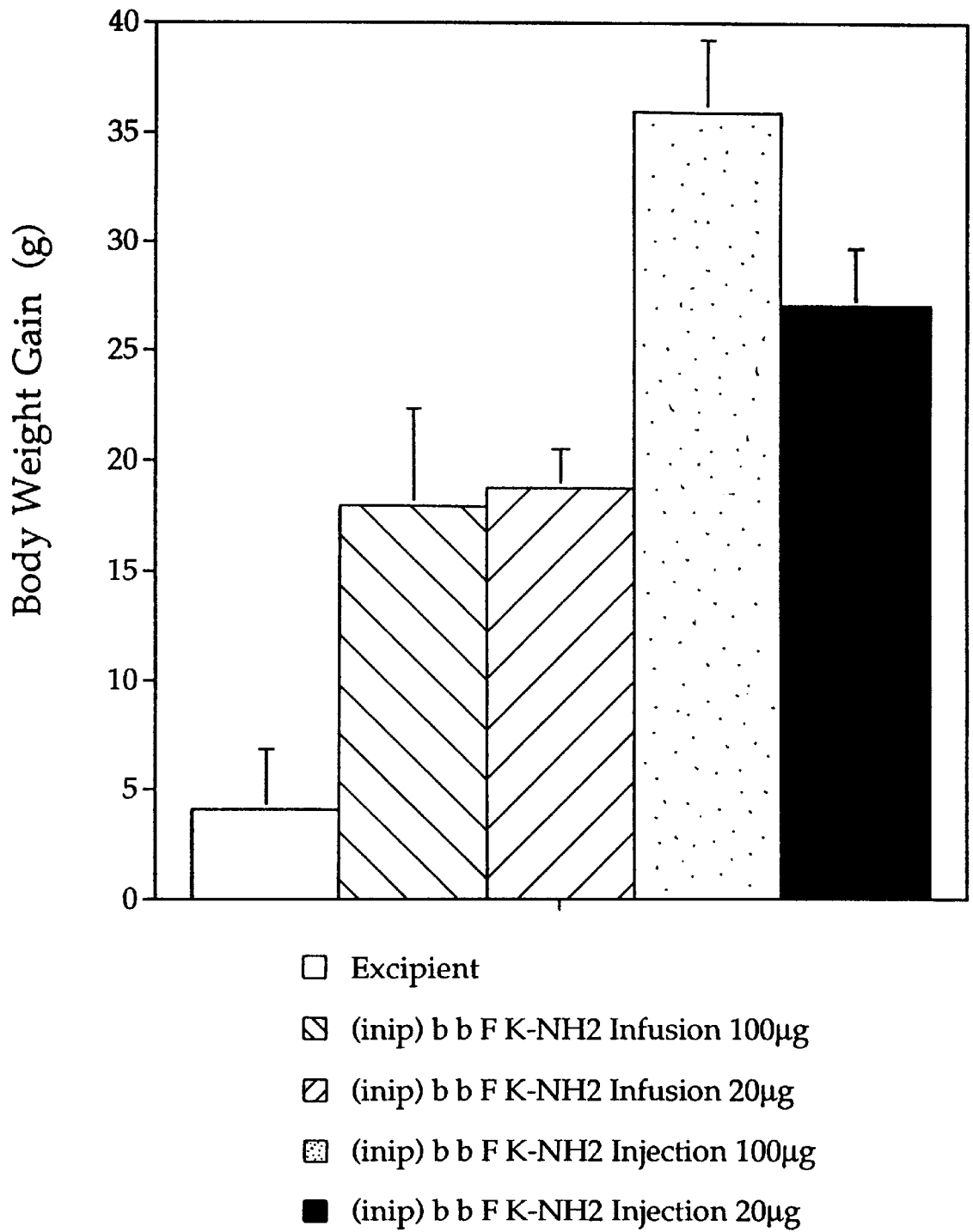
FIG. 20. Body weight gain in normal adult female rats treated for 14 days with excipient (open bar), two doses of (inip)bbFK-NH2 given subcutaneously by injection (shaded bar, 100 μg/d; solid bar, 20 μg/d) or infusion (lightly hatched bar, 100 μg/d; heavily hatched bar, 20 μg/d). Injections of (inip)bbFK-NH2 were more effective than infusions. Means and standard errors are shown.
Figure 26:
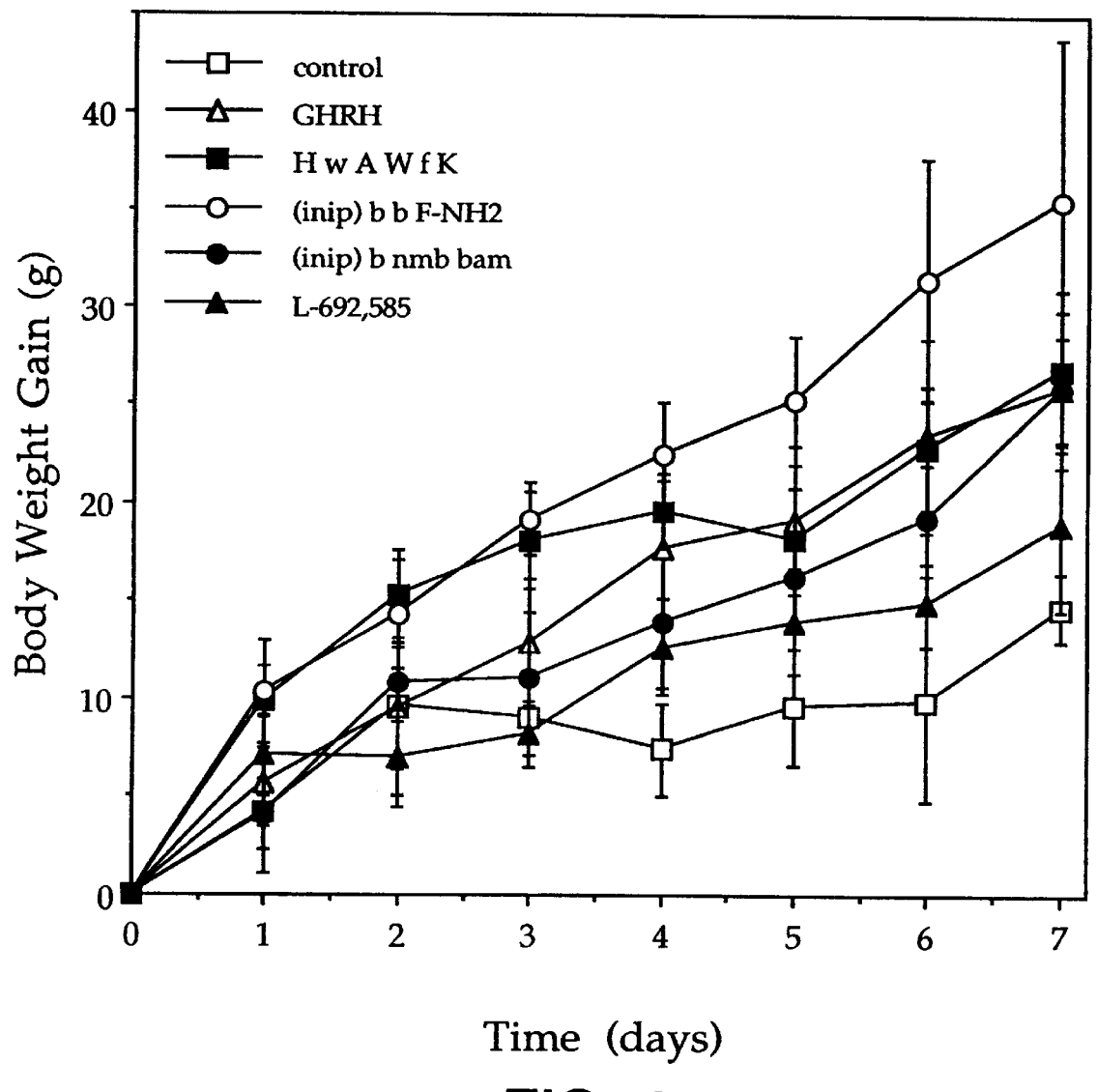
FIG. 26. Daily body weight gains in normal adult female rats treated for 7 days with twice daily subcutaneous injections of excipient (open squares), growth hormone releasing hormone (open triangles), HwAWfK (solid squares), (inip) bbF-NH2 (open circles), (inip)b nmb bam (solid circles), or L-692,585 (solid triangles). Significant weight gain occurred after treatment with all molecules except L-692,585. Means and standard errors are shown.

Body weight gains plotted against time for the groups of normal adult female rats treated with other GH secretagogues are shown in FIG. 26. The groups treated with GHRH and GHRPs 6, (inip)bbF-NH$_2$, and (inip)b(nmb) (bam) showed significant body weight gain but the group treated with L-692,585 showed no significant weight gain. Although the response to GHRP (inip)bbF-NH$_2$ appears to be larger than that to the other secretagogues, this difference was not statistically different. The weight gain in response to GHRP (inip)bbF-NH$_2$ (36±8 g in 7 days) was similar to that to GHRP (inip)bbFK-NH$_2$ (36±3 g in 14 days) shown in FIG. 20.

These studies show the various classes of GH secretagogues of this invention have significant anabolic effects in normal rats with intact pituitary function. One prior art molecule with minimal activity was L-692,585 a molecule of relatively low potency both in vitro and in vivo. It is believed, however, that if a larger amount of this molecule had been given significant anabolic effects would have resulted.

B. Organ Weight Gain in Young Normal Rats

Organs were weighed at sacrifice in these experiments to measure the effects of these treatments on the major organ systems. The pituitary and the kidney weight were not affected by treatment. Spleen weight was increased by high dose (inip)bbFK-NH$_2$ (100 µg/day) and by GHRH (excipient 532±25 mg; high dose (inip)bbFK-NH$_2$, 628±26 mg; GHRH 624±23 mg). Heart weight was increased by GHRH treatment (p<0.05) and tended to be increased by high dose (inip)bbFK-NH$_2$ (p<0.10 but >0.05) compared to excipient treated controls. The thymus was also increased in weight by both (inip)bbFK-NH$_2$ and GHRH. Thymus weight in excipient treated rats was 485±21 mg, 584±34 mg in high dose (inip)bbFK-NH$_2$ treated rats, and 575±39 mg in GHRH treated rats. The liver increased in weight in a dose-dependent manner with (inip)bbFK-NH$_2$. The weight of the liver in the excipient treated rats was 8.75±0.24 g, and with increasing doses of (inip)bbFK-NH$_2$ liver weight increased from 9.40±0.37 g to 9.70±0.29 g and 10.14±0.29 g for low medium and high doses of (inip)bbFK-NH$_2$, respectively. Liver weight was also significantly increased by treatment with GHRH. In these experiments there was no statistically significant increase in epiphyseal plate width with either (inip)bbFK-NH$_2$ or GHRH treatment.

C. Organ and Body Weight Gain Summary

These experiments shows that (inip)bbFK-NH$_2$ has a range of anabolic effects in normal young female rats. This anabolic effect was seen by increases in body weight, liver weight, spleen weight and thymus weight, with a tendency for heart weight to also increase compared to excipient treated control rats. The effect of the GHRP (inip)bbFK-NH$_2$ was also dose related with doses of 4, 20 and 100 μg/rat/day all being effective anabolic doses. In these experiments the two highest doses of (inip)bbFK-NH$_2$ had equivalent effects. Therefore as little as 166 ng/hr of (inip)bbFK-NH$_2$ (for 200 g rats; 0.83 μg/kg/hr) was effective at inducing an anabolic effect.

The dose-related effect of (inip)bbFK-NH$_2$ on the liver is a good indicator of the amount of GH secretion caused by the GHRP (inip)bbFK-NH$_2$. Liver growth is particularly sensitive to stimulation by GH, and the increased liver weight is the expected response to an increased secretion of GH caused by both (inip)bbFK-NH$_2$ and GHRH. Kidney shows a relatively poor growth response to GH treatment; the lack of an effect of (inip)bbFK-NH$_2$ on this organ is therefore the expected result. Wagner and Scow, *Endocrinology* 61:419–425 (1957); Clark et al., *Endocrinology and Metabolism* 1:49–54 (1994).

The effects of (inip)bbFK-NH$_2$ on the weight of the thymus and spleen indicate that the instant novel GHRPs would be expected to stimulate immune function. Other studies have shown that GH and IGF-1 can significantly stimulate immune function, so it would be expected that GHRPs of this invention, by increasing GH secretion, would also stimulate immune function (Kelley,*Ann, N.Y. Acad. Sci.* 594:95–118 (1990), Clark et al., *J. Clin. Invest* 92:540–548 (1993).

(inip)bbFK-NH$_2$ tended to increase cardiac weight, indicating a significant anabolic effect of this GHRP on the heart. GH and IGF-1 have been shown to be efficacious in animal models of congestive heart failure, and there is data that GH is effective in humans at improving cardiac function in growth hormone deficient adults. This data suggests that (inip)bbFK-NH$_2$ would also be effective at improving cardiac function and in the treatment of cardiac congestive heart failure (sacca et al., *Endocrine Reviews* 15:555–573 [1994]).

The GHRP (inip)bbFK-NH$_2$ was also effective at stimulating an anabolic response when delivered by continuous infusion. The delivery of (inip)bbFK-NH$_2$ by SC infusion is an effective treatment and a similar effect could be achieved by any method that maintained a near continuous exposure of the instant GHRP's. For example, oral delivery, transdermal patch, or other delivery systems designed to maintain a continuous exposure to these GHRP's would be appropriate.

D. Comparison of GHRP Infusion Versus Injections in Normal Rats

Body Weight Gain: The GHRP (inip)bbFK-NH$_2$ at 20 and 100 μg/day, delivered by both injection and infusion, induced significant body weight gain compared to excipient treated rats (see Example 42). By Day 2 of treatment, the weight gains of all the treated groups were statistically significantly greater than the excipient treated rats. The dose-related nature of the body weight gains to injections of (inip)bbFK-NH$_2$ can be seen in FIG. 20. In contrast there were similar weight gains in response to infusions of 20 and 100 μg/day of (inip)bbFK-NH$_2$. In addition, there were very different patterns of weight gain in response to infusions or injections of (inip)bbFK-NH$_2$ as can be seen in FIG. 21.

Figure 21:
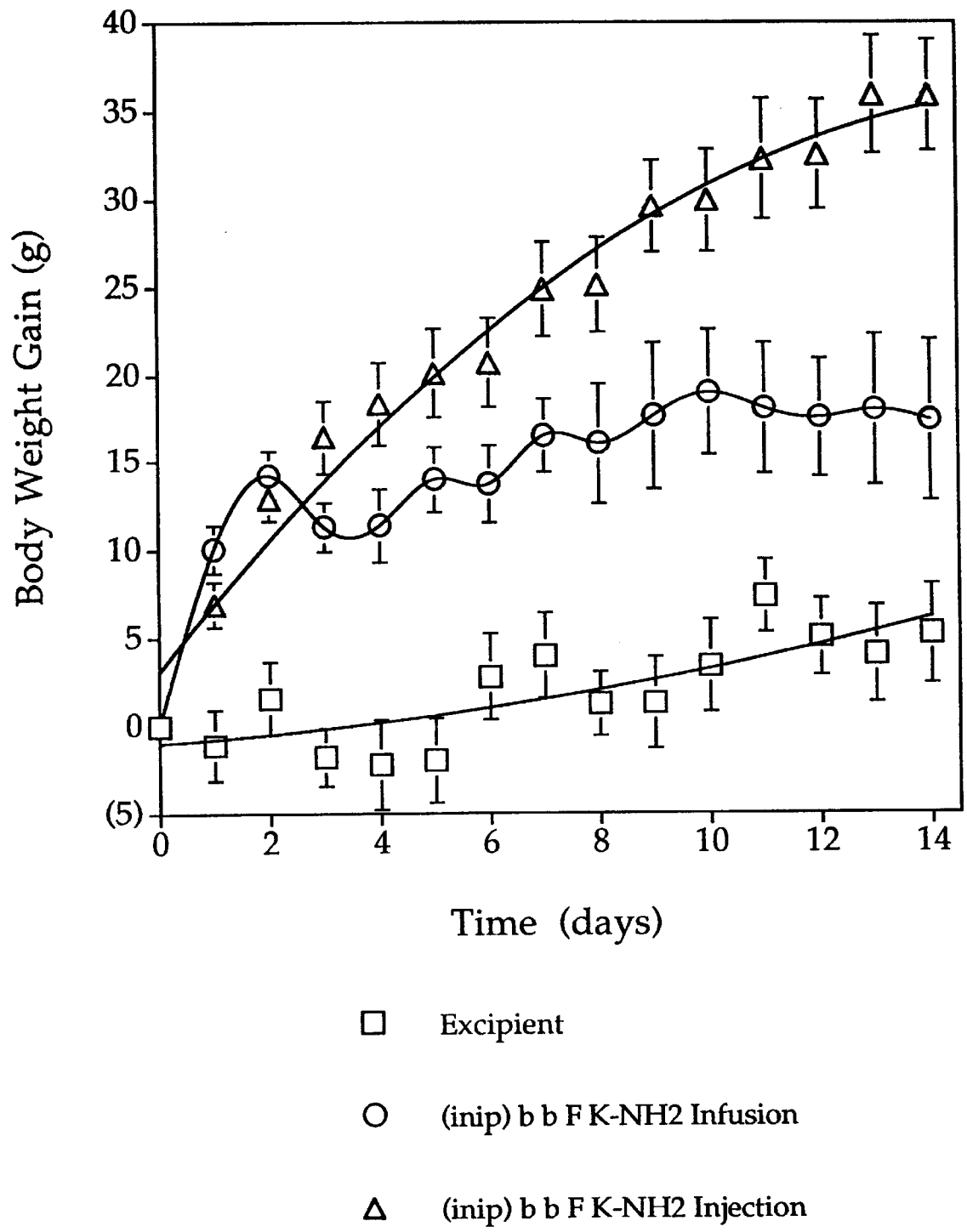
FIG. 21. Body weight gain in normal adult female rats treated for 14 days with excipient (open squares), or (inip) bbFK-NH2 given by subcutaneous injection (100 μg/d; open triangles) or infusion (100 μg/d; open circles). Injections of (inip)bbFK-NH2 produced a maintained growth response; infusions gave a large initial response that was not maintained. Means and standard errors are shown.

FIG. 21 also shows an initial rapid weight gain over 2 days in response to the high dose of infused (inip)bbFK-NH$_2$ (100 μg/d), followed by a marked absence of any further response for the duration of the experiment. This provides evidence that continuous exposure to high doses of GHRPs can induce tachyphalaxis and thus function as GH antagonists.

In contrast to infusions, periodic injections of (inip)bbFK-NH$_2$ maintained a significant growth response. Twice daily injections of 10 μg of the GHRP (inip)bbFK-NH$_2$ produced a large (30 gram) weight gain in adult female rats.

Organ Weights: Organ weights at sacrifice were measured to determine the effects of injection verses infusion of (inip)bbFK-NH$_2$ on major organ systems. The eviscerated and skinned carcass was significantly heavier in the high dose (152.4±2.5 g) and low dose (152.8±2.8 g) (inip)bbFK-NH$_2$ injected animals compared to controls (141.8±3 g). The skin was heavier in animals injected with (inip)bbFK-NH$_2$ and in those infused with low dose (inip)bbFK-NH$_2$ compared to control animals. When the skin and carcass weight were expressed as a percentage of body weight there was no significant effect due to treatment, indicating that the weight gain was due to a proportional increase in the whole body size of the rats. Soleus muscle, kidney, and liver were also unaffected by treatment. Injections of high dose (inip)bbFK-NH$_2$ significantly increased heart weight compared to controls (1.15±0.10 g vs. 0.96± 0.03 g). Thymus weight was increased by high dose injections of (inip)bbFK-NH$_2$ (0.33±0.02 g) compared to high dose infusion animals (0.25±0.03 g). Epiphyseal plate width was increased by high dose (inip)bbFK-NH$_2$ injections (191±8 μm) compared to low dose injections (160±11 μm) whereas (inip)bbFK-NH$_2$ infusions did not significantly increase cartilage growth. Serum IGF-1 concentrations were not significantly affected by either mode of delivering (inip)bbFK-NH$_2$.

Serum chemistries were measured in the blood samples obtained at sacrifice. Enzyme levels indicative of cardiac, liver, muscle and kidney function were measured. there were no statistically significant effects of (inip)bbFK-NH$_2$. In addition, metabolites (glucose, blood urea nitrogen, creatinine, total protein, albumen, cholesterol, bilirubin) and ions (calcium, phosphate, sodium, potassium and chloride) were measured. The only metabolite showing some evidence of changing was the serum triglyceride. There was some evidence that serum triglyceride was increased by high dose injections of the GHRP (inip)bbFK-NH$_2$ but not by low dose injections (control 126±11 mg %, high dose 183±17 mg %, low dose 128±11 mg %) although this effect failed to reach statistical significance.

This experiment clearly shows that the GHRP (inip) bbFK-NH$_2$ when given by either injections or infusions has a range of anabolic effects in normal adult female rats. This growth promoting effect was seen by increases in body weight gain, carcass weight, skin weight, heart weight and thymus weight compared to excipient treated control rats. In this experiment two injections per day of 10 $\mu$g of (inip)bbFK-NH$_2$ caused a weight gain nearly equal to that of two injections per day of 50 $\mu$g of (inip)bbFK-NH$_2$. Therefore 10 $\mu$g of (inip)bbFK-NH$_2$ (for 200 g rats; 50 $\mu$g/kg/day) appears to be a maximal dose of (inip)bbFK-NH$_2$ for inducing an anabolic response. Acute intravenous injection experiments with (inip)bbFK-NH$_2$ in 80 gram rats (Example 40) over a 25-fold range of doses (e.g. 1.0, 0.2, and 0.04 $\mu$g/injection) demonstrates that induction of GH secretion occurs within this dose-response range (ED$_{50}$ 0.2 $\mu$g/rat). In 200 g rats this suggests that a 10 $\mu$g dose of GHRP (inip)bbFK-NH$_2$ would be well above the effective doses-responses range.

There were differences between the anabolic effects of (inip)bbFK-NH$_2$ in 90 vs. 150 day old rats. In the older rats there was no clear effect on liver weight or spleen weight as seen with GHRP (inip)bbFK-NH$_2$ infusion in the younger rats. (inip)bbFK-NH$_2$ injections increased thymus weight, suggesting that these GHRPs can stimulate growth of immune tissue and therefore increase immune function. Other studies have shown that GH and IGF-1 can significantly stimulate immune function, so it would be expected that GHRP's of this invention, by increasing GH secretion, would also stimulate immune function. Kelley, *Ann. N.Y. Acad. Sci.* 594:95–118 (1990), Clark et al., *J. Clin. Invest.* 92:540–548 (1993). GHRP (inip)bbFK-NH$_2$ tended to increase cardiac weight, indicating an effect on the heart structure and function. GH and IGF-1 have been shown to be efficacious in models of congestive heart failure and this data suggests that (inip)bbFK-NH$_2$ would also be effective in the treatment of congestive heart failure. Sacca et al., *Endocrine Reviews* 15:555–573 (1994).

The GHRP (inip)bbFK-NH$_2$ was clearly effective at stimulating an anabolic response when delivered by both injections and continuous infusion. The delivery of (inip)bbFK-NH$_2$ by twice daily subcutaneous injection appears to be an effective method of GHRP delivery. Other methods of delivery that would produce a similar blood profile of GHRP, for example oral delivery, delivery to the lung, or other delivery systems designed to maintain an intermittent exposure to GHRP would also be an effective means of inducing GH secretion and thereby the effects of GH.

The normal serum chemistries indicate that the effects of (inip)bbFK-NH$_2$ can occur without perturbing the normal balance of blood metabolites and ions. The one possible exception was the tendency for serum triglyceride to be increased by high dose injections, but not by low dose injections of the GHRP (inip)bbFK-NH$_2$. This may indicate that very high doses of (inip)bbFK-NH$_2$ can impact the ACTH system and induce corticosterone activity. However 10 $\mu$g injections of (inip)bbFK-NH$_2$ did not seem to affect serum lipids, indicating that this dose, while maximally stimulating GH secretion, has a minimal effect on corticosterone secretion.

E. Combination GHRP and IGF-1 Treatment of Normal Rats

Normal adult female rats were chosen to study the anabolic effect of GHRP's 6, (inip)bbF-NH$_2$, (inip)b(nmb)(bam), and L-692,585 when given in combination with IGF-1. Details of the protocols for this study are described in Example 44.

The body weight gain responses to the GH secretagogues given in combination with IGF-1 (FIG. 27) were much greater than those to the GH secretagogues given by themselves (FIG. 26). In addition, the responses to the combination of the GH secretagogues and IGF-1 tended to be greater than to IGF-1 alone.

This study shows for the first time that GHRP has significant anabolic activity when given in combination with chronically administered IGF-1. Furthermore, there is an additional anabolic benefit of administering the combination of GH secretagogues and IGF-1.

3. In Vivo Activity in ZDF Rats

A. Combination GHRP and IGF-1 Therapy in Obese Rats

It is known that IGF-1 inhibits GH secretion by a feedback mechanism either acting indirectly on the hypothalamus or directly on the pituitary. Tannenbaum et al., *Science* 220:77–79 (1981). It is also known that GHRH induced GH secretion is suppressed by IGF-1 administration (Bermann et al., *Program and Abstracts 76th annual Meeting US Endocr. Soc*, Abstract 565, (1994). It was however unknown if GHRP could induce GH secretion, or produce effects, in combination with IGF-1 administration. The protocol for IGF-1 administration in combination with GHRP and GH is provided in Example 43. Rat GHRH, which has been shown to increase body weight in normal female rats was used as a positive control in the experiment.

Figure 22:
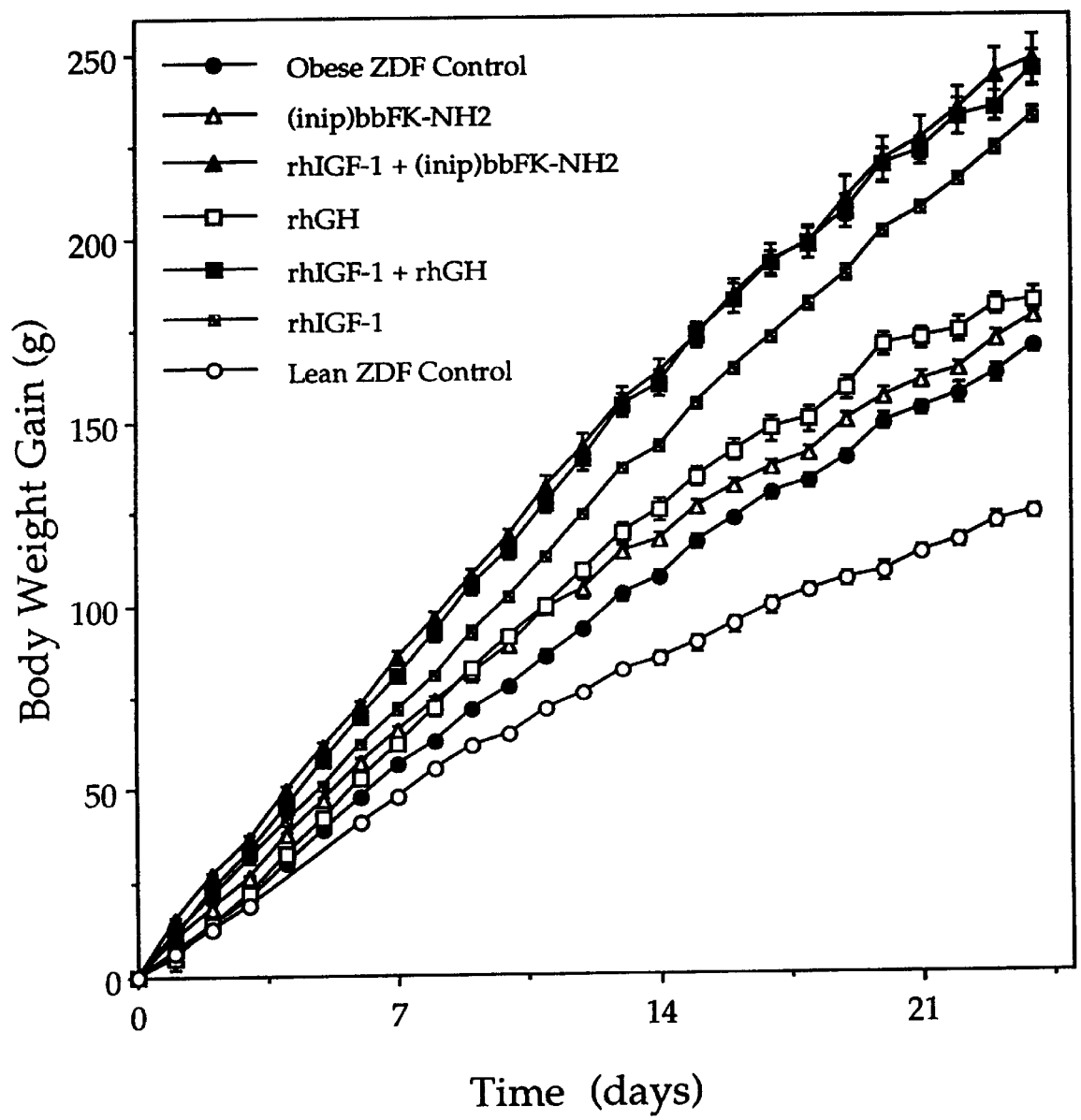
FIG. 22. Body weight gain in lean (open circles) and obese Type II Zucker Diabetic Fatty (ZDF) male rats treated subcutaneously for 24 days with excipient (solid circles), recombinant human growth hormone (rhGH, large open squares, 500 μg/d), recombinant human insulin-like growth factor-1 (rhIGF-1, small squares, 758 μg/d), (inip)bbFK-NH2 given by injection (100 μg/d; open triangles), the combination of rhGH plus rhIGF-1 (solid squares), or the combination of rhIGF-1 plus (inip)bbFK-NH2 (solid triangles). The combination of (inip)bbFK-NH2 plus rhIGF-1 produced a maintained growth response equal to that of rhIGF-1 plus rhGH. Means and standard errors are shown.
Figure 23:
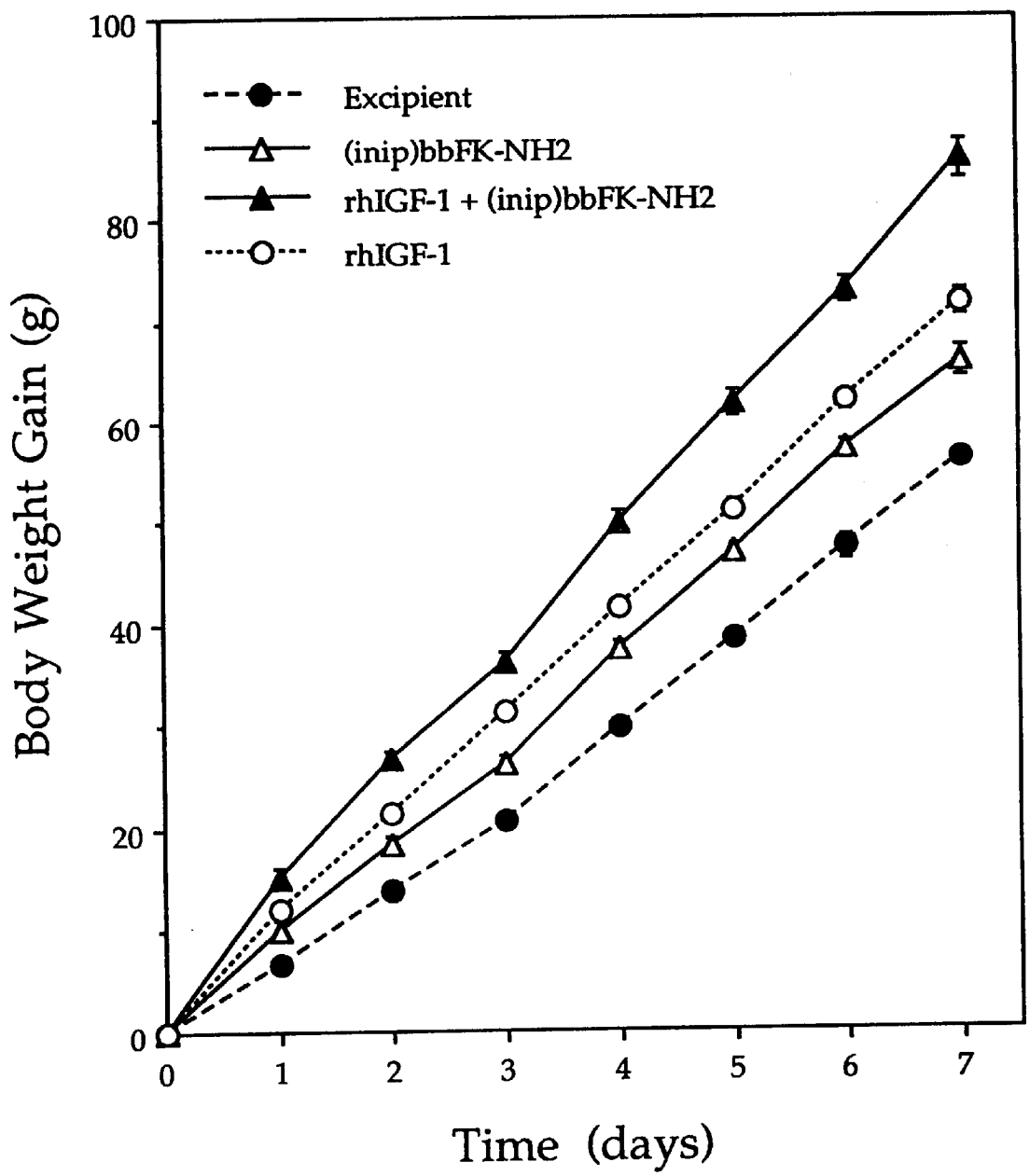
FIG. 23. Body weight gain in obese Type II Zucker Diabetic Fatty (ZDF) male rats treated subcutaneously for 7 days with excipient (solid circles), recombinant human insulin-like growth factor-1 (rhIGF-1, open circles, 758 μg/d), (inip)bbFK-NH2 given by injection (100 μg/d; open triangles), or the combination of rhIGF-1 and (inip)bbFK-NH2 (solid triangles). The combination of (inip)bbFK-NH2 plus rhIGF-1 produced a maintained growth response that was at least additive compared to each agent given alone. Means and standard errors are shown.

Body Weight Gain: The body weight gains plotted against time for all treatment groups over the entire study (i.e. 24 days) are shown in FIG. 22. Body weight gains for the first 7 days for the GHRP (inip)bbFK-NH$_2$ and IGF-1 treatment groups are shown in FIG. 23. Both (inip)bbFK-NH$_2$ and rhIGF-1 induced significant body weight gain compared to the vehicle treated rats, so that by Day 2 (see FIG. 23) of treatment, the weight gains were statistically significantly greater than the excipient treated rats ((inip)bbFK-NH$_2$: 18.3±1.0 g, rhIGF-1:21.5±0.7 g, and obese controls: 13.8±0.4 g). Treatment with rhGH had not increased weight gain by this time (13.6±2.5 g). The weight gain in response to the GHRP (inip)bbFK-NH$_2$ plus rhIGF-1(26.8+0.8 g) was greater (p<0.05) than that to the combination of rhGH+rhIGF-1 (23.3±1.2 g). At day 7 of treatment these differences in weight gain were maintained. By day 24 of treatment (FIG. 22) the weight gain response to (inip)bbFK-NH$_2$ plus IGF-1 (247.4±7.1 g) was similar to that to rhGH+rhIGF-1 (245.2±4.9 g) and much greater than that of obese controls (169.0±1.6 g) and significantly greater (p<0.05) than for rhIGF-1 treatment alone (232±2 g). It was surprising that GHRP (inip)bbFK-NH$_2$ could induce a weight gain when given in combination with IGF-1, and that this weight gain was equal to that of a large dose of rhGH and that the effects of the combination of GHRP and rhIGF-1 gave weight gains greater than or equal to those of the combination of rhGH and rhIGF-1.

B. Combination GHRP and IGF-1 Treatment of Diabetic Rats

Obese Zucker Diabetic Fatty (ZDF) rats were chosen to study the diabetogenic effect of GHRP when given in combination with IGF-1. Details of the protocols for this study are described in Example 43.

Figure 24:
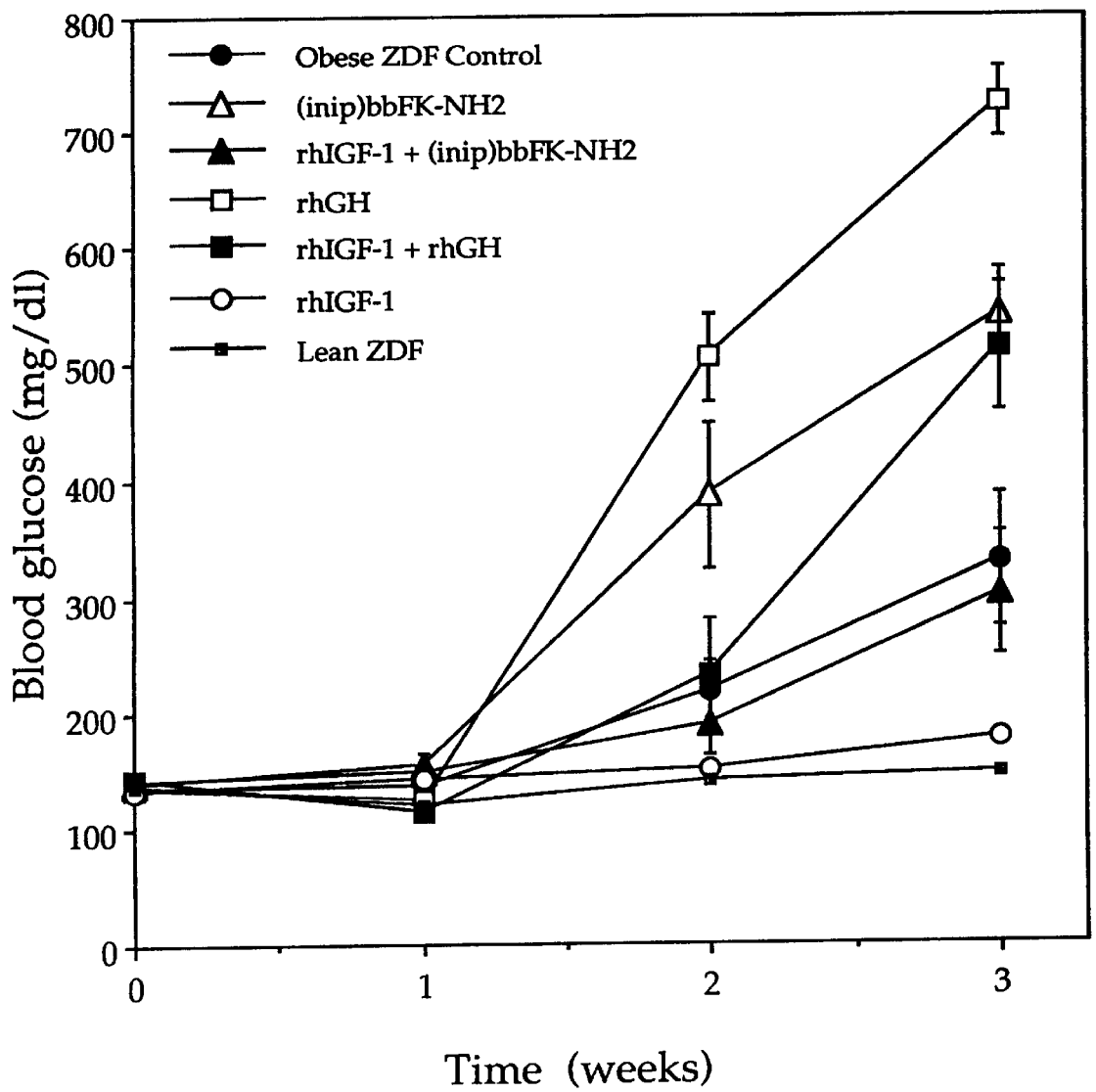
FIG. 24. Basal blood glucose levels obtained weekly in lean (small squares) and obese Type II Zucker Diabetic Fatty (ZDF) male rats treated for 3 weeks subcutaneously with excipient (controls, solid circles), recombinant human growth hormone (rhGH, open squares, 500 μg/d), recombinant human insulin-like growth factor-1 (rhIGF-1, open circles, 758 μg/d), (inip)bbFK-NH2 given by injection (100 μg/d; open triangles), or the combination of rhGH and rhIGF-1 (solid squares), or the combination of rhIGF-1 and (inip)bbFK-NH2 (solid triangles). When given alone, or in combination with rhIGF-1, (inip)bbFK-NH2 had lesser effect on blood glucose (diabetogenic effect) than rhGH at doses with similar somatogenic effects (FIG. 22). Means and standard errors are shown.

Blood glucose: High concentrations of blood glucose were used to define the diabetic state of an animal. Rats were started on treatment before diabetes had developed (there was no difference between lean and obese blood glucose values at day 0). FIG. 24 shows the changes with time in fasting blood glucose for the 6 obese groups and the lean controls. By day 14 the obese rats were clearly diabetic (obese controls 218±27 mg %, lean controls 140±3 mg %). Treatment with rhGH gave a greater (p<0.05) increase in blood glucose (504±38 mg %) than did the GHRP (inip)bbFK-NH$_2$ (386±63 mg %). In addition the combination of GHRP (inip)bbFK-NH$_2$ plus IGF-1 resulted in a blood glucose value of 190±27 mg % comparable to that for rhGH+IGF-1 treatment of 233±49 mg %.

On Day 24 the blood glucose of the obese diabetic rats had risen to more that twice that of the lean controls (147±4 mg % vs. 30±57 mg %) and values were significantly (p<0.05) higher for rhGH treated rats (725±30 mg %) than for GHRP treated rats (542±37 mg %). This difference between rhGH and GHRP was also observed in combination treatment with rhIGF-1. GHRP plus rhIGF-1 resulted in a lower blood glucose measurement (301±53 mg %) than did rhGH+rhIGF-1 treatment (512±55 mg %). However the glucose values in the GHRP+IGF-1 treated group were elevated (p<0.05) compared to animals receiving rhIGF-1 alone (177±4 mg %).

Serum Insulin: At Day 0 the levels in obese rats were elevated compared to lean controls, but there were no differences between the levels in the obese treatment groups. At week 1 IGF-1 treatment significantly reduced serum insulin (obese control, 21±2 ng/ml; IGF-1 treated, 8±1 ng/ml). By itself GHRP (inip)bbFK-NH$_2$ elevated serum insulin 35±6 ng/ml as did rhGH treatment (48±6 ng/ml). However the combination of GHRP (inip)bbFK-NH$_2$ plus IGF-1 significantly lowered insulin (to 10±2 ng/ml) compared to the combination of rhGH plus IGF-1 (25±3 ng/ml, p<0.05). Therefore there was evidence that the combination of GHRP (inip)bbFK-NH$_2$ and IGF-1 stimulated insulin secretion to a lesser extent (was less diabetogenic) than the combination of GH and IGF-1.

Figure 25:
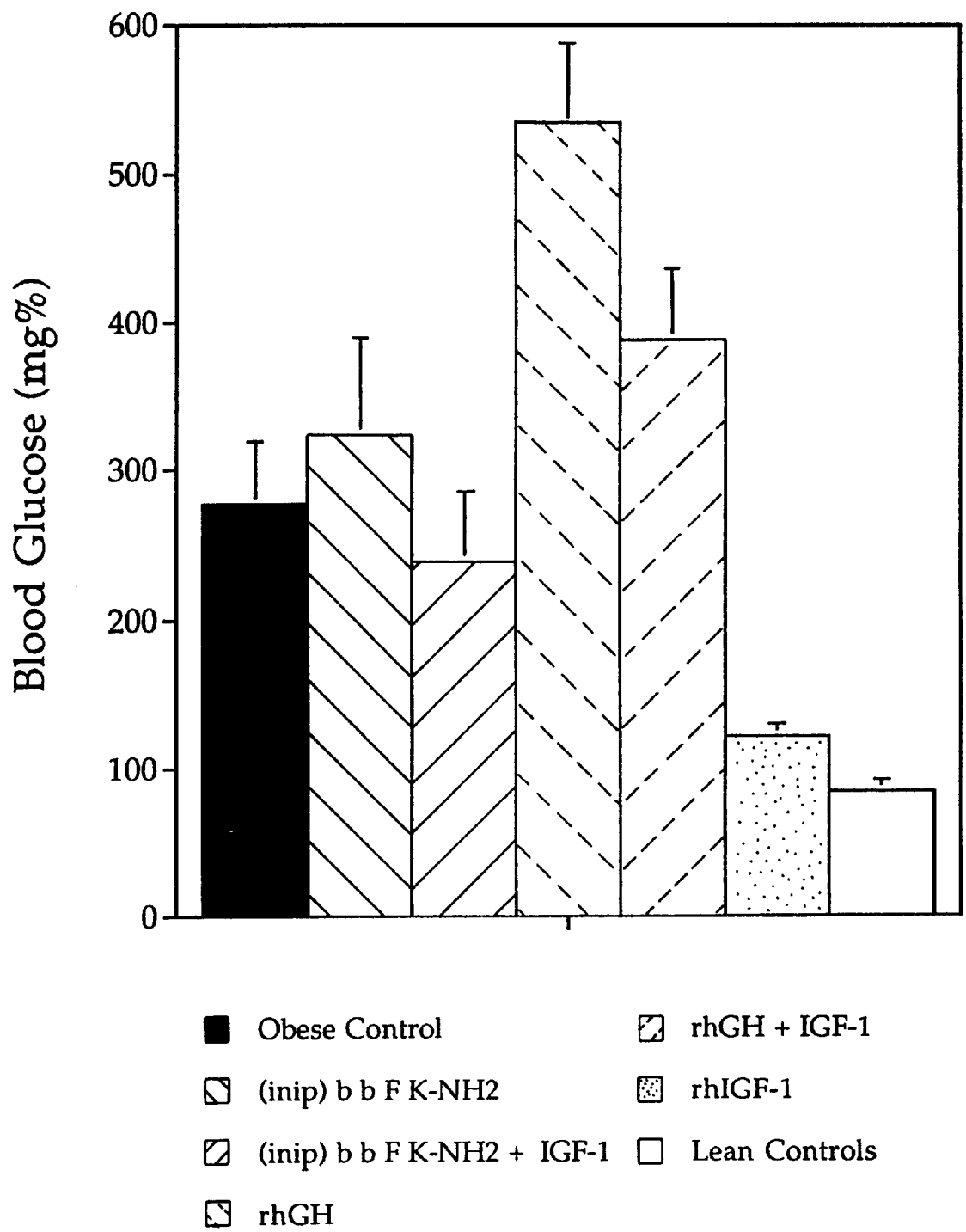
FIG. 25. Blood glucose concentrations following an intravenous insulin challenge (insulin tolerance test) in lean control male rats (open bar), obese Type II Zucker Diabetic Fatty (ZDF) rats treated subcutaneously with excipient (solid bar), recombinant human growth hormone (rhGH, light left-right ascending hatching, 500 μg/d), recombinant human insulin-like growth factor-1 (rhIGF-1, light shaded bar, 758 μg/d), (inip)bbFK-NH2 given by injection (100 μg/d; light left-right descending hatching), or the combination of rhGH and rhIGF-1 (heavy left-right ascending hatching), or the combination of rhIGF-1 and (inip)bbFK-NH2 (heavy left-right descending hatching). When given alone, or in combination with rhIGF-1, (inip)bbFK-NH2 had a greatly reduced effect on insulin sensitivity (diabetogenic effect) than rhGH at doses with similar somatogenic effects (FIG. 22). Means and standard errors are shown.

Insulin Sensitivity: At Day 2 the sensitivity of the animals to insulin was gauged by measuring blood glucose 30 minutes after an insulin challenge (FIG. 25). Following insulin, absolute blood glucose values were again higher in obese diabetic animals (277±42 mg %) than in lean animals (84±8 mg %). However, blood glucose was now reduced in GHRP treated animals to levels (323±67 mg %) not different from those of the obese controls. In contrast, in rhGH treated rats, glucose remained significantly (p<0.05) elevated (533±55 mg %) compared to obese controls or GHRP treated rats. A similar difference between rhGH and GHRP treatment was seen when they were combined with rhIGF-1 treatment. Blood glucose was significantly (p<0.05) lower in GHRP+rhIGF-1 treated rats (238±47 mg %) than in rhGH+ rhIGF-1 treated rats (388±48 mg %).

These experiments compare the anabolic and diabetogenic effects of administered GH and GHRP in a rat model of Type II diabetes. These experiments show for the first time that administered GHRP's have significant anabolic activity when given in combination with IGF-1. This anabolic activity was equivalent to that induced by treatment with GH plus IGF-1. In contrast, administering GH caused significantly greater insulin resistance, as measured by serum glucose and insulin, and by an insulin challenge, than did administered GHRP, even when they were given in combination with rhIGF-1. This study shows that the diabetogenic effect of GHRP (inip)bbFK-NH$_2$ was significantly less than that of rhGH, at doses that produced similar anabolic effects.

F. Administration

The present invention also provides compositions containing an effective amount of compounds of the present invention, including the nontoxic addition salts, amides and esters thereof, which may, alone, serve to provide the above-recited therapeutic benefits. Such compositions can be provided together with physiologically tolerable liquid, gel or solid diluents, adjuvants and excipients.

The compounds and compositions can be administered to mammals including humans in a manner similar to other therapeutic agents. The dosage to be administered will depend on the usual factors including; age, weight, sex, condition of the patient and route of administration. In general, the dosage required for therapeutic efficacy will range from about 0.001 to 1000 μg/kg, more usually 0.01 to 2.5 μg/kg of the host body weight. Alternatively, dosages within these ranges can be administered by constant infusion over an extended period of time until the desired therapeutic benefits have been obtained.

Typically, such compositions are prepared as injectable liquid solutions or suspensions. Compositions may also be emulsified. The active ingredient is often mixed with diluents or excipients which are physiologically tolerable and compatible with the active ingredient. Suitable diluents and excipients are, for example, water saline, dextrose, glycerol, or the like, and combinations thereof. In addition, if desired the compositions may contain minor amounts of auxiliary substances such as wetting or emulsifying agents, stabilizing or pH-buffering agents, and the like. For a more detailed description of the foregoing see a standard pharmaceutical text such as *Remington's Pharmaceutical Sciences,* Mack Publishing Co. Easton, Pa. (1970).

The compositions of this invention are conventionally administered parenterally by injection, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10% preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contain 10%–95% if active ingredient, preferably 25%–70%.

The peptidomimetic compounds may be formulated into the compositions as neutral or salt forms. Pharmaceutically acceptable nontoxic salts include the acid addition salts (formed with the free amino groups) and which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropyl amine, 2-ethylamino ethanol, histidine, procaine, and the like.

EXAMPLES

General Experimental

The compounds synthesized via the routes shown in Scheme I–VI followed standard solid-phase methodologies (Barany, G. and Merrifield, R. B. (1980) in "The Peptides", 2,1–284. Gross, E. and Meienhofer, J. Eds. Academic Press, New York.).

The chemical name abbreviations for common reagents and unusual amino acids used in the examples below are defined as follows (for the definition of acronyms specific to the Tables of Example 39, see Table I):

αNal L-α-Naphthylalanine or (L-3-(1-naphthyl)-Alanine)
BOC tert-Butyloxycarbonyl
BOP benzotriazol-1-yloxy-tri-(dimethylamino)-phosphonium-hexafluorophosphate
BOP-Cl bis(2-oxo-3-oxazolidinyl)phosphinic chloride CBZ Benzyloxycarbonyl
βNal L-β-Naphthylalanine or (L-3-(2-naphthyl)-Alanine)
DβNal D-β-Naphthylalanine or (D-3-(2-naphthyl)-Alanine)
DCM Dichloromethane
DIPC Diisopropylcarbodiimide
DIPEA Diisopropylethylamine
DMF N,N-Dimethylformamide
DMA N,N-Dimethylacetamide
DMSO Dimethylsulfoxide
EDC 1-(3-dimethylaminopropyl)-3-ethylcarbodiimide hydrochloride
FMOC Fluorenyloxymethylcarbonyl
HBTU [2-(1H-benzotriazol-1-yl)-1,1,3,3-tetramethyluronium] hexafluorophosphate
HOBt Hydroxybenzotriazole
inip Isonipecotic acid (Piperidine-4-carboxylic acid)
NBHA p-methylbenzhydrylamine
MeOH Methanol
MS Mass Spectrometry
N-Me N-Methyl
NMM N-Methyl morpholine
NMP N-Methyl pyrolidinone
TEA triethylamine
TFA Trifluoroactic acid
THF Tetrahydrofuran Note: Standard three letter codes are used to designate the natural amino acids with a "D" placed before it signifying the dextrorotatory enantiomer (i.e. D-Phe is D-Phenylalanine)

The generally preferred solid phase chemistry protocols for the synthesis of peptidic compounds of this invention using both BOC- and FMOC- alpha-amine protecting group protocols are shown below. In the absence of a detailed experimental procedure to the contrary, the following chemistry was employed for the synthesis of compounds in the examples:

Standard BOC Chemistry Cycle
1) 3×1 min. DCM
2) check ninhydrin, recouple if positive
3) 1×1 min. 45% TFA*
4) 1×25 min. 45% TFA
5) 1×30 sec DCM
6) 1×1 min. MeOH
7) 2×1 min. DCM
8) 1×1 min. 10% TEA/DCM
9) 1×8 min. 10% TEA/DCM
10) 3×1 min. DCM
11) add preactivated amino acid and couple for 1 h
12) go to step 1

*45% TFA=45% TFA, 45% DCM, 5% anisole, 5% ethane dithiol (by volume)

Notes
a) For peptide amides, use MBHA resin and start the synthesis at step 7.
b) For the coupling of standard amino acids, premix 3 equiv. of amino acid, BOP, and HOBt in DMA for 10 min., add 3 equiv. of NMM, then add mixture to the peptide resin. Gentle bubbling of nitrogen into the slurry my means of a glass frit is a preferred method of agitation during the reaction and washing steps.
c) For coupling to N-α-alkyl-amino acids, use 3 equiv. of amino acid and DIPC, overnight. Alternatively, 3 equiv. of amino acid, BOP-Cl, and DIPEA in DCM, overnight, may be used.

To fully deblock and cleave the peptide from the resin, add (per 1 g resin) 10 mL of HF, 1 mL of anisole, and 0.5 mL of ethylmethylsulfide and stir at 0° C. for 1 h (for peptides containing Trp, 0.25 g of p-cresol must be added). After the HF is removed, the residue is triturated with ether, collected on a glass frit, and washed several times with ether. The crude peptide is extracted off the resin by washing successively with 10% HOAc/water, HOAc, acetonitrile, 10% HOAc/water, and water. The combined filtrates are frozen and lyophilized. Purification, preferably via reverse phase (C-18) HPLC using an acetonitrile (0.1% TFA)/water (0.1% TFA) gradient, provides the pure peptide.

Standard FMOC Chemistry Cycle
1) 5×1 min. DMA
2) check ninhydrin, recouple if positive
3) 1×1 min. 20% piperidine/DCM*
4) 1×15 min. 20% piperidine/DCM
5) 5×1 min. DMA
6) 1×1 min. DCM
7) add preactivated amino acid and couple for 30 min. to 1 h
8) go to step 1

*For the synthesis of peptide acids, the following protocol may be used after deprotection of the second amino acid to prevent the formation of diketopiperizine.

Continue from step 3
4a) 1×30 sec DMA
5a) 1×30 sec DCM
6a) 1×30 sec DMA
7a) 1×30 sec DCM
8a) Add preactivated amino acid and couple for 30 min.–1 h
9a) go to step 1 above Notes
a) For peptide amides, use FMOC-Am-resin (see below for synthesis), pre-swelled with DCM, and start the synthesis at step 3.
b) For coupling of standard amino acids, premix 3 equiv. of the amino acid and BOP in DMA/DCM (1:1) for 10 min., add 3 equiv. of NMM, and add the mixture to the peptide-resin slurry in DMA/DCM (1:1), under gentle nitrogen bubbling.
c) For coupling to N-α-alkyl-amino acids, use 3 equiv. of amino acid and DIPC in DCM, overnight. Alternatively, 3 equiv. of amino acid, BOP-Cl, and DIPEA in DCM, overnight, may be used.
d) To fully deblock and cleave the peptide from the resin, add (per 1 g of resin) 10–15 mL of 95% TFA/triethylsilane (v/v) and shake or stir at room temperature for 1 h. The TFA is removed under vacuum and the residue is triturated with ether, collected on a glass frit, and washed several times with ether. The crude peptide is extracted off the resin by washing successively with 10% HOAc/water, HOAc, acetonitrile, 10% HOAc/water, and water. The combined filtrates are frozen and lyophilized. Purification, preferably via reverse phase (C-18) HPLC using an acetonitrile (0.1% TFA)/water (0.1% TFA) gradient, provides the pure peptide.
e) FMOC-Am-resin was prepared as follows: 60.5 g (0.47 mmol/g, 28.4 mmol, Advanced Chemtech #SA5002) of aminomethylated polystyrene resin was placed in a sintered glass funnel reaction vessel and swelled with DCM for 20 min while being agitated with nitrogen bubbling. The solvent was removed by applying a vacuum to the bottom of the funnel and 10% TEA in DCM added. After 20 min., the resin was washed with three portions of DCM and a solution of 23.0 g of p-[(R, S)-α-[1-(9H-Fluoren-9-yl) methoxyformamido]-2,4-dimethoxybenzyl]-PA (42.6 mmol, Novachem) in 100 mL of DMA added. 100 mL of a 1 M solution of DIPC in DCM (100 mmol) was added and the thick suspension agitated for 3.5 h. The resin was washed five times with DMA, twice with DCM, and twice with methanol. Drying in vacuo gave 70.2 g of FMOC-Am-resin at approximately 0.40 mmol/g substitution.

EXAMPLE 1

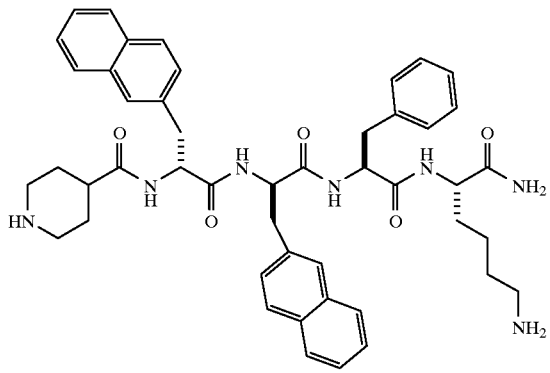

(inip)-DβNal-DβNal-Phe-Lys-amide, TFA Salt

Method A

Step A: (N-ε-BOC)Lys-(Am-resin)

FMOC-Am-resin (10 g, 0.50 mmol/g, 5.0 mmol) was deblocked by agitating with 20% piperidine in DMA for 15 min followed by successive washes with DMA (5x) and DCM (1x). The resin gave a positive test with ninhydrin. A solution of 9.37 g (20.0 mmol) of FMOC-(N-ε-BOC)-L-Lysine, 8.85 g (20.0 mmol) of BOP, and 3.31 mL (30.0 mmol) of NMM in 30 mL of DMA was added and the solution agitated for 1 h. The resin was washed (5x) with DMA and shown to give a negative ninhydrin test. The N-α-FMOC protecting group was removed with 20% piperidine in DMA for 15 min, followed by successive washings with DMA (5x) and DCM (1x) to give (N-ε-BOC)Lys-(Am-resin).

Step B: Phe-(N-ε-BOC)Lys-(Am-resin)

A solution of FMOC-L-Phenylalanine (7.75 g, 20.0 mmol) and BOP (8.85 g, 20.0 mmol) in 50 mL of DMA/DCM (1:1) was preactivated for 10 min and added to the (N-ε-BOC)Lys-(Am-resin) from Step A, followed by NMM (3.31 mL, 30.0 mmol). After 1 h, the resin was washed with DMA (5x, ninhydrin negative), deblocked with 20% piperidine in DMA for 15 min, and washed again with DMA (5x) and DCM (1x) to give Phe-(N-ε-BOC)Lys-(Am-resin), displaying a positive ninhydrin test.

Step C: DβNal-Phe-(N-ε-BOC)-Lys-(Am-resin)

FMOC-D-β-naphthylalanine (4.37 g, 10.0 mmol) and 4.42 g (10.0 mmol) of BOP in 50 mL of DMA/DCM (1:1) was preactivated for 10 min, 1.65 mL (15.0 mmol) of NMM was added, and the mixture added to the Phe-(N-ε-BOC) Lys-(Am-resin) from step B. After agitation for 2 h, the resin was washed with DMA (5x, ninhydrin negative), deblocked with 20% piperidine in DMA for 15 min, and washed again with DMA (5x) and DCM (1x), to give DβNal-Phe-(N-ε-BOC)Lys-Am-resin), displaying a positive ninhydrin test.

Step D: FMOC-DβNal-DβNal-Phe-(N-ε-BOC)Lys-(Am-resin)

FMOC-DβNal (4.37 g, 10.0 mmol) and 4.42 g (10.0 mmol) of BOP in 50 mL of DMA/DCM (1:1) was preactivated for 10 min and added to the DβNal-Phe-(N-ε-BOC) Lys-(Am-resin) from step C, followed by 1.65 mL (15.0 mmol) of NMM. After agitation for 3 h, the resin was washed with DMA (5x, ninhydrin negative), DCM (2x), and methanol (2x). The resin was dried in vacuo to give 15.6 g of FMOC-DβNal-DβNal-Phe-(N-ε-BOC)Lys-(Am-resin) with a substitution level of approximately 0.32 mmol/g.

Step E: N-FMOC-Isonipecotic acid

To a solution of 10.0 g (77.4 mmol) of isonipecotic acid (Aldrich) in 1 N sodium carbonate/dioxane (1:1) at 0° C., was added 21.1 g (77.4 mmol) of 9-fluorenylmethylsuccinimidyl carbonate, portionwise. After 14 h, the dioxane was removed in vacuo, and the suspension diluted with 1200 mL of water. After extraction with 2 portions of ether (discarded), the aqueous solution was cooled in an ice bath and acidified to pH 3 with concentrated hydrochloric acid. The slurry was extracted twice with ethyl acetate and the combined organics washed with water, brine, dried over anhydrous magnesium sulfate, and filtered. The filtrate was concentrated to 500 mL, diluted with 700 mL of hexane, and placed in a refrigerator overnight. The product was collected on a filter and dried in vacuo to give 25.8 g (95%) of N-FMOC-isonipecotic acid as a colorless solid.

Step F: (inip)-DβNal-DβNal-Phe-Lys-amide, TFA salt

FMOC-DβNal-DβNal-Phe-(N-ε-BOC)-Lys-(Am-resin) (1.0 g, 0.32 mmol) was swelled with DCM for 15 min, deblocked with 20% piperidine in DMA for 15 min, and washed with DMA (5x) and DCM (1x), to give DβNal-DβNal-Phe-(N-ε-BOC)-Lys-(Am-resin), displaying a positive ninhydrin test. A preactivated solution of N-FMOC-isonipecotic acid (462 mg, 1.32 mmol), 583 mg (1.32 mmol) of BOP, and 0.217 mL (1.98 mmol) of NMM in 10 mL of DMA/DCM (1:1) was added. After agitation for 2 h, the resin was washed with DMA (5x, ninhydrin negative) and deblocked with 20% piperidine in DMA for 15 min. The resin was washed again with DMA (5x) and DCM (3x) then dried in vacuo. The dry resin was suspended in 10 mL of TFA and 0.50 mL of triethylsilane added. The mixture was agitated for 1 h, concentrated in vacuo, and the resin washed 3x with ether. The crude peptide was recovered from the resin by washing with 10% aqueous HOAc, followed by acetonitrile. The combined filtrates were lyophilized to give 140 mg of a solid. A 70 mg aliquot was purified by reverse phase HPLC (15–20 μ, 300 Å, Vydac C-18, 1×50 cm, gradient: 23–38% acetonitrile (0.1% TFA) in water (0.1% TFA) in 60 min at 9 mL/min,rt=30 min) to give 34 mg of (inip)-DβNal-DβNal-Phe-Lys-amide, TFA salt as a colorless powder after lyophilization. MS (electrospray, M+H) 798.4.

Method B

Step A: BOC-(2-Cl-CBZ)Lys-(MBHA-resin)

A 20.0 g sample of MBHA-resin (substitution @ 1.04 mmol/g, 20.8 mmol) was washed successively with NMP, DCM (2x), 5% DIPEA/DCM (1×1 min), 5% DIPEA/DCM (1×10 min), and DCM (4x). A solution of 25.8 g (3 eq) of BOC-L-(N-ε-(2Cl-CBZ))-Lysine in NMP/DCM (1:1) was added, followed by 8.40 g (3 eq) of HOBt in NMP and 62.4 mL (3 eq) of a 1.0 M solution of DIPC in DCM. After agitation for 1 h, the resin was washed with NMP (1x), DCM (2x), and the coupling judged complete by a ninhydrin test. The resin was neutralized with 5% DIPEA/DCM (1×1 min), 5% DIPEA/DCM (1×10 min), DCM (4x), and capped by the addition of 19.7 mL (10 eq) of acetic anhydride and 14.4 mL (4 eq) of DIPEA in DCM for 10 min. Washing the resin with DCM (3x) gave BOC-(2-Cl-CBZ)Lys-(MBHA-resin).

Step B: BOC-Phe-(2-Cl-CBZ)Lys-(MBHA-resin)

Note: The following synthesis cycle was used for all subsequent couplings to this sample of resin:

1) Deprotect with 50% TFA/DCM for 1 min
2) Deprotect with 50% TFA/DCM for 20 min
3) Wash resin 4× with DCM
4) Neutralize with 5% DIPEA/DCM for 1 min
5) Neutralize with 5% DIPEA/DCM for 5–10 min
6) Wash resin 3× with DCM
7) Wash resin 1× with NMP
8) Preactivate the BOC-amino acid (3 eq) with BOP (3 eq) and HOBt (3 eq) in NMP for 10 min, add NMM (4.5 eq) and transfer to vessel with resin. Couple for 1 h.
9) Wash resin 1× with NMP
10) Wash resin 2× with DCM
11) check ninhydrin for completion of coupling
12) Recouple, if neccessary (steps 4–11)
13) If coupling is complete, proceed with steps 1–11 for coupling of the next residue.

Specifically, BOC-(2-Cl-CBZ)Lys-(MBHA-resin), vide supra, was deblocked, washed, and coupled with 16.4 g (3 eq) of BOC-L-Phe, 27.6 g of BOP, 8.4 g of HOBt, and 10.3 mL of NMM for 40 min to give BOC-Phe-(2-Cl-CBZ)Lys-(MBHA-resin) (ninhydrin negative).

Step C: BOC-DβNal-Phe-(2-Cl-CBZ)Lys-(MBHA-resin)

The above sample of BOC-Phe-(2-Cl-CBZ)Lys-(MBHA-resin) was deblocked, washed, and coupled with 13.1 g (2 eq) of BOC-D-β-naphthylalanine, 18.3 g of BOP, 5.6 g of HOBt, and 6.85 mL of NMM for 1 h giving an incomplete reaction (ninhydrin positive). The resin was recoupled (c.f. step 12 above) using 6.55 g (1 eq) of BOC-D-β-napthylalanine, 9.2 g of BOP, 2.8 g of HOBt, and 3.43 mL of NMM for 1 h to give BOC-DβNal-Phe-(2-Cl-CBZ)Lys-(MBHA-resin) (ninhydrin negative).

Step D: BOC-DβNal-DβNal-Phe-(2-Cl-CBZ)Lys-(MBHA-resin)

The above sample of BOC-DβNal-Phe-(2Cl-CBZ)Lys-MBHA-resin) was deblocked, washed, and coupled with 13.1 g (2 eq) of BOC-D-β-naphthylalanine, 18.3 g of BOP, 5.6 g of HOBt, and 6.85 mL of NMM for 3 h giving BOC-DβNal-DβNal-Phe-(2-Cl-CBZ)Lys-(MBHA-resin) (ninhydrin negative).

Step E: N-BOC-Isonipecotic acid

To a cold solution of 12.4 g (0.31 mmol, 1.0 eq) of sodium hydroxide in 300 ml of water and 600 ml of dioxane was added 40.0 g (0.31 mmol, 1.0 eq) of isonipecotic acid, followed by 84.0 g (38 mmol, 1.2 eq) of di-t-butyl dicarbonate. The mixture was stirred at ambient temperature for 5 h then partitioned between ethyl acetate and 0.5 N citric acid. The organic phase was washed with water, brine, dried over sodium sulfate, and concentrated. The crystalline product was collected by filtration, washed with hexane, and dried under vacuum. Yield: 64.0 g (90%), 1H NMR (300 MHz, CDCl$_3$) δ 10.78 (1H, exc), 4.0 (2H, d), 2.85 (2H,t), 2.48 (1H, m), 1.9 (2H, m), 1.65 (2H, m), 1.42 (9H, s). MS (FAB, M+H) 230.1.

Step F: BOC-(inip)-DβNal-DβNal-Phe-(2-Cl-CBZ)Lys-MBHA-resin)

The above sample of BOC-DβNal-DβNal-Phe-(2Cl-CBZ)Lys-(MBHA-resin) was deblocked, washed, and coupled with 9.54 g (2 eq) of BOC-isonipecotic acid, 18.3 g of BOP, 5.6 g of HOBt, and 6.85 mL of NMM for 1 h, giving BOC-(inip)-DβNal-DβNal-Phe-(2-Cl-CBZ)Lys-(MBHA-resin) (ninhydrin negative).

Step G: (inip)-DβNal-DβNal-Phe-Lys-amide

The above sample of BOC-(inip)-DβNal-DβNal-Phe-(2-Cl(CBZ)Lys-(MBHA-resin) was deblocked, washed, neutralized, washed with DCM (4×), ethanol (4×), and dried in vacuo to yield 40.4 g of (inip)-DβNal-DβNal-Phe-(2Cl-CBZ)Lys-(MBHA-resin). The resin was transfered to a teflon reaction vessel and stirred with a mixture of 200 mL of HF, 20 mL of anisole, and 20 mL of ethyl methyl sulfide at 0° C. for 1 h. The volitiles were removed in vacuo, the resin transfered to a glass fritted funnel and washed repeatedly with ether. The product was extracted from the resin by successive washings with 10% HOAc/water, acetonitrile, and water. The washings were pooled and lyophilized to afford 7.5 g of a powder that was purified by reverse phase HPLC (15–20 μ, 300 Å, Vydac C-18, 5×25 cm, gradient: 25–45% acetonitrile (0.1% TFA) in water (0.1% TFA) in 200 min at 50 mL/min, rt-=50 min) to give 4.39 g of (inip)-DβNal-DβNal-Phe-Lys-amide, TFA salt as a colorless powder after lyophilization. MS (electrospray, M+H) 798.7.

EXAMPLE 2

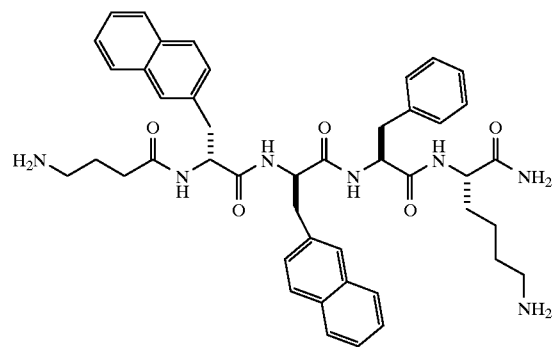

(4-aminobutanoyl)-DβNal-DβNal-Phe-Lys-amide, TFA Salt

FMOC-DβNal-DβNal-Phe-(N-ε-BOC)Lys-(Am-resin) (1.0 g, 0.32 mmol), from Example 1, Method A, step D, was swelled with DCM for 15 min, deblocked with 20% piperidine in DMA for 15 min, and washed with DMA (5×) and DCM (1×) to give DβNal-DβNal-Phe-(N-ε-BOC)Lys-(Am-resin), displaying a positive ninhydrin test. A preactivated solution of N-BOC-4-aminobutyric acid (403 mg, 1.98 mmol), 875 mg (1.98 mmol) of BOP, and 0.33 mL (2.97 mmol) of NMM in 15 mL of DMA/DCM (1:1) was added. After agitation for 1 h, the resin was washed with DMA (5×, ninhydrin negative), DCM (3×), MeOH (2×) and dried in vacuo. The dry resin was suspended in 10 mL of TFA and 0.50 mL of triethylsilane added. The mixture was agitated for 1 h, concentrated in vacuo, and the resin washed with ether. The crude peptide was recovered from the resin by washing with 10% aq HOAc, followed by acetonitrile. The combined filtrates were lyophilized to give 245 mg of a solid. A 50 mg aliquot was purified by reverse phase HPLC (15–20 μ, 300 Å, Vydac C-18, 1×50 cm, gradient: 23–38% acetonitrile (0.1% TFA) in water (0.1% TFA) in 60 min at 9 mL/min, rt=25 min) to give 28 mg of (4-aminobutanoyl)-DβNal-DβNal-Phe-Lys-amide, TFA salt as a colorless powder after lyophilization. MS (electrospray, m+h) 772.4.

EXAMPLE 3

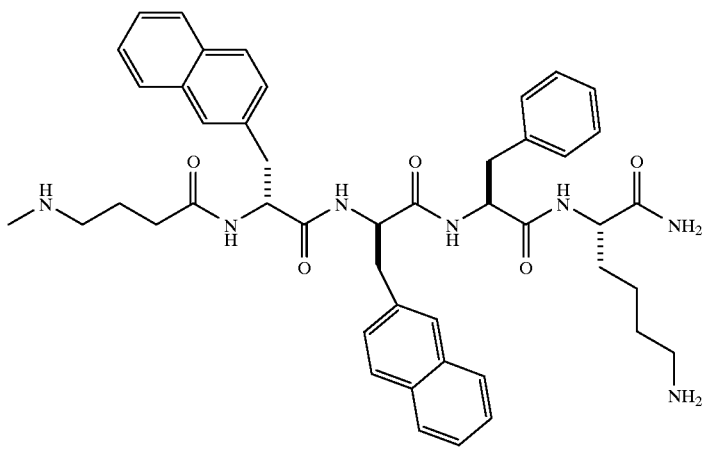

[4-(N-Methylamino)butanoyl]-DβNal-DβNal-Phe-Lys-amide, TFA Salt

Step A: BOC-4-(N-Methylamino)butyric Acid

To a 0° C. solution of 5.00 g (24.6 mmol) of BOC-4-aminobutyric acid in 75 mL of dry THF, was added 12.2 mL (197 mmol) of methyl iodide followed by 2.95 g (73.8 mmol, 60% dispersion in mineral oil) of sodium hydride, portionwise. The reaction was rapidly stirred at room temperature for 12 h and quenched by the careful addition of water. The mixture was partitioned between ether and water, and the organic phase extracted with 1 N aq sodium bicarbonate. The combined aqueous phases were chilled and acidified to pH 3 with 1 N sodium hydrogen sulfate, then extracted with two portions of ethyl acetate. The combined organics were washed successively with water, 5% aq sodium thiosulfate, water, brine, and then dried over anhydrous magnesium sulfate. Concentration in vacuo afforded 5.00 g (94%) of BOC-4-(N-methylamino)butyric acid. $^1$H NMR: (300 MHz, CDCl$_3$) δ 3.28 (2H, bt, J=7 Hz), 2.84 (3H,s), 2.36 (2H,t,J=7.5 Hz), 1.85 (2H, m), 1.45 (9H, s).

Step B: [4-(N-Methylamino)butanoyl]-DβNal-DβNal-Phe-Lys-amide, TFA salt

Following the procedure of Example 2, FMOC-DβNal-DβNal-Phe-(N-ε-BOC)Lys-(Am-resin) (0.50 g, 0.17 mmol, (from Example 1, Method A, Step D) was deblocked and coupled to BOC-4-(N-methylamino)butyric acid (Step A) (147 mg, 0.68 mmol) using 300 mg (0.68 mmol) of BOP and 0.11 mL (1.02 mmol) of NMM. Cleavage from the resin afforded 120 mg of a solid after lyophilization. A 62 mg aliquot was purified by reverse phase HPLC (15–20 μ, 300 Å, Vydac C-18, 1×50 cm, gradient: 23–38% acetonitrile (0.1% TFA) in water (0.1% TFA) in 60 min at 9 mL/min, rt=23 min) to give 27 mg of pure [4-(N-methylamino)butanoyl]-DβNal-DβNal-Phe-Lys-amide, TFA salt. MS (electrospray, M+H) 786.4.

EXAMPLE 4

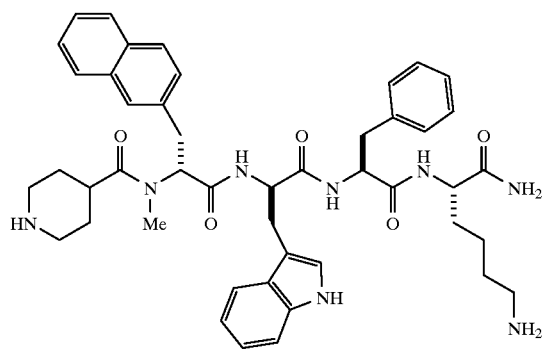

(inip)-(N-Me-DβNal)-DTrp-Phe-Lys-amide, TFA Salt

Step A: DTrp-Phe-(N-ε-BOC)Lys-(Am-resin)

A 1 g (approx. 0.4 mmol) sample of Phe-(N-ε-BOC)Lys-(Am-resin) (Example 1, Method A, Step B) was reacted with a preactivated solution of 0.85 g (2.0 mmol) of FMOC-D-Tryptophan, 0.88 g of BOP, and 0.33 mL of NMM for 1 h. Washing and deprotection as per the general protocol above gave DTrp-Phe-(N-ε-BOC)Lys-(Am-resin), displaying a positive ninhydrin test.

Step B: BOC-N-Methyl-D-β-naphthylalanine (BOC-N-Me-DβNal)

To a cold (0° C.), stirred, THF solution of N-BOC-D-β-naphthylalanine (15.0 g, 47.6 mmol) and methyl iodide (14.8 ml, 238 mmol) was added sodium hydride (5.70 g of 60% dispersion in mineral oil, 143 mmol) in portions over 45 min. The mixture was allowed to warm slowly to ambient temperature over 16 h then partially concentrated and poured into 1 L of dilute aqueous sodium bicarbonate. Neutral species were extracted into ethyl acetate and discarded. The aqueous phase was acidified with citric acid and the separated product extracted into ethyl acetate, washed with dilute sodium bisulfite, brine, dried over magnesium sulfate, and concentrated. The crude product was crystallized from DCM/hexane to yield 14.9 g (95%) of the title compound. $^1$H NMR (300 MHz, CDCl$_3$, rotational isomers evident) δ 1.31 (9H, 2s, BOC), 2.70 (3H, 2s, N-Me), 3.32 (2H, m, CH$_2$Ar), 4.8 (1H, m, CH), 7.54 (7H, m, Ar). MS (FAB,M+H) 330.2.

Step C: FMOC-N-Methyl-D-β-naphthylalanine (FMOC-N-Me-DβNal)

BOC-N-methyl-D-βnaphthylalanine (10.0 g, 30.4 mmol) was dissolved in TFA (100 ml) and stirred for 1 h. The TFA was removed under vacuum and the residue combined with 9-fluorenylmethyl-succinimidylcarbonate (13.3 g, 40.0 mmol), potassium carbonate (6.2 g, 45 mmol), THF (300 ml), water (124 ml), and stirred at ambient temperature for 18 h. The reaction mixture was partitioned between ethyl acetate and dilute aq HCl, and the organic phase washed with brine, dried over magnesium sulfate, and concentrated. The crystalline product was collected by filtration and washed with hexane to yield 12.9 g (94%) of the title compound. $^1$H NMR (300 MHz, DMSO-$d_6$, rotational isomers evident) δ 2.70 (3H, 2s, NMe), 3.20 (2H, m, $CH_2Ar$), 4.18 (3H, m, $OCH_2$ and CHAr), 4.90 (1H, m, COCHN), 7.0 to 8.0 (15H, m, Ar), 13.0 (1H, s, COOH). $[α]^{20}_d$=+48.0° (c=1.625 in MeOH/DCM 1:1). MS (FAB, M+H) 452.3.

Step D: (N-Me-DβNal)-DTrp-Phe-(N-ε-BOC)Lys-(Am-resin)

The DTrp-Phe-(N-ε-BOC)Lys-(Am-resin) from Step A was agitated with a preactivated solution of 0.68 g (1.5 mmol) of FMOC-(N-Me-DβNal), 0.88 g of BOP, and 0.33 mL of NMM for 3 h. Washing and deprotection as per the general FMOC protocol above gave (N-Me-DβNal)-DTrp-Phe-(N-ε-BOC)Lys-(Am-resin) displaying a faint orange ninhydrin test.

Step E: (inip)-(N-Me-DβNal)-DTrp-Phe-Lys-amide, TFA salt (N-Me-DβNal)-DTrp-Phe-(N-ε-BOC)Lys-(Am-resin) (1.0 g, 0.32 mmol, Step D) was treated with a preactivated solution of 0.88 g (2.5 mmol) of N-FMOC-isonipecotic acid, 1.10 g of BOP, and 0.66 mL of NMM for 4 h. After washing with DMA (5×), a ninhydrin test showed the reaction to be incomplete. The resin was recoupled using 0.88 g (2.5 mmol) of N-FMOC-isonipecotic acid, 0.56 g of BOP-Cl, and 0.87 mL of DIPEA for 12 h (ninhydrin negative). The resin was washed, deblocked with 20% piperidine in DMA, washed, and dried in vacuo. Cleavage with TFA and extraction as per the general protocol gave 75 mg of a solid after lyophilization, which was purified by reverse phase HPLC (15–20 μ, 300 Å, Vydac C-18, 1×50 cm, gradient: 17–32% acetonitrile (0.1% TFA) in water (0.1% TFA) in 60 min at 9 mL/min, rt=45 min) to give 23 mg of impure product. Rechromatography (15–20 μ, 300 Å, Vydac C-18, 1×50 cm, gradient: 35–55% methanol (0.1% TFA) in water (0.1% TFA) in 80 min at 10 mL/min, rt=30 min) gave 11 mg of the pure title compound. MS (electrospray,M+H) 801.6.

EXAMPLE 5

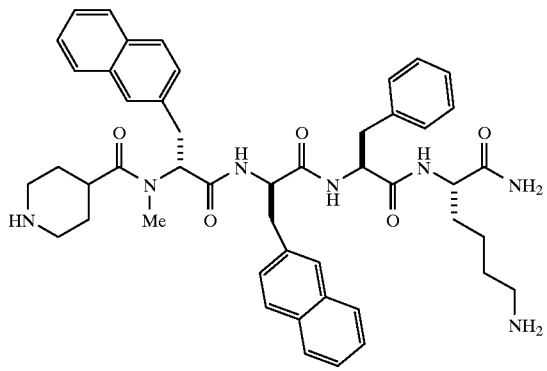

(inip)-(N-Me-DβNal)-DβNal-Phe-Lys-amide, TFA salt

Step A: (N-Me-DβNal)-DβNal-Phe-(2-Cl-CBZ)Lys-(MBHA-resin)

A 0.8 g (approx. 0.3 mmol) sample of BOC-DβNal-Phe-(2-Cl-CBZ)Lys-(MBHA-resin) (Example 1, Method B, Step C) was deblocked, washed, and reacted with a preactivated DMA solution of 0.33 g (1.0 mmol) of BOC-(N-Me-DβNal) (Example 4, step B), 0.44 g of BOP, 0.14 g of HOBt, and 0.11 mL of NMM for 1.5 h. Washing and deprotection as per the general BOC protocol above gave the title compound displaying a light orange, positive ninhydrin test.

Step B: (inip)-(N-Me-DβNal)-DβNal-Phe-Lys-amide, TFA salt

The intermediate from step A was treated with 0.23 g (1.0 mmol) of N-BOC-isonipecotic acid (Example 1, Method B, Step E), 0.29 g of BOP-Cl, and 0.20 mL of DIPEA in DCM for 12 h. Washing, drying, and cleavage as per the general BOC protocol above gave 250 mg of a powder. A 102 mg aliquot was purified by reverse phase HPLC (15–20 μ, 300 Å, Vydac C-18, 1×50 cm, gradient: 23–38% acetonitrile (0.1% TFA) in water (0.1% TFA) in 60 min at 9 mL/min, rt=32 min) to give 23 mg of the title compound. MS (electrospray,M+H) 812.4.

EXAMPLE 6

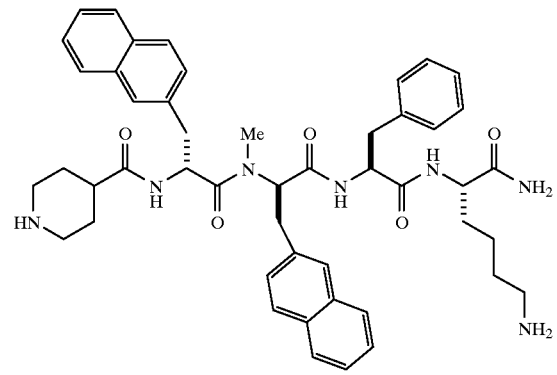

(inip)-DβNal-(N-Me-DβNal)-Phe-Lys-amide, TFA salt

Step A: (N-Me-DβNal)-Phe-(2-Cl-CBZ)Lys-(MBHA-resin)

A 0.80 g (approx. 0.30 mmol) sample of BOC-Phe-(2-Cl-CBZ)Lys-(MBHA-resin (Example 1, Method B, Step B) was deblocked, washed, and reacted with a preactivated DMA solution of 0.33 g (1.0 mmol) of BOC-(N-Me-DβNal) (Example 4, step B), 0.44 g of BOP, 0.14 g of HOBt, and 0.11 mL of NMM for 1.5 h. Washing and deprotection as per the general BOC protocol above gave the title compound displaying a light orange positive ninhydrin test.

Step B: DβNal-(N-Me-DβNal)-Phe-(2-Cl-CBZ)Lys-(MBHA-resin)

The intermediate from step A was treated with 0.32 g (1.0 mmol) of N-BOC-D-β-naphthylalanine, 0.29 g of BOP-Cl, and 0.20 mL of DIPEA in DCM for 12 h. Washing and deprotection as per the general BOC protocol above gave the title compound displaying a positive ninhydrin test.

Step C: (inip) -DβNal-(N-Me-DβNal)-Phe-Lys-amide, TFA salt

The intermediate from step B was reacted with a preactivated DMA solution of 0.23 g (1.0 mmol) of N-BOC-isonipecotic acid, 0.44 g of BOP, 0.14 g of HOBt, and 0.11 mL of NMM for 1 h. Deblocking, washing, drying, and HF cleavage, as per the general BOC protocol above gave 200 mg of a powder. A 67 mg aliquot was purified by reverse phase HPLC (15–20 μ, 300 Å, Vydac C-18, 1×50 cm, gradient: 13–28% acetonitrile (0.1% TFA) in water (0.1% TFA) in 60 min at 9 mL/min, rt=30 min) to give 25 mg of the title compound. MS (electrospray,M+H) 812.4.

EXAMPLE 7

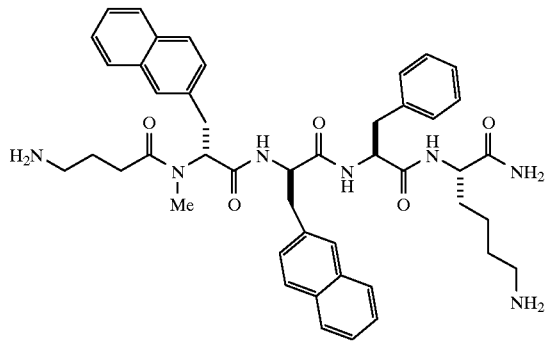

(5-Aminovaleryl)-(N-Me-DβNal)-DβNal-Phe-Lys-amide, TFA salt

Step A: BOC-(N-Me-D-DβNal)-DβNal-Phe-(2-Cl-CBZ)Lys-(MBHA-resin)

A 0.33 mmol sample of BOC-DβNal-Phe-(2-Cl-CBZ)Lys-(MBHA-resin) (Example 1, Method B, Step C) was treated with TFA deblock, neutralized, washed, and coupled with 3 eq of BOC-(N-Me-DβNal) (from Example 4, Step B), 3 eq of BOP, 3 eq of HOBt and 4.5 eq of NMM in DMA/DCM for 1 h. The resin was washed with DMA (5×) to give the title compound (ninhydrin negative).

Step B: (5-Aminovaleryl)-(N-Me-DβNal)-DβNal-Phe-Lys-amide, TFA salt

The above sample of BOC-(N-Me-DαNal)-DβNal-Phe-(2-Cl-CBZ)Lys-(MBHA-resin) was deblocked with TFA, neutralized, washed, and coupled with 4 eq of N-BOC-5-aminovaleric acid, 4 eq of BOP-Cl, and 6 eq of DIPEA in DCM overnight. After confirming complete coupling with the ninhydrin test, the peptide was deblocked with TFA, washed, and dried in vacuo to give (5-aminovaleryl)-(N-Me-DβNal)-DβNal-Phe-(2-Cl-CBZ)Lys-(MBHA-resin). The peptide was cleaved from the resin and lyophilized, using the methods described in the general procedure, to provide 193 mg of a crude solid. A 53 mg aliquot was purified by reverse phase HPLC (15–20 μ, 300 Å, Vydac C-18, 1×50 cm, gradient: 23–38% acetonitrile (0.1% TFA) in water (0.1% TFA) in 60 min at 9 mL/min, rt=43 min) to give 7.4 mg of pure (5-aminovaleryl)-(N-Me-DβNal)-DβNal-Phe-Lys-amide, TFA salt as a colorless powder after lyophilization. MS (electrospray, M+H) 800.2.

EXAMPLE 8

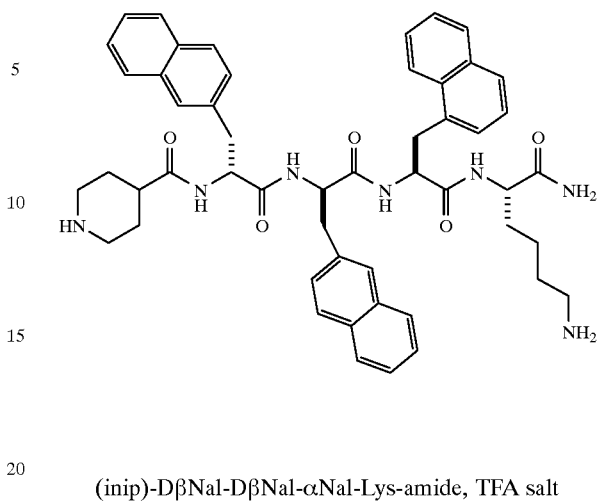

(inip)-DβNal-DβNal-αNal-Lys-amide, TFA salt

Step A: BOC-αNal-(2-Cl-CBZ)Lys-(MBHA-resin)

A 1.0 g sample of BOC-(2-Cl-CBZ)Lys-(MBHA-resin) from Example 1, Method B, Step A, was deblocked, washed, neutralized with 5% DIPEA/DCM, washed, and coupled with 945 mg (3 mmol) of BOC-L-α-napthylalanine, 1.32 g of BOP, and 0.45 mL of NMM for 1 h, giving BOC-αNal-(2Cl-CBZ)Lys-(MBHA-resin) (ninhydrin negative).

Step B: BOC-DβNal-αNal-(2-Cl-CBZ)lys-(MBHA-resin)

The intermediate from Step A was deblocked, washed, neutralized with 5% DIPEA/DCM, washed, and coupled with 945 mg (3 mmol) of BOC-D-β-napthylalanine, 1.32 g of BOP, and 0.45 mL of NMM for 1 h, giving BOC-DβNal-αNal-(2-Cl-CBZ)Lys-(MBHA-resin) (ninhydrin negative).

Step C: BOC-DβNal-DβNal-αNal-(2-Cl-CBZ)Lys-(MBHA-resin)

The resin from Step B was deblocked, washed, neutralized with 5% DIPEA/DCM, washed, and coupled with 945 mg (3 mmol) of BOC-D-β-napthylalanine, 1.32 g of BOP, and 0.45 mL of NMM for 1 h, giving BOC-DβNal-DβNalαNal-(2-Cl-CBZ)Lys-(MBHA-resin) (ninhydrin negative).

Step D: (inip)-DβNal-DβNal-αNal-(2Cl-CBZ)Lys-(MBHA-resin)

The resin from Step C was deblocked, washed, neutralized with 5% DIPEA/DCM, washed, and coupled with 690 mg (3 mmol) of N-BOC-isonipecotic acid, 1.32 g of BOP, and 0.45 mL of NMM for 1 h, giving BOC-(inip)-DβNal-DβNal-αNal-(2-Cl-CBZ)Lys-(MBHA-resin) (ninhydrin negative). The resin was deblocked, washed with methanol, and dried in vacuo to give 1.1 g of the title compound.

Step E: (inip)-DβNal-DβNal-αNal-Lys-amide, TFA salt

The above resin (1.1 g) was cleaved with HF according to the general procedure to afford 87 mg of a solid that was purified by reverse phase HPLC (15–20 μ, 300 Å, Vydac C-18, 1×50 cm, gradient: 25%–40% acetonitrile (0.1% TFA) in water (0.1% TFA) in 60 min at 9 mL/min, rt=min) to give 11 mg of pure (inip)-DβNal-DβNal-αNal-Lys-amide, TFA salt. MS (electrospray,M+H) 848.4.

EXAMPLE 9

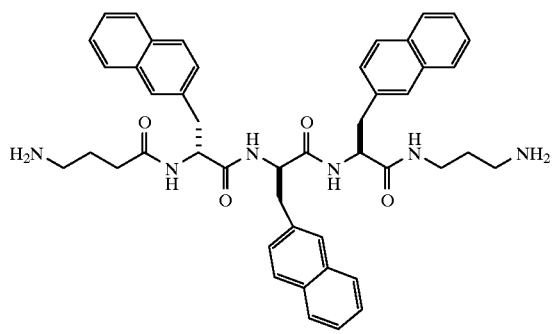

(4-Aminobutanoyl)-DβNal-DβNal-DβNal-[N-(3-aminopropyl)] amide, TFA salt

Step A: 1,3-Propanediamine-carbonylbenzyloxy-resin (PDA-COO-resin)

Hydroxymethyl resin (10 g, 1 meq/g, 100-14 200 mesh, Bachem RMIS35) was washed with 5% DIPEA/DCM, toluen (6×), suspended in 60 ml of toluene and gently agitated with nitrogen bubbling. A solution of phosgene in toluene (70 mL, 1.93 m, Fluka) was added and, after 20 min, the resin was washed with toluene (6×), resuspended in 60 mL of dry THF, and 1,3-Propanediamine (5.0 g, Fluka) was added. The mixture was agitated for 1 h, washed with DMA (5×), and shown to give a positive ninhydrin test. A solution of 10% TFA in DCM was added and the resin was washed with DCM (4×), methanol (2×), and dried in vacuo.

Step B: BOC-βNal-(PDA-COO-resin)

A 3.0 g sample of PDA-COO-resin was neutralized with 5% DIPEA/DCM, washed, and coupled with 2.84 g (9.0 mmol) of BOC-βNal, 3.96 g of BOP, and 1.5 mL of NMM for 1 h (ninhydrin negative). After washing with DCM, the resin was washed with methanol and dried.

Step C: BOC-DβNal-βNal-(PDA-COO-resin)

A 1.0 g sample of the resin from Step B was deblocked, washed, neutralized with 5% DIPEA/DCM, washed, and coupled with 945 mg (3 mmol) of BOC-DβNal, 1.32 g of BOP, and 0.45 mL of NMM for 1 h, giving BOC-DβNal-βNal-(PDA-COO-resin) (ninhydrin negative).

Step D: BOC-DβNal-DβNal-βNal-(PDA-COO-resin)

The above sample was washed, deblocked, washed, neutralized with 5% DIPEA/DCM, washed, and coupled with 945 mg (3 mmol) of BOC-DβNal, 1.32 g of BOP, and 0.45 mL of NMM for 1 h giving BOC-DβNal-DβNal-βNal-(PDA-COO-resin) (ninhydrin negative).

Step E: (4-Aminobutanoyl)-DβNal-DβNal-βNal-(PDA-COO-resin)

The above sample was washed, deblocked, washed, neutralized with 5% DIPEA/DCM, washed and coupled with 609 mg (3 mmol) of N-BOC-4-aminobutyric acid, 1.32 g of BOP, and 0.45 mL of NMM for 1 h (ninhydrin negative). The resin was washed, deblocked, washed with methanol, and dried in vacuo to give 1.3 g of the title compound.

Step F: (4-Aminobutanoyl)-DβNal-DβNal-βNal-[N-(3-aminopropyl)] amide, TFA salt

The above resin (1.3 g) was cleaved with HF to afford 225 mg of a solid after lyophilization. A 60 mg sample was purified by reverse phase HPLC (15–20 μ, 300 Å, Vydac C-18, 1×50 cm, gradient: 25–40% acetonitrile (0.1% TFA) in water (0.1% TFA) in 60 min at 9 mL/min, rt=30 min) to give 29 mg of the title compound. MS (electrospray,M+H) 751.4.

EXAMPLE 10

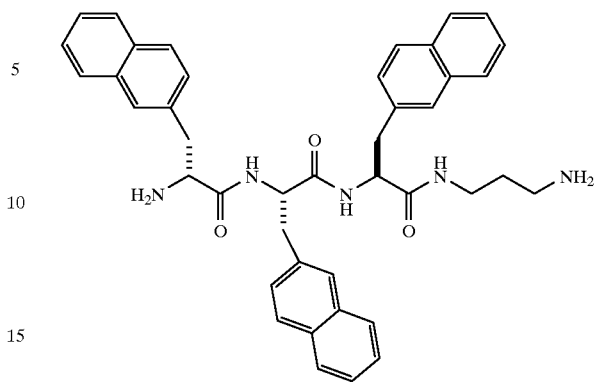

DβNal-βNal-βNal-[N-(3-aminopropyl)] amide, TFA salt

Step A: BOC-βNal-βNal-(PDA-COO-resin)

A 2 g sample of BOC-βNal-(PDA-COO-resin) (from Example 9, Step B) was washed, deblocked, washed, neutralized with 5% DIPEA/DCM, washed, and coupled with 1.89 g (6.0 mmol) of BOC-βNal, 2.64 g of BOP, and 0.90 mL of NMM for 1 h, giving BOC-βNal-βNal-(PDA-COO-resin) (ninhydrin negative). The resin was washed with methanol, and dried in vacuo to give the title compound.

Step B: BOC-DβNal-βNal-βNal-(PDA-COO-resin)

One gram of the above sample was deblocked, washed, neutralized with 5% DIPEA/DCM, washed, and coupled with 945 mg (3 mmol) of BOC-DβNal, 1.32 g of BOP, and 0.45 mL of NMM for 1 h, giving BOC-DβNal-βNal-βNal-(PDA-COO-resin) (ninhydrin negative). The resin was washed, deblocked, washed with methanol, and dried in vacuo.

Step C: DβNal-βNal-βNal-[N-(3-aminopropyl)] amide, TFA salt

The above resin (1.15 g) was cleaved with HF to afford 99 mg of a solid after lyophilization. The sample was purified as per Example 2 (gradient 27%–42% in 60 min (rt=22 min)) to give 58 mg of DβNal-βNal-βNal-[N-(3-aminopropyl)] amide, TFA salt. MS (electrospray,M+H) 666.4.

EXAMPLE 11

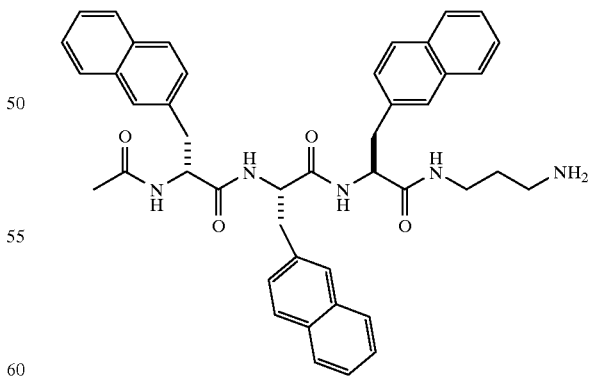

Acetyl-DβNal-βNal-βNal-[N-(3-aminopropyl)] amide, TFA salt

Step A: Acetyl-DβNal-βNal-βNal-(PDA-COO-resin)

A 1.0 g sample of the product of Example 10, Step B was deblocked, neutralized with 5% DIPEA/DCM, and coupled with acetic anhydride (2 mL) in 5% DIPEA/DCM (10 mL) giving Acetyl-DβNal-βNal-βNal-(PDA-COO-resin) (ninhydrin negative). The resin was washed with methanol and dried in vacuo to give 1.23 g of resin.

Step B: Acetyl-DβNal-βNal-βNal-[N-(3-aminopropyl)] amide, TFA salt

The above resin (1.23 g) was cleaved with HF to afford 155 mg of a powder after lyophilization. A 68 mg sample was purified as per Example 2 (gradient 30%–45% in 60 min (rt=40 min)) to give 31 mg of the title compound. MS (electrospray,M+H) 708.4.

EXAMPLE 12

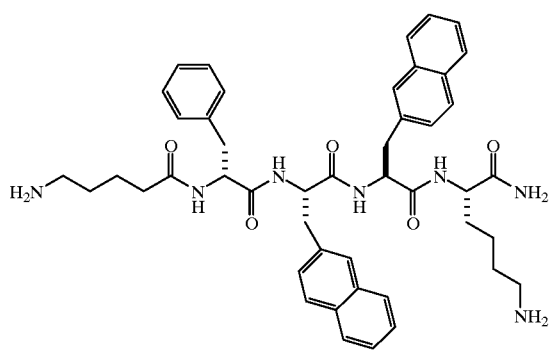

(5-Aminovaleryl)-DPhe-βNal-βNal-Lys-amide, TFA salt

Step A: βNal-(N-ε-BOC)Lys-(Am-resin)

A 0.5 g (approx. 0.25 mmol) sample of (N-ε-BOC)Lys-(Am-resin) (Example 1, Method A, Step A) was reacted with a preactivated solution of 0.44 g (1.0 mmol) of FMOC-L-βNal, 0.44 g of BOP, and 0.17 mL of NMM for 1 h. Washing and deprotection as per the general protocol above gave the title compound.

Step B: βNal-βNal-(N-ε-BOC)Lys-(Am-resin)

The product of step A was reacted with a preactivated solution of 0.44 g (1.0 mmol) of FMOC-L-βNal, 0.44 g of BOP, and 0.17 mL of NMM for 1 h. Washing and deprotection as per the general protocol above gave the title compound.

Step C: DPhe-βNal-βNal-(N-ε-BOC)Lys-(Am-resin)

The produce of step B was reacted with a preactivated solution of 0.39 g (1.0 mmol) of FMOC-D-Phenylalanine, 0.44 g of BOP, and 0.17 mL of NMM for 1 h. Washing and deprotection as per the general protocol above gave the title compound.

Step D: (5-Aminovaleryl)-DPhe-βNal-βNal-Lys-amide, TFA salt

The product of step C was reacted with a preactivated solution of 0.22 g (1.0 mmol) of N-BOC-5-aminovaleric acid, 0.44 g of BOP, and 0.17 mL of NMM for 1 h. Washing, drying, and cleavage as per the general FMOC protocol above gave 100 mg of a powder. A 51 mg aliquot was purified by reverse phase HPLC (15–20 μ, 300 Å, Vydac C-18, 1×50 cm, gradient: 25–40% acetonitrile (0.1% TFA) in water (0.1% TFA) in 60 min at 9 mL/min, rt=25 min) to give 23 mg of the title compound. MS (electrospray, M+H) 786.5.

EXAMPLE 13

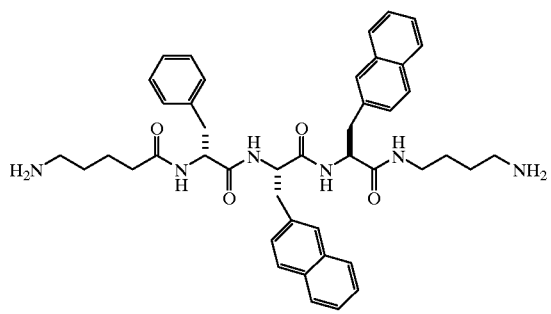

(5-Aminovaleryl)-DPhe-βNal-βNal-[N-(4-aminobutyl)]amide, TFA salt

Step A: 1,4 Butanediamine-carbonylbenzyloxy-resin (BDA-COO-resin

Hydroxymethyl resin (10 g, 1 meq/g, 100–200 mesh, Bachem RMIS35) was washed with 5% DIPEA/CM, toluene (6×), suspended in 60 ml of toluene and gently agitated with nitrogen bubbling. A solution of phosgene in toluene (70 mL, 1.93 M, Fluka) was added and, after 20 min, the resin was washed with toluene (6×), resuspended in 60 mL of dry THF, and 1,4-Diaminobutane (5.0 g, Fluke) was added. The mixture was agitated for 1 h, washed with DMA (5×), and shown to give a positive ninhydrin test. A solution of 10% TFA in DCM was added and the resin was washed with DCM (4×), methanol (2×), and dried in vacuo.

Step B: BOC-βNal-(BDA-COO-resin)

A 1 g sample of BDA-COO-resin from Step A was neutralized with 5% DIPEA/DCM, washed, and coupled with 945 mg (3 mmol) of BOC-βNal, 1.32 g of BOP, and 0.45 mL of NMM for 1 h, giving BOC-βNal-(BDA-COO-resin) (ninhydrin negative).

Step C: BOC-βNal-βNal-(BDA-COO-resin)

The above sample was deblocked, washed, neutralized with 5% DIPEA/DCM, washed, and coupled with 945 mg (3 mmol) of BOC-βNal, 1.32 g of BOP, and 0.45 mL of NMM for 1 h giving BOC-βNal-βNal-(BDA-COO-resin) (ninhydrin negative).

Step D: BOC-DPhe-βNal-βNal-(BDA-COO-resin)

The above sample was deblocked, washed, neutralized with 5% DIPEA/DCM, washed, and coupled with 795 mg (3 mmol) of BOC-D-Phenylalanine, 1.32 g of BOP, and 0.45 mL of NMM for 1 h, giving BOC-DPhe-βNal-βNal-(BDA-COO-resin) (ninhydrin negative).

Step E: BOC-(5Aminovaleryl)-DPhe-βNal-βNal-(BDA-COO-resin)

The the resin from Step D was deblocked, washed, neutralized with 5% DIPEA/DCM, washed, and coupled with 621 mg (3 mmol) of N-BOC-5-aminovaleric acid, 1.32 g of BOP, and 0.45 mL of NMM for 1 h giving BOC-(5-aminovaleryl)-DPhe-βNal-βNal-(BDA-COO-resin) (ninhydrin negative). The resin was washed, deblocked, washed with methanol, and dried in vacuo.

Step F: (5-aminovaleryl)-DPhe-βNal-βNal-[N-(4-aminobutyl)] amide, TFA salt

The above resin (1.1 g) was deblocked with HF to afford 72 mg of solid after lyophilization. The sample was purified as per Example 2 with a 25%–40% gradient (r=22 min) to give 16 mg of the title compound. MS (electrospray,M+H) 729.5.

EXAMPLE 14

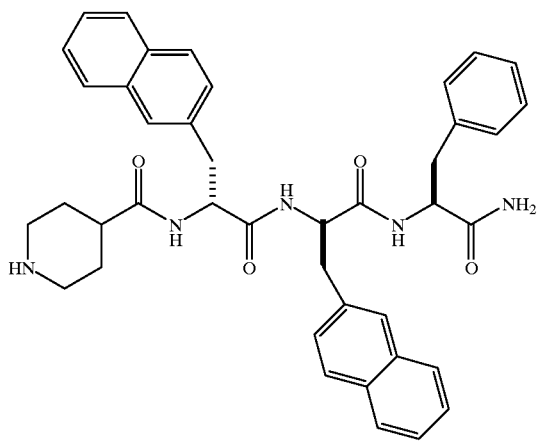

(inip)-DβNal-DβNal-Phe-amide, TFA salt

Step A: Phe-(MBHA-resin)

An 8.0 g sample of MBHA resin (substitution @0.57 mmol/g, 4.56 mmol) was neutralized, washed, and reacted with a preactivated DMA solution of 5.30 g (13.7 mmol) of BOC-L-Phenylalanine, 6.05 g of BOP, 1.85 g of HOBt, and 1.50 mL of NMM for 1.5 h. Washing and deprotection as per the general BOC protocol above gave the title compound.

Step B: DβNal-Phe-(MBHA-resin)

The intermediate from step A was reacted with a preactivated DMA solution of 2.87 g (9.12 mmol) of N-BOC-D-βnaphthylalanine, 4.03 g of BOP, 1.23 g of HOBt, and 1.00 mL of NMM for 1.5 h. Washing and deprotection gave the title compound.

Step C: DβNal-DβNal-Phe-(MBHA-resin)

The intermediate from step B was reacted with a preactivated DMA solution of 2.87 g (9.12 mmol) of N-BOC-D-β-naphthylalanine, 4.03 g of BOP, 1.23 g of HOBt, and 1.00 mL of NMM for 1.5 h. Washing and deprotection as per the general BOC protocol above gave the title compound.

Step D: (inip)-DβNal-DβNal-Phe0amide, TFA salt

One half of the intermediate resin from step C (2.28 mmol) was reacted with a preactivated DMA solution of 1.57 g (6.84 mmol) of N-BOC-isonipecotic acid, 3.02 g of BOP, and 1.00 mL of NMM for 3 h. Deblocking, washing, drying, and HF cleavage as per the general BOC protocol above gave 560 mg of a powder which was purified by reverse phase HPLC (15–20 μ, 300 Å, Vydac C-18, 1×50 cm, gradient: 30–44% acetonitrile (0.1% TFA) in water (0.1% TFA) in 150 min at 9 mL/min, rt=60 min) to give 436 mg of the title compound. MS (electrospray,M+H) 670.4.

EXAMPLE 15

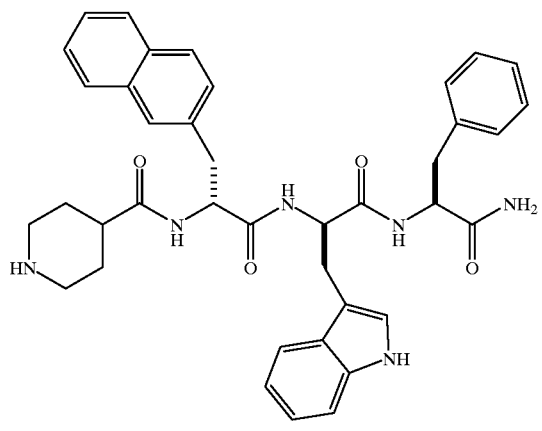

(inip)-DβNal-DTrp-Phe-amide, TFA salt

Step A: DTrp-Phe-(MBHA-resin)

A 2.0 g (approx. 1.14 mmol) sample of Phe-(MBHA-resin) (from Example 14, Step A) was reacted with a preactivated DMA solution of 1.04 g (3.42 mmol) of N-BOC-D-Tryptophan, 1.51 g of BOP, 0.46 g of HOBt, and 0.36 mL of NMM for 1.5 h. Washing and deprotection as per the general BOC protocol above gave the title compound.

Step B: DβNal-(D-Trp)-Phe-(MBHA-resin)

The intermediate from step A was reacted with a preactivated DMA solution of 1.08 g (3.42 mmol) of N-BOC-D-βnaphthylalanine, 1.51 g of BOP, 0.46 g of HOBt, and 0.38 mL of NMM for 1.5 h. Washing and deprotection as per the general BOC protocol above gave the title compound.

Step C: (inip)-DβNal-(D-Trp)-Phe-amide, TFA salt

The intermediate from step B was reacted with a preactivated DMA solution of 0.78 g (3.42 mmol) of N-BOC-isonipecotic acid, 1.51 g of BOP, 0.46 g of HOBt, and 0.38 mL of NMM for 2 h. Deblocking, washing, drying, and HF cleavage as per the general BOC protocol above gave 240 mg of a powder. A 50 mg aliquot was purified by reverse phase HPLC (15–20 μ, 300 Å, Vydac C-18, 1×50 cm, gradient: 23–38% acetonitrile (0.1% TFA) in water (0.1% TFA) in 60 min at 9 mL/min, rt=30 min) to give 23 mg of the title compound. MS (electrospray,M+H) 659.2.

EXAMPLE 16

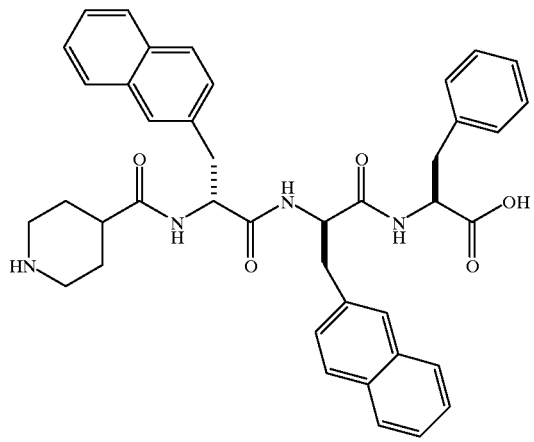

(inip)-DβNal-DβNal-Phe, TFA salt

Step A: BOC-DβNal-Phe-(O-resin)

Commercially available N-BOC-Phe-(O-resin) (8.0 g, 0.55 mmol/g, 4.41 mmol, 1.0 eq) was swelled in DCM, deblocked, washed, and coupled with 2.78 g (8.82 mmol, 2.0 eq) of N-BOC-D-βnaphthylalanine using 7.8 g of BOP, 1.2 g of HOBt, and 1.45 ml of NMM for 3 h, to give N-BOC-DβNal-Phe-(O-resin) (ninhydrin negative) after washing.

Step B: BOC-DβNal-DβNal-Phe-(O-resin)

The above sample of BOC-DβNal-Phe-(O-resin) was deblocked, washed, and coupled with 2.78 g (8.82 mmol, 2.0 eq) of BOC-D-β-naphthylalanine using 7.8 g of BOP, 1.2 g of HOBt, and 1.45 ml of NMM for 3 h to give BOC-DβNal-DβNal-Phe-(O-resin) (ninhydrin negative).

Step C: BOC-(inip)-DβNal-DβNal-Phe-(O-resin)

The above sample of BOC-DβNal-DβNal-Phe-(O-resin) was deblocked, washed, and coupled with 3.0 g (13.2 mmol, 3.0 eq) of N-BOC-isonipecotic acid (from Example 1, Method B, Step E) using 7.8 g of BOP, 1.2 g of HOBt, and 1.45 ml of NMM for 2 h to give BOC-(inip)-DβNal-DβNal-Phe-(O-resin) (ninhydrin negative), which was washed with methanol and dried in vacuo. Yield: 10.1 g Step D: (inip)-DβNal-DβNal-Phe, TFA salt A 3.0 g sample of the above BOC-(inip)-DβNal-DβNal-Phe-(O-resin) was swelled in DCM, deblocked, washed with methanol, dried, and the product cleaved from the resin by the general HF procedure to give 790 mg of (inip)-DβNal-DβNal-Phe of approximately 90% purity. A 37 mg aliquot was purified by HPLC (Vydac C-18, 27 to 42% acetonitrile in water over 60 min, 0.1% TFA, 9 mL/min, 214 nm, rt=41–51 min) to give 4.3 mg of the title compound. MS (electrospray,M+H) 671.2.

EXAMPLE 17

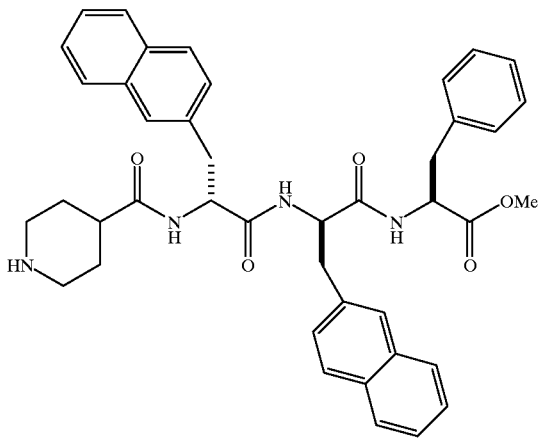

(inip)-DβNal-DβNal-Phe methyl ester, TFA salt

To a solution of 50 mg of (inip)-DβNal-DβNal-Phe (from Example 16, Step D) in 20 ml of methanol was added 10 drops of 1 M HCl in diethyl ether. After stirring overnight, the reaction mixture was concentrated and the product purified by HPLC to give 22 mg of the title compound (Vydac C-18, 1×50 cm, 9 mL/min, 27 to 42% acetonitrile in water over 60 min, 0.1% TFA, 214 nm, rt=39–52 min). MS (electrospray,M+H) 685.4.

EXAMPLE 18

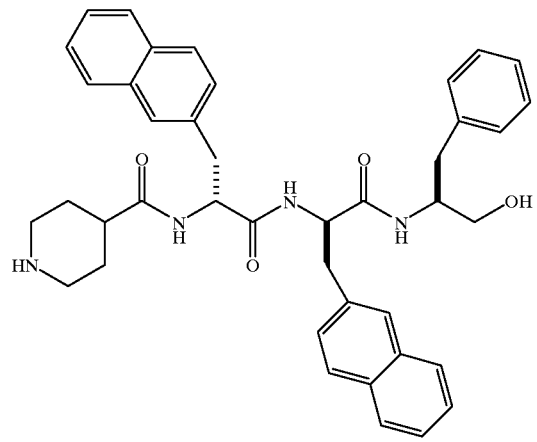

(inip)-DβNal-DβNal-(L-Phenylalanol), TFA salt

Step A: BOC-(inip)-DβNal-DβNal-(L-Phenylalanol)

To 50 ml of dry THF was added 1.5 g (ca. 0.8 mmol, 1.0 eq) of BOC-(inip)-DβNal-DβNal- Phe-(O-resin) (from Example 16, Step C) and 4.0 ml (80 mmol, 10 eq) of 2.0 M lithium borohydride solution in THF. The reaction mixture was gently stirred for 1.5 h, 10 ml of HOAc added dropwise, and stirring continued for another 0.5 h. The resin was filtered off, washed with methanol, and the combined filtrates partially evaporated. The product was partitioned between ethyl acetate and water and the organic phase was washed with brine, dried, evaporated, and the product crystallized from ethyl acetate. IR (cm$^{-1}$): 3409, 3289, 3957, 2930, 1695, 1635, 1536, 1164, 739, 699. MS (FAB, M+H) 757.4.

Step B: (inip)-DβNal-DβNal-(L-Phenylalanol), TFA salt

A solution of 50 mg of BOC-(inip)-DβNal-DβNal-L-Phenylalanol (step A) in 2 ml of DCM was treated with 2 ml of TFA for 1 h, concentrated, and the product purified by HPLC (Vydac C-18, 1×50 cm, 31 to 45% acetonitrile in water over 60 min, 0.1% TFA, 9 mL/min, 214 nm, rt=38–45 min). MS (electrospray,M+H) 657.4.

EXAMPLE 19

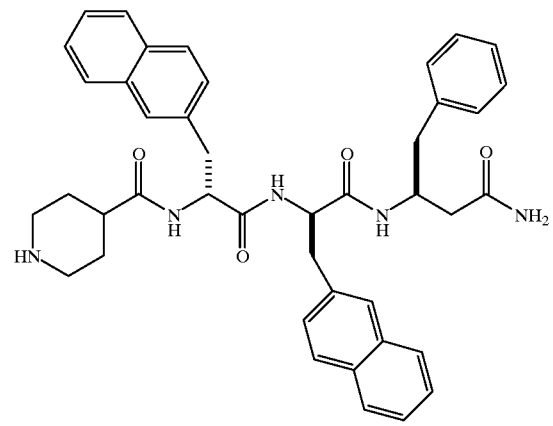

(inip)-DβNal-DβNal-(3(S)-3-benzyl-β-Ala) amide, TFA salt

Step A: 3(S)-3-(t-Butoxycarbonylamino)-4-phenylpropionic acid (N-BOC-3(S)-3-benzyl-β-Ala)

This compound was most conveniently prepared by the method of Ondetti and Engel, *J. Med. Chem.* 18(7), (1975), 761–763. Using this procedure, 2.0 g of commercially available N-BOC-L-Phenylalanine was converted to 760 mg of the title compound in 36% overall yield. $^1$H NMR (300 MHz, CDCl$_3$) δ 11.3 (1H, s, exch), 7.2 (5H, m), 5.1 (1H, d), 2.85 (2H, m), 2.5 (2H, m), 1.4 (9H, s). IR (cm$^{-1}$) 3316, 2977, 2930, 1709, 1662, 1496, 1370, 1164, 1050, 1025, 746, 699. MS (FAB,M+H) 280.0.

Step B: BOC-(3(S)-3-benzyl-β-Ala)-(MBHA-resin)

A 2.54 g sample of MBHA-resin (0.64 mmol/g, 2.06 mmol) was swelled in 1:1 DCM/DMA and coupled with 0.60 g (2.15 mmol, 1.1 eq) of N-BOC-(3(S)-3-benzyl-β-Ala) (from Step A) using 1.44 g of BOP, 241 mg of HOBt, and 196 μl of NMM for 72 h. the resin was washed and capped by acetylation with a mixture of acetic anhydride, TEA, and pyridine in DCM for 15 min, giving the title compound after washing (ninhydrin negative).

Step C: BOC-DβNal-(3(S)-3-benzyl-β-Ala)-(MBHA-resin)

The above sample of BOC-(3(S)-3-benzyl-β-Ala)-(MBHA-resin) was deblocked, washed, and coupled with N-BOC-D-β-napthylalanine using 2.85 g of BOP, 290 mg of HOBt, and 708 μl of NMM for 2 h, according to the general procedure, to give BOC-DβNal-(3(S)-3-benzyl-β-Ala)-(MBHA-resin) (ninhydrin negative).

Step D: BOC-DβNal-DβNal-(3(S)-3-benzyl-β-Ala)-MBHA-resin)

The above sample of BOC-DβNal-(3(S)-3-benzyl-β-Ala)-(MBHA-resin) was deblocked, washed, and coupled with N-BOC-D-β-naphthylalanine, using 2.85 g of BOP, 290 mg of HOBt, and 708 μl of NMM for 2 h to give the title compound (ninhydrin negative).

Step E: BOC-(inip)-DβNal-DβNal-(3(S)-3-benzyl-β-Ala)-(MBHA-resin)

The product of Step D was deblocked, washed, and coupled with N-BOC-isonipecotic acid, using 2.85 g of BOP, 581 mg of HOBt, and 708 μl of NMM for 18 h to give BOC-(inip)-DβNal-DβNal-(3(S)-3benzyl-β-Ala)-(MBHA-resin) (ninhydrin negative).

Step F: (inip)-DβNal-DβNal-(3(S)-3benzyl-β-Ala)-amide, TFA salt

The above sample of BOC-(inip)-DβNal-DβNal-(3(S)-3-benzyl-βAla)-(MBHA-resin) was deblocked, washed with methanol, and dried. The product was cleaved from the resin with HF according to the general procedure to give 280 mg of a solid. A 56 mg portion was purified by HPLC (Vydac C-18, 1×50 cm, 27 to 42% acetonitrile in water over 60 min, 9 mL/min, 0.1% TFA, rt=28–38 min) to give 23 mg of the title compound. MS(electrospray,M+H) 684.2.

EXAMPLE 20

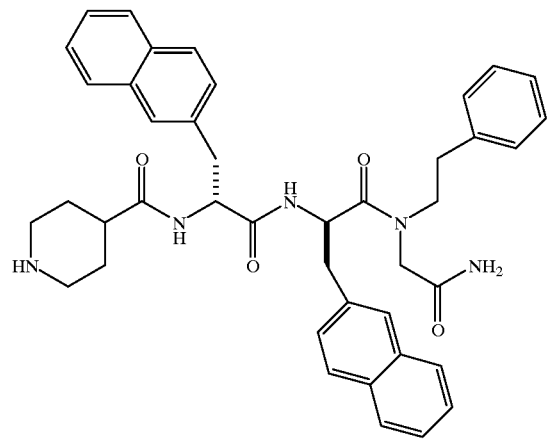

(inip)-DβNal-DβNal-(N-2-phenylethyl-Gly) amide, TFA salt

Step A: 2-Bromoacetyl-(MBHA-resin)

A 2.0 g sample of MBHA-resin (0.64 mmol/g, 1.28 mmol) was swelled in DCM and coupled with 0.36 g (2.56 mmol, 2.0 eq) of bromoacetic acid using 3.84 ml (3.84 mmol, 3.0 eq) of 1M DIPC in DCM for 2 h. The resin was washed with DCM (5×) to give 2-bromoacetyl-(MBHA-resin) (ninhydrin negative).

Step B: BOC-DβNal-(N-2-phenylethyl-Gly)-(MBHA-resin)

The above sample of 2-Bromoacetyl-(MBHA-resin) was taken up in DCM and 4.0 ml of phenethylamine added. After 5 h, the resin was washed (ninhydrin positive) and coupled with 806 mg (2.56 mmol, 2.0 eq) of N-BOC-D-β-naphthylalanine using 1.70 g of BOP, 346 mg of HOBt, and 421 μl of NMM for 18 h, to give the title compound (ninhydrin negative).

Step C: BOC-DβNal-DβNal-(N-2-phenylethyl-Gly)-(MBHA-resin)

The product of step B was deblocked, washed, and coupled to 806 mg (2.56 mmol, 2.0 eq) of N-BOC-D-β-naphthylalanine using 1.70 g of BOP, 346 mg of HOBt, and 421 μl of NMM for 4 h to give BOC-DβNal-DβNal-(N-2-phenylethyl-Gly)-(MBHA-resin) (ninhydrin negative).

Step D: BOC-(inip)-DβNal-DβNal-(N-2-phenylethyl-Gly)-(MBHA-resin)

The above sample of BOC-DβNal-DβNal-(N-2-phenylethyl-Gly)-(MBHA-resin) was deblocked, washed, and coupled to 586 mg (2.56 mmol, 2.0 eq) of N-BOC-isonipecotic acid using 1.70 g of BOP, 346 mg of HOBt, and 421 μl of NMM for 4 h to give BOC-(inip)-DβNal-DβNal-(N-2-phenylethyl-Gly)-(MBHA-resin) (ninhydrin negative).

Step E: (inip)-DβNal-DβNal-(N-2-phenylethyl-Gly) amide, TFA salt

The resin from Step D was deblocked, washed with methanol, dried, and cleaved with HF according to the general procedure to give 802 mg of a solid. A 70 mg portion was purified by HPLC (Vydac C-18, 1×50 cm, 25 to 40% acetonitrile in water over 60 min, 0.1% TFA, 9 mL/min, rt=33–50 min) to give 42 mg of the title compound. MS (electrospray,M+H) 684.2.

EXAMPLE 21

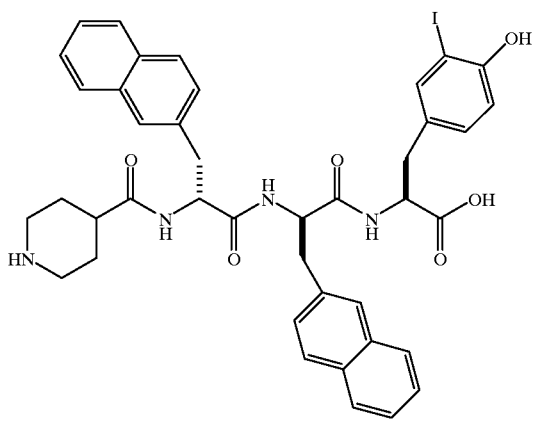

(inip)-DβNal-DβNal-(3-I-Tyr), TFA salt

Step A: [3-I-Tyr(3-BrBzl)]-(O-resin)

N-BOC-(O-3-Bromobenzyl)-3-Iodo-L-Tyrosine [Peninsula Labs, BOC-(3-I-Tyr(3-BrBzl)] was coupled to Hydroxymethyl-resin (Bachem, 1% DVB, 100–200 mesh, 1.0 mmol/g) with DIPC (3 eq) and DMAP (0.25 eq) in DMA for 3 h. The resin was washed, deblocked, and washed again, according to the general procedure to give the title compound (ninhydrin positive).

Step B: DβNal-[3-BrBzl)]-(O-resin)

BOC-DβNal (SyntheTech, 3 eq) was activated with HTU (Richelieu Biotechnologies, 4 eq) and DIPEA in DMA and coupled to the resin for 1 h (ninhydrin negative). The resin was washed, deblocked, and washed again, to give the title compound (ninhydrin positive).

Step C: DβNal-DβNal-[3-BrBzl)]-(O-resin)

BOC-DβNal (3 eq) was activated with HBTU (4 eq) and DIPEA in DMA and coupled to the resin for 1 h (ninhydrin negative). The resin was washed, deblocked, and washed again, to give the title compound (ninhydrin positive).

Step D: (inip)-DβNal-DβNal-[3-I-Tyr(3-BrBzl)]-(O-resin)

N-BOC-isonipecotic acid (3 eq) was activated with HBTU (4 eq) and DUPEA in DMA and coupled to the above resin for 1 h (ninhydrin negative). The resin was washed, deblocked, washed with DCM, MeOH, and dried in vacuo to give the title compound (ninhydrin positive).

Step E: (inip)-DβNal-DβNal-(3-I-Tyr), TFA salt

The intermediate from step D was cleaved with anhydrous HF according to the general procedure to give 350 mg of a solid, which was purified by reverse phase HPLC (15–20μ, 300 Å, Vydac C-18, 2.5×27 cm, gradient: 32–46% acetonitrile (0.1% TFA) in water (0.1% TFA) in 80 min at 18 mL/min, rt=20 min) to give 101 mg of (inip)-DβNal-DβNal-(3-I-Tyr), TFA salt as a colorless powder after lyophilization. MS (electrospray, M+H) 813.0.

EXAMPLE 22

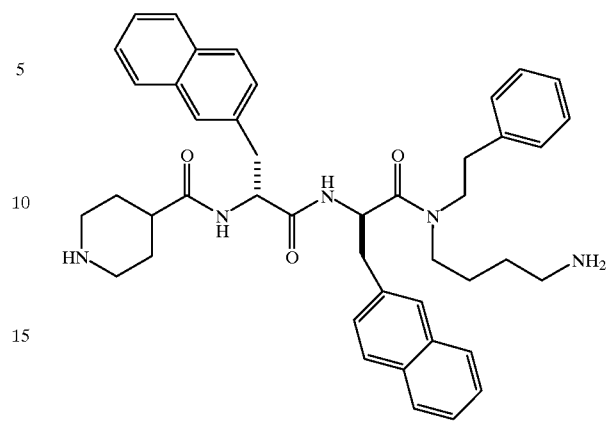

(inip)-DβNal-DβNal-[N-(2-phenylethyl), N-(4-aminobutyl)]amide, TFA salt

Step A: DβNal-[4-N-(2-phenylethyl)]-(BDA-COO-resin)

A 1.0 g sample of the BDA-COO-resin from (Example 13, Step A) was swelled with DCM, and a solution of 1% HOAc in DMF added, followed by 69 mg (1.2 eq) of phenylacetaldehyde and 60 mg of sodium cyanoborohydride. After 14 h, the resin was washed repeatedly with DMA and DCM (ninhydrin test showed a red color replacing the deep blue of the starting resin), and the resin neutralized. To a DCM slurry of the resin was added 0.45 g (1.44 mmol) of BOC-D-β-naphthylalanine, 0.43 g of BOP-Cl, and 0.30 mL of DIPEA. After 14 h, the resin was washed, deblocked, and washed again to give the title compound (ninhydrin positive).

Step B: DβNal-DβNal-[4-N-(2-phenylethyl)]-(BDA-COO-resin)

The intermediate from step A was reacted with a preactivated DMA solution of 0.45 g (1.44 mmol) of BOC-D-β-naphthylalanine, 0.64 g of BOP, 0.19 g of HOBt, and 0.21 mL of NMM for 1.5 h. The resin was washed, deblocked, and washed again, giving the title compound (ninhydrin negative).

Step C: (inip)-DβNal-DβNal-[N-(2-phenylethyl), N-(4-aminobutyl)]amide, TFA salts The intermediate from step B was reacted with a preactivated DMA solution of 0.33 g (1.44 mmol) of N-BOC-isonipecotic acid, 0.64 g of BOP, 0.19 g of HOBt, and 0.21 mL of NMM for 2 h. The resin was washed, deblocked, washed with methanol, and dryed in vacuo. HF cleaveage as per the general BOC protocol above gave 100 mg of a powder, that was purified by reverse phase HPLC (15–20μ, 300 Å, Vydac C-18, 1×50 cm, gradient: 23–38% acetonitrile (0.1% TFA) in water (0.1% TFA) in 60 min at 9 mL/min. rt=35 min) to give 10 mg of the title compound. MS (electrospray, M+H) 698.4.

EXAMPLE 23

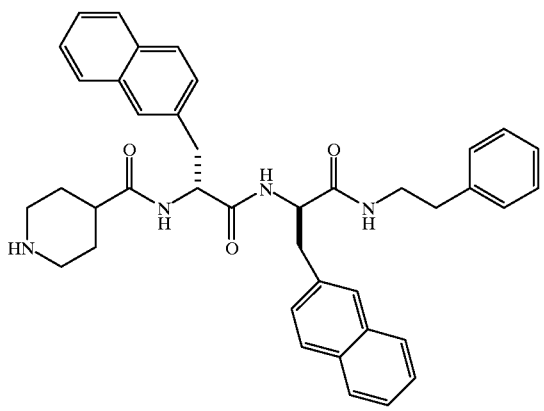

(inip)-DβNal-DβNal-(N-2-phenylethyl)amide, TFA salt

Step A: FMOC-DβNal-(Wang resin)

Wang resin (6.0 g, 0.63 mmol/g, 3.78 mmol) was swelled in DCM and coupled with 2.48 g (5.67 mmol) of N-FMOC-D-β-naphthylalanine using DIPC (11.3 mL of a 1 M solution in DCM, 11.3 mmol) and 100 mg of DMAP in DCM for 6 h, to give the title compound, after washing with methanol and drying in vacuo (yield 8.14 g).

Step B: Dβ-Nal-DβNal-(Wang resin)

Employing the standard FMOC chemistry cycle above, a 4.0 g sample of FMOC-DβNal-(Wang resin) (0.63 mmol/g, 2.52 mmol) was swelled in DCM, deblocked, washed, and coupled with 2.20 g (5.04 mmol) of N-FMOC-DβNal using 2.23 g of BOP, and 0.83 ml of NMM for 1.5 h. The sample was then deblocked and washed to give DβNal-DβNal-(Wang resin) (ninhydrin positive).

Step C: BOC-(inip)-Dβ-Nal-DβNal-(Wang resin)

The above sample of Dβ-Nal-DβNal-(Wang resin) was coupled with 2.31 g (10.1 mmol) of N-BOC isonipecotic acid (from Example 1, Method B, Step E) using 4.45 g of BOP and 1.38 ml of NMM for 2 h to give BOC-(inip)-Dβ-Nal-(Wang-resin) (ninhydrin negative), which was washed with methanol and dried in vacuo.

Step D: (inip) NβNal-DβNal-(N-2-phenylethyl) amide, TFA salt

A 0.30 g sample of the above BOC-(inip)-DβNal-(Wang resin) was suspended in 5 mL of phenethylamine (Aldrich) and 5 mL of DMA. The stirred mixture was placed in a 50° C. oil bath under nitrogen for 18 h, filtered, and the resin washed with DCM. The filtrate was concentrated and partitioned between 1 N sodium hydrogen sulfate and ethyl acetate. The organic phase was washed successively with 1 N sodium bicarbonate, water, brine, and dried over magnesium sulfate. Concentration gave an oil that was treated with 6 mL of DCM/TFA (1:1) for 1 h at ambient temperature and concentrated to give 30 mg of a gum. Purification by reverse phase HPLC (15–20μ, 300 Å, Vydac C-18, 1×50 cm, gradient: 23–38% acetonitrile (0.1% TFA) in water (0.1% TFA) in 60 min at 9 mL/min, rt=33 min) gave 7.6 mg of the title compound. MS (electrospray, M+H) 627.6.

EXAMPLE 24

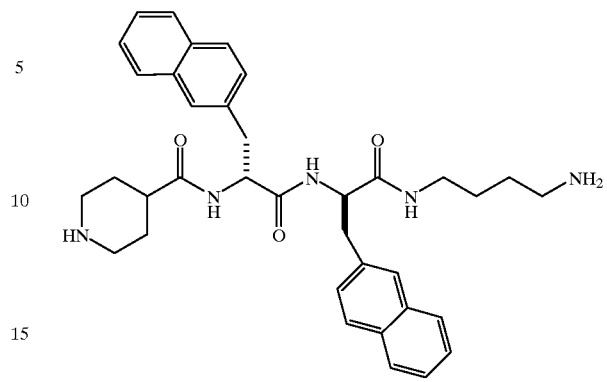

(inip)-DβNal-DβNal-[N-(4-aminobutyl)]amide, TFA salt

Step A: BOC-DβNal-(BDA-COO-resin)

A 5.0 g (0.24 mmol/g, 1.2 mmol) sample of the BDA-COO-resin from Example 13, Step A was neutralized, washed with DCM, and coupled with 0.76 g (2.4 mmol) of BOC-Dβ-Nal, 1.06 g of BOP, 0.32 g of HOBt, and 0.40 mL of NMM for 2 h according to the general BOC chemistry protocols given above. The resin was washed, giving BOC-Dβ-Nal-(BDA-COO-resin) (ninhydrin negative).

Step B: BOC-DβNal-DβNal-(BDA-COO-resin)

The above sample was deblocked, washed, neutralized, washed, and coupled with 0.76 g (2.4 mmol) of BOC-Dβ-Nal, 1.06 g of BOP, 0.32 g of HOBt, and 0.40 mL of NMM for 2 h, giving BOC-DβNal-DβNal-(BDA-COO-resin) (ninhydrin negative).

Step C: (inip)-DβNal-DβNal-(BDA-COO-resin)

The resin from Step B was washed, deblocked, washed, neutralized, washed, and coupled with 0.55 g (2.4 mmol) of N-BOC-isonipecotic acid (Example 1, Method B, step E), 1.06 g of BOP, 0.32 g of HOBt, and 0.40 mL of NMM for 2h, giving BOC-(inip)-DβNal-DβNal-(BDA-COO-resin) (ninhydrin negative). The resin was washed with DCM, deblocked, washed with DCM, methanol, and dried in vacuo.

Step D: (inip)-DβNal-DβNal-[N-(4-aminobutyl)]amide, TFA salt

The above resin (6 g) was cleaved with HF according to the general procedure and afforded 320 mg of a solid after lyophilization. The sample was purified by reverse phase HPLC (15–20μ, 300 Å, Vydac C-18, 1×50 cm, gradient: 12%–26% acetonitrile (0.1% TFA) in water (0.1% TFA) in 80 min at 9 mL/min, rt=18 min) to give 138 mg of the title compound. MS (electrospray, M+H) 594.2.

EXAMPLE 25

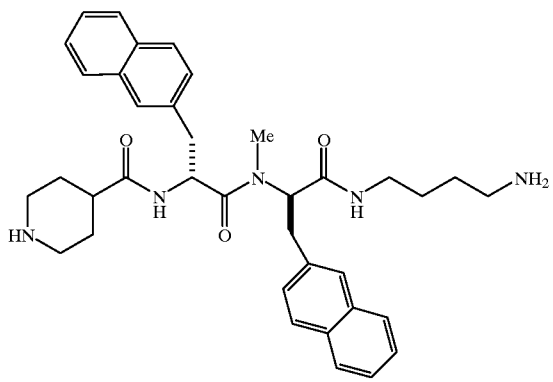

(inip)-DβNal-(N-Me-DβNal)-[N-4-aminobutyl)]
amide, TFA salt

Step A: BOC-(N-Me-DβNal)-(BDA-COO-resin)

A 1.0 g sample of BDA-COO-resin from Example 13, Step A was washed, neutralized with 5% DIPEA/DCM, washed, and coupled with 981 mg (3 mmol) of BOC-(N-Me-DβNal), 1.32 g of BOP, and 0.45 mL of NMM for 1 h giving BOC-(N-Me-DβNal)-BDA-COO-resin) (ninhydrin negative).

Step B: BOC-DβNal-(N-Me-DβNal)-(BDA-COO-resin)

The above sample was washed, deblocked, washed, neutralized with 5% DIPEA/DCM, and washed. BOC-DβNal (3.29 g, 10 mmol) was activated with DIPC (5.0 mL, 1.0 M in DCM) in 15 mL DCM for 4 min, then added to the resin. After 6 h, the resin was washed, giving BOC-DβNal-(N-Me-DβNal)-(BDA-COO-resin) (ninhydrin negative).

Step C: (inip)-DβNal-(N-Me-DβNal)-(BDA-COO-resin)

The above sample was deblocked, washed, neutralized with 5% DIPEA/DCM, washed, and coupled with 648 mg (3 mmol) of N-BOC-isonipecotic acid, 1.32 g of BOP, and 0.45 mL of NMM for 1 h, giving BOC-(inip)-DβNal-(N-Me-DβNal)-(BDA-COO-resin) (ninhydrin negative). The resin was washed with DCM, deblocked, washed with DCM, methanol, and dried in vacuo to give 1.2 g of the title compound.

Step D: (inip)-DβNal-(N-Me-DβNal)-[N-(4-aminobutyl)] amide, TFA salt

The above resin (1.2 g was cleaved with HF according to the general procedure to afford 100 mg of a solid after lyophilization. A 57 mg sample was purified by reverse phase HPLC (15–20μ, 300 Å, Vydac C-18, 1×50 cm, gradient: 20–35% acetonitrile (0.1% TFA) in water (0.1% TFA) in 60 min at 9 mL/min, rt=28 min) to give 27 mg of the pure title compound. MS electrospray, M+H) 607.7.

EXAMPLE 26

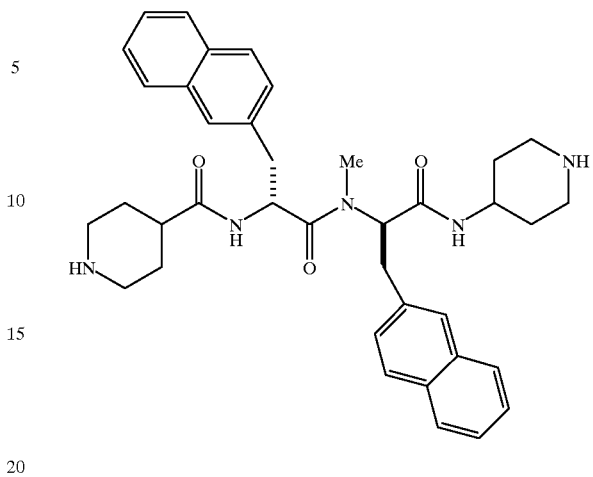

(inip)-DβNal-(N-Me-DβNal)-N-(4-piperidinyl) amide, TFA salt

Step A: N-CBZ-isonipecotic acid

Benzyl chloroformate (16.4 mL, 115 mmol) in toluene (50 mL) was added dropwise to a stirred solution of 12.9 g (100 mmol) of isonipecotic acid (Aldrich) and 21.0 g (250 mmol) of sodium bicarbonate in 200 mL of water. After 14 h, the mixture was extracted with ether (3×50 ml) and the ether layers were discarded. The aqueous layer was acidified with conc. HCl to pH 2, causing the product to precipitate. The product was partitioned into ethyl acetate (3×50 mL) and the combined organic layers were washed with brine, dried over magnesium sulfate, and concentrated in vacuo to yield 22.6 g (86%) of N-CBZ-isonipecotic acid as a viscous oil.

Step B: N-CBZ-4-(BOC-amino)-piperidine

A solution of N-CBZ-isonipecotic acid (10.3 g, 38.9 mmol) in tert-butyl alcohol (100 mL) and DCM (100 mL) was treated with diphenylphosphoryl azide (11.8 g, 42.8 mmol), TEA (5.97 mL, 42.8 mmol), and the resulting mixture was heated at reflux for 3 days. The solution was concentrated in vacuo and the residue was partitioned between ether and water. The organic layer was washed successively with 10% aq citric acid, sat. sodium bicarbonate, brine, dried over magnesium sulfate, and concentrated to an oil. This residue was purified by silica gel flash chromatography (gradient elution, 7:3 to 1:1 hexane-ether) to afford 3.2 g (25%) of the title compound as a colorless crystalline solid: TLC R$_f$ 0.21 (1:1 hexane/ethyl ether).

Step C: 4-(BOC-amino)-piperidine

N-CBZ-4-(BOC-amino)-piperidine (3.0 g, 9.0 mmol) was dissolved in ethanol (100 mL) and transferred into a Parr shaker bottle. After adding 10% palladium on carbon (0.5 g), the mixture was shaken under an atmosphere of hydrogen at 50 psi for 0.75 h on a Parr apparatus. The catalyst was removed by filtration through a pad of Celite. The filter cake was washed with ethanol and the combined filtrate and washings were concentrated in vacuo to yield 1.8 g (100%) of crude 4-(BOC-amino)-piperidine as a pale yellow oil. This product was used immediately in the next step without further purification.

Step D: [4-(BOC-amino)-piperidine]-(COO-resin)

Hydroxymethyl resin (4.0 g of 0.45 mmol/g, 1.8 mmol) was rinsed several times with tolune. A solution of 20% phosgene in toluene (50 mL) was added to the hydroxymethyl resin (2×30 min) to generate the chloroformate intermediate. After rinsing the resin several times with toluene and dioxane, a solution of 4-(BOC-amino)-piperidine (Step C, 1.8 g, 9.0 mmol) in dioxane was added, and the resulting mixture was agitated for 3 h. The resin was rinsed with dioxane, DCM, and dried in vacuo, to provide 4.4 g of the title compound.

Step E: BOC-(N-Me-DβNal)-[4-(4-amino-piperidine)]-(COO-resin)

An aliquot (0.82 g, ~0.33 mmol) of the resin from Step D was treated with TFA deblock, neutralized, washed, and coupled with 3 eq of BOC-N-Me-DβNal) (from Example 4, Step B), 3 eq of BOP, 3 eq of HOBt and 4.5 eq of NMM in DMA/DCM for 1 h, after which a negative ninhydrin test was observed.

Step F: FMOC-DβNal-(N-Me-DβNal)-[4-(4-amino-piperidine)]-(COO-resin)

The above sample of BOC-(N-Me-DβNal)-[4-(4- amino-piperidine)]-(COO-resin) was deblocked with TFA, neutralized, washed, and coupled with 4 eq of FMOC-D-β-naphthylalanine, 4 eq of BOP-Cl, and 6 eq of DIPEA in DCM overnight, after which a negative ninhydrin test was observed.

Step G: (inip)-DβNal-(N-Me-DβNal)-N-(4-piperidinyl) amide, TFA salt

The above sample of FMOC-DβNal-(N-Me-DβNal)-[4-(4-amino-piperidine)]-(COO-resin) was deblocked with 20% piperidine/DMA, washed, and coupled with 3 eq of N-BOC-isonipecotic acid (from Example 1, Method B, Step E), 3 eq of BOP, 3 eq of HOBt, and 4.5 eq of NMM in DMA/DCM for 1 h, after which a negative ninhydrin test was observed. The peptide was deblocked with TFA, washed, and dried in vacuo to give (inip)-DβNal-(N-Me-DβNal)-[4-(4-amino-piperidine)]-(COO-resin). This peptide was cleaved from the resin with HF and lyophilized as per the general procedure to provide 88 mg of a crude solid. This solid was purified by reverse phase HPLC (15–20μ, 300 Å, Vydac C-18, 1×50 cm, gradient: 23–38% acetonitrile (0.1% TFA) in water (0.1% TFA) in 60 min at 9 mL/min, rt=43 min) to give 39 mg of the title compound as a colorless powder after lyophilization. MS (electrospray, M+H) 619.4.

EXAMPLE 27

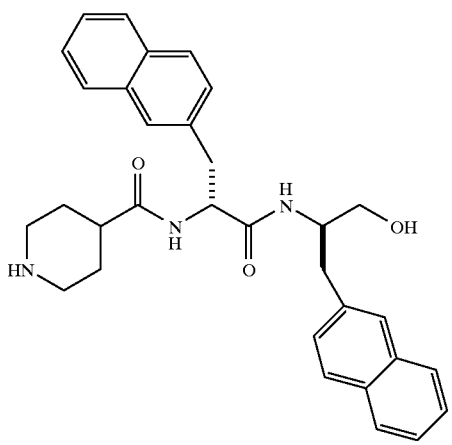

(inip)-DβNal-(D-β-napthylalanol), TFA salt

A 0.30 g sample of BOC-(inip)-DβNal-DβNal-(Wang resin) (from Example 23, Step C) was suspended in 5 mL of THF under nitrogen and 0.90 mL of a 2.0 M solution of lithium borohydride in THF (Aldrich) added. After 1.5 h, 2 mL of HOAc was added carefully, the suspension filtered, and the resin washed with MeOH. The combined filtrates were concentrated three times from MeOH to give a solid, which was treated with 9 mL of TFA/DCM (3:1) containing a few drops of triethylsilane for 1 h. The solution was concentrated to give 270 mg of a solid, which was purified by reverse phase HPLC (15–20μ, 300 Å, Vydec C-18, 2.5×27 cm, gradient: 25–39% acetonitrile (0.1% TFA) in water (0.1% TFA) in 80 min at 18 mL/min, rt=50 min) to give 39 mg of the title compound. MS (electrospray, M+H) 510.0.

EXAMPLE 28

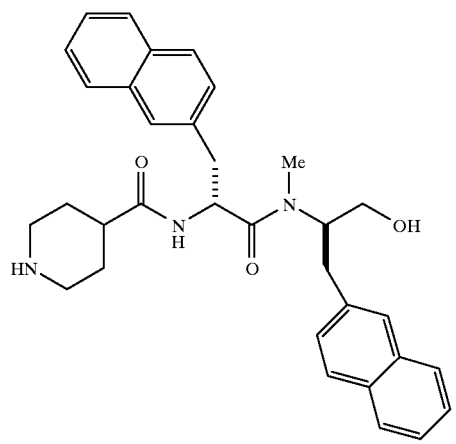

(inip)-DβNal-(N-Methyl-D-β-naphthylalanol), TFA salt

Step A: (N-Me-DβNal)-(O-resin)

A 1.48 g (4.50 mmol) sample of BOC-N-Methyl-D-β-naphthylalanine (from Example 4, Step B) was coupled to 1.5 g (1.0 mmol/g, 1.5 mmol) of hydroxymethyl-resin with DIPC (4.50 mL of a 1.0 M solution in DCM, 4.50 mmol) and 55 mg (0.45 mmol) of DMAP in DMA/DCM (1:1) for 2 h. The resin was washed, deblocked, and washed according to the general BOC procedure, to give the title compound (beads give an orange ninhydrin test).

Step B: DβNal-(N-Me-DβNal)-(O-resin)

The above (D-Me-DβNal)-(O-resin) was coupled with 1.42 g (4.50 mmol) of BOC-D-β-naphthylalanine, 1.01 g of BOP-Cl, and 1.46 mL of DIPEA in DCM for 12 h. The resin was washed and deblocked (ninhydrin positive) to give the title compound.

Step C: BOC-(inip)-DβNal-(N-Me-DβNal)-(O-resin)

To a slurry of the above DβNal-(N-Me-DβNal)-(O-resin) in DCM/DMA (1:1) was added 1.03 g (4.50 mmol) of N-BOC-isonipecotic acid, 1.99 g of BOP, and 0.61 g of HOBt, followed by 1.0 mL of NMM. After 1 h, the resin was washed, washed again with methanol, and dried in vacuo to give 2.33 g of the title compound.

Step D: (inip)-DβNal-(N-Methyl-D-β-naphthylalanol), TFA salt

A 1.0 g (0.64 mmol) sample of the above BOC-(inip)-DβNal-(n-Me-DβNal)-(O-resin) was suspended in 10 mL of THF under nitrogen and 3.2 mL of a 2.0 M solution of lithium borohydride in THF (Aldrich) added. After 1.5 h, 2 mL of HOAc was added carefully, the suspension filtered, and the resin washed with MeOH. The combined filtrates were concentrated 3x from MeOH to give a solid, which was treated with 6 mL of TFA/DCM (1:1), containing a few drops of triethylsilane, for 1 h. The solution was concentrated to give 700 mg of a solid containing salts. A 386 mg aliquot was purified by reverse phase HPLC (15 20µ, 300 Å, Vydac C-18, 1×50 cm, gradient: 23–38% acetonitrile (0.1% TFA) in water (0.1% TFA) in 60 min at 9 mL/min, rt=40 min) to give 21 mg of the title compound. MS (electrospray, M+H) 525.0.

EXAMPLE 29

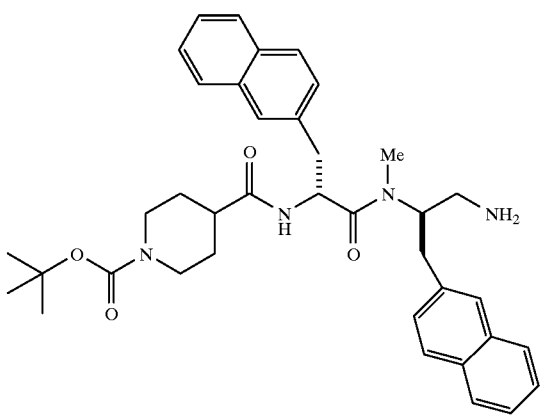

BOC-(inip)-DβNal-{N-methyl, N-[(2R)-2-(1-amino-3-(2-naphthyl)propyl]}amide, TFA salt Step A: BOC-(inip)-DβNal To a stirred solution of 10.0 g (44.0 mmol, 1.0 eq) of N-BOC-isonipecotic acid (from Example 1, Method B, Step E) in 200 ml of DCM was added 100 mg of DMAP and 4.53 g (22 mmol, 0.5 eq) of DCC. After 1 h, the dicyclohexylurea was filtered off and the filtrate added to a solution of 4.7 g (22.0 mmol, 0.5 eq) of D-β-naphthyalanine and 35 ml of NMM in 200 ml of DCM. The reaction was stirred overnight, concentrated, and the residue partitioned between ethyl acetate and 0.5 N citric acid. The organic phase was washed with water, brine, evaporated, and the product recrystallized from ethyl acetate, to give 3.95 g of BOC-(inip)-DβNal. Another 2.14 g was obtained by chromatography of the mother liquors on silica (ethyl acetate/HOAc, 98:2), combined yield: 65%. $^1$H NMR (300 MHz, $d_6$-acetone) δ7.8 (3H, m), 7.65 (1H, s), 7.4 (3H, m), 7.2 (1H, d), 4.8 (1H, m), 3.88 (2H, m), 3.35 (1H, m), 3.15 (1H, m), 2.62 (2H, m), 2.35 (1H, m), 1.6–1.4 (4H, m), 1.35 (9H, s). MS (FAB, M+H) 427.2.

Step B: BOC-(N-Me-D-β-naphthylalanol)

To a cold solution of 3.25 g (9.9 mmol, 1.0 eq) of BOC-(N-Me-DβNal) (from Example 4, Step B) and 1.10 g (10.9 mmol, 1.1 eq) of TEA in 50 ml of dry THF, was added dropwise over 30 min, a solution of 1.19 g (10.9 mmol, 1.1 eq) of ethyl chloroformate in 10 ml of dry THF. The reaction turned bright red and TEA hydrochloride precipitated and was filtered off. The red filtrate was added dropwise to a cold, stirred solution of 1.50 g (39.6 mmol, 4.0 eq) of sodium borohydride in 50 ml of methanol/water (1:1). After stirring overnight, the reaction mixture was concentrated to ½ the initial volume and partitioned between ethyl acetate and 0.5 N citric acid. The organic phase was washed successively with water, 10% potassium carbonate, saturated sodium bicarbonate, brine, dried over sodium sulfate, filtered, and concentrated to yield 2.91 g of an oil (94%). $^1$H NMR (300 MHz, CDCl$_3$) δ 7.75 (3H, m), 7.6 (1H, s), 7.4 (3H, m), 4.3 (1H), 3.7 (2H, m), 3.0–2.8 (6H, m), 1.3 (9H, 2s). IR (cm$^{-1}$) 3428, 3050, 2977, 1689, 1669, 1363, 1144. MS (EI, e/m) 427.2.

Step C: (2R)-1-Azido-2-BOC-methylamino)-3-(2-naphthyl) propane

A cold solution of hydrazoic acid (4.14 mmol, 1.5 eq) in benezene was prepared by acidification of a stirred mixture of 269 mg (4.14 mmol) of sodium azide, 5 ml of water and 5 ml of benzene with 5 ml of 3.6 N sulfuric acid at 10° C. The benzene phase was separated, dried with sodium sulfate, and filtered. This solution was added to a stirred mixture of 867 mg (3.31 mmol, 1.2 eq) of triphenylphosphine and 669 mg of diisopropylazodicarboxylate (3.31 mmol, 1.2 eq) in dry THF at −78° C. A solution of 870 mg (2.76 mmol, 1.0 eq) of BOC-(N-Me-D-β-naphthylalanol (step B) in 10 ml of dry THF was added and the reaction mixture allowed to come to room temperature over 2 h. Saturated sodium bicarbonate (20 mL) was added and the reaction mixture partially concentrated to remove the THF. The mixture was partitioned between ethyl acetate and saturated sodium bicarbonate and the organic phase was washed with brine, dried over sodium sulfate, filtered, and evaporated. Flash chromatography on silica (hexane/ethyl acetate, 80:20) gave 600 mg (64%) of the title compound. $^1$H NMR (300 MHz, CDCl$_3$) δ 7.75 (3H, m), 7.6 (1H, d), 7.42 (2H, m), 7.25 (1H, m), 4.4 (1H, m), 3.6–2.8 (4H, m), 2.7 (3H, 2s), 2.3 (9H, 2s). IR (cm$^{-1}$) 3057, 2977, 2094, 1689.

Step D: BOC-(inip)-DβNal-{N-methyl, N-[(2R)-2-(1-azido-3-(2-naphthyl)propyl]}amide A solution of 300 mg of (2R)-1-azido-2-(BOC-methylamino)-3-(2-naphthyl) propane (0.88 mmol. 1.0 eq) (step C) in 2.0 ml of DCM was treated with 2.0 ml of TFA for 1 h then evaporated several times from DCM. The residue was dissolved in a solution of 5 ml of DCM and 250 µl of NMM then added to a previously prepared mixture of 751 mg (1.76 mmol, 2.0 eq) of N-BOC-(inip)-DβNal (step A), 363 mg (1.76 mmol, 2.0 eq) of DCC, 238 mg (1.76 mmol, 2.0 eq) of HOBt, and 250 µl of NMM in 15 ml of DCM/DMF (2:1). The reaction was stirred overnight, triturated with 1 mL of water and the precipitated dicyclohexylurea was filtered off. The reaction mixture was taken up in ethyl acetate and washed successively with 0.5 N citric acid, water, 10% potassium carbonate, water, saturated sodium bicarbonate, brine, dried over sodium sulfate, filtered, and evaporated. Flash chromatography on silica (ethyl acetate/hexane (1:1), Rf=0.4) gave 380 mg (67%) of the title compound. IR (cm$^{-1}$) 3309, 3057, 2977, 2930, 2100, 1689, 1635, 1171. MS (FAB, M+H) 649.4.

Step E: BOC-(inip)-DβNal-{N-methyl, N-[(2R)-2-(1-amido-3-(2-naphthyl)propyl]}amide, TFA salt A solution of 280 mg (0.43 mmol) of the azine from step D in 15 ml of methanol and 1 ml HOAc was hydrogenated over 100 mg of 10% palladium on carbon at 30 psi for 8 hrs. The catalyst was filtered off and the filtrate evaporated to give 250 mg of crude product. A 20 mg aliquot was purified by reverse phase HPLC (15–20µ, 300 Å, Vydac C-18, 1×50 cm, gradient: 30–45% acetonitrile (0.1% TFA) in water (0.1% TFA) in 60 min at 9 mL/min, rt=39–48 min) to give 8 mg of the title compound. IR (cm$^{-1}$) 3409, 3296, 3057, 2977, 1675, 1430, 1204, 1171, 1131. MS (electrospray, M+H) 624.5.

EXAMPLE 30

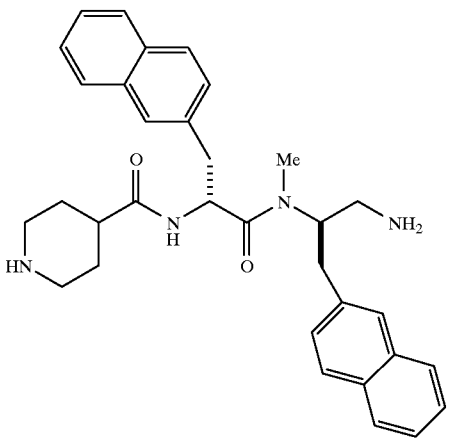

(inip)-DβNal-{N-methyl, N-[(2R)-2-(1-amino-3-(2-naphthyl)propyl]}amide, TFA salt A solution of 200 mg of BOC-(inip)-DβNal-{N-methyl, N-[(2R)-2-(1-amino-3-(2-naphthyl)propyl]} amide, TFA salt (from Example 29, step E) in 2 ml of DCM was treated with 2 ml of TFA, stirred for 1 h, and concentrated to give 490 mg of crude product. A 100 mg aliquot was purified by HPLC (Vydac C-18, 1×50 cm, 20 to 35% acetonitrile in water, 60 min, 0.1% TFA, 9 mL/min, rt=21–31 min) giving 17 mg of the title compound. MS (electrospray, M+H) 523.2.

EXAMPLE 31

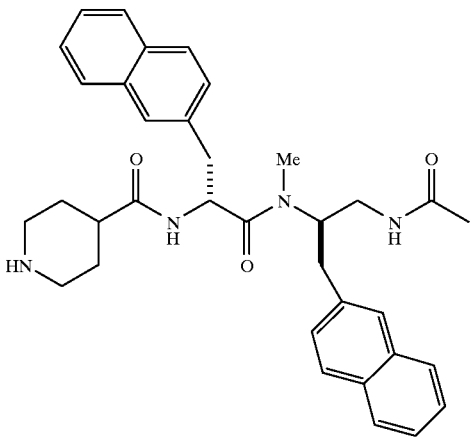

(inip)-DβNal-{N-methyl, N-[(2R)-2-(1-acetamido-3-(2-naphthyl)propyl]}amide, TFA salt To a solution of 33 mg (0.05 mmol) of BOC-(inip)-DβNal-{N-methyl, N-[(2R)-2-(1-amino-3-(2-naphthyl)propyl]} amide, TFA salt (from Example 29, step E) in 0.5 ml of DCM was added 0.5 ml of TEA and 0.5 ml of acetic anhydride. The reaction mixture was stirred for 1 h then evaporated and partitioned between ethyl acetate and water. The organic phase was dried over sodium sulfate and evaporated. The residue was taken up in 2 ml of DCM and 2 ml of TFA added. The mixture was stirred for 1 h, evaporated and the crude product (48 mg) was purified by HPLC (Vydac C-18, 1×50 cm, 25 to 50% acetonitrile in water over 60 min, 9 mL/min, 0.1% TFA, rt=29 min) giving 15 mg of the title compound. MS (electrospray, M+H) 565.4.

EXAMPLE 32

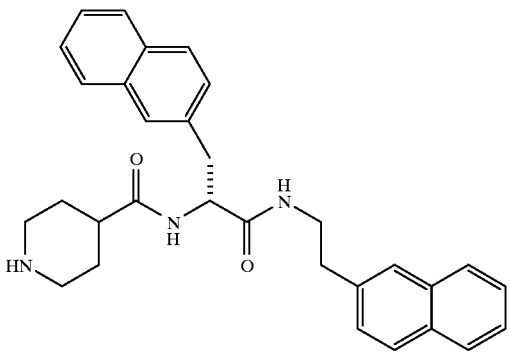

(inip)-DβNal-[N-1-{2-(2-naphthyl)ethyl}]amide, TFA salt

Step A: 2-(2-Naphthyl)ethylamine hydrochloride

A solution of lithium aluminum hydride (LAH, 100 mmol, 3.0 eq) in 300 ml of dry ether at 0° C. was stirred and a solution of 2-naphthylacetonitrile (5.0 g, 30 mmol, 1.0 eq) in 200 ml of dry ether added over 2 h. To the resultant bright orange slurry, was added dropwise, 25 ml of cold (0° C.) 12 N sulfuric acid, and the mixture stirred until colorless. The reaction mixture was partitioned between ether and water and the ether phase, containing mostly unreacted 2-naphthylacetonitrile, discarded. The aqueous phase was basified with sodium hydroxide and the separated free amine extracted into ether, dried over sodium sulfate, filtered, and acidified with anhydrous HCl in dioxane. The precipitated HCl salt was collected by filtration to give 890 mg of the title compound. $^1$H NMR (300 MHz, D$_2$O) δ 7.82 (3H, t), 7.7 (1H, s), 7.45 (2H, m), 7.38 (1H, d) 3.25 (2H, t), 3.05 (2H, t). MS (FAB), M+H) 172.1.

Step B: BOC-(inip)-DβNal-[N-1-{2-(2-naphthyl)ethyl}]amide

A mixture of 100 mg (0.23 mmol, 1.0 eq) of N-BOC-(inip)-DβNal (from Example 29, step A), 42 mg (0.23 mmol, 1.0 eq) of 2-(2-naphthyl)ethylamine hydrochloride (step A), 132 mg (0.69 mmol, 3.0 eq) of EDC, 31 mg (0.23 mmol, 1.0 eq) of HOBt, 87 μl (0.69 mmol, 3.0 eq) of NMM, and 5.0 ml of DMF was stirred overnight at ambient temperature. The reaction mixture was partitioned between ethyl acetate and dilute hydrochloric acid and the separated organic phase washed successively with water, saturated sodium bicarbonate, brine, dried over sodium sulfate, filtered, and evaporated. The crude product was chromatographed on silica (ethyl acetate/hexane (70:30), Rf=0.5) to give 110 mg of the title compound. IR (cm$^{-1}$) 3289, 3057, 2977, 2930, 2857, 1695, 1642, 1423, 1171, 819, 739. MS (FAB, M+H) 580.3.

Step C: (inip)-DβNal-[N-1-{2-(2-naphthyl)ethyl}]amide, TFA salt

A solution of 110 mg of N-BOC-(inip)-DβNal-[N-1-{2-(2-naphthyl)ethyl}]amide (step B) in 4 ml of DCM was treated with 2 ml of TFA and stirred for 2 h. The concentrated crude product (121 mg) was purified by HPLC (1×50 cm, Vydac C-18, 25 to 40% acetonitrile in water over 60 min, 9 mL/min, 0.1% TFA, rt=25–30 min) to give 29 mg of the title compound. MS (electrospray, M+H) 479.8.

EXAMPLE 33

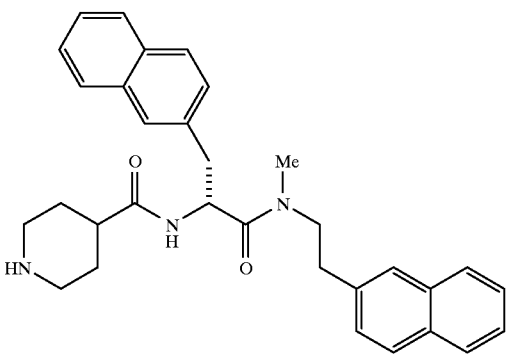

(inip)-DβNal-[N-methyl, N-1-{2-(2-naphthyl)ethyl}]amide, TFA salt

Step A: N-Methyl-N-2-(2-naphthyl)ethylamine, TFA salt

A solution of 2-(2-naphthyl)ethylamine (1.4 mmol, 1.0 eq) in DCM was prepared by partitioning 250 mg of 2-(2-naphthyl)ethylamine hydrochloride (from Example 32, step A) between 5 ml of DCM and 5 ml of 10% aq sodium hydroxide. The organic phase was dried over sodium sulfate, filtered, and 363 mg (1.67 mmol, 1.2 eq) of di-t-butyldicarbonate added, followed by 1.0 ml of TEA. After stirring for 30 min, the reaction mixture was concentrated and the product crystallized from hexane at −78° C.

Yield: 250 mg.

This product was dissolved in 10 ml of dry THF, 262 μl (4.2 mmol, 3.0 eq) of methyl iodide added, and the solution cooled to 0° C. Sodium hydride (47 mg, 60% dispersion in mineral oil, 1.96 mmol) was added in portions with stirring over 10 min, and the reaction allowed to warm to ambient temperature overnight. The solvents were evaporated and the crude product taken up in ethyl acetate/hexane and washed successively with saturated sodium bicarbonate, 1 N sodium bisulfite, water, brine, dried over sodium sulfate, filtered, and evaporated. Treatment with TFA/DCM (1:1) for 1 h and concentration gave 190 mg of the title compound as an oil. $^1$H NMR (300 MHz, CDCl$_3$) δ 7.78 (3H, t), 7.62 (1H, s), 7.4 (2H, m), 7.32 (1H, d), 2.9 (4H, m), 2.4 (3H, s), 1.55 (1H, s). MS (FAB, M+H) 186.0.

Step B: BOC-(inip)-DβNal-[N-methyl, M-1-{2-(2-naphthyl)ethyl}]amide

A mixture of 525 mg (1.23 mmol, 1.2 eq) of BOC-(inip)-DβNal (from Example 29, step A), 190 mg (1.02 mmol, 1.0 eq) of N-methyl-N-2-(2-naphthyl)ethylamine (step A), 584 mg (3.06 mmol, 3.0 eq) of EDC, 138 mg (1.02 mmol, 1.0 eq) of HOBt, 412 mg of (4.08 mmol, 4.0 eq) of NMM, and 15 ml of DMF was stirred overnight at ambient temperature. The reaction mixture was partitioned between ethyl acetate and dilute citric acid and the separated organic phase washed successively with water, saturated sodium bicarbonate, brine, dried over sodium sulfate, filtered, and evaporated. The crude product was chromatographed on silica (80:20, ethyl acetate/hexane) to give 550 mg of the title product. IR (cm$^{-1}$) 3302, 3050, 2977, 2930, 1689, 1629, 1423, 1164, 819, 732.

Step C: (inip)-DβNal-[N-methyl, M-1-{2-(2-naphthyl)ethyl}]amide, TFA salt

A solution of 550 mg of BOC-(inip)-(inip)-DβNal-[N-methyl, M-1-{2-(2-naphthyl)ethyl}]amide (step B) in 4 ml of DCM was treated with 3 ml of TFA, stirred for 2 h, and concentrated to give 569 mg of crude product. A 90 mg aliquot was purified by HPLC (1×50 cm, Vydac C-18, 27 to 42% acetonitrile in water over 60 min, 0.1% TFA, 9 mL/min, 214 nm, rt=30–45 min) to give 29 mg of the title compound. MS (electrospray, M+H) 493.8.

EXAMPLE 34

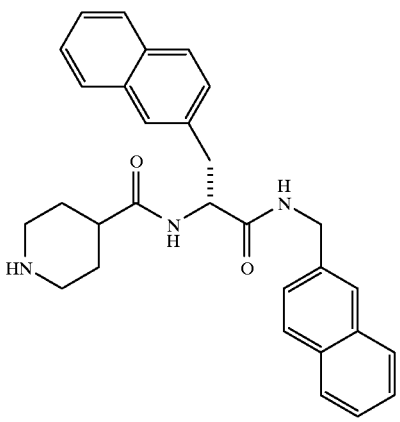

(inip)-DβNal-(N-(2-naphthyl)methyl) amide, TFA salt

Step A: 2-Aminomethylnaphthylene hydrochloride

A stirred 0° C. solution of 20.0 g of 2-naphthaldehyde (128 mmol) and 98.7 g (1.28 mol) of ammonium acetate in 200 mL of MeOH/HOAc (99:1) was treated with 5.62 g (90.0 mmol) of sodium cyanoborohydride, portionwise. The solution was stirred at ambient temperature for 24 h, concentrated in vacuo, resuspended in water, and basified with sodium hydroxide. The product was extracted into ether, washed with water, brine, dried over magnesium sulfate, and filtered. The filtrate was treated with a dry ethereal solution of HCl, and the precipitated product washed with ether and dried to give 16.5 g (65% of 2-aminomethylnaphthylene hydrochloride.

Step B: (inip)-DβNal-(2-aminomethylnaphthyl) amide, TFA salt

A mixture of 124 mg (0.29 mmol) of BOC-(inip)-DβNal (from Example 29, step A), 84.5 mg (0.54 mmol) of 2-aminomethylnaphthylene hydrochloride (step A), 67 mg (0.348 mmol) of EDC, 47 mg (0.348 mmol) of HOBt, and 140 μL of NMM in 5 ml of DMF was stirred overnight at ambient temperature. The reaction mixture was partitioned between ethyl acetate and water and the separated organic phase washed successively with 1 N sodium hydrogen sulfate, 1 N sodium bicarbonate, brine, dried over magnesium sulfate, filtered, and evaporated. The crude product was dissolved in 4 ml of DCM/TFA (1:1), stirred for 2 h, and reconcentrated to give 160 mg of crude product. An 85 mg aliquot was purified by HPLC (1×50 cm, Vydac C-18, 23 to 38% acetonitrile in water over 60 min, 0.1% TFA, 9 mL/min, rt=45 min) to give 4.6 mg of the title compound. MS (electrospray, M+H) 466.0.

EXAMPLE 35

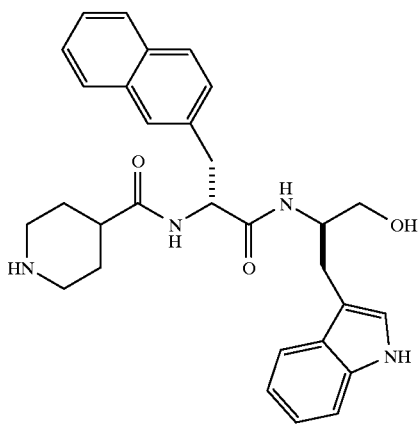

(inip)-DβNal-(D-Tryptophanol), TFA salt

Step A: BOC-DβNal-DTrp-(O-resin)

A 1.5 g sample of BOC-DTrp-(O-resin) (0.5 mmol/g, 0.75 mmol) was deblocked (TFA/DCM (1:1) containing 1 g/L of indole as a scavenger), washed, neutralized, and coupled with 0.71 g (3 eq) of BOC-DβNal, 1.02 g (3 eq) of BOP, 0.30 g (3 eq) of HOBt, and 0.37 mL (4.5 eq) of NMM for 1.5 h, according to the general BOC procedure, giving BOC-DβNal-DTrp-(O-resin) (ninhydrin negative).

Step B: BOC-(inip)-DβNal-DTrp-(O-resin)

The above sample of BOC-DβNal-DTrp-(O-resin) was deblocked, washed, and coupled with 0.52 g (3 eq) of N-BOC-isonipecotic acid, 1.02 g (3 eq) of BOP, 0.30 g (3 eq) of HOBt, and 0.37 mL (4.5 eq) of NMM for 1 h, giving 1.76 g of the title compound after washing with methanol and drying in vacuo (ninhydrin negative).

Step C: (inip)-DβNal-(D-Tryptophanol), TFA salt

The dry resin from step B (BOC-(inip)-DβNal-DTrp-(O-resin), 1.76 g) was suspended in 50 mL of THF under nitrogen and 4.80 mL of a 2.0 M solution of lithium borohydride in THF added. After 1.5 h, 4.5 mL of HOAc was added dropwise over 10 min. After 30 min, the suspension was filtered, and the resin washed with MeOH. The combined filtrates were concentrated and partitioned between ethyl acetate and water (a few drops of HOAc added). The organic phase was concentrated, and treated with 20 mL of TFA/DCM (1:1) for 30 min. The TFA was removed in vacuo and the product reconcentrated from DCM (3x) to give 700 mg of an oil. A 100 mg aliquot was purified by reverse phase HPLC (15–20μ, 300 Å, Vydac C-1, 1×50 cm, gradient: 23–38% acetonitrile (0.1% TFA) in water (0.1% TFA) in 60 min at 9 mL/min, rt=20 min) to give 23 mg of the title compound. MS (electrospray, M+H) 499.5.

EXAMPLE 36

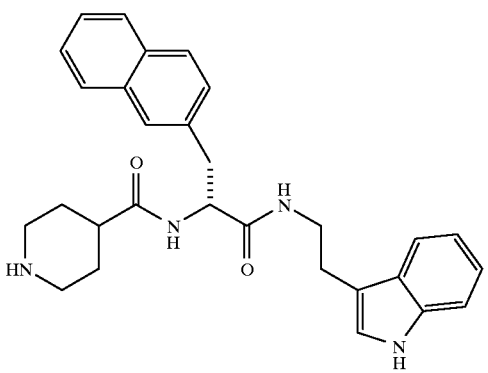

(inip)-DβNal-[N-tryptaminyl]amide, TFA salt

Step A: BOC-(inip)-DβNal-[N-tryptaminyl]amide

A mixture of 100 mg (0.23 mmol, 1.0 eq) of N-BOC-(inip)-DβNal (from Example 29, step A), 132 mg (0.69 mmol, 3.0 eq) of EDC, and 47 mg (0.35 mmol, 1.5 eq) of HOBt in 15 ml of DCM/DMF (2:1) was stirred for 10 min, then 40 mg (0.25 mmol, 1.1 eq) of tryptamine and 40 μl (0.35 mmol, 1.5 eq) of NMM were added. After 14 h at ambient temperature, the reaction mixture was partitioned between ethyl acetate and dilute citric acid and the separated organic phase was washed successively with water, saturated sodium bicarbonate, brine, dried over sodium sulfate, filtered, and evaporated. The crude product (160 mg) was chromatographed on silica (ethyl acetate/hexane (70:30), Rf=0.5) to give 90 mg of the title compound as a crystalline solid. IR (cm$^{-1}$) 3342, 3289, 3057, 2977, 2924, 2857, 1675, 136, 1556, 1436, 1224, 1164, 739. MS FAB, M+H) 569.3.

Step B: (inip)-DβNal-[N-tryptaminyl]amide, TFA salt

A solution of 70 mg of B-BOC-(inip)-DβNal-[N-tryptaminyl]amide (step A) in 4 ml of DCM was treated with 3 ml of TFA and stirred for 1 h. The concentrated crude product was purified by HPLC (1×50 cm, Vydac C-18, 20 to 35% acetonitrile in water over 60 min, 9 mL/min, 0.1% TFA, rt=30–48 min) to give 32 mg of the title compound. MS (electrospray, M+H) 469.4.

EXAMPLE 37

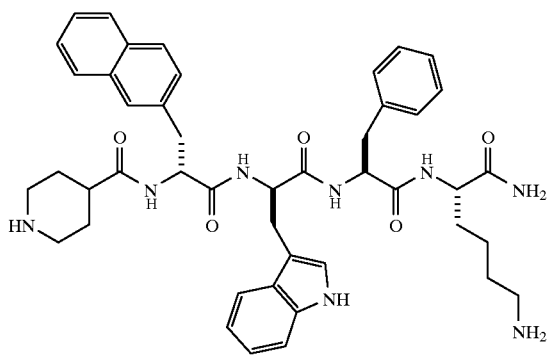

(inip)-DβNal-DTrp-Phe-Lys-amide, TFA salt

The title compound was prepared in an identical fashion to (inip)-DβNal-DβNal-Phe-Lys-amide, TFA salt (Example 1, method B) with the only change being substitution of BOC-D-Tryptophan for BOC-DβNal in the third coupling (step C). Washing, drying, and cleavage as per the general BOC protocol above gave 250 mg of a powder. A 102 mg aliquot was purified by reverse phase HPLC (15–20μ, 300 Å, Vydac C-18, 1×50 cm, gradient: 23–38% acetonitrile (0.1% TFA in water (0.1% TFA) in 60 min at 9 mL/min, rt=32 min) to give 23 mg of the title compound. MS (electrospray, M+H) 812.4.

EXAMPLE 38

Anterior Pituitary Cell Assays ("Pit"Cell Assays)

Dispersion

Adult female Sprague-Dawley (160–180 g., Charles River) rats were group-caged in a 12:12 light:dark cycle with food and water available ad libitum. Pituitaries from ten rates were removed, the posterior pituitary discarded and the anterior pituitary placed in Hanks' Balanced Salt Solution (HBSS: without calcium chloride, w/o magnesium chloride, w/o magnesium sulfate; Gibco) containing 20 mM HEPES (Gibco) and 100 U/ml penicillin streptomycin (PS; JRH Biosciences). Under sterile conditions, pituitaries were rinsed twice then minced into small fragments with a razon blade. Fragments were resuspended in 5 ml of HBSS/HEPES containing 20 mg collagenase (Serva 17449) and 200 ml of 1 mg/ml DNase (Sigma) for a 40 min. incubation in a 37° C. gyrotory water bath shaker (New Brunswick Scientific Model G76; setting 10). After the incubation, fragments were triturated to yield small clumps and single cells. The cells were centrifuged 1000×g. for 5 min, resuspended, counted and plated at a final cell concentration of 100,000 cells/ml. Incubation media was DME low glucose media w/NaHCO$_3$ (Gibco) containing 20 mM hepes, 100 U/ml PS and 10% FBS (Hyclone A-111-L). Cells were plated at 0.5 ml per well in 48 well plates (Falcon) and incubated at 37° C. in 5% C02 for three days. For challenges to determine release of other pituitary hormones cells were plated at 200,000 cells per ml with 2 ml per well of a 6-well plate (Corning).

Challenge

A (inip)bbFK—NH$_2$ stock (or other GHRP) concentration of 1 mM was made in DMSO and diluted with warmed media approximately 30 min prior to use. The highest concentration of DMSO in media was 0.1%. Stock solutions (1 mM) of rat GHRH, somatostatin (Sigma) and GHRP antagonist HwkWfK were made fresh in media and diluted appropriately. The media used in all challenges and washing steps was DME low glucose with 20 mM Hepes, 100 U/ml PS, 10% FBS. Media was warmed to 37° C. and gassed by placing it into the incubator prior to challenge. On day three, the media was discarded and fresh media (approximately 1 ml) added for the first of three washes. After the last wash, the plate was placed back in the incubator for a 15 min pre-incubation. Then cells were washed 2× (with warmed and gassed media) and fresh 0.5 ml media were added for the second 15 min. pre-incubation. After the second pre-incubation cells were washed 2× as above and 0.5 ml of control and test solutions were added for a final 15 min incubation. After this incubation, the media were removed for subsequent GH ELISA.

GH ELISA

A two-site ELISA was used to determine rat GH concentration in the media. Briefly, goat anti-rat GH antibody (lot# 19164-20) was used to coat Nunc immunoplates overnight. After blocking and washing, standard (rat GH reference preparation: Parlow) and challenge media is diluted 1:20 prior to GB assay were added for a 1 hr room temperature incubation.

Statistics

The mean for each group was determined an analyzed by one-way analysis of variance with a post-hoc Student-Newman-Keuls. Significance is defined as $P<0.05$. The $EC_{50}$ was calculated using a 4-parameter curve-fit program (Kaleidagraph). Three to four independent $EC_{50s}$ were used to derive the means and SEM.

RIA of Pituitary Hormones

LH, FSH, TSH, and Prolactin were determined with commercially available kits from Amersham, and ACTH levels were determined by a RIA kit from ICN.

Calcium Flux Experiment

Pituitary cells were plated on fibronectin (Collaborative Research) coated two-chambered slide wells (Nunc). After four days in monolayer culture cells were rinsed three times with HBSS (Gibco) in 1% BSA and 15 mM HEPES and then incubated for 30 min at 37° C. with 5 μM Indo-1 AM (Molecular Probes, Eugene) in HBSS also containing 1% pluronic F127 (Molecular Probes). The cells were rinsed once and fresh media added for RT incubation. Cells were challenged within 30 min with 10 nM (inip)bbFK—NH$_2$, vehicle or 2.5 uM ionomycin (Sigma). $Ca^{++}$ flux was imaged with a Meridian ACAS 570 using stage scanning at 21 second intervals. $Ca^{++}$ bound Indo-1 was measured at 405±22 nm and $Ca^{++}$ free Indol-1 was measured at 530±15 nm. The ratio of bound vs free Indo-1 was calculated and corrected with a standard curve created under identical instrument settings (Grynkiewicz G., M. Peonie, R.T. Tsien. A new generation of $Ca^{++}$ indicators with greatly improved flourescence properties. *Journal of Biological Chemistry* 260: 3440–3450, [1985]).

EXAMPLE 39

In vitro and In vivo Biological Data

Biological data for selected prior art compounds is provided in Table II

TABLE II

| Literature code | Structure | C-term | "Pit" Cell $EC_{50}$ (nM) | SE | n | Rat IV $ED_{50}$ (μg) |
|---|---|---|---|---|---|---|
| | Y w w F | amide | 1000 | | 3 | |
| "GHRP 6" | H w A W f K | amide | 6.2 | 1.5 | 5 | 1.0 |
| "GHRP 2" | a b A w f K | amide | 1.0 | 0.2 | 3 | 0.35 |
| — | (Ava) b A W f K | amide | 0.2 | 0.03 | 3 | 1.5 |
| "GHRP 1" | A H b A W f K | amide | 1.4 | | 2 | |
| L-692,429 | benzo-fused lactam | | 26.2 | 5.3 | 5 | 100 |
| L-692,585 | benzo-fused lactam | | 10.6 | 4.0 | 4 | 10 |

The following selected in vitro and in vivo biological data for compounds represented by formula IV is provided in Table III

TABLE III

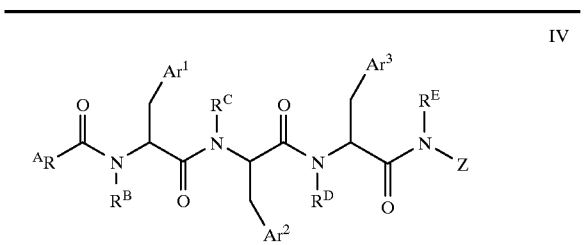

IV

| Structure | C-term | PIT Cell EC$_{50}$ (nM) | SE | n | RAT IV ED$_{50}$ (μg) |
|---|---|---|---|---|---|
| Y w w F K | amide | 1000 | | 3 | |
| H w w F K | amide | 25.8 | 3.9 | 3 | 50 |
| H b w F K | amide | 6.8 | 1.2 | 3 | 4.2 |
| H w b F K | amide | 15.0 | 5.0 | 3 | 50 |
| H b b F K | amide | 2.4 | 1.2 | 3 | 15.4 |
| G w w F K | amide | 2.1 | 0.3 | 3 | 2.5 |
| (Ava) w w F K | amide | 13.0 | 2.6 | 4 | 5 |
| a w w F K | amide | 4.1 | 2 | 3 | 1.47 |
| G b w F K | amide | 0.8 | | 2 | 4.8 |
| (Ava) b w F K | amide | 4.6 | 1.5 | 6 | 11.8 |
| H w w nmF K | amide | 37.3 | 11.3 | 3 | |
| G b b F K | amide | 14.9 | | 2 | 100 |
| bA b b F K | amide | 4.8 | 3.3 | 3 | 6.7 |
| (Ab) b b F K | amide | 0.4 | 0.1 | 3 | 1 |
| (Ava) b b F K | amide | 2.8 | 0.4 | 4 | 2.6 |
| (ahx) b b F K | amide | 1000 | | 2 | 250 |
| (ahp) b b F K | amide | 34.3 | 8.2 | 3 | 100 |
| (nba) b b F K | amide | 2.8 | | 2 | 100 |
| (inip) b b F K | amide | 0.18 | 0.04 | 3 | 0.2 |
| (pyc) b b F K | amide | >300 | | 4 | 200 |
| (pac) b b F K | amide | 100 | | 2 | |
| (Ava) b b F G | amide | 7.2 | 1.9 | 4 | 50 |
| (Ava) b b F N | amide | 7.7 | 4.5 | 3 | 200 |
| (Ava) b b F n | amide | 10 | | 1 | 12.5 |
| (Ava) b b F k | amide | 17 | | 1 | 33.3 |
| (Ava) b b F P | amide | 51 | | 1 | 50 |
| b b F K | amide | 1000 | | 2 | |
| (Ava) b b F K Y | amide | 13.6 | 2.6 | 3 | 20 |
| (Ava) b nmb F K | amide | 3.8 | 1.4 | 3 | 100 |
| (Ava) nmb b F K | amide | 1.8 | 0.6 | 3 | 0.4 |
| (Ava) b b B K | amide | 0.7 | | 1 | 50 |
| (Ava) b b hF K | amide | 5.0 | 1.7 | 3 | 50 |
| (Ava) a b F K | amide | >300 | | 2 | |
| (Ava) b b chA K | amide | 44.3 | 9.5 | 3 | |
| (Ava) b b (Pg) K | amide | >100 | | 1 | |
| (Ava) b b (pG) K | amide | >100 | | 1 | |
| (inip) b b npA K | amide | 0.1 | | 2 | 1 |
| (Ava) b b A K | amide | >150 | | 2 | |
| (Ava) b a F K | amide | >300 | | 3 | |
| a b b F K | amide | 3.5 | 1.5 | 3 | 10 |
| A b b F K | amide | 2.1 | 0.8 | 4 | 10 |
| (mab) b b F K | amide | 1.4 | | 1 | 0.7 |
| (inip) nmb nmb F K | amide | 1.4 | | 1 | |
| (inip) nmb b F K | amide | 0.27 | 0.06 | 4 | 0.4 |
| (inip) b nmb F K | amide | 0.2 | | 2 | 1 |
| (inip) b b F K Y | amide | 0.43 | 0.01 | 4 | 1 |
| (inip) b b F bA | amide | 0.2 | 0.05 | 4 | 2 |
| nmb b F K | amide | >100 | | 1 | 1000 |
| (Ab) nmb b F K | amide | 0.5 | | 2 | 1 |
| (inip) nmb w F K | amide | 0.2 | | 2 | 0.2 |
| (inip) b b F K GGSGGSY | amide | 0.4 | | 2 | |
| (inip) nmb b F dam | | 6.0 | | 1 | |
| (inip) nmb b F mor | | 0.8 | | 1 | 10 |
| nmb b Y K | amide | 1000 | | 4 | 500 |
| (Ava) b b npA K | amide | 1000 | | 1 | |
| (cho) b b F K | amide | 1000 | | 1 | |
| (Ab) b b B ram | | 2.4 | 1.1 | 3 | 10 |
| (inip) b b f dam | | 12 | | 1 | |
| (inip) b b F dam | | 12 | | 1 | 10 |
| (inip) b b F mam | | 7.0 | | 1 | |
| (inip) b b F mam | | 2.0 | | 1 | 2 |
| (inip) b b F tbm | | 10 | | 1 | 10 |
| (inip) b b Y(I) K | amide | | | | |
| (inip) b b Y K | | 0.2 | | 1 | |

TABLE III-continued

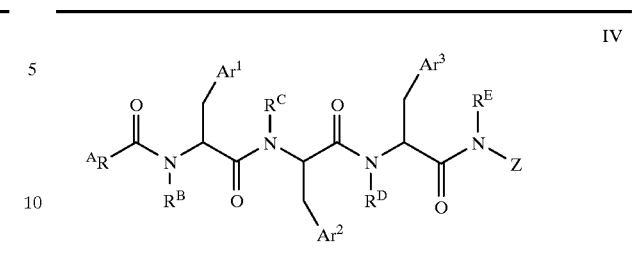

IV

| Structure | C-term | PIT Cell EC$_{50}$ (nM) | SE | n | RAT IV ED$_{50}$ (μg) |
|---|---|---|---|---|---|
| (inip) b b F K Y(I) | amide | 0.69 | 0.54 | 3 | |
| (inip) b w F K | amide | 1.1 | 0.5 | 3 | 0.070 |

The following selected in vitro and in vivo biological data for compounds represented by formula III is provided in Table IV

TABLE IV

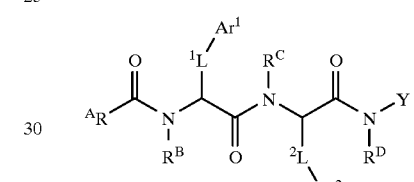

III

| Structure | C-term | PIT Cell ED50 (nM) | SE | n | RAT IV ED50 (μg) |
|---|---|---|---|---|---|
| H w w F | amide | 1000 | | 4 | |
| (Ava) f f F | amide | 1000 | | 1 | |
| (Ava) f w F | amide | >300 | | 3 | 1000 |
| (Ava) b b F | amide | 17.1 | 5.7 | 3 | 100 |
| (Ava) b b fem | | >200 | | 4 | |
| (inip) b b bam | | 18.5 | | 2 | 3.3 |
| (Ava) b f K | amide | >300 | | 4 | |
| (inip) b b fem | | 2.04 | 0.9 | 3 | |
| (inip) b b F | amide | 0.28 | 0.07 | 5 | 1.7 |
| (inip) nmb b F | amide | 0.5 | 0.2 | 4 | 5 |
| (inip) nl b F | amide | 101 | | 1 | |
| (inip) b nl F | amide | 72 | | 1 | |
| (inip) b b nL | amide | 4.3 | | 2 | 3.3 |
| (inip) b b P | amide | 9 | | 1 | 5 |
| (inip) b b amF | amide | 0.5 | | 1 | 5 |
| (inip) b b nmF | amide | 0.6 | | 2 | 5 |
| (inip) nmb b F | acid | 1.4 | | 1 | 5 |
| (inip) nmb b F | Me ester | 1.4 | | 2 | 10 |
| (inip) nmb B F | | >100 | | 1 | |
| (inip) b b feg | amide | 0.25 | 0.19 | 3 | 1 |
| (inip) b b feb | amide | 0.3 | | 2 | 0.67 |
| (inip) b b fbd | | 0.9 | | 2 | 0.67 |
| (inip) b b hcF | amide | 0.2 | 0.09 | 3 | 2.5 |
| (inip) hf b F | amide | 27 | | 1 | |
| (inip) b hf F | amide | 14 | | 1 | 10 |
| (inip) hf hf F | amide | >1000 | | 1 | |
| (inip) b f F | amide | 79 | | 1 | |
| (inip) b b (Tic) | amide | 12 | | 1 | 10 |
| (inip) b (tic) F | amide | >1000 | | 1 | |
| (Ava) nmb b F | amide | 1.6 | | 1 | 20 |
| (Ab) nmb b F | amide | 0.2 | | 2 | 20 |
| (inip) b b f | amide | 0.6 | | 1 | 20 |
| (inip) nmb B F | acid | 7 | | 1 | 100 |
| (inip) b b npA | amide | 0.2 | | 1 | 5 |
| (inip) b b B | amide | 0.1 | | 2 | 50 |
| (Ab) b b F | amide | 3.1 | | 1 | 10 |
| (inip) b b Pol | | 0.2 | 0.02 | 3 | 5 |
| (inip) b chf F | amide | 2.7 | | 1 | 5 |

TABLE IV-continued

III $$\text{A}_R\text{-C(=O)-N(R}^B\text{)-CH(}^1\text{L-Ar}^1\text{)-C(=O)-N(R}^C\text{)-CH(}^2\text{L-Ar}^2\text{)-C(=O)-N(R}^D\text{)-Y}$$

| Structure | C-term | PIT Cell ED50 (nM) | SE | n | RAT IV ED50 (μg) |
|---|---|---|---|---|---|
| (inip) chf b F | amide | 2.2 | | 1 | 10 |
| (inip) b nmb F | amide | 1 | | 2 | 5 |
| (inip) b b bA | amide | 10 | | 1 | 10 |
| (inip) b b F | Me ester | 2.8 | | 1 | 2 |
| (inip) b b F | acid | 0.2 | | 2 | 2 |
| (inip) w w F | amide | 0.9 | | 2 | 5 |
| (inip) b w F | amide | 0.1 | | 2 | 0.67 |
| (inip) b b Abx | amide | 13 | | 1 | 100 |
| (inip) b Abx F | amide | >100 | | 1 | |
| (inip) b b tam | | 11 | | 1 | 20 |
| (inip) b b ram | | 16 | | 1 | 5 |
| (inip) b b pam | | 43 | | 1 | |
| (inip) b b cxa | | 14 | | 1 | 10 |
| (inip) b b ppz | | 10 | | 1 | 10 |
| (inip) b b ab | amide | 10 | | 1 | 10 |
| (inip) b b apc | | 39 | | 1 | |
| (inip) b b api | | 2.7 | | 2 | 25 |
| (inip) b b O | amide | 5.9 | | 2 | 1 |
| (inip) b b o | amide | 10 | | 1 | |
| (inip) b b Y | acid | 5 | | 1 | 10 |
| (inip) b nmb bam | | 0.3 | | 2 | 1.67 |
| (inip) nmb B bam | | 1000 | | 1 | |
| (inip) nmb b bam | | n/d | | | |
| (inip) b nmb api | | 0.5 | | 2 | 2 |
| (inip) b b Y(I) | acid | 0.1 | | 2 | |

The following selected in vitro and in vivo biological data for compounds represented by formula II is provided in Table V

TABLE V

II

| Structure | C-term | PIT Cell EC50 (nM) | SE | n | RAT IV ED50 (μg) |
|---|---|---|---|---|---|
| (inip) b b | amide | 17.6 | 5.6 | 3 | |
| (inip) b Bmn | | 36 | | 1 | 20 |
| (inip) b b | acid | 82 | | 1 | |
| (inip) b bol | | 2 | | 2 | 10 |
| (inip) b b | Me ester | 5 | | 1 | 100 |
| (inip) b mbm | | 7 | | 1 | 20 |
| (inip) b Bol | | 100 | | 4 | |
| (inip) B Bol | | 1000 | | 1 | |
| (inip) B bol | | 1000 | | 1 | |
| (inip) b wol | | 10.6 | 6.2 | 3 | 0.8 |
| (inip) w wol | | 4 | | 1 | 20 |
| (inip) w bol | | 1000 | | 1 | |
| (inip) b npe | | 11 | | 2 | 500 |
| (inip) b men | | 12 | | 2 | 500 |
| (inip) b man | | 9 | | 1 | 500 |
| (inip) b tam | | 1000 | | 1 | |

TABLE V-continued

II

| Structure | C-term | PIT Cell EC50 (nM) | SE | n | RAT IV ED50 (μg) |
|---|---|---|---|---|---|
| (Ava) b bol | | 190 | | 1 | |
| (inip) b nbol | | 3 | | 1 | 20 |
| (amb) b bol | | 1000 | | 1 | |
| (inip) b miz | | 12 | | 1 | |
| (inip) b mbm Ac | | 90 | | 2 | |
| Boc (inip) b mbm | | 13 | | 1 | |
| (inip) b tra | | 100 | | 2 | 100 |

The following selected in vitro and in vivo biological data for the "retroinverso" compounds represented by formula V is provided in Table VI

TABLE VI

V

| Structure | C-term | PIT Cell EC50 (nM) | SE | n | RAT IV ED50 (μg) |
|---|---|---|---|---|---|
| (dhc) B B bam | | >200 | | 3 | |
| (Ava) f B B K | amide | 36 | | 1 | |
| (Ava) f B B bam | | 22 | | 1 | 100 |
| (Ab) b B B ram | | 2 | | 2 | |
| b B B ram | | 15.2 | | 1 | 100 |
| Ac b B B ram | | 4.8 | | 2 | 100 |
| (inip) B B api | | 96 | | 2 | |
| (inip) B B bam | | 1000 | | 1 | |

EXAMPLE 40

GHRP Induced Growth Hormone Secretion: Intravenous Administration

Immature weanling female Sprague Dawley rats were purchased from Charles River Labs (Portage, Oreg.) and group housed with water and food available ad libitum. When the rats were 24–30 days (weighing 50–90 g) they were anesthetized with pentobarbitone (4 mg in 0.5 ml, approximately 60 mg/kg) given by intraperitoneal injection. The rats were then placed briefly on a heated pad, to distend their tail veins, and given an intravenous tail vein injection of the peptides 20 minutes after receiving the anesthetic. The intravenous injection was of 0.1 ml using a 1 ml syringe. The injections contained graded doses of peptides or the vehicle (vehicle for all peptides given intravenously was a buffer of 20 mM sodium acetate, 45 g/l mannitol, pH 5.0). Ten minutes after the intravenous injection blood was taken by cardiac puncture, using a 3 ml syringe, and the rats were then sacrificed.

The blood was then clotted on ice, centrifuged, serum decanted and frozen for subsequent analysis using the rat GH ELISA described elsewhere in the application. For the rat GB ELISA the serum was diluted 1:50 or 1:250, depending on the expected serum GH concentration achieved, and assay in duplicate.

EXAMPLE 41

GHRP Induced Dose Dependent Weight Gain in Rats

Methods

Forty normal Sprague Dawley female rats (Supplier, Charles River, 90 days of age, average weight 200 g) were group housed in a room controlled for temperature and lighting and fed a standard pelletted rat diet and tap water ad libitum. The rats were weighed on the day of surgery (see below) and randomized into 5 groups of 8/group using a grouping program.

The GHRP (inip) b b F K—$NH_2$, was dissolved in sodium acetate (20 mM) buffer (pH 5.0) containing mannitol (45 g/l) at 8 g/l, 1.6 g/l and 0.33 g/l. Rat GHRH (1–43) was dissolved in the same buffer at 25 g/l. Osmotic minipumps (Alza, Palo Alto, model 2002, pump rate 0.52 µl/hr for 14 days, fill volume 230 µl) were filled with these solutions (1/rat for (inip) b b F K—$NH_2$ and 2/rat for rat GHRH); a fifth set of pumps were filled with the sodium acetate buffer. All the pumps were primed by being incubated in isotonic saline overnight in a refrigerator.

The next day these osmotic pumps were inserted into rats. To do this the rats were anesthetized with ketamine/xylazine (62.5 and 12.5 mg/kg/rat, respectively, by i.p. injection). The dorsal neck was then shaved, swabbed with betadine solution and cleaned with alcohol. An incision was then made on the dorsal neck and the a subcutaneous pocket created carefully by blunt dissection. The pumps were then inserted into the pocket with the end of the pump delivering the solution positioned away from the incision. The incision was then closed with wound clips, the rat placed on a heated pad and when ambulatory was returned to its home cage.

The rats were then weighed every day and on day 14 they were sacrificed using inhalation of carbon dioxide. They were then bled from the heart and organs taken. The pituitary, spleen, heart, kidney, liver, and thymus were taken and weighed while the tibias were removed and placed in 10% formalin for subsequent histological evaluation. To do this the tibias were sectioned longitudinally and the width of the epiphyseal plate was measured using a microscope fitted with an ocular micrometer.

Serum chemistries were measured by standard automated procedures. Serum insulin-like growth factor-1 (IGF-1) was measured by radioimmunoassay, using an antibody raised in rabbits, after acid ethanol extraction to remove the IGF-1 binding protein.

Statistical significance was gauged by analysis of variance, which if significant (p<0.05) was followed by a Duncan's New Multiple Range Test to test for differences between the individual treatment groups. Data are presented as mean±standard error of the mean with 8 rats per group.

The body weight gains plotted against time for the 5 treatment groups are shown in FIG. 19. Both (inip) b b F K—$NH_2$ and rat GHRH induced significant body weight and organ weight gain compared to the vehicle treated rats.

EXAMPLE 42

Comparison of SC Injections and SC Infusions

Methods

Forty normal Sprague Dawley female rates (supplier Charles River, 150 days of age, average weight 280 g) were group housed in a room controlled for temperature and lighting and fed a standard pelletted rat diet and tap water ad libitum. The rats were weighed on the day of surgery (see below) and randomized into 5 groups of 8/group using a grouping program.

GHRP (inip) b b F K—NH2 was dissolved in a sodium acetate (20 mM) buffer (pH 5.0) containing mannitol (45 g/l) at 8 g/l and 1.6 g/l to fill the minipumps and at 0.5 and 0.1 g/l for the injection solutions. Osmotic minipumps (Alza, Palo Alto, model 2002, pump rate 0.52 µl/hr for 14 days, fill volume 230 µl, once per rat) were filled with these solutions; a fifth set of pumps were filled with the sodium acetate buffer. All the pumps were primed by being incubated in isotonic saline overnight in a refrigerator.

The next day osmotic pumps were inserted into all rats. To do this the rats were anesthetized with ketamine/xylazine (62.5 and 12.5 mg/kg/rat, respectively, by i.p. injection). The dorsal neck was then shaved, swabbed with betadine solution and cleaned with alcohol. An incision was then made on the dorsal neck and the a subcutaneous pocket created caudally by blunt dissection. The pumps were then inserted into the pocket with the end of the pump delivering the solution positioned away from the incision. The incision was then closed with wound clips, the rat placed on a heated pad and when ambulatory was returned to its home cage.

The treatment groups were;

1) Excipient pump, excipient injections 2 times a day.
2) b b F K—$NH_2$ pump (100 µg/day), excipient injections 2 times a day.
3) (inip) b b F K—$NH_2$ pump (20 µg/day, excipient injections 2 times a day.
4) (inip) b b F K—$NH_2$ injections 50 µg 2 times a day.
5) (inip) b b F K—$NH_2$ injections 10 µg 2 times a day.

The rats were then weighed every day and injected twice daily with either excipient or the two doses of (inip) b b F K—$NH_2$. On day 14 they were sacrificed using inhalation of carbon dioxide. They were then bled from the heart and organs taken. The rats were skinned and eviscerated to weigh the amount of skin, muscle and bone (the carcass). The pituitary, spleen, heart, kidney, liver, thymus and the soleus muscle were also taken and weighed while the tibias were removed and placed in 10% formalin for subsequent histological evaluation. The Tibias were sectioned longitudinally and the width of the epiphyseal plate was measured using a microscope fitted with an ocular micrometer.

Serum chemistries were measured using standard automated techniques. Serum insulin-like growth factor-1 (IGF-1) was measured by radioimmunoassay, using an antibody raised in rabbits, after acid ethanol extraction to remove the IGF-1 binding protein.

Statistical significance was gauged by analysis of variance, which if significant (p<0.05) was followed by a Duncan's New Multiple Range Test to test for differences between the individual treatment groups. Data are presented as mean±standard error of the mean with 8 rats per group.

(inip) b b F K—$NH_2$ at 20 and 100 µg/day, delivered by both injection and infusion, induced significant body weight gain compared to vehicle treated rats. The dose-related nature of the body weight gains to injections of (inip) b b F K—NH$_2$ can be seen in FIG. 20. In contrast there were similar weight gains in response to infusions of both 20 and 100 μg/day of (inip) b b F K—NH$_2$. In addition there were very different patterns of weight gain in response to infusions or injections of 100 μg/day of (inip) b b F K—NH$_2$ as can be seen in FIG. 21.

EXAMPLE 43

Combination GHRP and IGF-1 Treatment of Obese Rats

Methods

Forty-eight (48)obese male Zucker Diabetic Fatty (ZDF) rats (Genetic Models Inc., Indianapolis, Ind. 46268) 6 weeks of age were group housed in a room controlled for temperature and lighting and fed a standard pelletted rat diet and tap water ad libitum. The rats were weighed on the day of surgery (see below) and randomized into 6 groups of 8/group using a grouping program. Ten lean ZDF rats served as an additional control group.

GHRP (inip) b b F K—NH$_2$ was dissolved in a sodium acetate (20 mM) buffer (pH 5.0) containing mannitol (45 g/l) at 0.5 g/l. This GHRP was given by sc. injection twice daily, each dose of 100 μl therefore containing 50 μg/injection or 100 μg/day.

Recombinant human IGF-1 (rhIGF-1) at 13.8 mg/ml in acetate buffer was loaded into osmotic minipumps (Alza, Palo Alto, model 2ML4, pump rate 2.29 μl/hr for 28 days, fill volume 2064 μl). Other pumps were filled with acetate buffer. The pumps were primed by being incubated in isotonic saline overnight in a refrigerator. The delivered dose of rhIGF-1 was therefore 758 μg/day. Recombinant human growth hormone (rhGH, Lot R9092AX, Genentech Inc.) was diluted in sterile water to 2.5 g/l and a 100 μl injection given twice daily (250 μg/injection, or 500 μg/day).

The next day the osmotic pumps were inserted into rats. To do this the rats were anesthetized with ketamine/xylazine (62.5 and 12.5 mg/kg/rat, respectively, by i.p. injection). The dorsal neck was then shaved, swabbed with betadine solution and cleaned with alcohol. An incision was then made on the dorsal neck an the a subcutaneous pocket created caudally by blunt dissection. The pumps were then inserted into the pocket with the end of the pump delivering the solution positioned away from the incision. All rats not receiving rhIGF-1 containing pumps were implanted with pumps delivering the acetate buffer excipient. The incision was then closed with would clips, the rat placed on a heated pad and when ambulatory was returned to its home cage.

The rats were then weighed every day, and injected twice daily with either active drug (GH or GHRP) or vehicle excipient. On day 24 blood was withdrawn after a 4 hour fast and 1.5 U/kg of regular insulin was injected i.p. and a second blood sample taken 30 minutes later. The rats were then sacrificed using carbon dioxide, bled from the heart, and organs taken. Serum glucose was measured by standard automated procedures.

Statistical significance was gauged by analysis of variance, which if significant (p<0.05) was followed by a Duncan's New Multiple Range Test to test for differences between the individual treatment groups. Data are presented as mean±standard error (SE) of the mean with 8 rats per group.

Body Weight Gain

The body weight gains plotted against time for all treatment groups over the whose study are shown in FIG. 22 and for the first 7 days for the GHRP (inip) b b F K—NH$_2$ and IFG-1 treatment groups are shown in FIG. 23. The basal blood glucose values plotted against time for all the treatment groups for the entire experiment are shown in FIG. 24 and the blood glucose responses to an intravenous insulin challenge at the end of the experiment are shown in FIG. 25.

EXAMPLE 44

Combination GHRP and IGF-1 Treatment of Normal Rats

Methods

Sixty normal adult female SD rats (Supplier, Charles River, 120 days of age, 250 to 320 g) were group housed in a room controlled for temperature and lighting and fed a standard pelletted rat diet and tap water ad libitum. The rats were weighed on the day of surgery and randomized into 12 groups of 5/group using a grouping program.

The GH secretagogues (GHRPs and GHRH) were dissolved in a sodium acetate (20 mM) buffer (pH 5.0) containing mannitol (45g/l) at 0.5 g/l. The GH secretagogues were given by sc. injection twice daily, each dose of 100 μl. Different doses of the molecules were given based on there potency in the IV assay (for example L-692,585 was given at 3-fold higher doses as it was less the least potent of the secretagogues). Recombinant human IGF-1 (rhIGF-1) at 2.5 mg/ml in acetate buffer was loaded into osmotic minipumps (Alza, Palo Alto, model 2ML1, pump rate 10.16 μ/hr for 7 days, fill volume 2086 μl). Other pumps were filled with acetate buffer. The pumps were primed by being incubated in isotonic saline overnight in a refrigerator. The delivered dose of rhIGF-1 was therefore 610 μg/day.

The next day the osmotic pumps were inserted into rats. To do this the rats were anesthetized with ketamine/xylazine (62.5 and 12.5 mg/kg/rat, respectively, by i.p. injection). The dorsal neck was then shaved, swabbed with betadine solution and cleaned with alcohol. An incision was then made on the dorsal neck and the a subcutaneous pocket created caudally by blunt dissection. The pumps were then inserted into the pocket with the end of the pump delivering the solution positioned away from the incision. All rats not receiving rhIGF-1 containing pumps were implanted with pumps delivering the acetate buffer excipient. The incision was then closed with wound clips, the rat placed on a heated pad and then when it was ambulatory returned to its home cage. The treatment groups were;

| | | |
|---|---|---|
| 1) Excipient | 2 injections/d | Excipient pump |
| 2) Excipient | 2 injections/d | IGF-1 Pump |
| 3) GHRH (300 μg/dose) | 2 injections/d | Excipient pump |
| 4) GHRH (300 μg/dose) | 2 injections/d | IGF-1 pump |
| 5) GHRP-6 (50 μg/dose) | 2 injections/d | Excipient pump |
| 6) GHRP-6 (50 μg/dose) | 2 injections/d | IGF-1 pump |
| 7) (inip) b b F-NH$_2$ (50 μg/dose) | 2 injections/d | Excipient pump |
| 8) (inip) b b F-NH$_2$ (50 μg/dose) | 2 injections/d | IGF-1 pump |
| 9) (inip) b nmb bam (50 μg/dose) | 2 injections/d | Excipient pump |
| 10) (inip) b nmb bam (50 μg/dose) | 2 injections/d | IGF-1 pump |
| 11) L-692,585 (150 μg/dose) | 2 injections/d | Excipient pump |
| 12) L-692,585 (150 μg/dose) | 2 injections/d | IGF-1 pump |

The rats were then weighed every day, and injected twice daily with either active drug (GHRH or GHRP) or vehicle excipient). The rats were sacrificed using carbon dioxide, bled from the heart and organs taken. Serum chemistries were measured by standard automated procedures.

Statistical significance was gauged by analysis of variance, which if significant (p<0.05) was followed by a Duncan's New Multiple Range Test to test for differences between the individual treatment groups. Data are presented as mean±standard error of the mean with 8 rats per group.

Body Weight Gain

Figure 27:
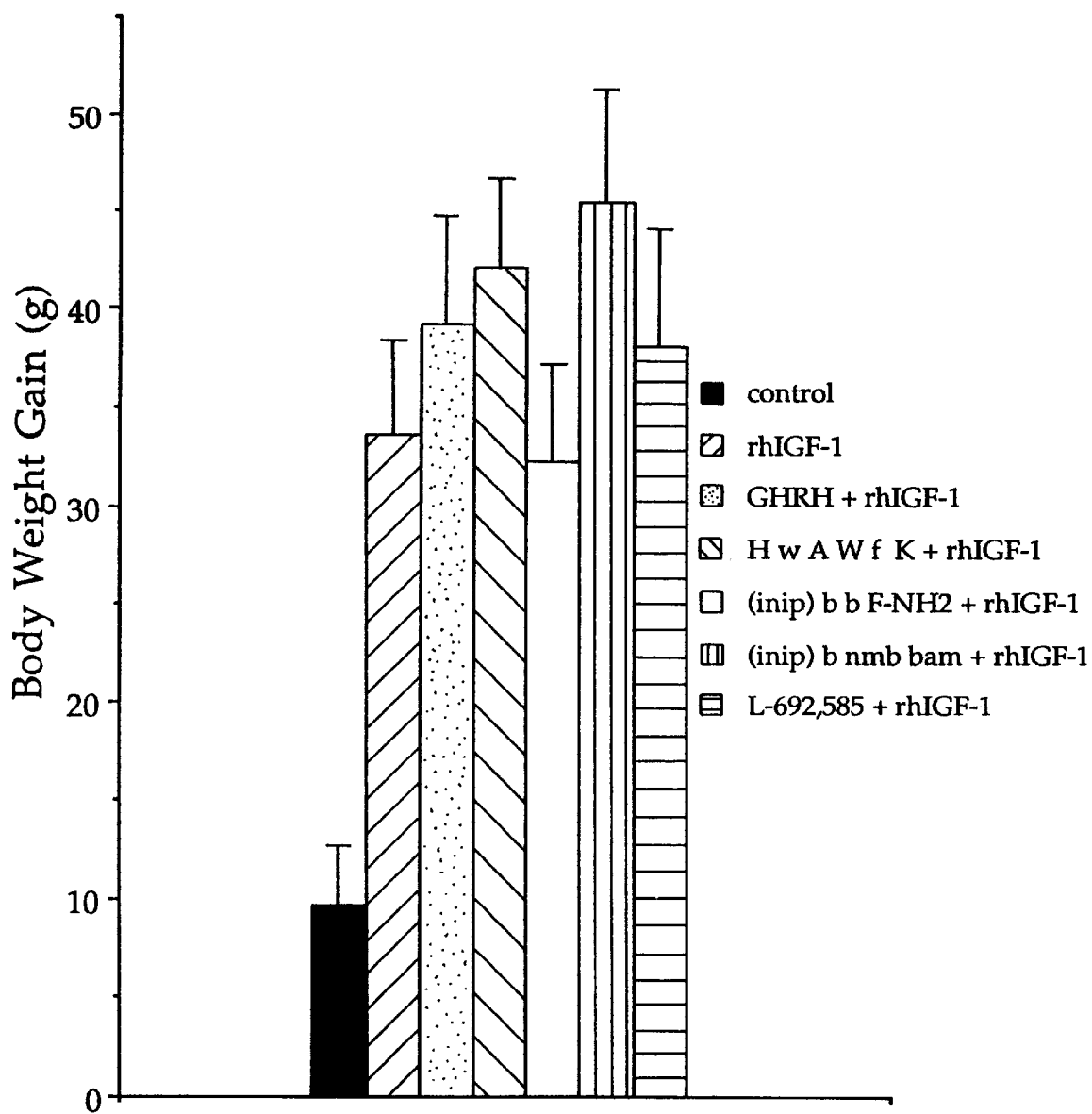
FIG. 27. Total body weight gain in normal adult rats treated for 7 days with twice daily subcutaneous injections of excipient (solid bar), infusions of recombinant human insulin-like growth factor-1 (rhIGF-1, broad hatching), or the combinations of rhIGF-1 plus growth hormone releasing hormone (light shading), HwAWfK plus rhIGF-1 (narrow hatching), (inip)bbF-NH2 plus rhIGF-1(open bar), (inip)b nmb bam plus rhIGF-1 (dark shading), or L-692,585 plus rhIGF-1 (horizontal lines). Weight gains tended to be greater after combination treatment. Means and standard errors are shown.

The body weight pains plotted against time for the groups treated only with the GH secretagogues are shown in FIG. 26. The responses to the combination of the GH secretagogues and IGF-1 tended to be greater than to IGF-1 alone (FIG. 27).

All references described herein are expressly incorporated by reference.

What is claimed is:
1. A compound represented by structural Formula IIIa–IIIi

[Structures IIIa through IIIi shown]

where
Ar$^1$ and Ar$^2$ are each independently selected from indolyl,

[structures shown with $(R^4)_n$ and $(R^5)_o$]

n and o are independently 1, 2 or 3;
R$^B$, R$^C$ and R$^D$ are selected from the group
  hydrogen,
  C$_1$–C$_6$alkyl optionally substituted with a group selected from
    NR$^2$R$^3$, and
    phenyl-C$_1$–C$_3$-NR$^2$R$^3$, and
  halo(F, Cl, Br, I)C$_1$–C$_6$alkyl;
R$^1$ is selected from
  hydrogen,
  C$_1$–C$_6$alkyl,
  C(=O)—C$_1$–C$_6$alkyl,
  C(=O)—NR$^2$R$^3$,
  C(=NR$^2$)—NR$^2$R$^3$,
  C(=O)O—C$_1$–C$_6$alkyl, and
  halo (F, Cl, Br, I)C$_1$–C$_6$alkyl;
R$^2$ and R$^3$ are selected from
  hydrogen,
  C$_1$–C$_6$alkyl,
  piperidinyl, and
  halo(F, Cl, Br, I)C$_1$–C$_6$alkyl;
R$^2$ and R$^3$ together with the N to which they are bonded may form a 5- or 6-member heterocycle, optionally containing one additional hetero atom selected from O, S, and N where any N is optionally substituted with R$^1$, any carbon is optionally substituted with R$^7$ and where the heterocycle is optionally fused to a phenyl ring, optionally substituted with R$^4$;
R$^4$ and R$^5$ are independently selected from the group hydrogen
halo (F, Cl, Br, and I),
cyano,
amino,
amido,
nitro,
hydroxy,
$C_1$–$C_4$perfluoroalkyl, and
$C_1$–$C_3$perfluoroalkoxy;
$R^7$ is selected from the group
  $COOR^2$,
  $CONR^2R^3$,
  cyano,
  $NR^2R^3$,
  $NR^2COR^3$,
  azido,
  nitro,
  hydroxy,
  $C_6$–$C_{10}$aryl optionally substituted with
    halo (F, Cl, Br, and I),
    cyano,
    amino,
    amido,
    nitro,
    hydroxy,
    $C_1$–$C_4$perfluoroalkyl, and
    $C_1$–$C_3$perfluoroalkoxy;
Y is selected from the group
  $C_1$–$C_6$alkyl substituted with 1–2 $R^7$,
  $C_2$–$C_6$alkynyl optionally substituted with 1–2$R^7$,
  $C_2$–$C_6$alkenyl optionally substituted with 1–2$R^7$,
  $C_1$–$C_6$alkyloxy optionally substituted with 1–2$R^7$, and
  piperidinyl; or
a pharmaceutically acceptable salt thereof.

2. The compound of claim 1 represented by structural Formula (IIIa)

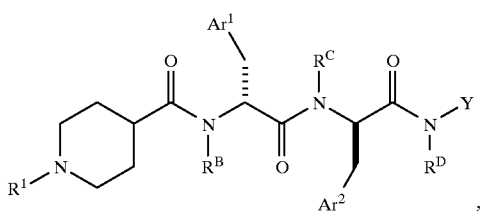

IIIa where
  $Ar^1$ and $Ar^2$ are each independently selected from indolyl, and

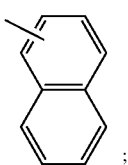

;

$R^B$, $R^C$ and $R^D$ are selected from the group
  hydrogen,
  $C_1$–$C_6$alkyl,
  $C_6$–$C_{10}$aryl—$C_1$–$C_6$alkyl, and
  halo (F, Cl, Br, I)$C_1$–$C_6$alkyl;
$R^2$ and $R^3$ are selected from
  hydrogen,
  $C_1$–$C_6$alkyl,
  piperidinyl, and
  halo (F, Cl, Br, I)$C_1$–$C_6$alkyl;
$R^2$ and $R^3$ together with the nitrogen to which they are attached may form on optionally mono- or di-substituted ring selected from
  piperidinyl,
  pyrroylidinyl,
  pyrryl,
  imidazolyl,
  piperazinyl, and
  morpholinyl
where the substituents are selected from $C_1$–$C_3$alkyl;
$R^7$ is selected from the group
  $COOR^2$,
  $CONR^2R^3$,
  cyano,
  $NR^2R^3$,
  $NR^2COR^3$,
  azido,
  nitro,
  hydroxy, and
  $C_6$–$C_{10}$aryl optionally substituted with
    halo (F, Cl, Br, and I),
    cyano,
    amino,
    amido,
    nitro,
    hydroxy,
    $C_1$–$C_4$perfluoroalkyl, and
    $C_1$–$C_3$perfluoroalkoxy;
Y is selected from the group
  $C_1$–$C_6$alkyl substituted with 1–2 $R^7$,
  $C_2$–$C_6$alkynyl optionally substituted with 1–2$R^7$,
  $C_2$–$C_6$alkenyl optionally substituted with 1–2 $R^7$,
  $C_1$–$C_6$alkyloxy optionally substituted with 1–2 $R^7$, and
  piperidinyl;
Y and $R^D$ together with the N to which they are bonded may form a 5- or 6-member heterocycle, optionally containing one additional hetero atom selected from O, S, and N where any N is optionally substituted with $R^1$, any carbon is optionally substituted with $R^7$ and where the heterocycle is optionally fused to a phenyl ring; or
a pharmaceutically acceptable salt thereof.

3. The compound of claim 2 selected from the group consisting of

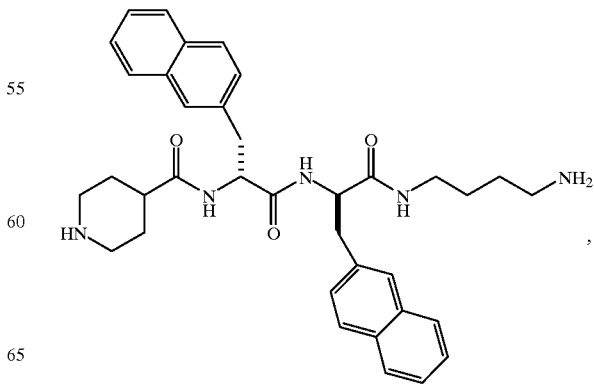

,

165
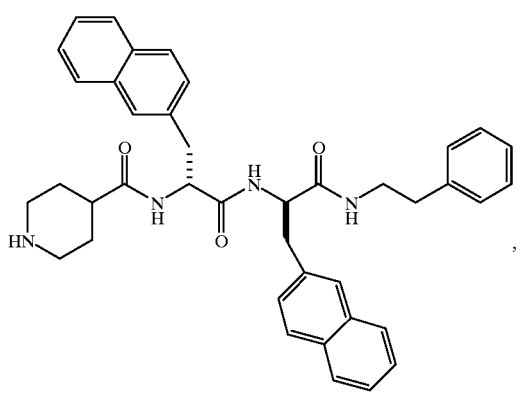
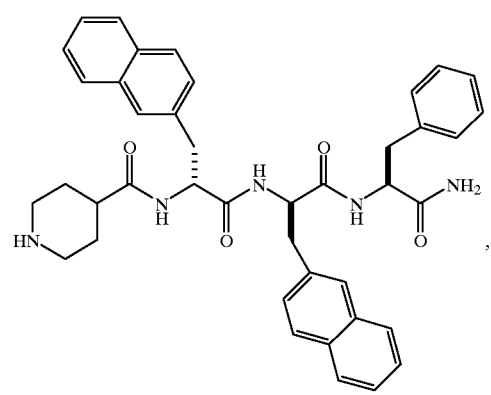
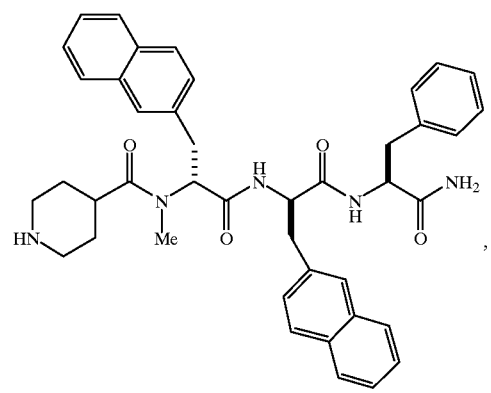
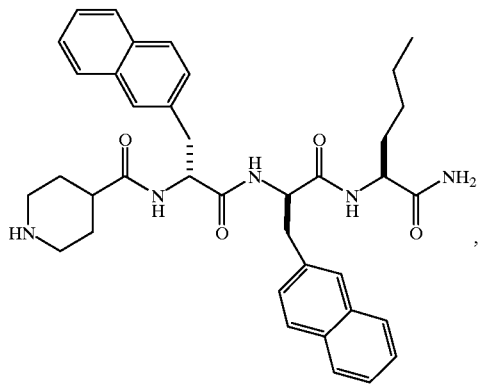
166
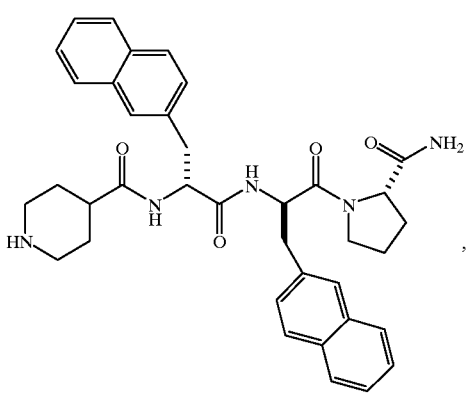
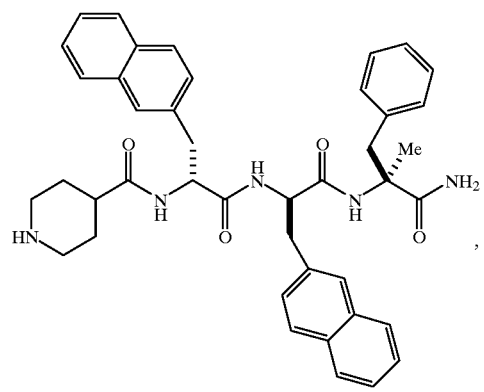
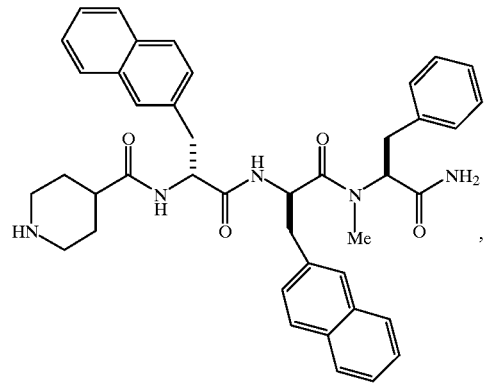
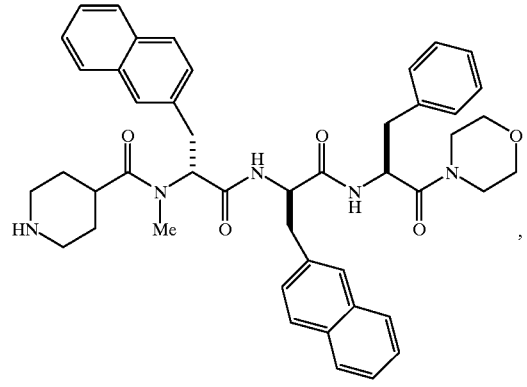

167
-continued
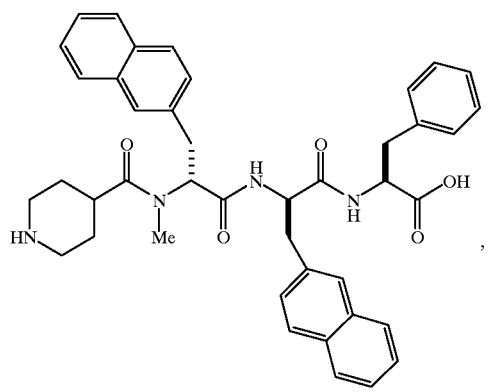
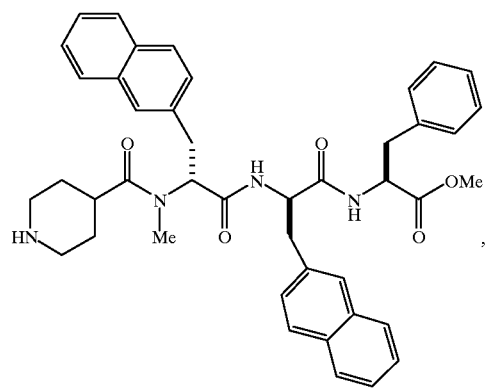
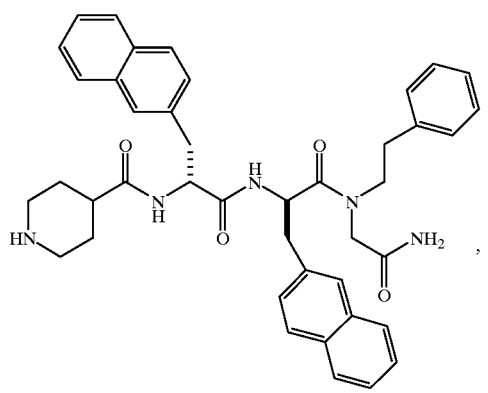
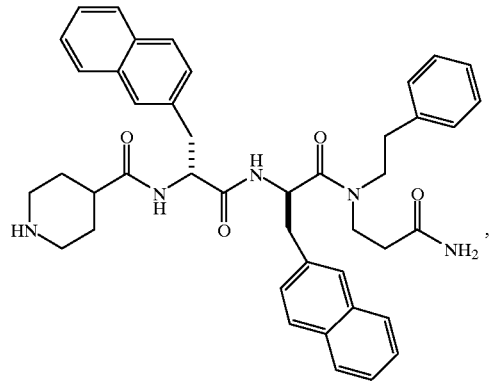
168
-continued
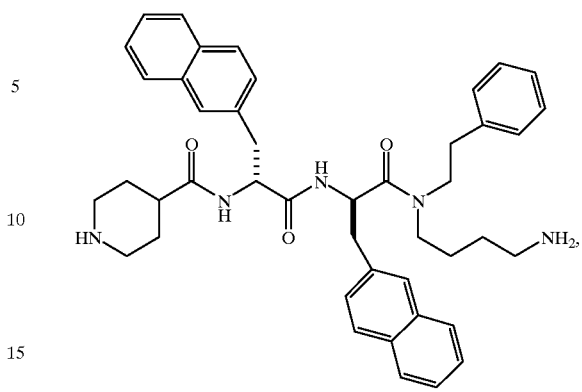
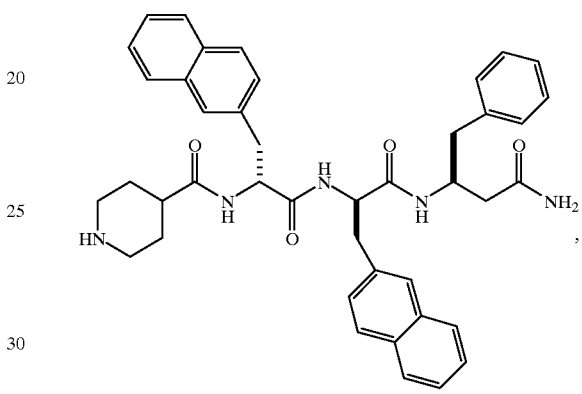
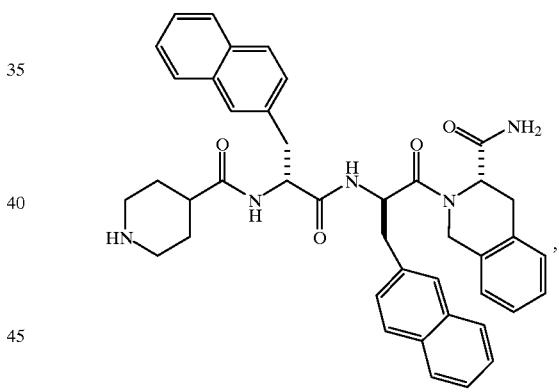
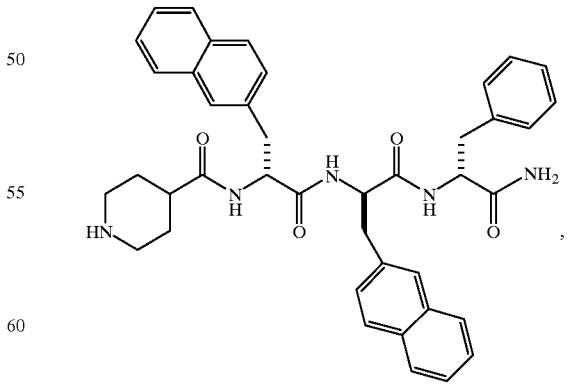

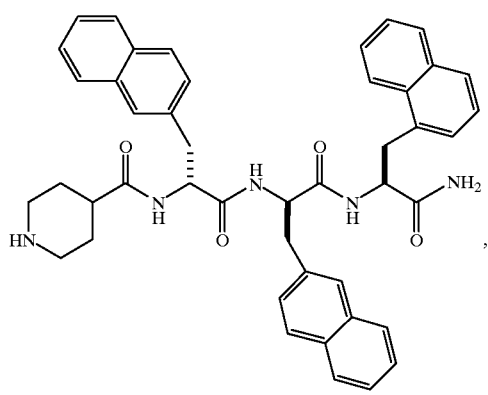
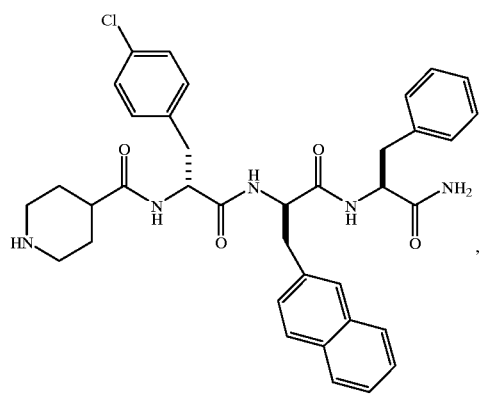
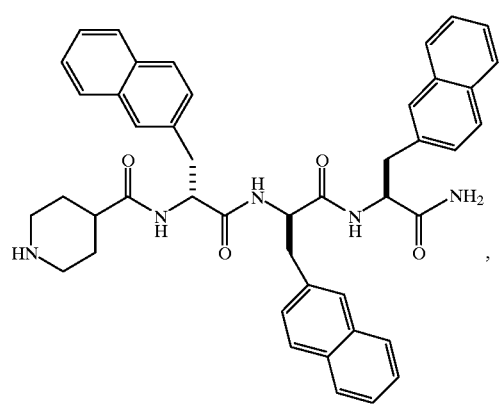
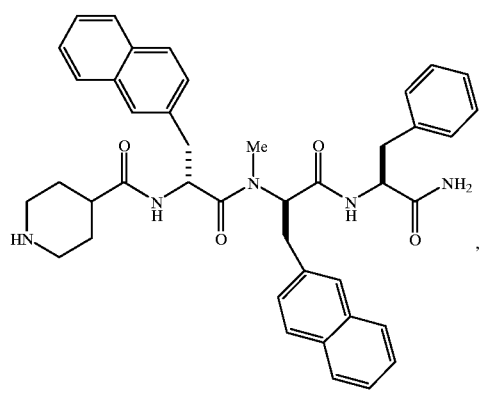
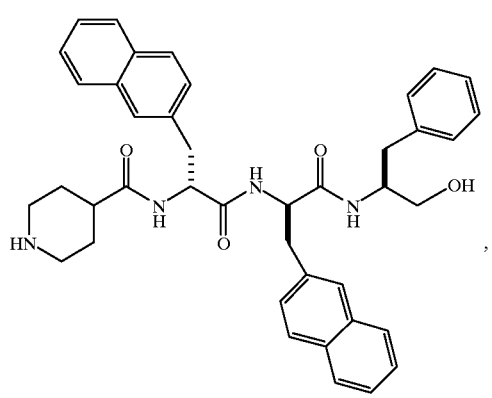
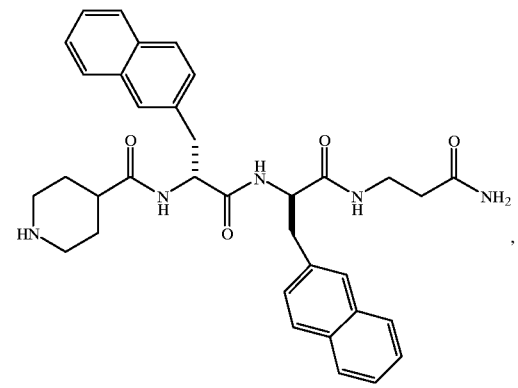
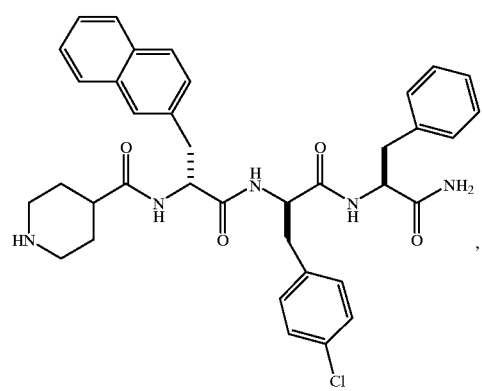
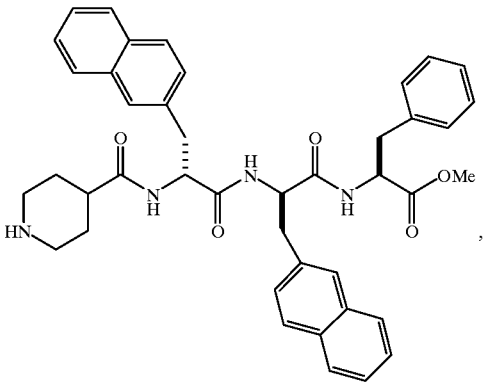

171
-continued
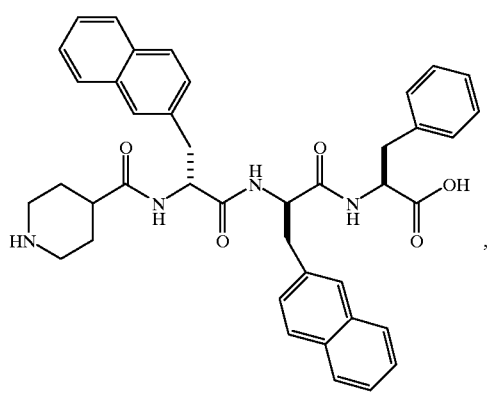
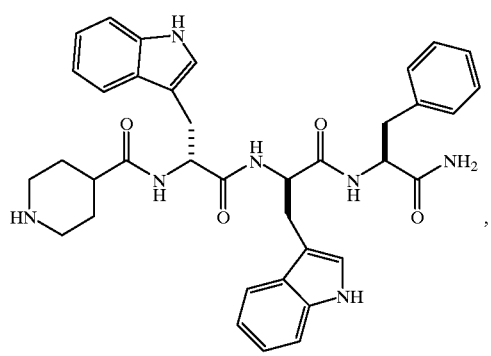
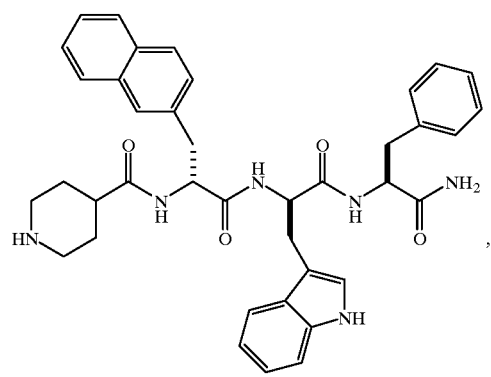
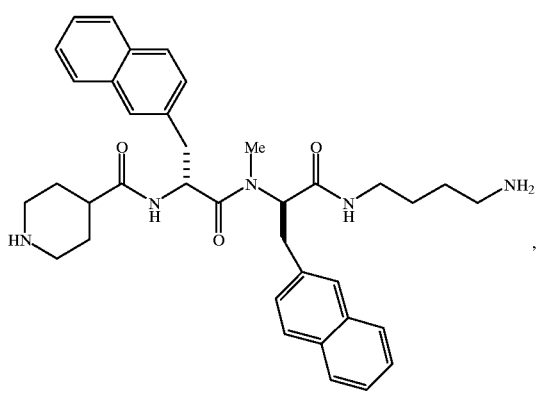
172
-continued
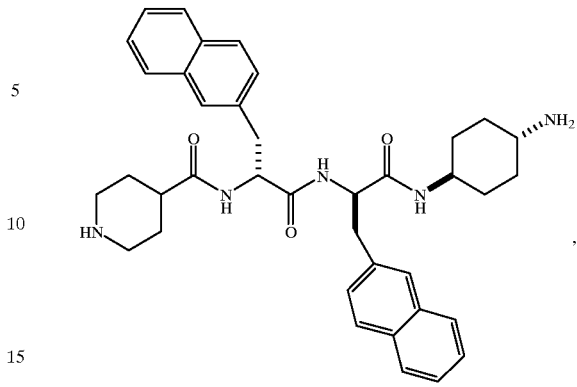
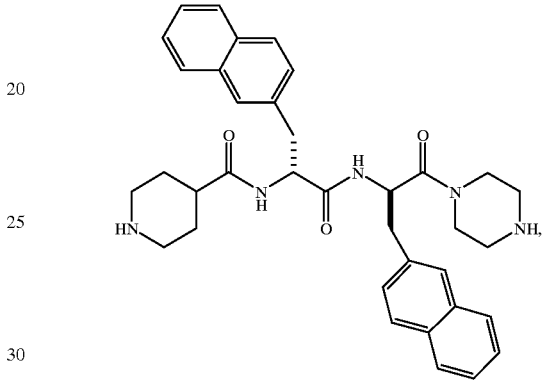
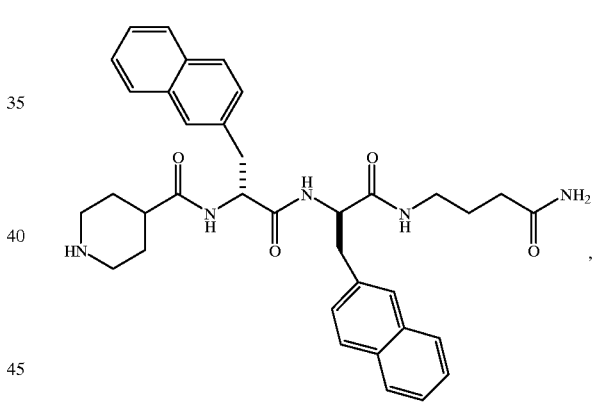
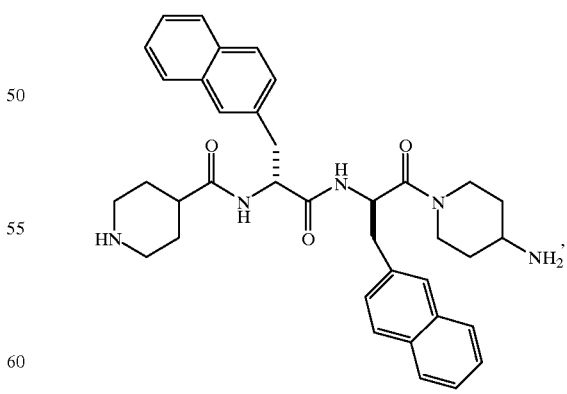

173
-continued

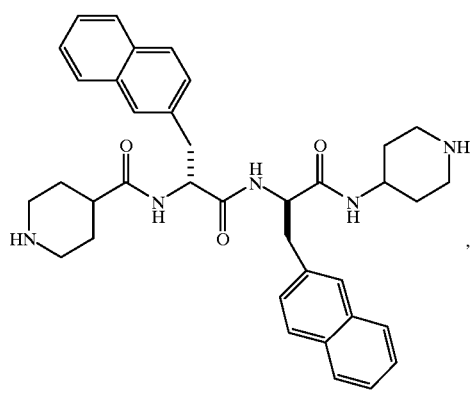
,

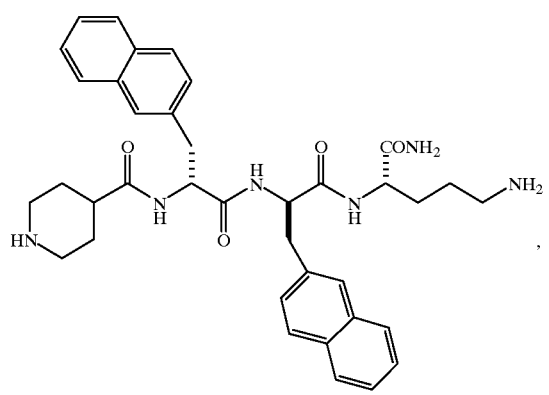
,

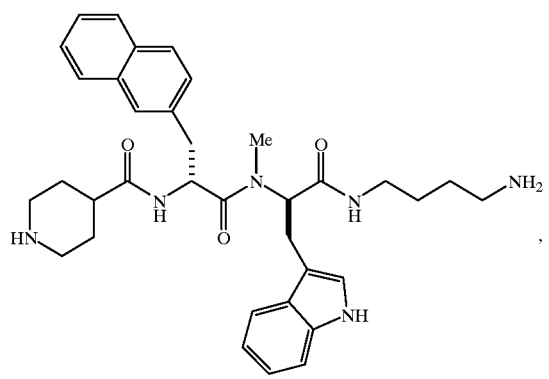
,

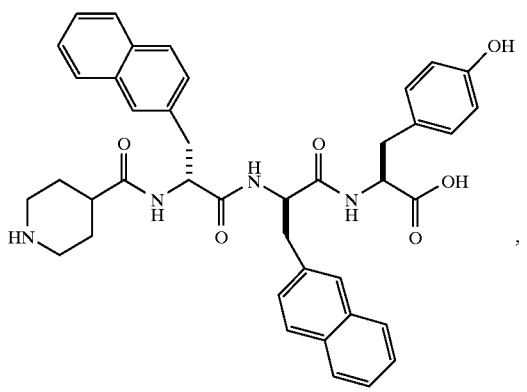
,

174
-continued

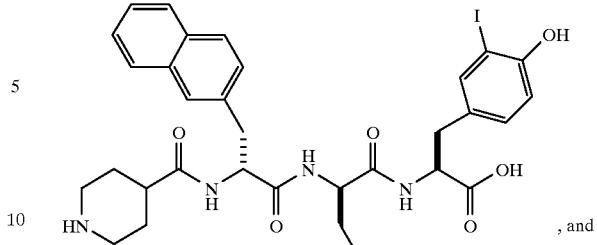
, and

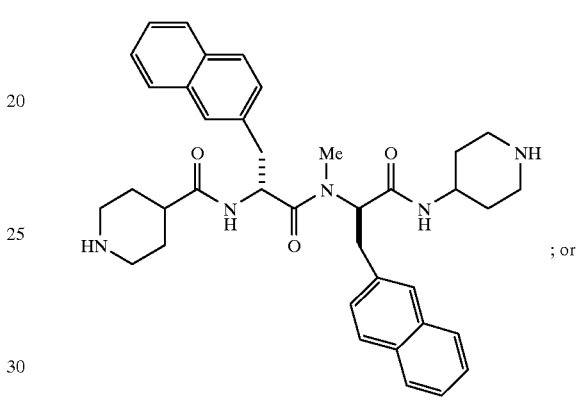
; or a pharmaceutically acceptable salt thereof.

4. A pharmaceutical composition comprising a pharmaceutically acceptable excipient and the compound of claim 1.

5. A method for increasing the level of endogenous growth hormone in a mammal comprising administering to the mammal a pharmaceutically effective amount of the composition of claim 4 to the mammal.

6. The method of claim 5, further comprising administering the composition in combination with a growth factor selected from the group consisting of growth hormone (GH), growth hormone releasing hormone (GHRH), insulin-like growth factor-1 (IFG-1) and insulin-like growth factor-2 (IGF-2).

7. A method for treating type II diabetes in a mammal in need of such treatment comprising administering to the mammal a pharmaceutically effective amount of the composition of claim 4 to the mammal.

* * * * *